US008187280B2

(12) United States Patent
May et al.

(10) Patent No.: US 8,187,280 B2
(45) Date of Patent: May 29, 2012

(54) KNEE JOINT PROSTHESIS SYSTEM AND METHOD FOR IMPLANTATION

(75) Inventors: Brian M. May, Warsaw, IN (US); Duke A. Fox, Warsaw, IN (US); Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 669 days.

(21) Appl. No.: 12/248,517

(22) Filed: Oct. 9, 2008

(65) Prior Publication Data

US 2009/0125114 A1 May 14, 2009

Related U.S. Application Data

(63) Continuation-in-part of application No. 11/972,359, filed on Jan. 10, 2008.

(60) Provisional application No. 60/978,949, filed on Oct. 10, 2007.

(51) Int. Cl.
*A61B 17/56* (2006.01)
*A61B 17/90* (2006.01)

(52) U.S. Cl. ........................................... 606/88

(58) Field of Classification Search ...................... 606/88
See application file for complete search history.

(56) References Cited

U.S. PATENT DOCUMENTS

| 538,987 A | 5/1895 | Turley |
|---|---|---|
| 3,806,961 A | 4/1974 | Muller et al. |
| 3,848,272 A | 11/1974 | Noiles |
| 3,859,992 A | 1/1975 | Amstutz |
| 3,878,566 A | 4/1975 | Bechtol |
| 3,964,106 A | 6/1976 | Hutter, Jr. et al. |
| 4,001,897 A | 1/1977 | Rambert et al. |
| 4,007,495 A | 2/1977 | Frazier |
| 4,012,796 A | 3/1977 | Weisman et al. |
| 4,041,550 A | 8/1977 | Frazier |
| 4,064,567 A | 12/1977 | Burstein et al. |
| 4,136,405 A | 1/1979 | Pastrick et al. |

(Continued)

FOREIGN PATENT DOCUMENTS

DE 3336004 6/1985

(Continued)

OTHER PUBLICATIONS

International Search Report and Written Opinion for PCT/US2008/079545 mailed Jan. 14, 2009 claiming priority to U.S. Appl. No. 60/978,949, filed Oct. 10, 2007.

(Continued)

*Primary Examiner* — Thomas C. Barrett
*Assistant Examiner* — Zade Coley
(74) *Attorney, Agent, or Firm* — Harness, Dickey

(57) ABSTRACT

A system for cooperating with an elongated IM member during preparation of a bone for receiving a prosthesis can include a scaffold, skeleton or frame. An alignment assembly can be selectively coupled to the frame. The alignment assembly can cooperate with the IM member to position the frame relative to the bone. A cutting block can be selectively coupled to the frame. According to other features, a posterior stabilized (PS) box guide assembly can have a PS box guide attachment portion that selectively couples with the first attachment portion of the frame. A posterior foot can selectively couple with a second attachment portion on the frame. The posterior foot can be positioned to occupy space of a joint line in an installed position.

29 Claims, 98 Drawing Sheets

U.S. PATENT DOCUMENTS

| | | |
|---|---|---|
| 4,151,615 A | 5/1979 | Hall |
| 4,202,055 A | 5/1980 | Reiner et al. |
| 4,219,893 A | 9/1980 | Noiles |
| 4,224,698 A | 9/1980 | Hopson |
| 4,284,080 A | 8/1981 | Rehder et al. |
| 4,305,394 A | 12/1981 | Bertuch, Jr. |
| 4,344,192 A | 8/1982 | Imbert et al. |
| 4,404,691 A | 9/1983 | Buning et al. |
| 4,475,549 A | 10/1984 | Oh |
| RE31,865 E | 4/1985 | Roux et al. |
| 4,523,587 A | 6/1985 | Frey |
| 4,549,319 A | 10/1985 | Meyer |
| 4,579,558 A | 4/1986 | Ramer |
| 4,619,658 A | 10/1986 | Pappas et al. |
| 4,624,674 A | 11/1986 | Pappas et al. |
| 4,632,111 A | 12/1986 | Roche |
| 4,655,777 A | 4/1987 | Dunn et al. |
| 4,659,331 A | 4/1987 | Matthews et al. |
| 4,661,112 A | 4/1987 | Muller et al. |
| 4,676,797 A | 6/1987 | Anapliotis et al. |
| 4,676,798 A | 6/1987 | Noiles |
| 4,676,799 A | 6/1987 | Legrand et al. |
| 4,678,470 A | 7/1987 | Nashef et al. |
| 4,698,063 A | 10/1987 | Link et al. |
| 4,711,233 A | 12/1987 | Brown |
| 4,711,639 A | 12/1987 | Grundei |
| 4,714,477 A | 12/1987 | Fichera et al. |
| 4,716,894 A | 1/1988 | Lazzeri et al. |
| 4,718,909 A | 1/1988 | Brown |
| 4,718,911 A | 1/1988 | Kenna |
| 4,718,915 A | 1/1988 | Epinette et al. |
| 4,718,916 A | 1/1988 | Morscher et al. |
| 4,728,333 A | 3/1988 | Masse et al. |
| 4,735,625 A | 4/1988 | Davidson |
| 4,737,411 A | 4/1988 | Graves, Jr. et al. |
| 4,764,171 A | 8/1988 | Harder et al. |
| 4,770,658 A | 9/1988 | Geremakis |
| 4,770,659 A | 9/1988 | Kendall |
| 4,770,660 A | 9/1988 | Averill |
| 4,770,661 A | 9/1988 | Oh |
| 4,778,473 A | 10/1988 | Matthews et al. |
| 4,778,474 A | 10/1988 | Homsy |
| 4,784,662 A | 11/1988 | Muller et al. |
| 4,784,663 A | 11/1988 | Kenna |
| 4,789,663 A | 12/1988 | Wallace et al. |
| 4,790,852 A | 12/1988 | Noiles |
| 4,790,854 A | 12/1988 | Harder et al. |
| 4,795,470 A | 1/1989 | Goymann et al. |
| 4,795,471 A | 1/1989 | Oh |
| 4,798,610 A | 1/1989 | Averill et al. |
| 4,801,301 A | 1/1989 | Noiles |
| 4,813,961 A | 3/1989 | Sostegni et al. |
| 4,822,366 A | 4/1989 | Bolesky |
| 4,827,919 A | 5/1989 | Barbarito et al. |
| 4,828,566 A | 5/1989 | Griss et al. |
| 4,842,606 A | 6/1989 | Kranz et al. |
| 4,846,839 A | 7/1989 | Noiles |
| 4,846,840 A | 7/1989 | Leclercq et al. |
| 4,851,007 A | 7/1989 | Gray |
| 4,871,368 A | 10/1989 | Wagner et al. |
| 4,878,916 A | 11/1989 | Rhenter et al. |
| 4,883,488 A | 11/1989 | Bloebaum et al. |
| 4,883,492 A | 11/1989 | Frey et al. |
| 4,888,021 A | 12/1989 | Forte et al. |
| 4,892,547 A | 1/1990 | Brown |
| 4,904,265 A | 2/1990 | MacCollum et al. |
| 4,908,033 A | 3/1990 | Frey et al. |
| 4,908,034 A | 3/1990 | Weightman et al. |
| 4,908,036 A | 3/1990 | Link et al. |
| 4,911,723 A | 3/1990 | Menschik et al. |
| 4,919,674 A | 4/1990 | Schelhas et al. |
| 4,923,472 A | 5/1990 | Ugolini et al. |
| 4,936,847 A | 6/1990 | Manginelli |
| 4,936,853 A | 6/1990 | Fabian et al. |
| 4,936,855 A | 6/1990 | Sherman |
| 4,936,861 A | 6/1990 | Muller et al. |
| 4,938,769 A | 7/1990 | Shaw |
| 4,938,772 A | 7/1990 | Frey et al. |
| 4,944,756 A | 7/1990 | Kenna |
| 4,944,757 A | 7/1990 | Martinez et al. |
| 4,950,297 A | 8/1990 | Elloy et al. |
| 4,950,298 A | 8/1990 | Gustilo et al. |
| 4,950,299 A | 8/1990 | Noiles |
| 4,959,071 A | 9/1990 | Brown et al. |
| 4,960,427 A | 10/1990 | Noiles |
| 4,961,748 A | 10/1990 | Frey et al. |
| 4,963,154 A | 10/1990 | Anapliotis et al. |
| 4,963,155 A | 10/1990 | Lazzeri et al. |
| 4,964,869 A | 10/1990 | Auclair et al. |
| 4,978,356 A | 12/1990 | Noiles |
| 4,985,037 A | 1/1991 | Petersen |
| 4,990,161 A | 2/1991 | Kampner |
| 4,994,064 A | 2/1991 | Aboczky |
| 4,995,158 A * | 2/1991 | Howell et al. .................. 29/723 |
| 4,995,883 A | 2/1991 | Demane et al. |
| 5,002,578 A | 3/1991 | Luman |
| 5,002,581 A | 3/1991 | Paxson et al. |
| 5,009,666 A | 4/1991 | Van Syckle et al. |
| 5,019,103 A | 5/1991 | Van Zile et al. |
| 5,019,105 A | 5/1991 | Wiley |
| 5,019,108 A | 5/1991 | Bertin et al. |
| 5,021,062 A | 6/1991 | Adrey et al. |
| 5,030,221 A | 7/1991 | Buechel et al. |
| 5,032,134 A | 7/1991 | Lindwer |
| 5,037,424 A | 8/1991 | Aboczsky |
| 5,037,438 A | 8/1991 | Davidson |
| 5,037,441 A | 8/1991 | Bouvet et al. |
| 5,041,140 A | 8/1991 | Teinturier et al. |
| 5,061,269 A | 10/1991 | Muller |
| 5,061,270 A | 10/1991 | Aboczky |
| 5,062,852 A | 11/1991 | Dorr et al. |
| 5,062,853 A | 11/1991 | Forte |
| 5,074,879 A | 12/1991 | Pappas et al. |
| 5,080,677 A | 1/1992 | Shelley et al. |
| 5,084,051 A | 1/1992 | Tormala et al. |
| 5,092,900 A | 3/1992 | Marchetti et al. |
| 5,098,437 A | 3/1992 | Kashuba et al. |
| 5,108,437 A | 4/1992 | Kenna |
| 5,108,439 A | 4/1992 | Morscher et al. |
| 5,108,445 A | 4/1992 | Ashby et al. |
| 5,108,446 A | 4/1992 | Wagner et al. |
| 5,108,450 A | 4/1992 | Horber et al. |
| 5,112,338 A | 5/1992 | Anspach, III |
| 5,116,339 A | 5/1992 | Glock |
| 5,116,378 A | 5/1992 | Carbone |
| 5,116,379 A | 5/1992 | McLardy-Smith et al. |
| 5,116,380 A | 5/1992 | Hewka et al. |
| 5,133,760 A | 7/1992 | Petersen et al. |
| 5,133,763 A | 7/1992 | Mullers et al. |
| 5,137,535 A | 8/1992 | Keller |
| 5,137,536 A | 8/1992 | Koshino et al. |
| 5,141,512 A | 8/1992 | Farmer et al. |
| 5,147,406 A | 9/1992 | Houston et al. |
| 5,152,796 A | 10/1992 | Slamin |
| 5,152,797 A | 10/1992 | Luckman et al. |
| 5,163,963 A | 11/1992 | Hewka et al. |
| 5,163,966 A | 11/1992 | Norton et al. |
| 5,169,399 A | 12/1992 | Ryland et al. |
| 5,171,243 A | 12/1992 | Kashuba et al. |
| 5,171,276 A | 12/1992 | Caspari et al. |
| 5,171,286 A | 12/1992 | Lawes et al. |
| 5,171,313 A | 12/1992 | Salyer |
| 5,171,323 A | 12/1992 | Willert et al. |
| 5,176,709 A | 1/1993 | Branemark et al. |
| 5,180,394 A | 1/1993 | Davidson |
| 5,181,925 A | 1/1993 | Houston et al. |
| 5,181,929 A | 1/1993 | Prats et al. |
| 5,192,331 A | 3/1993 | Spotorno et al. |
| 5,194,066 A | 3/1993 | Van Zile |
| 5,197,488 A | 3/1993 | Kovacevic |
| 5,197,987 A | 3/1993 | Koch et al. |
| 5,197,988 A | 3/1993 | Spotorno et al. |
| 5,201,769 A | 4/1993 | Schutzer |
| 5,211,664 A | 5/1993 | Tepic et al. |
| 5,211,666 A | 5/1993 | Fetto |
| 5,217,496 A | 6/1993 | Bruce et al. |
| 5,217,498 A | 6/1993 | Hensgge et al. |

| | | | | | | |
|---|---|---|---|---|---|---|
| 5,219,362 A | 6/1993 | Tuke et al. | 5,486,178 A * | 1/1996 | Hodge | 606/82 |
| 5,222,983 A | 6/1993 | Schmitz et al. | 5,486,181 A | 1/1996 | Cohen et al. | |
| 5,222,984 A | 6/1993 | Forte | 5,489,311 A | 2/1996 | Cipolletti | |
| 5,226,915 A | 7/1993 | Bertin | 5,507,745 A | 4/1996 | Logroscino et al. | |
| 5,242,445 A | 9/1993 | Ashman | 5,507,817 A | 4/1996 | Craig et al. | |
| 5,246,459 A | 9/1993 | Elias | 5,507,818 A | 4/1996 | McLaughlin | |
| 5,250,051 A | 10/1993 | Maryan | 5,507,820 A | 4/1996 | Pappas | |
| 5,258,034 A | 11/1993 | Furlong et al. | 5,507,826 A | 4/1996 | Besselink et al. | |
| 5,258,035 A | 11/1993 | Hofmann et al. | 5,507,829 A | 4/1996 | Thongpreda et al. | |
| 5,263,988 A | 11/1993 | Huebner | 5,507,832 A | 4/1996 | Michielli et al. | |
| 5,275,601 A | 1/1994 | Gogolewski et al. | 5,510,396 A | 4/1996 | Prewett et al. | |
| 5,282,867 A | 2/1994 | Mikhail | 5,522,902 A | 6/1996 | Yuan et al. | |
| 5,282,870 A | 2/1994 | Moser et al. | 5,527,317 A | 6/1996 | Ashby et al. | |
| 5,284,483 A | 2/1994 | Johnson et al. | 5,531,791 A | 7/1996 | Wolfinbarger, Jr. | |
| 5,290,311 A | 3/1994 | Baumann | 5,531,793 A | 7/1996 | Kelman et al. | |
| 5,290,313 A | 3/1994 | Heldreth | 5,534,032 A | 7/1996 | Hodorek | |
| 5,290,315 A | 3/1994 | DeCarlo, Jr. | 5,540,697 A | 7/1996 | Rehmann et al. | |
| 5,290,318 A | 3/1994 | Ling et al. | 5,549,684 A | 8/1996 | Amino et al. | |
| 5,292,322 A | 3/1994 | Faccioli et al. | 5,549,685 A | 8/1996 | Hayes | |
| 5,314,478 A | 5/1994 | Oka et al. | 5,549,689 A | 8/1996 | Epstein et al. | |
| 5,314,479 A | 5/1994 | Rockwood, Jr. et al. | 5,549,696 A | 8/1996 | Willi et al. | |
| 5,314,491 A | 5/1994 | Thongpreda et al. | 5,549,699 A | 8/1996 | MacMahon et al. | |
| 5,318,571 A | 6/1994 | Benson | 5,549,701 A | 8/1996 | Mikhail | |
| 5,320,625 A | 6/1994 | Bertin | 5,549,703 A | 8/1996 | Daigle et al. | |
| 5,326,358 A | 7/1994 | Aubriot et al. | 5,549,704 A | 8/1996 | Sutter et al. | |
| 5,326,359 A | 7/1994 | Oudard et al. | 5,549,706 A | 8/1996 | McCarthy | |
| 5,330,534 A | 7/1994 | Herrington et al. | 5,552,454 A | 9/1996 | Kretschmann et al. | |
| 5,336,267 A | 8/1994 | Kubein-Meesenburg et al. | 5,556,432 A | 9/1996 | Kubein-Meesenburg et al. | |
| 5,342,360 A | 8/1994 | Faccioli et al. | 5,556,433 A | 9/1996 | Gabriel et al. | |
| 5,343,877 A | 9/1994 | Park | 5,571,111 A | 11/1996 | Aboczky | |
| 5,344,460 A | 9/1994 | Turanyi et al. | 5,571,193 A | 11/1996 | Kampner | |
| 5,344,461 A | 9/1994 | Phlipot | 5,571,194 A | 11/1996 | Gabriel | |
| 5,356,629 A | 10/1994 | Sander et al. | 5,571,196 A | 11/1996 | Stein | |
| 5,358,529 A | 10/1994 | Davidson | 5,571,201 A | 11/1996 | Averill et al. | |
| 5,358,530 A | 10/1994 | Hodorek | 5,571,202 A | 11/1996 | Mathys, Sr. et al. | |
| 5,360,449 A | 11/1994 | Branemark et al. | 5,580,352 A | 12/1996 | Sekel et al. | |
| 5,360,451 A | 11/1994 | Keller et al. | 5,584,837 A | 12/1996 | Petersen | |
| 5,364,403 A | 11/1994 | Petersen et al. | 5,593,447 A | 1/1997 | Angeli et al. | |
| 5,370,692 A | 12/1994 | Fink et al. | 5,593,449 A | 1/1997 | Roberson, Jr. | |
| 5,370,693 A | 12/1994 | Kelman et al. | 5,593,450 A | 1/1997 | Scott et al. | |
| 5,370,698 A | 12/1994 | Heimke et al. | 5,593,451 A | 1/1997 | Averill et al. | |
| 5,370,701 A | 12/1994 | Finn | 5,609,641 A | 3/1997 | Johnson et al. | |
| 5,370,702 A | 12/1994 | Jones | 5,609,642 A | 3/1997 | Johnson et al. | |
| 5,376,122 A | 12/1994 | Pappas et al. | 5,609,645 A | 3/1997 | Vinciguerra | |
| 5,376,123 A | 12/1994 | Klaue et al. | 5,609,647 A | 3/1997 | Kalberer et al. | |
| 5,376,124 A | 12/1994 | Gustke et al. | 5,609,648 A | 3/1997 | Oehy et al. | |
| 5,383,938 A | 1/1995 | Rohr et al. | 5,624,444 A * | 4/1997 | Wixon et al. | 606/88 |
| 5,387,239 A | 2/1995 | Bianco et al. | 5,639,280 A | 6/1997 | Warner et al. | |
| 5,387,240 A | 2/1995 | Pottenger et al. | 5,641,323 A | 6/1997 | Caldarise | |
| 5,387,241 A | 2/1995 | Hayes | 5,645,593 A | 7/1997 | Woods et al. | |
| 5,397,360 A | 3/1995 | Cohen et al. | 5,645,594 A | 7/1997 | Devanathan et al. | |
| 5,405,392 A | 4/1995 | Deckner et al. | 5,645,604 A | 7/1997 | Schneider et al. | |
| 5,405,395 A | 4/1995 | Coates | 5,653,765 A | 8/1997 | McTighe et al. | |
| 5,405,400 A | 4/1995 | Linscheid et al. | 5,658,294 A | 8/1997 | Sederholm | |
| 5,405,401 A | 4/1995 | Lippincott, III et al. | 5,658,344 A | 8/1997 | Hurlburt | |
| 5,405,403 A | 4/1995 | Mikhail | 5,658,346 A | 8/1997 | Willi et al. | |
| 5,405,404 A | 4/1995 | Gardner et al. | 5,658,348 A | 8/1997 | Rohr, Jr. | |
| 5,411,555 A | 5/1995 | Nieder | 5,658,349 A | 8/1997 | Brooks et al. | |
| 5,413,605 A | 5/1995 | Ashby et al. | 5,662,656 A * | 9/1997 | White | 606/88 |
| 5,413,607 A | 5/1995 | Engelbrecht et al. | 5,676,700 A | 10/1997 | Black et al. | |
| 5,413,610 A | 5/1995 | Amino et al. | 5,676,704 A | 10/1997 | Ries et al. | |
| 5,417,696 A | 5/1995 | Kashuba et al. | 5,681,354 A | 10/1997 | Eckhoff | |
| 5,425,778 A | 6/1995 | Zichner et al. | 5,683,399 A | 11/1997 | Jones | |
| 5,425,779 A | 6/1995 | Schlosser et al. | 5,683,472 A | 11/1997 | O'Neil et al. | |
| 5,431,657 A | 7/1995 | Rohr | 5,702,463 A | 12/1997 | Pothier et al. | |
| 5,443,512 A | 8/1995 | Parr et al. | 5,702,475 A | 12/1997 | Zahedi et al. | |
| 5,443,516 A | 8/1995 | Albrektsson et al. | 5,702,476 A | 12/1997 | Limacher et al. | |
| 5,447,492 A | 9/1995 | Cartmell et al. | 5,702,477 A | 12/1997 | Capello et al. | |
| 5,458,637 A | 10/1995 | Hayes | 5,702,478 A | 12/1997 | Tornier et al. | |
| 5,462,563 A | 10/1995 | Shearer et al. | 5,702,482 A | 12/1997 | Thongpreda et al. | |
| 5,474,560 A | 12/1995 | Rohr, Jr. | 5,702,487 A | 12/1997 | Averill et al. | |
| 5,480,443 A | 1/1996 | Elias | 5,720,752 A | 2/1998 | Elliott et al. | |
| 5,480,444 A | 1/1996 | Incavo et al. | 5,725,589 A | 3/1998 | Pfaff et al. | |
| 5,480,445 A | 1/1996 | Burkinshaw | 5,725,591 A | 3/1998 | DeCarlo, Jr. et al. | |
| 5,480,446 A | 1/1996 | Goodfellow et al. | 5,725,597 A | 3/1998 | Hwang et al. | |
| 5,480,447 A | 1/1996 | Skiba | 5,735,901 A | 4/1998 | Maumy et al. | |
| 5,480,448 A | 1/1996 | Mikhail | 5,746,771 A | 5/1998 | Clement, Jr. et al. | |
| 5,480,451 A | 1/1996 | Grundei et al. | 5,749,877 A | 5/1998 | Young et al. | |
| 5,480,452 A | 1/1996 | Hofmann et al. | 5,755,794 A | 5/1998 | Benson | |

| Patent | Date | Inventor | Patent | Date | Inventor |
|---|---|---|---|---|---|
| 5,755,800 A | 5/1998 | O'Neil et al. | 5,997,576 A | 12/1999 | Copf et al. |
| 5,755,805 A | 5/1998 | Whiteside | 5,997,577 A | 12/1999 | Herrington et al. |
| 5,755,806 A | 5/1998 | Stalcup et al. | 5,997,579 A | 12/1999 | Albrektsson et al. |
| 5,755,807 A | 5/1998 | Anstaett et al. | 6,004,353 A | 12/1999 | Masini |
| 5,755,808 A | 5/1998 | DeCarlo et al. | 6,005,018 A | 12/1999 | Cicierega et al. |
| 5,766,255 A | 6/1998 | Slamin et al. | 6,007,580 A | 12/1999 | Lehto et al. |
| 5,766,256 A | 6/1998 | Oudard et al. | 6,008,432 A | 12/1999 | Taylor |
| 5,766,260 A | 6/1998 | Whiteside | 6,010,533 A | 1/2000 | Pope et al. |
| 5,766,262 A | 6/1998 | Mikhail | 6,010,534 A | 1/2000 | O'Neil et al. |
| 5,776,200 A | 7/1998 | Johnson et al. | 6,013,080 A | 1/2000 | Khalili |
| 5,776,201 A | 7/1998 | Colleran et al. | 6,013,081 A * | 1/2000 | Burkinshaw et al. ........... 606/88 |
| 5,776,202 A | 7/1998 | Copf et al. | 6,013,103 A | 1/2000 | Kaufman et al. |
| 5,782,920 A | 7/1998 | Colleran | 6,013,104 A | 1/2000 | Kampner |
| 5,782,921 A | 7/1998 | Colleran et al. | 6,015,937 A | 1/2000 | Branemark et al. |
| 5,782,924 A | 7/1998 | Johnson | 6,027,505 A | 2/2000 | Peter et al. |
| 5,782,925 A | 7/1998 | Collazo et al. | 6,039,764 A | 3/2000 | Pottenger et al. |
| 5,782,928 A | 7/1998 | Ries et al. | 6,042,611 A | 3/2000 | Noiles |
| 5,782,930 A | 7/1998 | Lin et al. | 6,045,583 A | 4/2000 | Gross et al. |
| 5,788,976 A | 8/1998 | Bradford | 6,053,945 A | 4/2000 | O'Neil et al. |
| 5,798,924 A | 8/1998 | Eufinger et al. | 6,056,779 A | 5/2000 | Noyer et al. |
| 5,800,554 A | 9/1998 | Scholz et al. | 6,059,833 A | 5/2000 | Doets et al. |
| 5,800,555 A | 9/1998 | Gray, III | 6,063,091 A | 5/2000 | Lombardo et al. |
| 5,800,556 A | 9/1998 | Sanders et al. | 6,063,124 A | 5/2000 | Amstutz |
| 5,800,558 A | 9/1998 | LaHaise, Sr. | 6,066,176 A | 5/2000 | Oshida |
| 5,800,560 A | 9/1998 | Draenert et al. | 6,071,311 A | 6/2000 | O'Neil et al. |
| 5,817,096 A | 10/1998 | Salyer | 6,074,424 A | 6/2000 | Perrone, Jr. et al. |
| 5,824,097 A | 10/1998 | Gabriel et al. | 6,074,425 A | 6/2000 | Pappas |
| 5,824,107 A | 10/1998 | Tschirren et al. | 6,080,195 A | 6/2000 | Colleran et al. |
| 5,824,108 A | 10/1998 | Huebner | 6,086,614 A | 7/2000 | Mumme |
| 5,830,215 A | 11/1998 | Incavo et al. | 6,087,553 A | 7/2000 | Cohen et al. |
| 5,858,020 A | 1/1999 | Johnson et al. | 6,090,146 A | 7/2000 | Rozow, III et al. |
| 5,865,850 A | 2/1999 | Matthews | 6,093,208 A | 7/2000 | Tian et al. |
| 5,871,547 A | 2/1999 | Abouaf et al. | 6,096,082 A | 8/2000 | Stegmuller et al. |
| 5,871,548 A | 2/1999 | Sanders et al. | 6,099,569 A | 8/2000 | Keller et al. |
| 5,876,459 A | 3/1999 | Powell | 6,099,571 A | 8/2000 | Knapp |
| 5,879,387 A | 3/1999 | Jones et al. | 6,113,640 A | 9/2000 | Tormala et al. |
| 5,879,390 A | 3/1999 | Kubein-Meesenburg et al. | 6,117,175 A | 9/2000 | Bosredon et al. |
| 5,879,391 A | 3/1999 | Slamin | 6,120,543 A | 9/2000 | Kubein-Meesenburg et al. |
| 5,879,398 A | 3/1999 | Swarts et al. | 6,120,545 A | 9/2000 | Hamelijnck et al. |
| 5,879,401 A | 3/1999 | Besemer et al. | 6,126,690 A | 10/2000 | Ateshian et al. |
| 5,879,402 A | 3/1999 | Lawes et al. | 6,126,691 A | 10/2000 | Kasra et al. |
| 5,879,404 A | 3/1999 | Bateman et al. | 6,126,692 A | 10/2000 | Robie et al. |
| 5,879,405 A | 3/1999 | Ries et al. | 6,126,693 A | 10/2000 | O'Neil et al. |
| 5,879,406 A | 3/1999 | Lilley | 6,126,694 A | 10/2000 | Gray, Jr. |
| 5,888,205 A | 3/1999 | Pratt et al. | 6,126,695 A | 10/2000 | Semlitsch et al. |
| 5,888,206 A | 3/1999 | Lob et al. | 6,129,765 A | 10/2000 | Lopez et al. |
| 5,888,211 A | 3/1999 | Sanders | 6,132,468 A | 10/2000 | Mansmann |
| 5,899,942 A | 5/1999 | Berman | 6,132,469 A | 10/2000 | Schroeder |
| 5,902,340 A | 5/1999 | White et al. | 6,136,029 A | 10/2000 | Johnson et al. |
| 5,904,688 A | 5/1999 | Gilbert et al. | 6,136,033 A | 10/2000 | Suemer et al. |
| 5,904,720 A | 5/1999 | Farrar et al. | 6,136,035 A | 10/2000 | Lob et al. |
| 5,906,644 A | 5/1999 | Powell | 6,139,584 A | 10/2000 | Ochoa et al. |
| 5,910,172 A | 6/1999 | Penenberg | 6,142,998 A | 11/2000 | Smith et al. |
| 5,916,269 A | 6/1999 | Serbousek et al. | 6,146,424 A | 11/2000 | Gray, Jr. et al. |
| 5,916,270 A | 6/1999 | Lipman | 6,149,687 A | 11/2000 | Gray, Jr. et al. |
| 5,919,236 A | 7/1999 | Pfaff et al. | 6,152,930 A | 11/2000 | Mastrorio |
| 5,928,286 A | 7/1999 | Ashby et al. | 6,152,961 A | 11/2000 | Ostiguy, Jr. et al. |
| 5,928,287 A | 7/1999 | Keller et al. | 6,156,070 A | 12/2000 | Incavo et al. |
| 5,931,870 A | 8/1999 | Cuckler et al. | 6,162,255 A | 12/2000 | Oyola |
| 5,935,171 A | 8/1999 | Schneider et al. | 6,162,256 A | 12/2000 | Ostiguy, Jr. et al. |
| 5,935,175 A | 8/1999 | Ostiguy, Jr. et al. | 6,165,220 A | 12/2000 | McKellop et al. |
| 5,938,702 A | 8/1999 | Lopez et al. | 6,165,222 A | 12/2000 | Hoeppner et al. |
| 5,944,756 A | 8/1999 | Fischetti et al. | 6,165,223 A | 12/2000 | Metzger et al. |
| 5,944,759 A | 8/1999 | Link et al. | 6,168,600 B1 | 1/2001 | Grace et al. |
| 5,951,603 A | 9/1999 | O'Neil et al. | 6,171,342 B1 | 1/2001 | O'Neil et al. |
| 5,954,727 A | 9/1999 | Collazo | 6,179,876 B1 | 1/2001 | Stamper et al. |
| 5,957,979 A | 9/1999 | Beckman et al. | 6,179,877 B1 | 1/2001 | Burke |
| 5,961,516 A | 10/1999 | Graf et al. | 6,193,759 B1 | 2/2001 | Ro et al. |
| 5,972,368 A | 10/1999 | McKay | 6,197,032 B1 | 3/2001 | Lawes et al. |
| 5,973,222 A | 10/1999 | Devanathan et al. | 6,200,324 B1 | 3/2001 | Regni, Jr. |
| 5,976,148 A | 11/1999 | Charpenet et al. | 6,206,929 B1 | 3/2001 | Ochoa et al. |
| 5,976,188 A | 11/1999 | Dextradeur et al. | 6,214,014 B1 | 4/2001 | McGann |
| 5,976,189 A | 11/1999 | Keller et al. | 6,214,052 B1 | 4/2001 | Burkinshaw |
| 5,977,204 A | 11/1999 | Boyan et al. | 6,214,053 B1 | 4/2001 | Ling et al. |
| 5,980,574 A | 11/1999 | Takei et al. | 6,217,615 B1 | 4/2001 | Sioshansi et al. |
| 5,984,968 A | 11/1999 | Park | 6,217,619 B1 | 4/2001 | Keller et al. |
| 5,984,969 A | 11/1999 | Matthews et al. | 6,221,110 B1 | 4/2001 | Copf et al. |
| 5,989,293 A | 11/1999 | Cook et al. | 6,224,633 B1 | 5/2001 | Kalberer et al. |
| 5,989,294 A | 11/1999 | Marlow et al. | 6,228,091 B1 | 5/2001 | Lombardo et al. |

| | | |
|---|---|---|
| 6,228,121 B1 | 5/2001 | Khalili |
| 6,231,611 B1 | 5/2001 | Mosseri et al. |
| 6,235,060 B1 | 5/2001 | Kubein-Meesenburg et al. |
| 6,245,111 B1 | 6/2001 | Shaffner |
| 6,248,132 B1 | 6/2001 | Harris |
| 6,264,698 B1 | 7/2001 | Lawes et al. |
| 6,264,699 B1 | 7/2001 | Noiles et al. |
| 6,267,785 B1 | 7/2001 | Masini |
| 6,281,264 B1 | 8/2001 | Salovey et al. |
| 6,284,001 B1 | 9/2001 | Knapp |
| 6,290,725 B1 | 9/2001 | Weiss et al. |
| 6,290,726 B1 | 9/2001 | Pope et al. |
| 6,290,727 B1 | 9/2001 | Otto et al. |
| 6,293,971 B1 | 9/2001 | Nelson et al. |
| 6,296,667 B1 | 10/2001 | Johnson et al. |
| 6,302,890 B1 | 10/2001 | Leone, Jr. |
| 6,306,172 B1 | 10/2001 | O'Neil et al. |
| 6,319,285 B1 | 11/2001 | Chamier et al. |
| 6,325,829 B1 | 12/2001 | Schmotzer et al. |
| 6,334,875 B1 | 1/2002 | Keller et al. |
| 6,340,370 B1 | 1/2002 | Willert et al. |
| 6,342,075 B1 | 1/2002 | MacArthur |
| 6,344,060 B1 | 2/2002 | Schmotzer et al. |
| 6,344,496 B1 | 2/2002 | Niederauer et al. |
| 6,352,559 B1 | 3/2002 | Church et al. |
| 6,358,282 B1 | 3/2002 | Wymann et al. |
| 6,361,566 B1 | 3/2002 | Al-Hafez et al. |
| 6,368,354 B2 | 4/2002 | Burstein et al. |
| 6,376,573 B1 | 4/2002 | White et al. |
| 6,379,389 B1 | 4/2002 | Koch et al. |
| 6,383,227 B1 | 5/2002 | Baroud et al. |
| 6,387,131 B1 | 5/2002 | Miehlke et al. |
| 6,391,251 B1 | 5/2002 | Keicher et al. |
| 6,413,279 B1 | 7/2002 | Metzger et al. |
| 6,413,280 B1 | 7/2002 | Feiler |
| 6,416,552 B1 | 7/2002 | Hoeppner et al. |
| 6,423,096 B1 | 7/2002 | Musset et al. |
| 6,425,921 B1 | 7/2002 | Grundei et al. |
| 6,428,578 B2 | 8/2002 | White |
| 6,432,141 B1 | 8/2002 | Stocks et al. |
| 6,436,145 B1 | 8/2002 | Miller |
| 6,436,146 B1 | 8/2002 | Hassler et al. |
| 6,447,549 B1 | 9/2002 | Taft |
| 6,447,550 B1 | 9/2002 | Hunter et al. |
| 6,451,058 B2 | 9/2002 | Tuke et al. |
| 6,468,281 B1 | 10/2002 | Badorf et al. |
| 6,475,243 B1 | 11/2002 | Sheldon et al. |
| 6,482,237 B2 | 11/2002 | Mosseri et al. |
| 6,485,519 B2 | 11/2002 | Meyers et al. |
| 6,488,713 B1 | 12/2002 | Hershberger |
| 6,488,715 B1 | 12/2002 | Pope et al. |
| 6,491,726 B2 | 12/2002 | Pappas |
| 6,494,914 B2 | 12/2002 | Brown et al. |
| 6,497,728 B2 | 12/2002 | Yong et al. |
| 6,500,207 B1 | 12/2002 | Keller |
| 6,500,208 B1 | 12/2002 | Metzger et al. |
| 6,503,281 B1 | 1/2003 | Mallory |
| 6,506,215 B1 | 1/2003 | Letot et al. |
| 6,517,583 B1 | 2/2003 | Pope et al. |
| 6,518,328 B2 | 2/2003 | Kumar |
| 6,520,995 B2 | 2/2003 | Church et al. |
| 6,524,344 B2 | 2/2003 | Yoon et al. |
| 6,524,345 B1 | 2/2003 | Valimaa et al. |
| 6,527,807 B1 | 3/2003 | O'Neil et al. |
| 6,527,808 B1 | 3/2003 | Albertorio et al. |
| 6,527,809 B1 | 3/2003 | Doursounian et al. |
| 6,527,810 B2 | 3/2003 | Johnson et al. |
| 6,537,321 B1 | 3/2003 | Horber et al. |
| 6,540,786 B2 | 4/2003 | Chibrac et al. |
| 6,558,427 B2 | 5/2003 | Leclercq et al. |
| 6,565,575 B2 | 5/2003 | Lewis |
| 6,565,606 B1 | 5/2003 | Bruce et al. |
| 6,589,248 B1 | 7/2003 | Hughes |
| 6,589,283 B1 | 7/2003 | Metzger et al. |
| 6,589,284 B1 | 7/2003 | Silberer et al. |
| 6,602,259 B1 | 8/2003 | Masini |
| 6,605,293 B1 | 8/2003 | Giordano et al. |
| 6,610,097 B2 | 8/2003 | Serbousek et al. |
| 6,613,092 B1 | 9/2003 | Kana et al. |
| 6,616,696 B1 | 9/2003 | Merchant |
| 6,620,198 B2 | 9/2003 | Burstein et al. |
| 6,623,488 B1 | 9/2003 | Leone, Jr. |
| 6,626,950 B2 | 9/2003 | Brown et al. |
| 6,629,999 B1 | 10/2003 | Serafin, Jr. |
| 6,641,617 B1 | 11/2003 | Merrill et al. |
| 6,652,533 B2 | 11/2003 | O'Neil |
| 6,652,586 B2 | 11/2003 | Hunter et al. |
| 6,652,589 B2 | 11/2003 | Schmotzer et al. |
| 6,652,590 B1 | 11/2003 | Zitnansky et al. |
| 6,660,040 B2 | 12/2003 | Chan et al. |
| 6,669,728 B2 | 12/2003 | Despres, III et al. |
| 6,679,890 B2 | 1/2004 | Margulies et al. |
| 6,682,566 B2 | 1/2004 | Draenert et al. |
| 6,682,567 B1 | 1/2004 | Schroeder |
| 6,682,568 B2 | 1/2004 | Despres, III et al. |
| 6,692,531 B1 | 2/2004 | Yoon et al. |
| 6,699,293 B2 | 3/2004 | White |
| 6,706,071 B1 | 3/2004 | Wolter et al. |
| 6,706,072 B2 | 3/2004 | Dwyer et al. |
| 6,712,857 B1 | 3/2004 | Roger et al. |
| 6,712,858 B1 | 3/2004 | Grundei et al. |
| 6,716,248 B2 | 4/2004 | Huene |
| 6,719,800 B2 | 4/2004 | Meyers et al. |
| 6,723,129 B2 | 4/2004 | Dwyer et al. |
| 6,726,725 B2 | 4/2004 | Hunter et al. |
| 6,740,092 B2 | 5/2004 | Lombardo et al. |
| 6,743,258 B1 | 6/2004 | Keller et al. |
| 6,755,864 B1 | 6/2004 | Brack et al. |
| 6,758,864 B2 | 7/2004 | Storer et al. |
| 6,761,741 B2 | 7/2004 | Iesaka |
| 6,764,516 B2 | 7/2004 | Pappas |
| 6,770,097 B2 | 8/2004 | Leclercq et al. |
| 6,773,461 B2 | 8/2004 | Meyers et al. |
| 6,783,550 B2 | 8/2004 | MacArthur |
| 6,786,933 B2 | 9/2004 | Merrill et al. |
| 6,793,681 B1 | 9/2004 | Pope et al. |
| 6,800,670 B2 | 10/2004 | Shen et al. |
| 6,802,866 B2 | 10/2004 | Bunz et al. |
| 6,811,568 B2 | 11/2004 | Minamikawa et al. |
| 6,811,569 B1 | 11/2004 | Afriat et al. |
| 6,818,019 B2 | 11/2004 | Horber et al. |
| 6,818,020 B2 | 11/2004 | Sun et al. |
| 6,827,739 B2 | 12/2004 | Griner et al. |
| 6,827,742 B2 | 12/2004 | Hayes, Jr. et al. |
| 6,840,944 B2 | 1/2005 | Suddaby |
| 6,843,805 B2 | 1/2005 | Webb et al. |
| 6,843,806 B2 | 1/2005 | Hayes, Jr. et al. |
| 6,863,692 B2 | 3/2005 | Meulink |
| 6,866,683 B2 | 3/2005 | Gerbec et al. |
| 6,866,685 B2 | 3/2005 | Chan et al. |
| 6,869,447 B2 | 3/2005 | Lee et al. |
| 6,875,237 B2 | 4/2005 | Dye |
| 6,881,229 B2 | 4/2005 | Khandkar et al. |
| 6,887,276 B2 | 5/2005 | Gerbec et al. |
| 6,896,702 B2 | 5/2005 | Collazo |
| 6,905,515 B1 | 6/2005 | Gilbertson |
| 6,908,486 B2 | 6/2005 | Lewallen |
| 6,916,340 B2 | 7/2005 | Metzger et al. |
| 6,916,341 B2 | 7/2005 | Rolston |
| 6,923,833 B2 | 8/2005 | Wasielewski |
| 6,926,738 B2 | 8/2005 | Wyss |
| 6,926,739 B1 | 8/2005 | O'Connor et al. |
| 6,926,740 B2 | 8/2005 | Lewis et al. |
| 6,944,518 B2 | 9/2005 | Roose |
| 6,953,479 B2 | 10/2005 | Carson et al. |
| 6,962,607 B2 | 11/2005 | Gundlapalli et al. |
| 6,966,932 B1 | 11/2005 | Schroeder |
| 6,969,406 B2 | 11/2005 | Tornier et al. |
| 6,972,021 B2 | 12/2005 | Raugel et al. |
| 6,972,039 B2 | 12/2005 | Metzger et al. |
| 6,981,991 B2 | 1/2006 | Ferree |
| 6,986,791 B1 | 1/2006 | Metzger |
| 7,004,946 B2 | 2/2006 | Parker et al. |
| 7,022,142 B2 | 4/2006 | Johnson |
| 7,025,788 B2 | 4/2006 | Metzger et al. |
| 7,037,310 B2 | 5/2006 | Murphy |
| 7,044,974 B2 | 5/2006 | Garber et al. |
| 7,051,417 B2 | 5/2006 | Michelson |

| Patent/Publication | Date | Inventor |
|---|---|---|
| 7,056,577 B1 | 6/2006 | Bruce et al. |
| 7,070,622 B1 | 7/2006 | Brown et al. |
| 7,074,241 B2 | 7/2006 | McKinnon |
| 7,105,026 B2 | 9/2006 | Johnson et al. |
| 7,108,719 B2 | 9/2006 | Horber |
| 7,125,193 B2 | 10/2006 | Despres, III et al. |
| 7,131,995 B2 | 11/2006 | Biedermann et al. |
| 7,153,326 B1 | 12/2006 | Metzger |
| 7,156,880 B2 | 1/2007 | Evans et al. |
| 7,166,133 B2 | 1/2007 | Evans et al. |
| 7,179,295 B2 | 2/2007 | Kovacevic |
| 7,189,263 B2 | 3/2007 | Erbe et al. |
| 7,192,448 B2 | 3/2007 | Ferree |
| 7,198,642 B2 | 4/2007 | Hazebrouck et al. |
| 7,445,639 B2 | 11/2008 | Metzger et al. |
| 7,497,874 B1 | 3/2009 | Metzger et al. |
| 2001/0014828 A1 | 8/2001 | Yoon |
| 2001/0014829 A1 | 8/2001 | Yoon |
| 2001/0016780 A1 | 8/2001 | Yong San |
| 2001/0018616 A1 | 8/2001 | Schwab |
| 2001/0032021 A1 | 10/2001 | McKinnon |
| 2001/0037156 A1 | 11/2001 | Burstein et al. |
| 2001/0039456 A1 | 11/2001 | Boyer et al. |
| 2001/0039457 A1 | 11/2001 | Boyer et al. |
| 2001/0041941 A1 | 11/2001 | Boyer et al. |
| 2001/0051830 A1 | 12/2001 | Tuke et al. |
| 2002/0007294 A1 | 1/2002 | Bradbury et al. |
| 2002/0022889 A1 | 2/2002 | Chibrac et al. |
| 2002/0022890 A1 | 2/2002 | Jacobsson et al. |
| 2002/0040244 A1 | 4/2002 | Despres et al. |
| 2002/0040245 A1 | 4/2002 | Lester et al. |
| 2002/0042656 A1 | 4/2002 | Hunter et al. |
| 2002/0045949 A1 | 4/2002 | Ling et al. |
| 2002/0049500 A1 | 4/2002 | Draenert |
| 2002/0052659 A1 | 5/2002 | Hayes et al. |
| 2002/0059000 A1 | 5/2002 | Dwyer et al. |
| 2002/0068980 A1 | 6/2002 | Serbousek et al. |
| 2002/0072799 A1 | 6/2002 | Despres et al. |
| 2002/0082706 A1 | 6/2002 | Raugel |
| 2002/0107577 A1 | 8/2002 | Storer et al. |
| 2002/0116007 A1 | 8/2002 | Lewis |
| 2002/0116068 A1 | 8/2002 | McLean |
| 2002/0120340 A1 | 8/2002 | Metzger et al. |
| 2002/0120341 A1 | 8/2002 | Stumpo et al. |
| 2002/0128653 A1 | 9/2002 | Haidukewych |
| 2002/0138148 A1 | 9/2002 | Hyde |
| 2002/0138151 A1 | 9/2002 | Hubbard et al. |
| 2002/0139818 A1 | 10/2002 | McGuffey |
| 2002/0143402 A1 | 10/2002 | Steinberg |
| 2002/0143403 A1 | 10/2002 | Vaidyanathan et al. |
| 2002/0151978 A1 | 10/2002 | Zacouto et al. |
| 2002/0156536 A1 | 10/2002 | Harris et al. |
| 2002/0165615 A1 | 11/2002 | Abouaf et al. |
| 2002/0173853 A1 | 11/2002 | Corl et al. |
| 2003/0009232 A1 | 1/2003 | Metzger et al. |
| 2003/0009234 A1 | 1/2003 | Treacy et al. |
| 2003/0014120 A1 | 1/2003 | Carson et al. |
| 2003/0022069 A1 | 1/2003 | Karube et al. |
| 2003/0033018 A1 | 2/2003 | Merchant |
| 2003/0040805 A1 | 2/2003 | Minamikawa |
| 2003/0050645 A1 | 3/2003 | Parker et al. |
| 2003/0050703 A1 | 3/2003 | Harris et al. |
| 2003/0050705 A1 | 3/2003 | Cueille et al. |
| 2003/0055508 A1 | 3/2003 | Metzger et al. |
| 2003/0055509 A1 | 3/2003 | McCue et al. |
| 2003/0060889 A1 | 3/2003 | Tarabishy |
| 2003/0060890 A1 | 3/2003 | Tarabishy |
| 2003/0065397 A1 | 4/2003 | Hanssen et al. |
| 2003/0074078 A1 | 4/2003 | Doubler et al. |
| 2003/0093156 A1 | 5/2003 | Metzger et al. |
| 2003/0105529 A1 | 6/2003 | Synder et al. |
| 2003/0109933 A1 | 6/2003 | Weissman et al. |
| 2003/0114934 A1 | 6/2003 | Steinberg |
| 2003/0114935 A1 | 6/2003 | Chan et al. |
| 2003/0120346 A1 | 6/2003 | Mercinek et al. |
| 2003/0120347 A1 | 6/2003 | Steinberg |
| 2003/0125810 A1 | 7/2003 | Sullivan et al. |
| 2003/0130740 A1 | 7/2003 | Stocks et al. |
| 2003/0139818 A1 | 7/2003 | Rogers et al. |
| 2003/0149485 A1 | 8/2003 | Tornier |
| 2003/0153981 A1 | 8/2003 | Wang et al. |
| 2003/0153982 A1 | 8/2003 | Pria |
| 2003/0158606 A1 | 8/2003 | Coon et al. |
| 2003/0163202 A1 | 8/2003 | Lakin |
| 2003/0171815 A1 | 9/2003 | Kana et al. |
| 2003/0171817 A1 | 9/2003 | Rambert et al. |
| 2003/0181984 A1 | 9/2003 | Abendschein |
| 2003/0181987 A1 | 9/2003 | Muirhead-Allwood |
| 2003/0204262 A1 | 10/2003 | Ferguson et al. |
| 2003/0204263 A1 | 10/2003 | Justin et al. |
| 2003/0204268 A1 | 10/2003 | Gerbec et al. |
| 2003/0204269 A1 | 10/2003 | Gerbec et al. |
| 2003/0208276 A1 | 11/2003 | Berelsman et al. |
| 2003/0212458 A1 | 11/2003 | Harris et al. |
| 2003/0220697 A1 | 11/2003 | Justin et al. |
| 2003/0220699 A1 | 11/2003 | Hunter et al. |
| 2003/0225457 A1 | 12/2003 | Justin et al. |
| 2003/0225458 A1 | 12/2003 | Donkers et al. |
| 2003/0229356 A1 | 12/2003 | Dye |
| 2003/0229398 A1 | 12/2003 | Iesaka |
| 2004/0002766 A1 | 1/2004 | Hunter et al. |
| 2004/0019380 A1 | 1/2004 | Baege et al. |
| 2004/0019382 A1 | 1/2004 | Amirouche et al. |
| 2004/0019386 A1 | 1/2004 | Ferree |
| 2004/0024460 A1 | 2/2004 | Ferree |
| 2004/0030344 A1 | 2/2004 | Dye et al. |
| 2004/0030394 A1 | 2/2004 | Horber |
| 2004/0030400 A1 | 2/2004 | Horber |
| 2004/0034432 A1 | 2/2004 | Hughes et al. |
| 2004/0039449 A1 | 2/2004 | Tornier |
| 2004/0039451 A1 | 2/2004 | Southworth |
| 2004/0049284 A1 | 3/2004 | German et al. |
| 2004/0049285 A1 | 3/2004 | Haas |
| 2004/0049286 A1 | 3/2004 | German et al. |
| 2004/0054418 A1 | 3/2004 | McLean et al. |
| 2004/0059427 A1 | 3/2004 | Serbousek et al. |
| 2004/0068324 A1 | 4/2004 | Grundei |
| 2004/0073226 A1 | 4/2004 | Cotting et al. |
| 2004/0073315 A1 | 4/2004 | Justin et al. |
| 2004/0078083 A1 | 4/2004 | Gibbs et al. |
| 2004/0083004 A1 | 4/2004 | Wasielewski |
| 2004/0098133 A1 | 5/2004 | Carignan et al. |
| 2004/0098134 A1 | 5/2004 | Meulink |
| 2004/0102851 A1 | 5/2004 | Saladino |
| 2004/0102852 A1 | 5/2004 | Johnson et al. |
| 2004/0107594 A1 | 6/2004 | Afriat |
| 2004/0117023 A1 | 6/2004 | Gerbec et al. |
| 2004/0117024 A1 | 6/2004 | Gerbec et al. |
| 2004/0117029 A1 | 6/2004 | Lewis et al. |
| 2004/0122521 A1 | 6/2004 | Lee et al. |
| 2004/0122524 A1 | 6/2004 | Hunter et al. |
| 2004/0143336 A1 | 7/2004 | Burkinshaw |
| 2004/0143341 A1 | 7/2004 | McLean |
| 2004/0147926 A1 | 7/2004 | Iversen |
| 2004/0153063 A1 | 8/2004 | Harris |
| 2004/0162619 A1 | 8/2004 | Blaylock et al. |
| 2004/0162620 A1 | 8/2004 | Wyss |
| 2004/0162621 A1 | 8/2004 | Crofford |
| 2004/0172137 A1 | 9/2004 | Blaylock et al. |
| 2004/0172139 A1 | 9/2004 | Dwyer et al. |
| 2004/0186580 A1 | 9/2004 | Steinmann |
| 2004/0186586 A1 | 9/2004 | Seyer et al. |
| 2004/0193282 A1 | 9/2004 | Hanes |
| 2004/0199257 A1 | 10/2004 | Dooney |
| 2004/0199259 A1 | 10/2004 | Pichon et al. |
| 2004/0204760 A1 | 10/2004 | Fitz et al. |
| 2004/0204767 A1 | 10/2004 | Park et al. |
| 2004/0210316 A1 | 10/2004 | King et al. |
| 2004/0225368 A1 | 11/2004 | Plumet et al. |
| 2004/0225370 A1 | 11/2004 | Cruchet et al. |
| 2004/0225371 A1 | 11/2004 | Roger |
| 2004/0226343 A1 | 11/2004 | Babler et al. |
| 2004/0236428 A1 | 11/2004 | Burkinshaw et al. |
| 2004/0243249 A1 | 12/2004 | Ishihara et al. |
| 2004/0255749 A1 | 12/2004 | Hayden |
| 2004/0260396 A1 | 12/2004 | Ferree et al. |
| 2004/0267374 A1 | 12/2004 | Friedrichs |
| 2004/0267375 A1 | 12/2004 | Friedrichs |

| | | |
|---|---|---|
| 2005/0004677 A1 | 1/2005 | Johnson |
| 2005/0004678 A1 | 1/2005 | Richards |
| 2005/0010288 A1 | 1/2005 | Merrill et al. |
| 2005/0010303 A1 | 1/2005 | Nogier |
| 2005/0010304 A1 | 1/2005 | Jamali |
| 2005/0021149 A1 | 1/2005 | Borruto et al. |
| 2005/0027302 A1 | 2/2005 | Cueille et al. |
| 2005/0033442 A1 | 2/2005 | Fisher et al. |
| 2005/0033445 A1 | 2/2005 | Siebel |
| 2005/0038443 A1 | 2/2005 | Hedley et al. |
| 2005/0043807 A1 | 2/2005 | Wood |
| 2005/0043812 A1 | 2/2005 | Corl et al. |
| 2005/0049524 A1 | 3/2005 | Lefevre et al. |
| 2005/0049713 A1 | 3/2005 | Garber et al. |
| 2005/0055102 A1 | 3/2005 | Tornier et al. |
| 2005/0059972 A1 | 3/2005 | Biscup |
| 2005/0060040 A1 | 3/2005 | Auxepaules et al. |
| 2005/0071014 A1 | 3/2005 | Barnett et al. |
| 2005/0071015 A1 | 3/2005 | Sekel |
| 2005/0075641 A1 | 4/2005 | Singhatat et al. |
| 2005/0080490 A1 | 4/2005 | Bertram |
| 2005/0085823 A1 | 4/2005 | Murphy |
| 2005/0090903 A1 | 4/2005 | Khandkar et al. |
| 2005/0102032 A1 | 5/2005 | Beynnon et al. |
| 2005/0102033 A1 | 5/2005 | Lambert et al. |
| 2005/0102034 A1 | 5/2005 | E. Hayes et al. |
| 2005/0102038 A1 | 5/2005 | Grundei |
| 2005/0107884 A1 | 5/2005 | Johnson et al. |
| 2005/0119755 A1 | 6/2005 | Kristensen |
| 2005/0125067 A1 | 6/2005 | Sweeney |
| 2005/0131540 A1 | 6/2005 | Trieu |
| 2005/0137603 A1 | 6/2005 | Belew et al. |
| 2005/0137708 A1 | 6/2005 | Clark |
| 2005/0137711 A1 | 6/2005 | Southworth et al. |
| 2005/0143828 A1 | 6/2005 | Collins et al. |
| 2005/0143835 A1 | 6/2005 | Gilbertson |
| 2005/0143836 A1 | 6/2005 | Steinberg |
| 2005/0149043 A1 | 7/2005 | Parry et al. |
| 2005/0149047 A1 | 7/2005 | Parry et al. |
| 2005/0154470 A1 | 7/2005 | Sekel |
| 2005/0154471 A1 | 7/2005 | Aram et al. |
| 2005/0165490 A1 | 7/2005 | Tornier |
| 2005/0165491 A1 | 7/2005 | Diaz |
| 2005/0165492 A1 | 7/2005 | Fitz |
| 2005/0171612 A1 | 8/2005 | Rolston |
| 2005/0177172 A1 | 8/2005 | Acker et al. |
| 2005/0177242 A1 | 8/2005 | Lotke |
| 2005/0177244 A1 | 8/2005 | Steinberg |
| 2005/0187635 A1 | 8/2005 | Metzger |
| 2005/0187637 A1 | 8/2005 | Karrer et al. |
| 2005/0192675 A1 | 9/2005 | Robinson |
| 2005/0202371 A1 | 9/2005 | McGuire |
| 2005/0203535 A1 | 9/2005 | Parry et al. |
| 2005/0203629 A1 | 9/2005 | Cipolletti et al. |
| 2005/0209604 A1 | 9/2005 | Penenberg et al. |
| 2005/0211562 A1 | 9/2005 | Rowe et al. |
| 2005/0216091 A1 | 9/2005 | Wasielewski |
| 2005/0228394 A1 | 10/2005 | Bihary et al. |
| 2005/0228395 A1 | 10/2005 | Auxepaules et al. |
| 2005/0228502 A1 | 10/2005 | Deloge et al. |
| 2005/0228503 A1 | 10/2005 | Gundolf |
| 2005/0240275 A1 | 10/2005 | Chappuis |
| 2005/0240276 A1 | 10/2005 | Shea et al. |
| 2005/0246026 A1 | 11/2005 | Lewis et al. |
| 2005/0246027 A1 | 11/2005 | Metzger et al. |
| 2005/0246028 A1 | 11/2005 | Pappas et al. |
| 2005/0246030 A1 | 11/2005 | Yao |
| 2005/0256576 A1 | 11/2005 | Moskowitz et al. |
| 2005/0256584 A1 | 11/2005 | Farrar |
| 2005/0261776 A1 | 11/2005 | Taylor |
| 2005/0267584 A1 | 12/2005 | Burdulis et al. |
| 2005/0267585 A1 | 12/2005 | Sidebotham |
| 2005/0267590 A1 | 12/2005 | Lee |
| 2005/0278034 A1 | 12/2005 | Johnson et al. |
| 2005/0283252 A1 | 12/2005 | Coon et al. |
| 2005/0283253 A1 | 12/2005 | Coon et al. |
| 2005/0283254 A1 | 12/2005 | Hayes et al. |
| 2005/0288791 A1 | 12/2005 | Tornier et al. |
| 2005/0288793 A1 | 12/2005 | Dong et al. |
| 2006/0004463 A1 | 1/2006 | Lewis et al. |
| 2006/0009774 A1 | 1/2006 | Goble et al. |
| 2006/0009853 A1 | 1/2006 | Justin et al. |
| 2006/0009854 A1 | 1/2006 | Justin et al. |
| 2006/0009855 A1 | 1/2006 | Goble et al. |
| 2006/0009857 A1 | 1/2006 | Gibbs et al. |
| 2006/0015188 A1 | 1/2006 | Grimes |
| 2006/0030945 A1 | 2/2006 | Wright |
| 2006/0052876 A1 | 3/2006 | Wozencroft et al. |
| 2006/0058883 A1 | 3/2006 | Aram et al. |
| 2006/0058884 A1 | 3/2006 | Aram et al. |
| 2006/0058886 A1 | 3/2006 | Wozencroft |
| 2006/0064169 A1 | 3/2006 | Ferree |
| 2006/0074491 A1 | 4/2006 | Smith et al. |
| 2006/0085079 A1 | 4/2006 | Carroll |
| 2006/0100714 A1 | 5/2006 | Ensign |
| 2006/0129247 A1 | 6/2006 | Brown et al. |
| 2006/0142865 A1 | 6/2006 | Hyde |
| 2006/0142867 A1 | 6/2006 | Metzger et al. |
| 2006/0149285 A1 | 7/2006 | Burgi et al. |
| 2006/0167462 A1 | 7/2006 | Raugel et al. |
| 2006/0167554 A1 | 7/2006 | Heck et al. |
| 2006/0167556 A1 | 7/2006 | Lazennec et al. |
| 2006/0167557 A1 | 7/2006 | Terrill |
| 2006/0167559 A1 | 7/2006 | Johnstone et al. |
| 2006/0167560 A1 | 7/2006 | Heck et al. |
| 2006/0173547 A1 | 8/2006 | Ensign |
| 2006/0173548 A1 | 8/2006 | Auxepaules et al. |
| 2006/0178749 A1 | 8/2006 | Pendleton et al. |
| 2006/0178750 A1 | 8/2006 | Chieng |
| 2006/0184249 A1 | 8/2006 | Tarabishy |
| 2006/0190086 A1 | 8/2006 | Clemow et al. |
| 2006/0195196 A1 | 8/2006 | Pendleton et al. |
| 2006/0206210 A1 | 9/2006 | Abicht et al. |
| 2006/0229734 A1 | 10/2006 | Yoon |
| 2006/0235538 A1 | 10/2006 | Rochetin et al. |
| 2006/0241776 A1 | 10/2006 | Brown et al. |
| 2006/0241781 A1 | 10/2006 | Brown et al. |
| 2006/0265079 A1 | 11/2006 | D'Alessio |
| 2007/0010890 A1 | 1/2007 | Collazo |
| 2007/0021838 A1 | 1/2007 | Dugas et al. |
| 2007/0088443 A1 | 4/2007 | Hanssen et al. |
| 2007/0129809 A1 | 6/2007 | Meridew et al. |
| 2007/0173948 A1 | 7/2007 | Meridew et al. |
| 2007/0196230 A1 | 8/2007 | Hamman et al. |
| 2008/0167722 A1 | 7/2008 | Metzger et al. |
| 2009/0062806 A1 | 3/2009 | Scott et al. |
| 2009/0125114 A1 | 5/2009 | May et al. |
| 2009/0149964 A1 | 6/2009 | May et al. |
| 2009/0299482 A1 | 12/2009 | Metzger et al. |
| 2010/0174378 A1 | 7/2010 | Metzger et al. |

FOREIGN PATENT DOCUMENTS

| | | |
|---|---|---|
| EP | 0000549 A1 | 2/1979 |
| EP | 0378928 | 7/1990 |
| EP | 0538987 A1 | 4/1993 |
| EP | 0555003 | 8/1993 |
| EP | 0689796 | 1/1996 |
| EP | 0797417 A1 | 10/1997 |
| EP | 853930 | 7/1998 |
| EP | 0947181 | 10/1999 |
| EP | 0985386 A2 | 3/2000 |
| EP | 993813 | 4/2000 |
| EP | 01004283 A2 | 5/2000 |
| EP | 1398007 A2 | 3/2004 |
| EP | 1430856 A1 | 6/2004 |
| FR | 2718953 | 10/1995 |
| FR | 2793677 | 11/2000 |
| GB | 1553836 A | 10/1979 |
| GB | 2223172 A | 4/1990 |
| JP | 58141847 | 8/1983 |
| WO | WO-9613233 A1 | 5/1996 |
| WO | WO-0038598 | 7/2000 |
| WO | WO-0205732 | 1/2002 |
| WO | WO-03065939 | 8/2003 |
| WO | WO-2004078069 A2 | 9/2004 |
| WO | WO-2004080340 | 9/2004 |

OTHER PUBLICATIONS

European Search Report for EP 02 25 1274 completed on Sep. 12, 2003 (mailed on Sep. 22, 2003).
International Search Report and Written Opinion for PCT/US2008/000374 mailed Jun. 6, 2008.
"Advantim® Total Knee System," brochure,1996 (pp. 1-14) Wright Medical Technology, Inc.
"AGC Total Knee System, Tradition™ Series," brochure, (11 pages) 1995. Biomet Orthopedics, Inc.
"Ascent™ Total Knee System, Revision Surgical Technique," (pp. 1-24) 2001. Biomet Orthopedics, Inc.
"FINN® Knee System Modularity and Surgical Latitude, Product Ordering Information," catalog, (4 pages) 1994. Biomet, Inc.
"FINN® Knee System Modularity and Surgical Latitude," brochure (pp. 1-20) 1995 Biomet, Inc.
"FINN® Knee System Modularity and Surgical Latitude," brochure, (11 pages) 1990. Biomet, Inc.
"Kinemax® Plus Total Stabiliser (TS) Revision Surgical technique, Xcelerate Instrumentation," brochure/catalog. Stryker Howmedica Osteonics (Dated at least as early as Apr. 4, 2005.).
"OSS™ Orthopaedic Salvage System, Femoral/Tibial Augmentation," brochure, pp. 1-9. 2003, 2004 Biomet Orthopedics, Inc.
"Passport™ Revision Instrumentation, Howmedica Osteonics Total Knee Revision System Surgical Protocol," brochure, Jun. 2000 (pp. 1-27) Stryer® Howmedica Osteonics.
"S-Rom Total Hip System Surgical Technique," (19 pages) located at http://www.rpa.spot.pt/Main-Sections/Informacao-ao-Profissional-de-Saude.aspx?lang=en-GB, web site copyrighted 2008; accessed Oct. 13, 2010. DePuy.
"S-Rom Total Hip System Surgical Technique," brochure (17 pages) 2000. DePuy Orthopaedics, Inc.
"The RHK™ System, RHK™ controlled rotation," brochure (2 sheets) 2004. ArCom™. Biomet Europe.
"Vanguard Complete Knee System, Cruciate Retaining," brochure (6 pages) 2007. Biomet Orthopedics, Inc.
"Vanguard Complete Knee System, System Summary," brochure, (4 sheets) 2007. Biomet Orthopedics, Inc.
International Preliminary Report on Patentability and Written Opinion issued Jul. 14, 2009 for PCT/US2008/000374 claiming benefit of U.S. Appl. No. 60/879,733, filed Jan. 10, 2007; and U.S. Appl. No. 60/978,949, filed Oct. 10, 2007.
International Preliminary Report on Patentability for PCT/US2008/079545 issued Apr. 13, 2010, claiming priority to U.S. Appl. No. 60/978,949, filed Oct. 10, 2007.
International Search Report and Written Opinion mailed Jan. 25, 2011 for PCT/US2010/044395 Invitation to Pay Additional Fees mailed Oct. 15, 2010 for PCT/US2010/044395 which claims benefit of U.S. Appl. No. 12/729,852, filed Mar. 23, 2010; which claims benefit of CIP of U.S. Appl. No. 12/536,056, filed Aug. 5, 2009; which claims benefit of CIP of U.S. Appl. No. 12/248,517, filed Oct. 9, 2008; which claims benefit of CIP of U.S. Appl. No. 11/972,359, filed Jan. 10, 2008; which claims benefit of CIP of U.S. Appl. No. 12/248,509, filed Oct. 9, 2008.
Invitation to Pay Additional Fees mailed Oct. 15, 2010 for PCT/US2010/044395 which claims benefit of U.S. Appl. No. 12/729,852, filed Mar. 23, 2010; which claims benefit of CIP of U.S. Appl. No. 12/536,056, filed Aug. 5, 2009; which claims benefit of CIP of U.S. Appl. No. 12/248,517, filed Oct. 9, 2008; which claims benefit of CIP of U.S. Appl. No. 11/972,359, filed Jan. 10, 2008; which claims benefit of CIP of U.S. Appl. No. 12/248,509, filed Oct. 9, 2008.

* cited by examiner

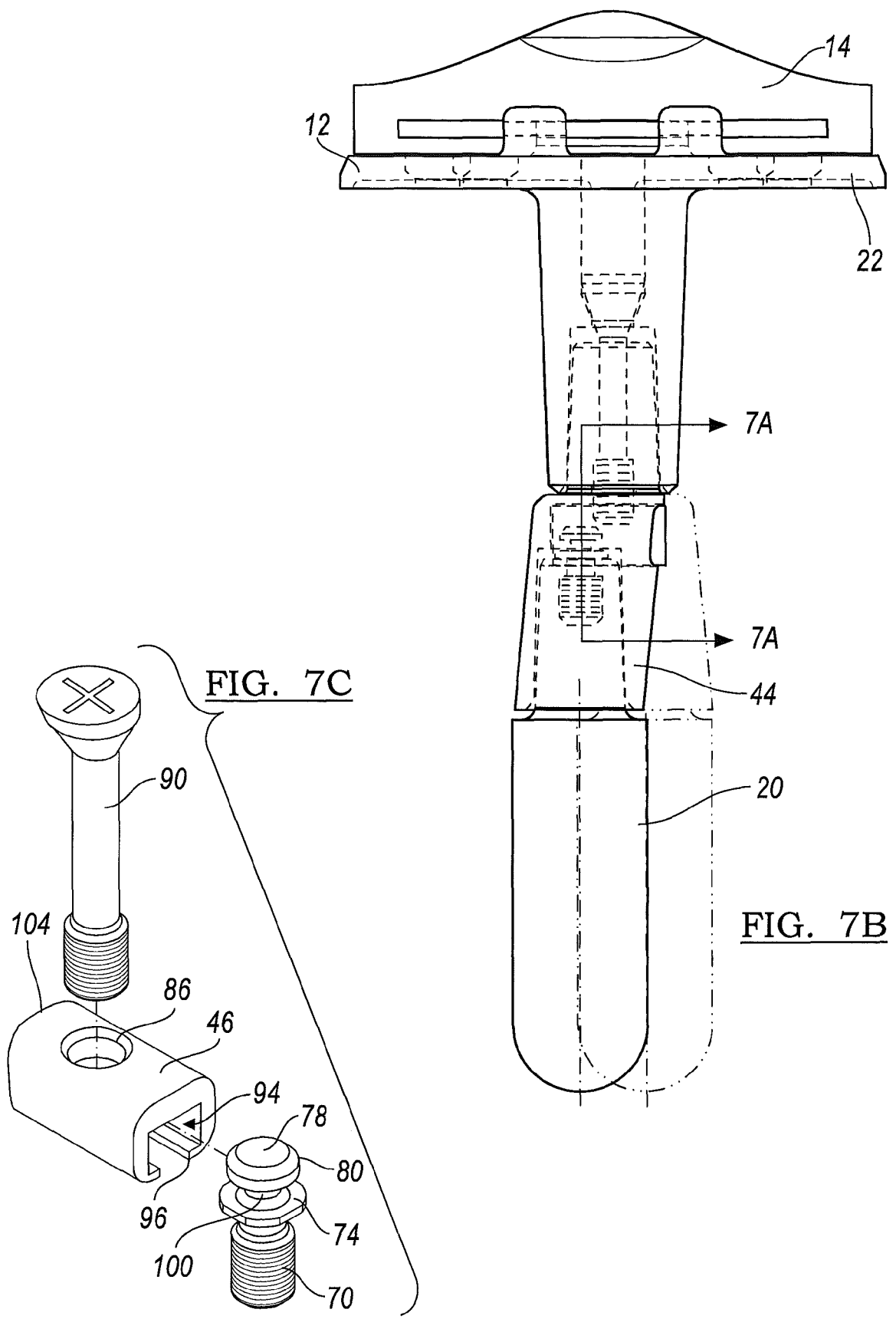

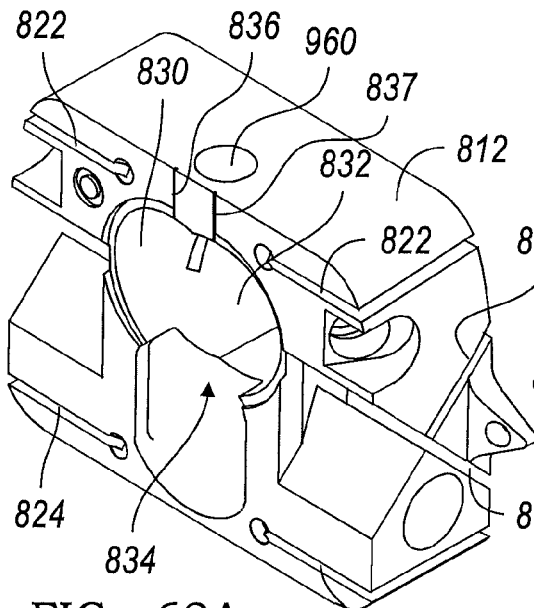
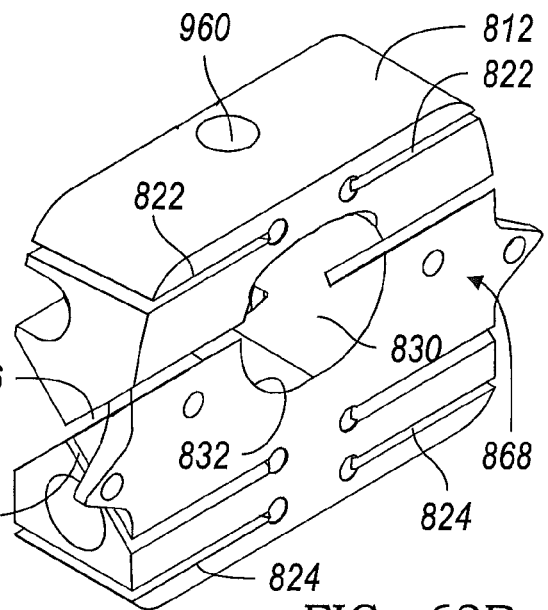
FIG. 62A
FIG. 62B
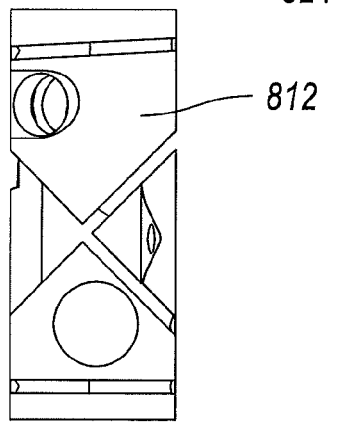
FIG. 62C
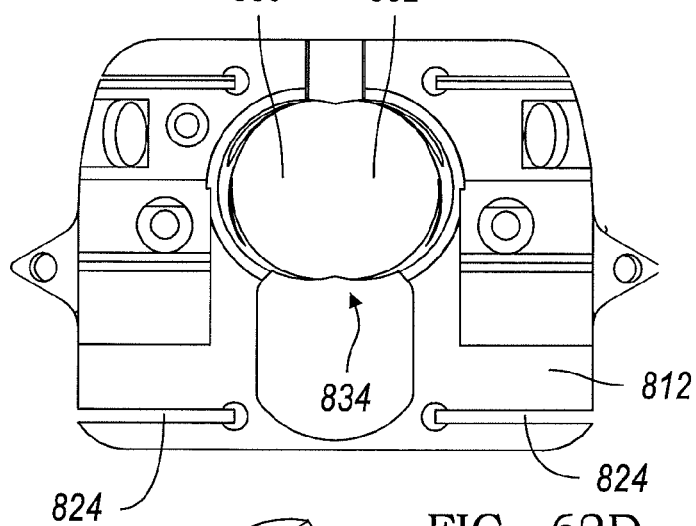
FIG. 62D
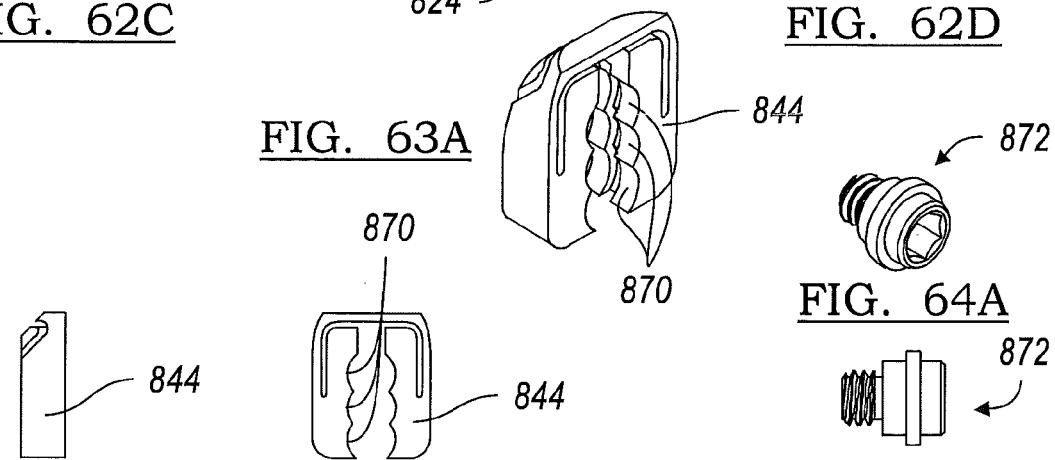
FIG. 63A
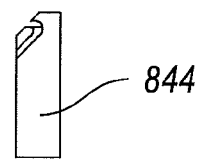
FIG. 63B
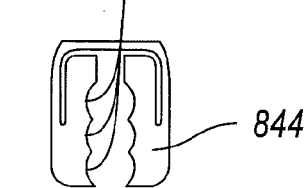
FIG. 63C
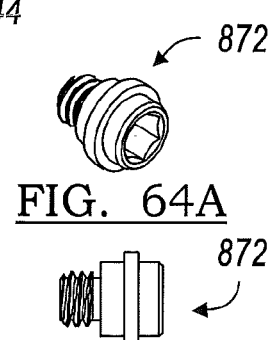
FIG. 64A
FIG. 64B

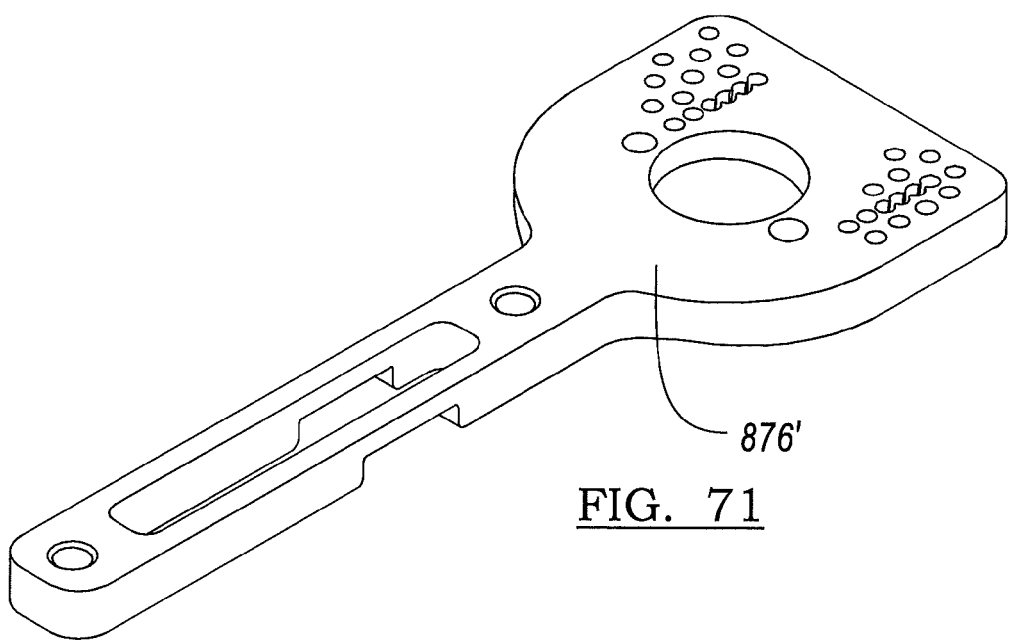
FIG. 71
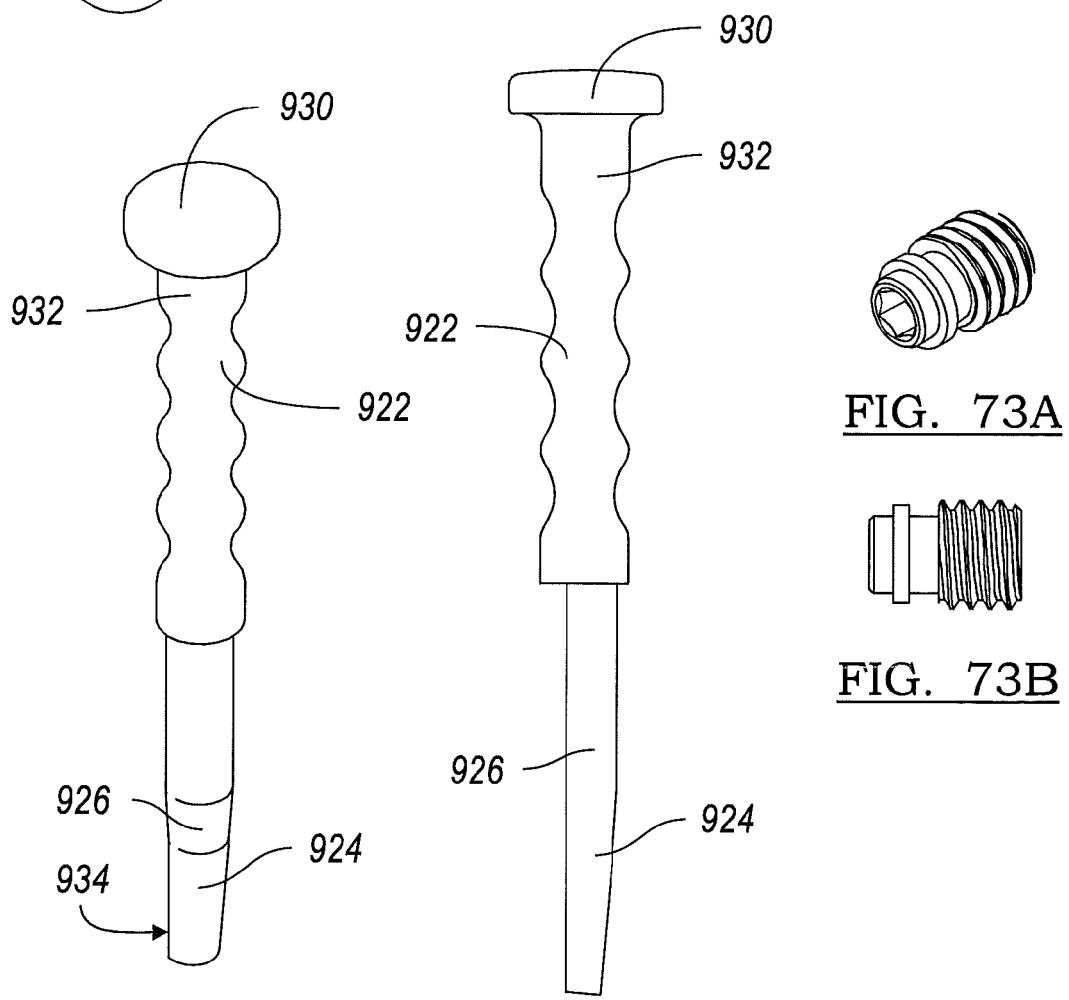
FIG. 72A
FIG. 72B
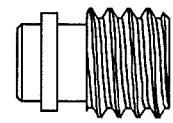
FIG. 73A
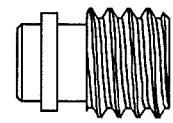
FIG. 73B

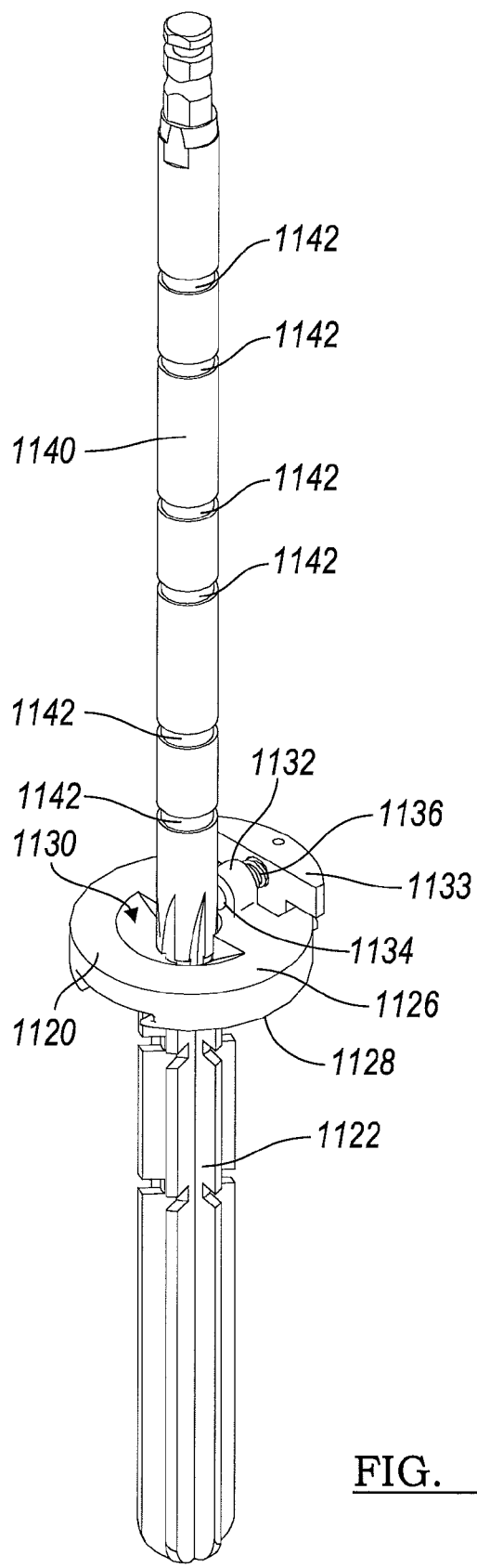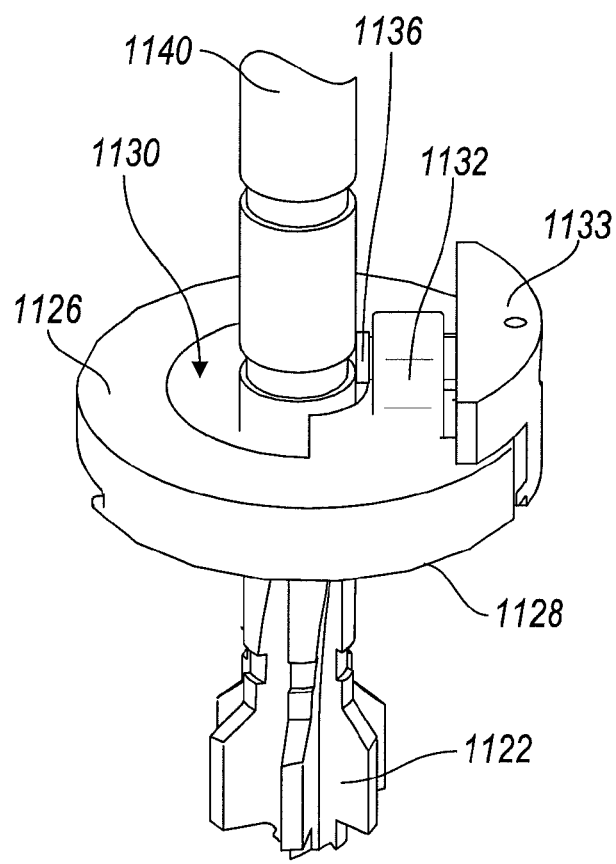
FIG. 110B
FIG. 110A

US 8,187,280 B2

KNEE JOINT PROSTHESIS SYSTEM AND METHOD FOR IMPLANTATION

CROSS-REFERENCE TO RELATED APPLICATIONS

This application is a continuation-in-part of U.S. Ser. No. 11/972,359, filed Jan. 10, 2008 and claims the benefit of U.S. Provisional Application No. 60/978,949, filed on Oct. 10, 2007. The disclosures of the above applications are incorporated herein by reference.

FIELD

The present disclosure relates generally to knee joint prostheses and more particularly to various tibial and femoral components and modular augments for cooperating with such tibial and femoral components.

BACKGROUND

A knee joint prosthesis typically comprises a femoral component and a tibial component. The femoral component and tibial component are designed to be surgically attached to the distal end of the femur and the proximal end of the tibia, respectively. The femoral component is further designed to cooperate with the tibial component in simulating the articulating motion of an anatomical knee joint. Such knee joint prostheses are generally referred to as primary knee prostheses.

Knee joint prostheses, in combination with ligaments and muscles, attempt to duplicate natural knee motion as well as absorb and control forces generated during the range of flexion. In some instances however, it may be necessary to replace an existing prosthesis. Such replacement prostheses are generally referred to as revision knee prostheses. Depending on the degree of damage or deterioration of the primary knee prosthesis, knee tendons and ligaments, however, it may be necessary for a revision knee joint prosthesis to eliminate one or more of these motions in order to provide adequate stability. In this way, it may be desirable to provide a cruciate retaining (CR) revision knee, a fully constrained revision knee, a posterior stabilized (PS) revision knee or a hinged revision knee for example. Furthermore, in some instances it may be necessary to account for bone loss in areas adjacent to such knee joint prostheses.

SUMMARY

A system for cooperating with an elongated IM member during preparation of a bone for receiving a prosthesis can include a scaffold, skeleton or frame. An alignment assembly can be selectively coupled to the frame. The alignment assembly can cooperate with the IM member to position the frame relative to the bone. A cutting block can be selectively coupled to the frame.

According to other features, a posterior stabilized (PS) box guide assembly can have a PS box guide attachment portion that selectively couples with the first attachment portion of the frame. A posterior foot can selectively couple with a second attachment portion on the frame. The posterior foot can be positioned to occupy space of a joint line in an installed position.

The alignment assembly can include an alignment member having a receiving portion and a bushing selectively received by the receiving portion of the alignment member. The bushing can define a longitudinal axis and a bore configured to accept the IM member therethrough. An engaging portion can be formed on the alignment member. The bushing can be selectively received by the receiving portion of the alignment member. The engaging portion can be movable from a disengaged position to an engaged position. In the engaged position, the engaging portion substantially inhibits movement of the bushing along the longitudinal axis while permitting rotation of the bushing around the longitudinal axis.

According to additional features, the bushing can define an annular groove. The engaging portion can nest in the annular groove of the bushing in the engaged position. The engaging portion can comprise a knob coupled to a foot. The knob can be movable between the disengaged and engaged positions causing the foot to move from a position generally within the body of the alignment member to a position generally into the receiving portion of the alignment member.

BRIEF DESCRIPTION OF THE DRAWINGS

The present disclosure will become more fully understood from the detailed description and the accompanying drawings, wherein:

FIG. 7B is a view of the knee joint prosthesis of FIG. 1 illustrating various offsets;

FIG. 7C is an exploded view of a locking assembly shown in FIG. 7A;

FIGS. 61-80B illustrate various instruments used for preparing a femur and tibia for receipt of the implants disclosed herein;

FIGS. 108-120 illustrate various instruments and a related sequence for preparing a tibia for receipt of a tibial prosthesis;

DETAILED DESCRIPTION

At the outset, the instant disclosure provides a knee joint prosthesis system having various knee joint prostheses that may be adapted for use in a revision knee procedure. Various tibial and femoral components are described that may be used alone or as part of a cruciate retaining (CR) knee revision, posterior stabilized (PS) knee revision, fully constrained knee revision and hinged knee revision. As will be described, the instant disclosure further provides various modular adapters, stems and augments that may be used in any combination with any of the tibial and femoral components disclosed herein. In other words, all of the components disclosed that are above and below the joint line, such as the stems, adapters, augments, etc., can be inter-changeably used with any of the knee prostheses disclosed herein and on the tibial or femoral side. Moreover, selection of any of the knee prostheses and related components from the knee joint prosthesis system may be selected intra-operatively by the surgeon performing the procedure.

Figure 1:
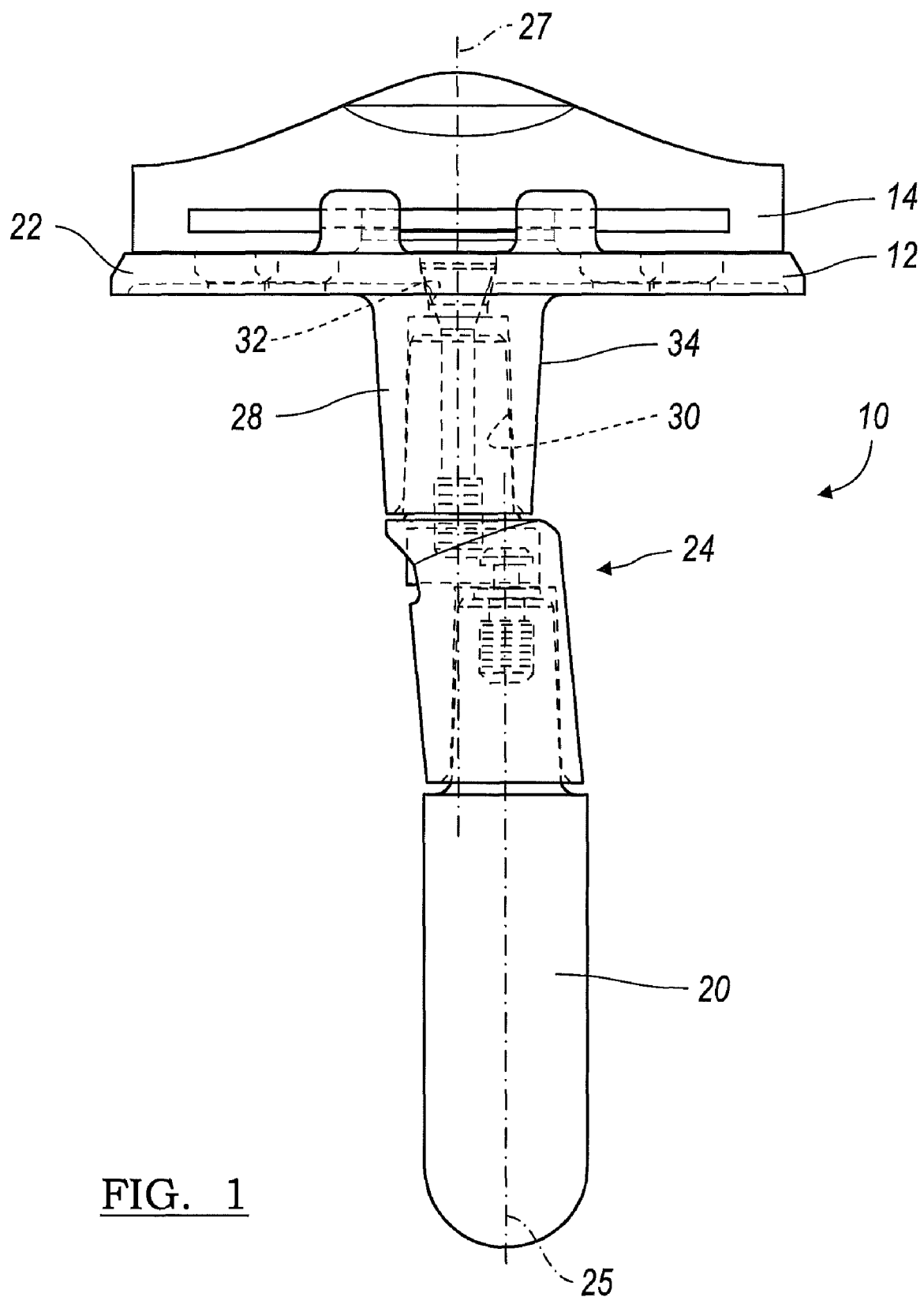
FIG. 1 is an anterior view illustration of a knee joint prosthesis including a modular tibial component having a first adapter assembly for providing a first predetermined offset according to the present teachings.

With initial reference to FIG. 1, a knee joint prosthesis constructed in accordance with the present teachings is illustrated and generally identified at reference number 10. The knee joint prosthesis 10 is generally shown to include a tibial component 12 that supports a bearing 14 which engages an articulation surface of a femoral component (not shown). Insofar as the present teachings are concerned, it will be understood that the tibial tray 12 and bearing 14 can be adapted for use with any suitable femoral component. For example, a first cruciate retaining (CR) bearing 14 is illustrated that is designed to articulate with a CR femoral component. However, a fixed PS bearing may be employed that is designed to articulate with a PS femoral component.

Figure 29:
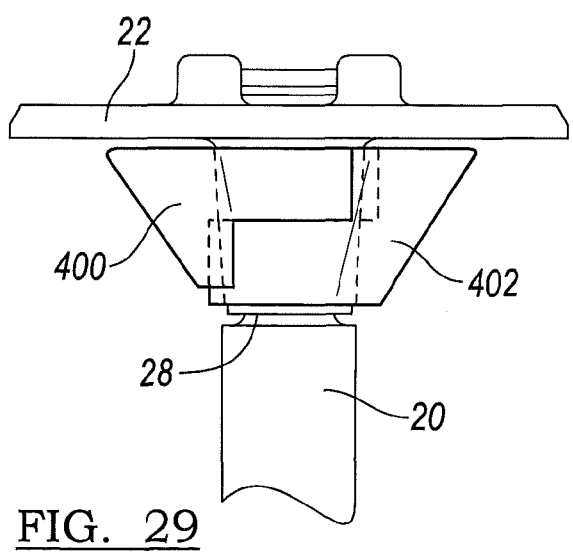
FIG. 29 is an anterior view of the tibial component of FIG. 1 shown with the first and second augments assembled on an inferiorly extending portion and without the adapter assembly.

The tibial component 12 illustrated in FIG. 1 will be understood to be modular in construction and generally include a stem 20, a tray 22, and a first adapter assembly 24. In a manner which will be discussed more fully below, the adapter assembly 24 can connect the tray 22 and the stem 20 so as to provide an offset to the stem 20 in the transverse or coronal plane or in any other plane. Explaining further, when the stem 20 is attached to the tray 22 through the first adapter assembly 24, a central axis 25 of the stem 20 can be offset from a central axis 27 of an inferiorly extending portion 28 of the tray 22. In the embodiment illustrated, the first adapter assembly 24 can provide a first offset of approximately 5 mm. It is appreciated that the offset can range from 0 mm to approximately 5 mm or more and can be in any rotational direction relative to the central axis 27. Alternatively, a stem 20 can be attached directly to the tray 22 (FIG. 29). In other words, the offset axis 25 can be rotated 360 degrees relative to the central axis 27 to provide the surgeon with various intra-operative options to select depending on the patient's needs. Alternatively, the adapter assembly 24 or stem 20 can be rotational keyed to provide only a limited range of adjustment, such as providing only a single offset or two offset positions.

Figure 2:
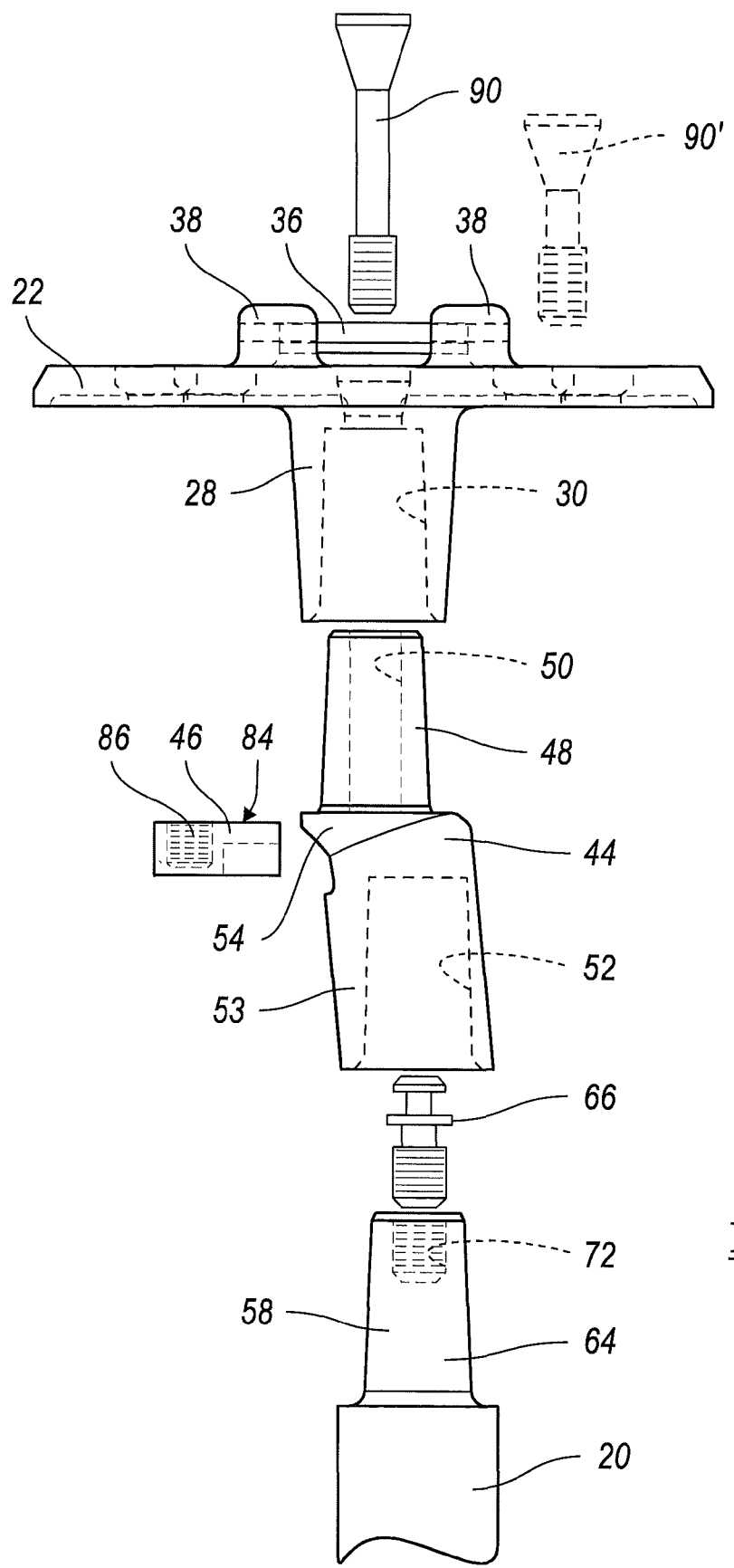
FIG. 2 is an exploded view of the modular tibial component of FIG. 1.
Figure 3A:
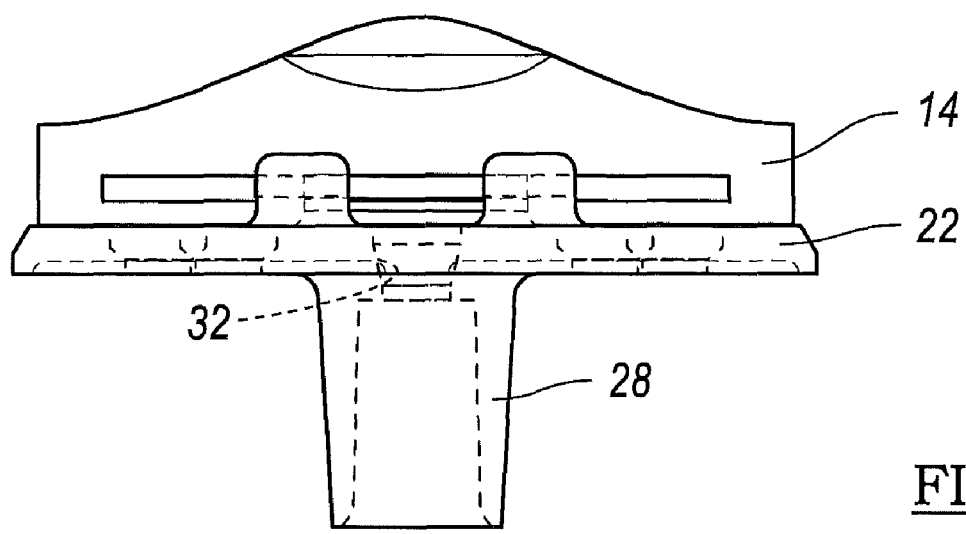
FIG. 3A is an anterior view of the tibial component of FIG. 1.
Figure 3B:
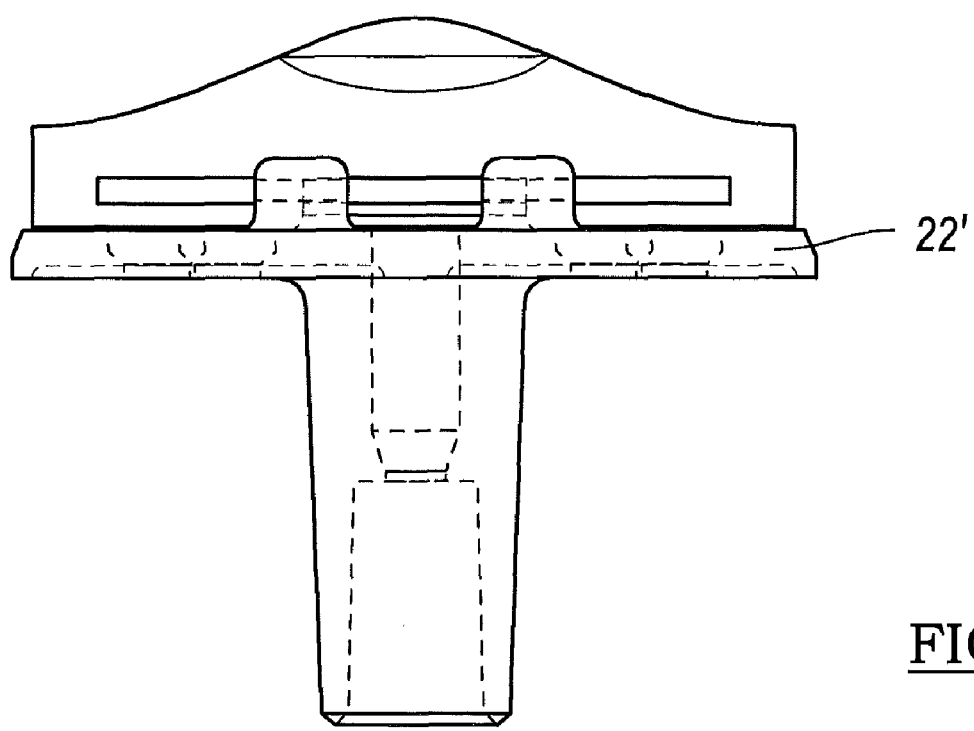
FIG. 3B is an anterior view of a tibial component according to additional features.
Figure 3C:
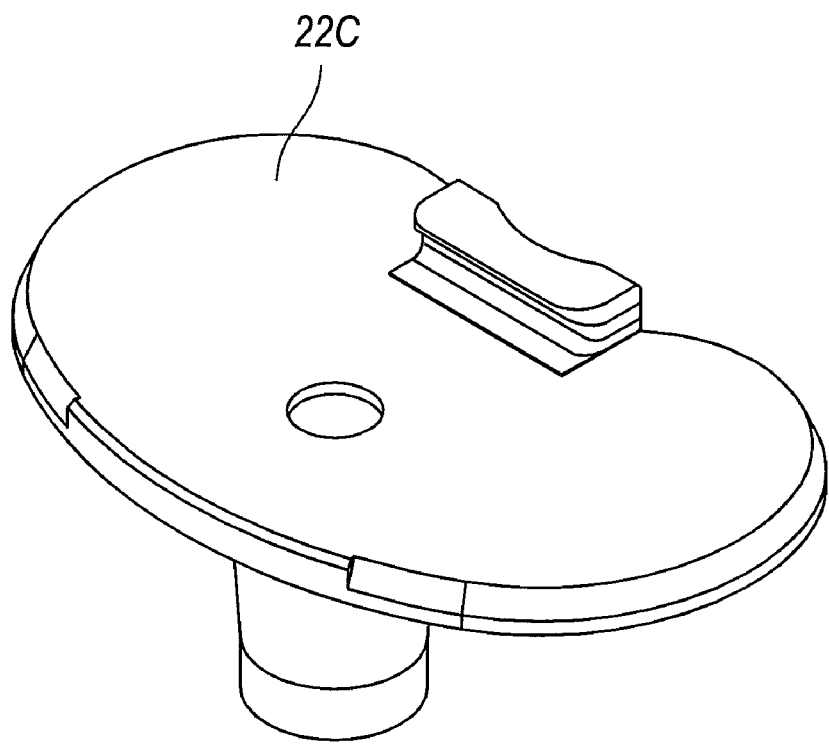
FIG. 3C is a perspective view of a tibial component according to additional features.
Figure 3D:
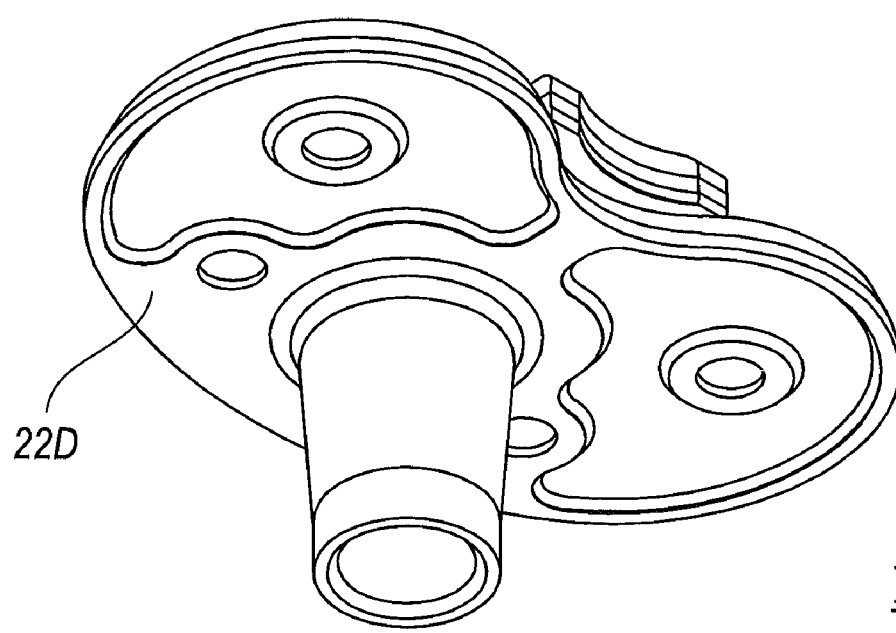
FIG. 3D is a perspective view of a tibial component according to additional features.

With reference to FIGS. 2 and 3A, the inferiorly extending portion 28 of the tibial tray 22 can define a female tapered receiving portion 30. The female tapered receiving portion 30 can taper slightly as it extends into the inferiorly extending portion 28. A central aperture 32 can be formed through the tray 22 and the inferiorly extending portion 28 into the female tapered receiving portion 30. The inferiorly extending portion 28 may also define an exterior tapered augment receiving surface 34. A retaining rail 36 (FIG. 2) can extend superiorly from a posterior edge of the tray 22. The tibial tray 22 can further include a pair of posts 38 integrally formed on a superior surface at an anterior edge thereof. The posts 38 and rail 36 can cooperate to retain the modular bearing 14 in a fixed position on the tray 22. An alternate tibial tray 22' is shown in FIG. 3B.

The modular bearing 14 can be formed of ultra-high molecular weight polyethylene (UHMWPE) with anterior and posterior recesses (not specifically shown) to receive the posts 38 and rail 36, respectively, and with a uniformly flat inferior surface on its intercondylar and medial/lateral portions for direct contact with the superior surface of the tray 22. The modular bearing 14 can be designed to be locked in position with a transverse slide-in locking bar or clip 40 wedged between the posts 38 and the bearing 14 in opposed grooves provided therein for that purpose. A more detailed discussion of how the locking bar cooperates with the posts and bearing may be found in commonly owned U.S. Pat. No. 5,330,534 entitled "Knee Joint Prosthesis With Interchangeable Components", which is hereby incorporated by reference. Modular tibial trays and bearings as generally described above are commercially available from Biomet Inc., the assignee of the present disclosure, as components of the Vanguard® Complete Knee System, which includes various sizes and configurations of trays, bearings and other knee components for different patient requirements. The articulating surfaces of the modular bearing 14 can be substantially the same as provided by the Vanguard® Complete Knee System.

Figure 4:
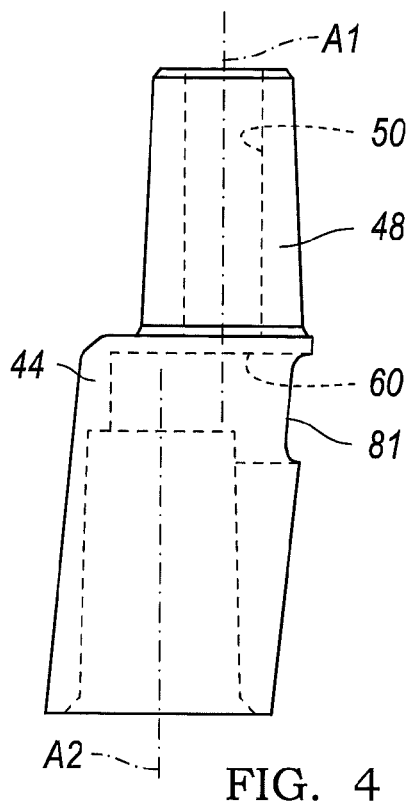
FIG. 4 is a view of a first adapter body according to the present teachings.
Figure 5:
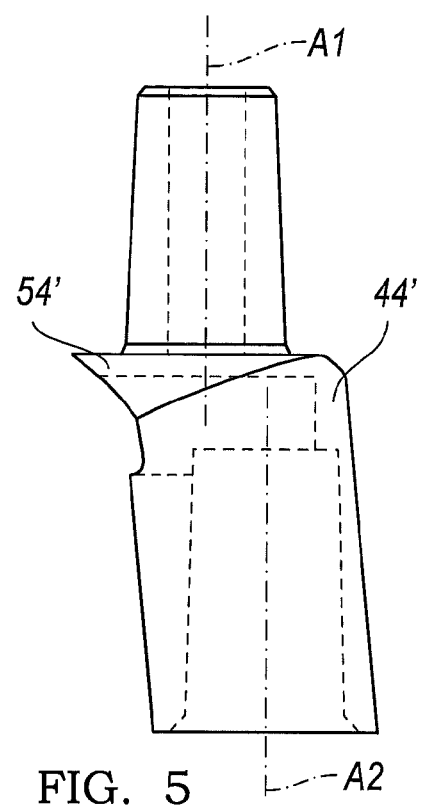
FIG. 5 is a view of another adapter body according to additional features.

Turning now to FIGS. 2, 4 and 5, the adapter assembly 24 can generally include an adapter body 44 and a locking member or element 46 (FIG. 2). The adapter body 44 of the adapter assembly 24 can define a male tapered insertion portion 48 having a passage 50 formed therethrough. A female tapered receiving portion 52 can be formed in an offset body portion 53 of the adapter body 44 for receiving a male tapered insertion portion 58 of the stem 20. In one example, the female tapered receiving portion 52 can be generally cylindrical. A skirt 54 can be defined at a transition between the male tapered insertion portion 48 and the offset body portion 53.

With reference to FIG. 4, the male tapered insertion portion 48 of the adapter body 44 defines a first axis $A_1$ and the female tapered receiving portion 52 defines a second axis $A_2$. Further, in the embodiment illustrated, the first axis $A_1$ and the second axis $A_2$ are parallel to one another and spaced apart to provide the desired offset. In this regard, multiple adaptors each having a different offset can be provided to provide the surgeon with intra-operative selection depending on the patient's needs. Insofar as the adapter body 44 provides a 5 mm offset, the first and second central axes $A_1$ and $A_2$ are spaced apart 5 mm. The adapter body 44' can define a skirt 54' having an alternate configuration. Other geometries are contemplated for the skirt 54, 54'.

The male tapered insertion portion 48 can taper slightly as it extends away from the adapter body 44. The female tapered receiving portion 52 similarly tapers slightly as it extends into the adapter body 44 from an end of the adapter body 44. As will become appreciated from the following discussion, various male tapered insertion portions (such as portion 48) can be inserted in various female tapered receiving portions (such as portion 52) to form a locking taper or Morse taper. The adapter body 44 is illustrated to further define a laterally extending channel 60 which intersects both the aperture 50 and the female tapered receiving portion 52. In a manner to be described further below, the locking element 46 can extend into the laterally extending channel 60 where it ultimately couples the tray 22 to the stem 20.

Figure 6:
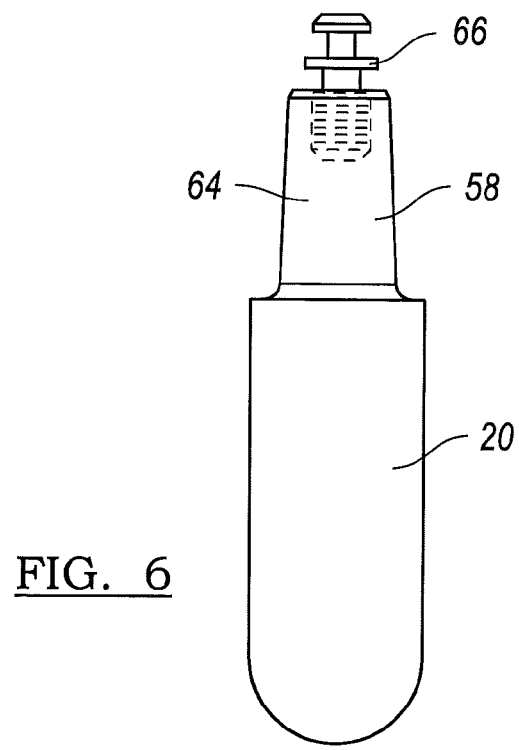
FIG. 6 is a view of an exemplary stem and fastener insert.

As shown in FIGS. 2 and 6, the stem 20 can include an upper portion 64 that cooperatively engages with the locking element 46. In the embodiment illustrated, the upper portion 64 of the stem 20 can include a fastener insert 66. Alternatively, the fastener insert 66 of the stem 20 may be integrally formed to cooperate with the locking element 46.

The fastener insert 66 can include a distal portion 70 which can be externally threaded for engaging an internally threaded aperture 72 of the male tapered insertion portion 58 of the stem 20. The fastener insert 66 can further include a central portion 74 having a hexagonal or other suitable cross-section which can be engaged by a tool (not shown) for rotating the fastener insert 66 into the stem 20. Further, the fastener insert 66 can include a proximal end 78 including an enlarged diameter head 80.

The locking element 46 can be sized and configured to be inserted through an opening 81 in the sidewall of the adapter body 44 and into the channel 60 for coupling of the stem 20 and the tray 22. The locking element 46 can include an upper surface 84 (see FIG. 2) having an internally threaded aperture 86. The internally threaded aperture 86 can threadably receive a fastener 90 which can extend through the central aperture 32 provided in the tray 22. The fastener 90 can align with the central longitudinal axis 27 of the inferior portion 28 of the tray 22.

Figure 7A:
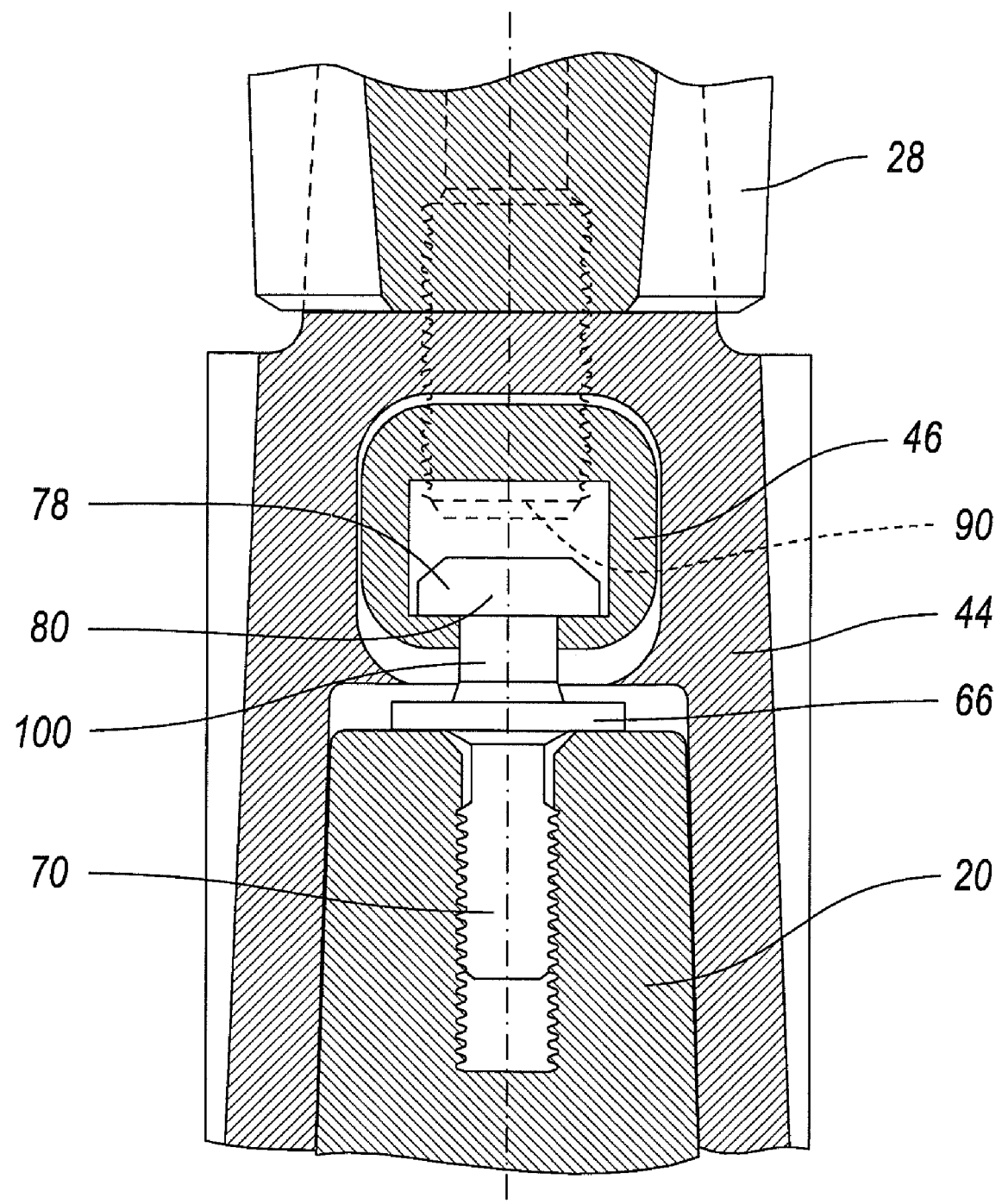
FIG. 7A is a cross-sectional view taken along a superior/inferior line through the adapter of FIG. 1.

With additional reference to FIG. 7C, the locking element 46 can additionally include an open end 94 and a bottom surface having a slot 96. The slot 96 can intersect the open end 94. The open end 94 can receive the head 80 of the stem insert 66 as the locking element 46 is inserted through the opening 60. The slot 96 can accommodate a reduced diameter, central portion 100 of the fastener insert 66. The head 80 of the fastener insert 66 can have a diameter greater than a width of the slot 94 for coupling of the fastener insert 66 with the locking element 46.

The locking element 46 can further include a closed end 104. The closed end 104 can be convexly curved. When the locking element 46 is completely inserted into the channel 60, the closed end 104 can be flush with the sidewall of the adapter body 44.

In use, the fastener insert 66 can be screwed into the stem 20. Next, the adapter body 44 can be placed over the male insertion portion 64 of the stem 20 such that the male insertion portion 64 is received in a press fit within the female tapered receiving portion 52 of the adapter body 44 and the upper end 78 of the fastener insert 66 extends into the laterally extending channel 60.

The male taper extension 48 of the adapter 44 can now be press fit onto the female tapered receiving portion 30 of the tray 12 with the adapter body 44 oriented to provide the offset in the desired direction. As viewed in FIG. 7B, the adapter body 44 may be rotated about the axis $A_1$ prior to fastening to orient the stem 20 at the desired offset for a particular patient. As a result, the stem 20 may extend at a plurality of positions around a radius defined by the axes $A_1$ and $A_2$. Alternatively, the stem 20 may be keyed with the adapted body thus, precluding rotation. In addition, a set of stems may be provided having various lengths suitable for a range of patients. Likewise, a set of adapter bodies may be provided for providing various offsets.

At this point, the locking element 46 can be inserted into the laterally extending channel 60 through the opening 81. Upon complete insertion, the locking element 46 can engage the fastener insert 66. The tray 22 can be secured to the adapter body 44 by the threaded fastener 90 which extends through the central aperture 32 of the tray 22 and threadably engages the internally threaded aperture 86 of the locking element 46. A further discussion of offset stems and their application with respect to various tibial and femoral components may be found in commonly owned U.S. patent application Ser. No. 10/934,282 filed Sep. 3, 2004 and entitled "Knee Joint Prosthesis", which is hereby incorporated by reference. In this commonly owned Application, the tibial tray defines an inferiorly extending male portion whereas in the instant application, the tibial tray 22 defines the inferiorly extending female receiving portion 30. In addition, while not specifically shown, the adapter body 44 may alternatively define an axis $A_2$ that defines an angle with respect to the axis $A_1$.

In another example, the male insertion portion 58 may be inserted directly into the female receiving portion 30 of the tray 22. In this example, another threaded fastener 90' may be used that has a shorter shaft for spanning an appropriate distance to mate directly with the threaded aperture 72 of the stem 20. As shown in FIGS. 3A-3D, other tibial trays 22A, 22B, 22C and 22D, are shown for accommodating various combinations of fasteners 90, 90', adapters 44, 44' and stems 20.

Figure 8:
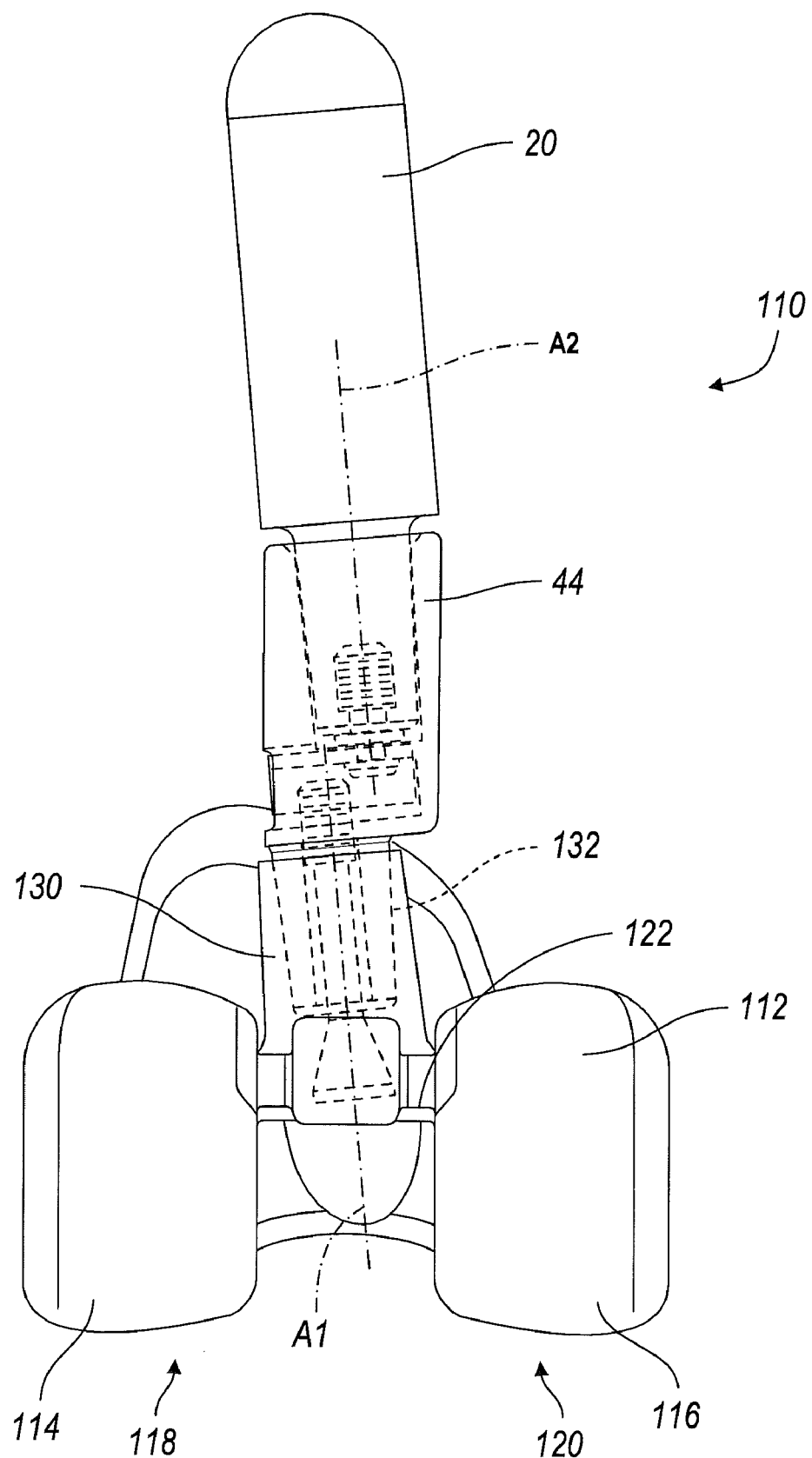
FIG. 8 is an anterior view of an exemplary femoral component according to the present teachings and shown with the adapter assembly of FIG. 1.
Figure 9:
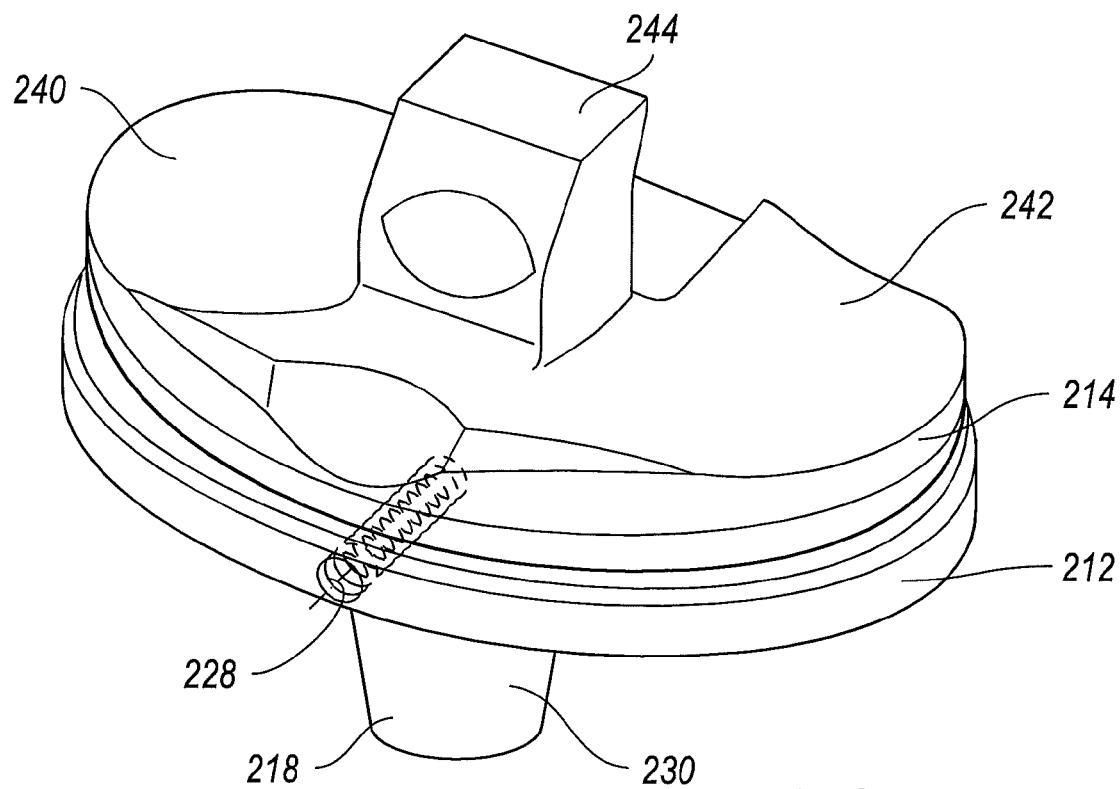
FIG. 9 is a perspective view of a tibial tray and bearing according to additional features.
Figure 10:
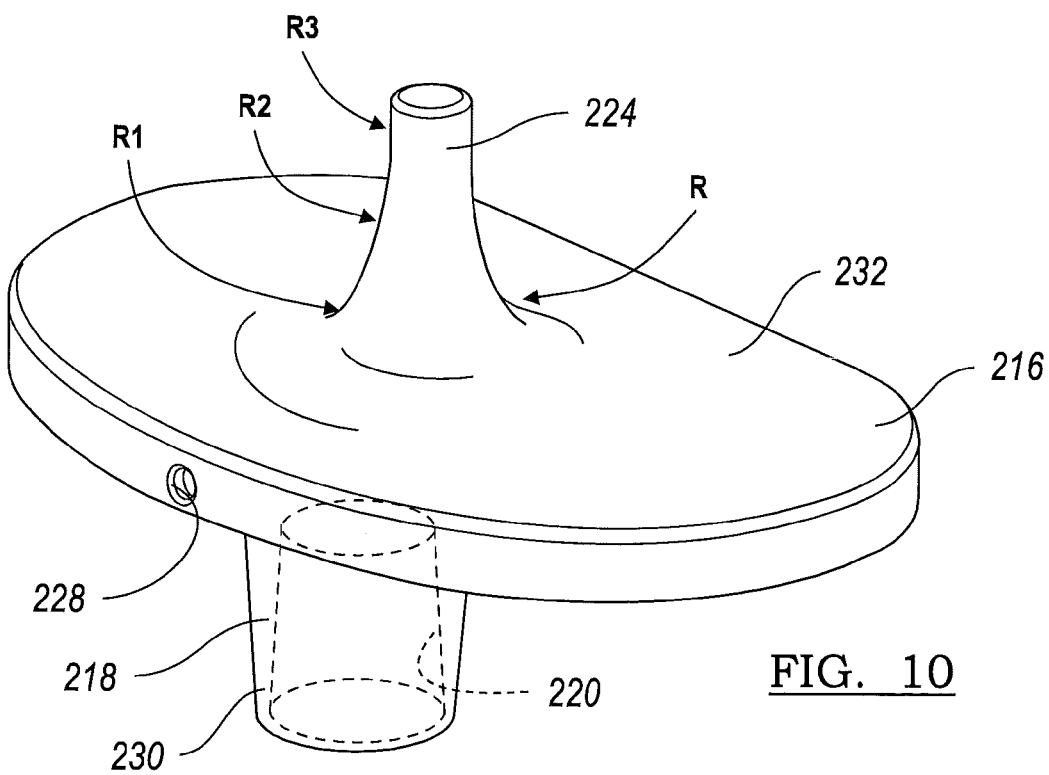
FIG. 10 is a perspective view of the tibial tray of FIG. 9.
Figure 11:
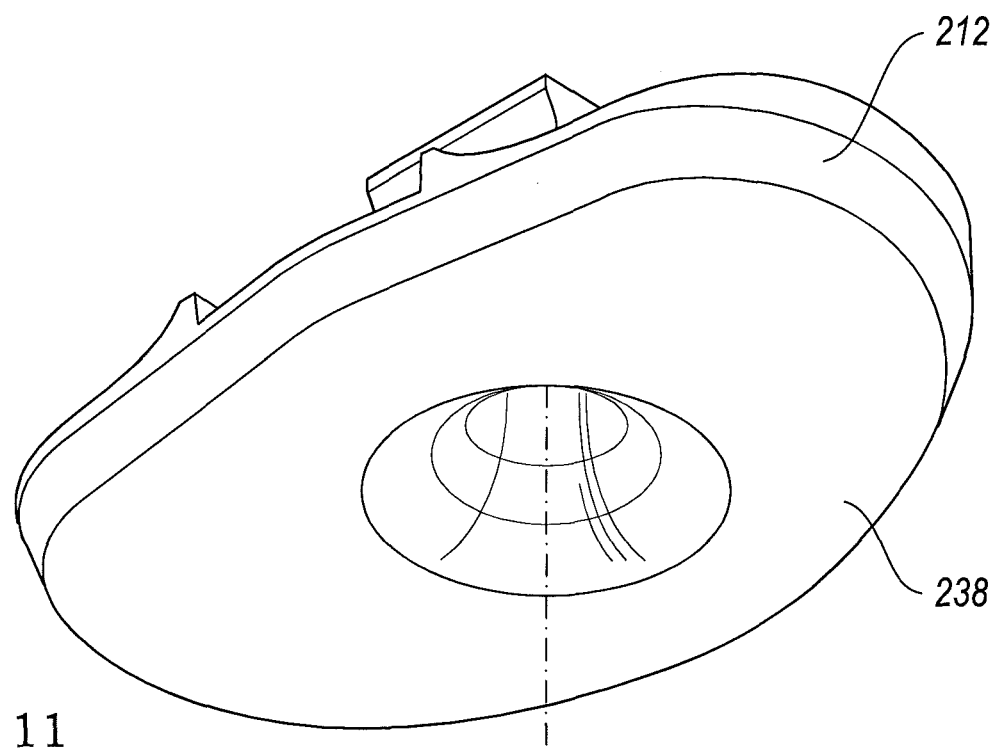
FIG. 11 is a perspective view of an inferior surface of the bearing of FIG. 9.
Figure 12:
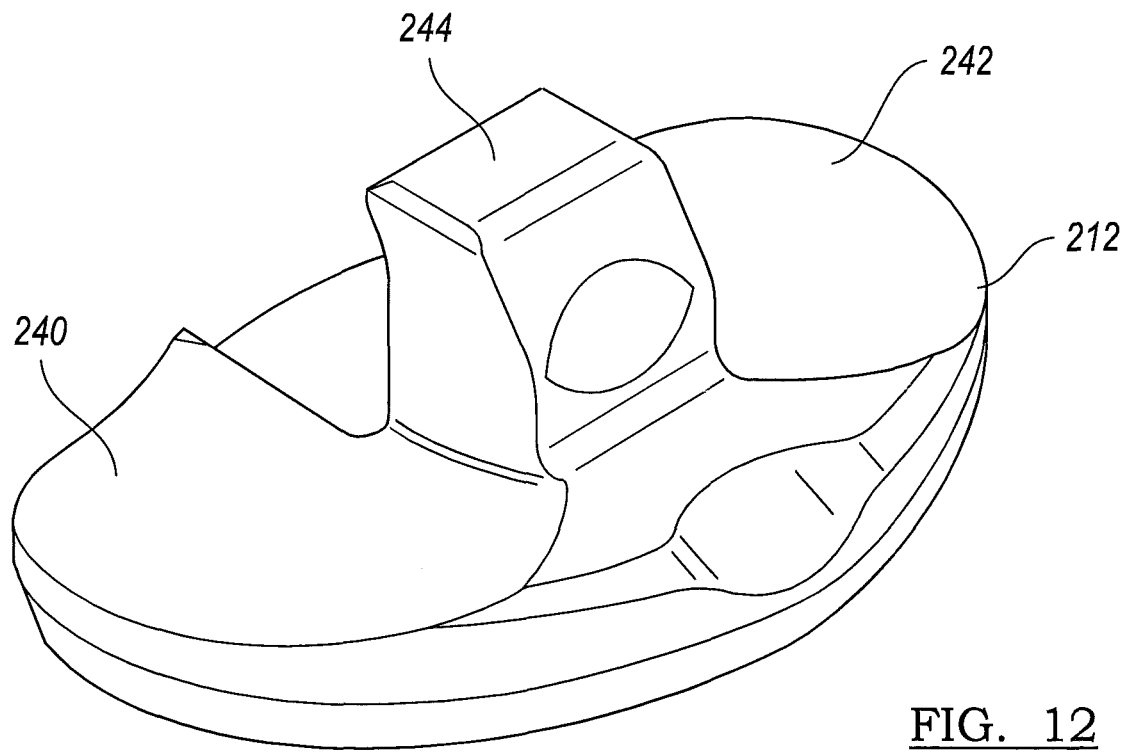
FIG. 12 is a perspective view of a superior surface of the bearing of FIG. 9.

Turning now to FIG. 8, a knee joint prosthesis according to another example is shown and generally identified at reference number 110. The knee joint prosthesis 110 includes a femoral component 112. The femoral component 112 may be used as part of a posterior stabilized (PS) knee joint prosthesis. A PS knee joint prosthesis can provide adequate stability in case of moderate deterioration or instability of a knee. This most typically occurs when the anterior and posterior cruciate ligaments are sacrificed or dysfunctional and the medial and lateral collateral ligaments remain functionally intact. The femoral component 112 can include a first condylar portion 114 and a second condylar portion 116 that provide a first femoral bearing surface 118 and a second femoral bearing surface 120, respectively. The first and second condylar portions 114 and 116 of the femoral component 112 can be interconnected by an inner condylar portion 122 that defines an intercondylar recess 124. A superiorly extending portion 130 may be formed on the femoral component 112. The superiorly extending portion 130 can include a generally tapered outer body to receive the augments described herein and define a female tapered receiving portion 132.

According to the present teachings, the female tapered receiving portion 132 of the femoral component 112 may be configured to accept one of the adapter bodies 44, 44' described above. In this way, the male tapered insertion portion 48 of the adapter body 44 can be adapted to be inserted and press-fit into the female tapered receiving portion 132 of the femoral component 112. As can be appreciated, the first axis $A_1$ and the second axis $A_2$ are parallel to one another and spaced apart. Again, the exemplary adapter assembly 24 has been described as having a 5 mm offset however, other adapter bodies may be provided having various offsets. A locking element 46 and stem 20 may be used according to the description above.

Turning now to FIGS. 9-14, a knee joint prosthesis according to another example is shown and generally identified at reference number 210. The knee joint prosthesis 210 is generally shown to include a tibial component 212 that supports a rotating constrained bearing 214. The tibial component 212 can generally include a substantially planar platform-like tibial tray 216 (FIG. 10) and an inferiorly extending portion 218. The inferiorly extending portion 218 can define a tapered female receiving portion 220 and an outer tapered body for receiving augments disclosed herein.

The tibial tray 216 can further include a superiorly extending post 224. A transition between the tibial tray 216 and the superiorly extending post 224 can be defined by a varying radius R, or more specifically transition between a radius $R_1$ having a radius of approximately 0.50 inches, and a radius $R_3$ having a radius of approximately 1.50 inches. An intermediate radius $R_2$ can have a radius of approximately 0.38 inches. It is appreciated that the radius R may define other dimensions. The transition of the varying radius R can minimize stresses experienced on the superiorly extending post 224. An axis $A_3$ (FIG. 14) defined through the post 224 can be laterally offset in the posterior direction relative to an axis $A_4$ defined through the inferiorly extending portion 218. A threaded aperture 228 can be formed through the anterior portion of the tibial tray 216. The threaded aperture 228 can extend generally perpendicular to the axis $A_4$.

The inferiorly extending portion 218 can define a tapered augment receiving surface 230. The tibial tray 216 can be formed from cobalt-chromium-molybdenum or any other suitable biocompatible material. A top 232 (FIG. 10) of the tibial tray 216 can be highly polished to provide a substantially smooth tibial bearing surface 234.

Figure 13:
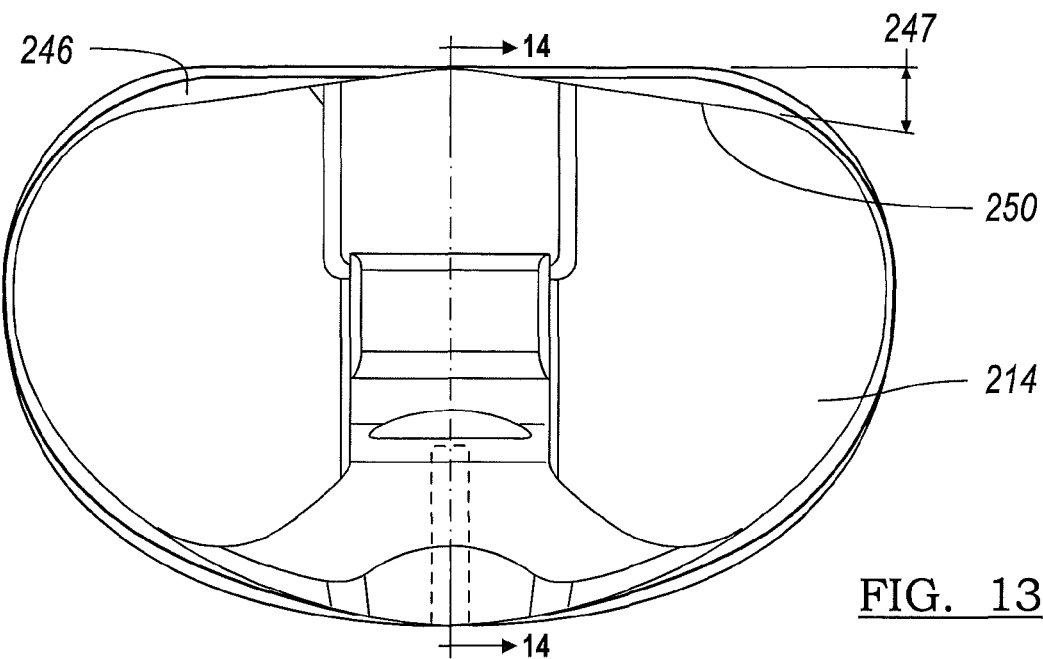
FIG. 13 is a top view of the tibial tray and bearing of FIG. 9.

The rotating bearing 214 can have a substantially planar inferior bearing surface 238 (FIG. 11) which can rotatably move relative to the highly polished tibial bearing surface 234. The rotating bearing 212 can further include a first superior articulating or bearing surface 240 and a second superior articulating or bearing surface 242. The bearing surfaces 240 and 242 can be formed anteriorly and laterally from a central superiorly extending portion 244. The first bearing surface 240 and the second bearing surface 242 can articulate with respective bearing surfaces of a first and second condyle of a constrained femoral component (not shown). The rotating bearing 212 can be formed from a surgical grade, low friction, and low wearing plastic, such as UHMWPE or other suitable material. As shown in FIG. 13, a posterior edge 246 of the tibial tray 216 can define a surface that defines an angle 247 relative to a posterior edge 250 of the bearing 214. The angle 247 can be approximately 8 degrees. Other angles are contemplated.

Figure 14:
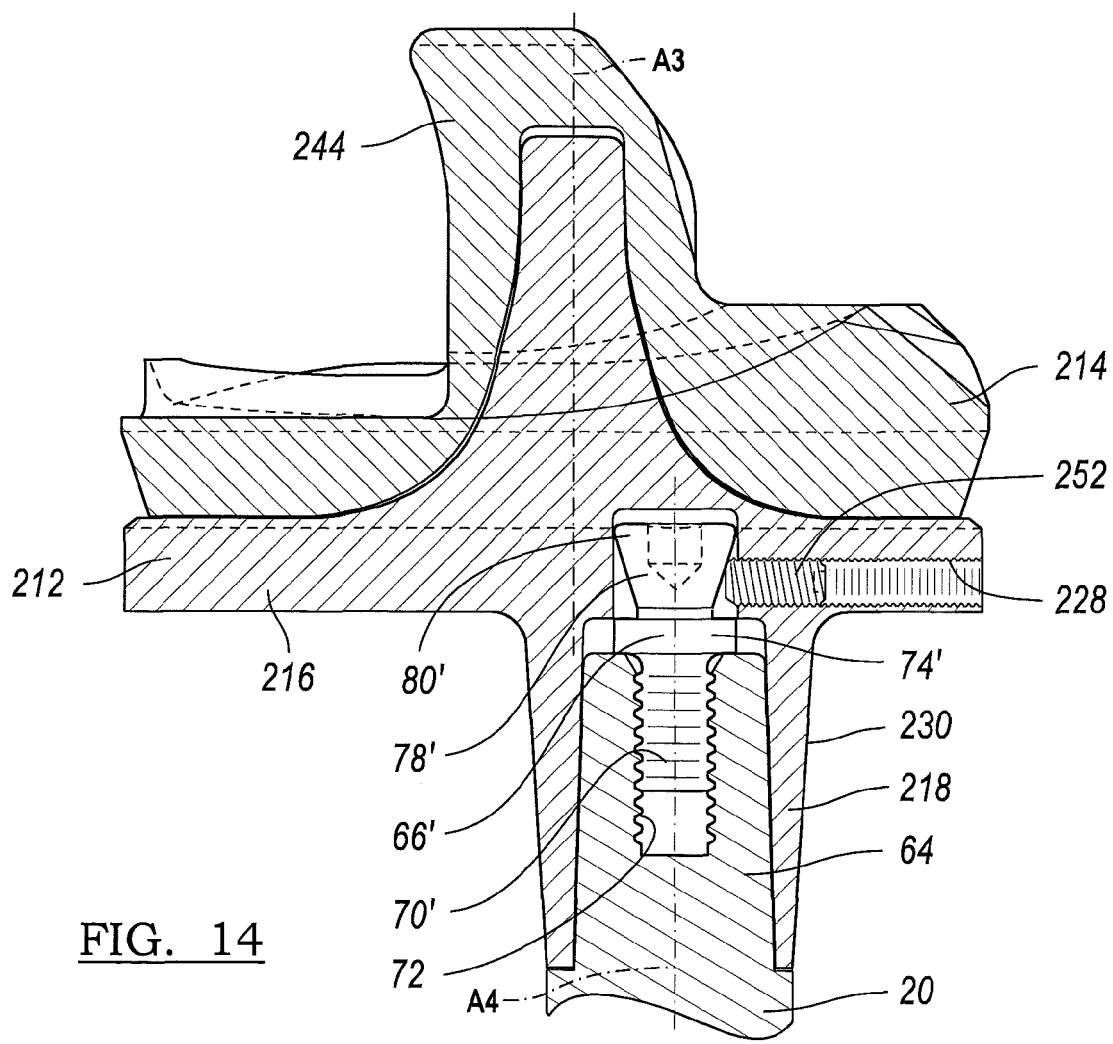
FIG. 14 is a cross-sectional view taken along the line 14-14 of FIG. 13.
Figure 15:
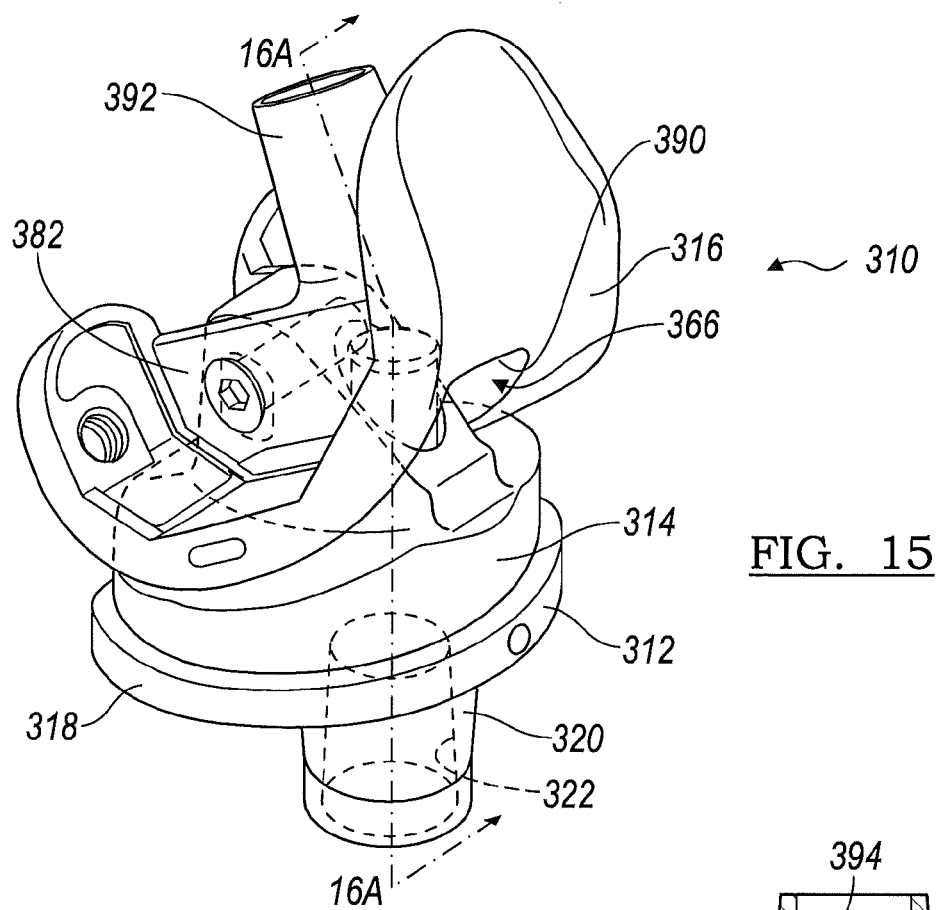
FIG. 15 is a perspective view of a hinged knee joint prosthesis according to additional features.

Turning now to FIG. 14, a stem 20 is shown received directly into the female tapered receiving portion 220 of the tray 216. Again, instead of inserting a stem 20 directly into the female tapered receiving portion 220 of the tray 216, an adapter body 44 or 44' may be used. The stem 20 can include a fastener insert 66'. The fastener insert 66' can include a distal portion 70' which is externally threaded for engaging an internally threaded aperture 72 of the male tapered insertion portion 64 of the stem 20. The fastener insert 66' can further include a central portion 74' having a hexagonal or other suitable cross-section which can be engaged by a tool (not shown) for rotating the fastener insert 66' into the stem 20. Further, the fastener insert 66' can include an upper end 78' including a conical engaging head 80'. A set screw 252 can be advanced through the threaded aperture 228 of the tibial tray 216 to engage the conical engaging head 80'. In this way, advancement of the set screw 252 can secure the fastener insert 66', and therefore, the stem 20 in a secure position. It is appreciated that when utilizing the adapter body 44, a fastener such as fastener insert 66' but having a longer shank, may alternately be used for threadably securing to the locking element 46.

Turning now to FIGS. 15-20, a hinged knee joint prosthesis constructed in accordance with the present teachings is illustrated and generally identified at reference number 310. The knee joint prosthesis 310 is generally shown to include a tibial component 312 that supports a bearing 314 which engages an articulation surface of a femoral component 316. The tibial component 312 can generally include a substantially planar platform-like tibial tray 318 and an inferiorly extending portion 320. The inferiorly extending portion 320 can define a tapered female receiving portion 322.

Figure 16A:
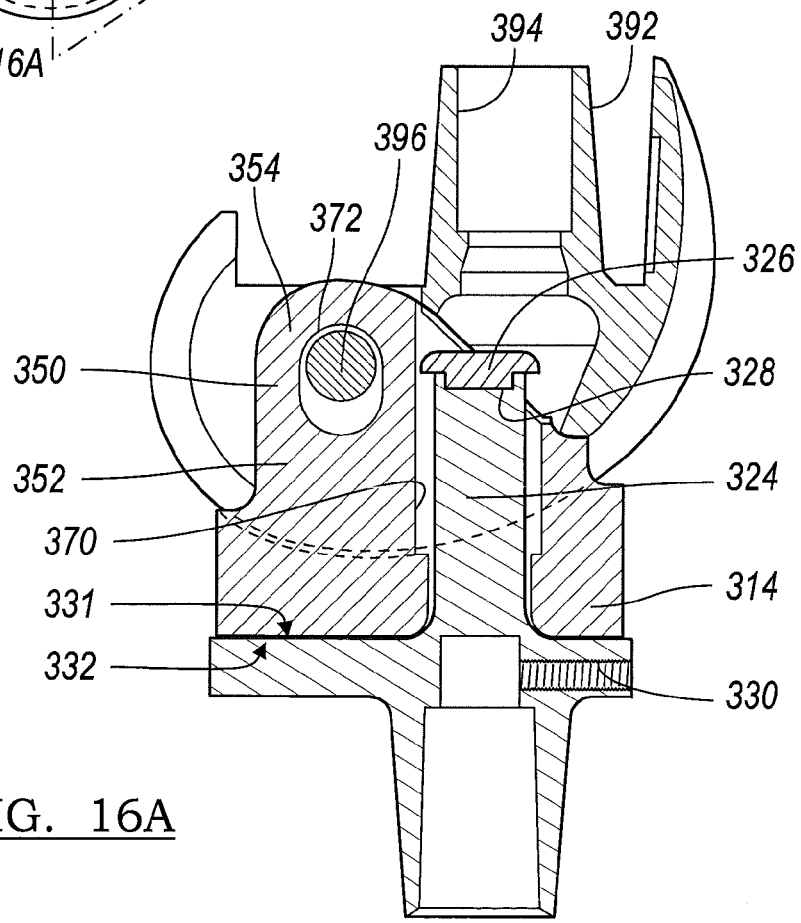
FIG. 16A is a cross-sectional view taken along the line 16-16 of FIG. 15 and shown with the femoral component rotated.

With additional reference to FIG. 16A, the tibial tray 318 can further include a superiorly extending post 324. As will be described, a cap 326 can be securely inserted into an elongate bore 328 defined at a terminal opening of the superiorly extending post 324. A threaded aperture 330 can be formed through the tibial tray 318. The threaded aperture 330 can extend generally perpendicular to an axis defined by the superiorly extending post 324. The tibial tray 318 can be formed from cobalt-chromium-molybdenum or any other suitable biocompatible material. A set screw (not shown) can be advanced through the threaded aperture 330 of the tibial tray 318 to engage a conical engaging head of a fastener insert (as described in detail above regarding FIG. 14). In this way, advancement of the set screw can secure the fastener insert, and therefore the adapter body 44 or the stem 20 in a secure position. The top of the tibial tray 318 can be highly polished to provide a substantially smooth tibial bearing surface 331.

Figure 17:
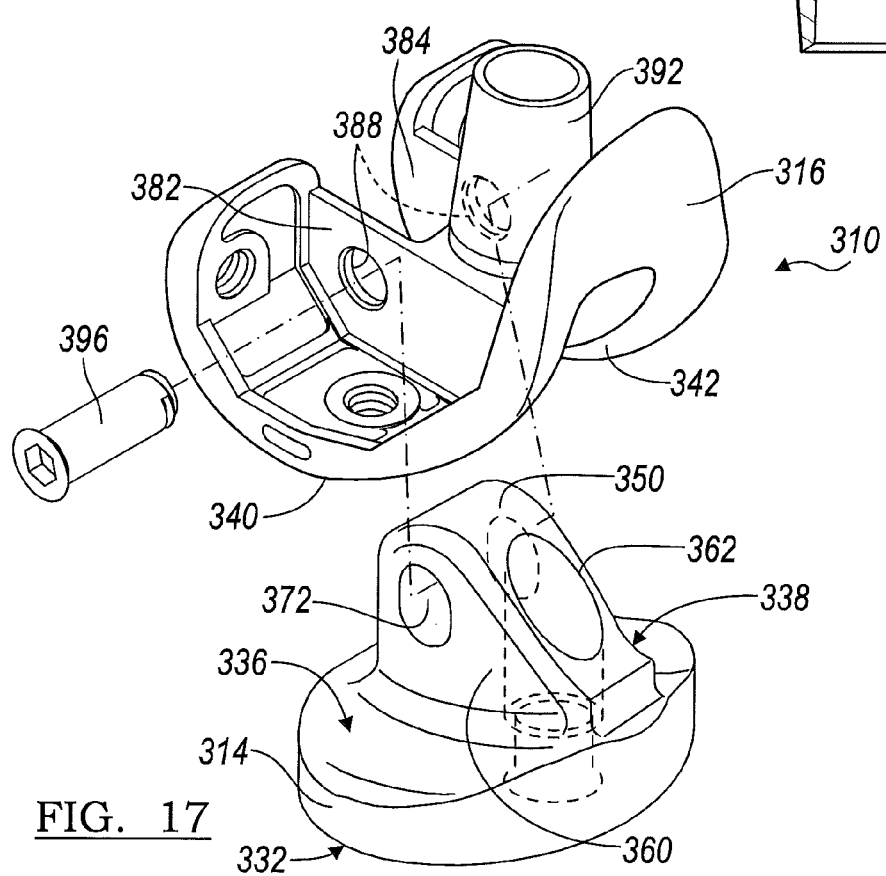
FIGS. 17-20 show an exemplary sequence of assembling the knee joint prosthesis of FIG. 15.
Figure 18:
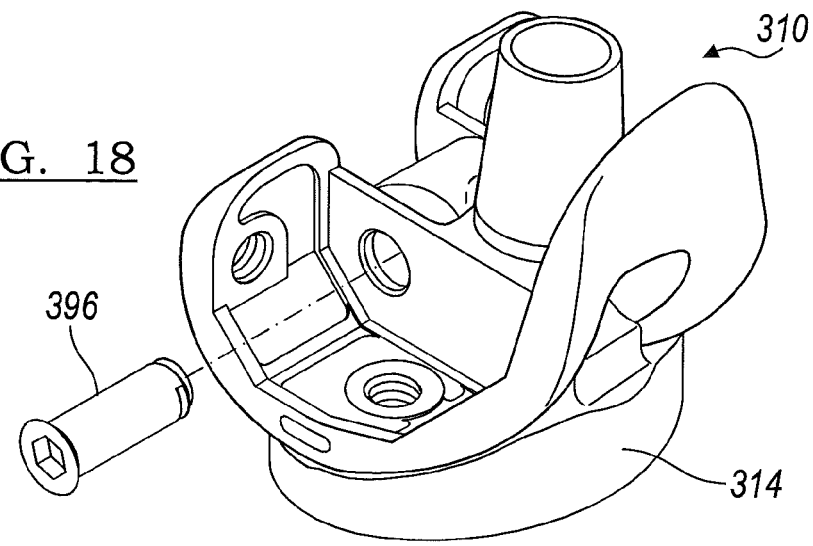

The rotating bearing 314 can have a substantially planar inferior bearing surface 332 which can rotatably move relative to the highly polished tibial bearing surface 331. The rotating bearing 314 can further include a first superior articulating or bearing surface 336 and a second superior articulating or bearing surface 338. The first bearing surface 336 and the second bearing surface 338 can articulate with respective bearing surfaces of a first and second condyle 340 and 342, respectively of the femoral component 316. Again, as described above, the bearing surfaces may be similar to those provided in the Vanguard® Complete Knee System. To accommodate guiding movement of the femoral component 316, the bearing 314 can include a stabilizing post 350 which can project superiorly from the bearing surface. The stabilizing post 350 can include a fin-like body 352 having a raised posterior portion 354 and a lower anterior portion 356. The body 350 can define a first and second laterally spaced-apart sides 360 and 362 (FIG. 17). The first and second sides 360 and 362 of the stabilizing post 350 can be positioned so as to extend into an intercondylar recess 366 (FIG. 15) of the femoral component 316. A stabilizing post aperture 370 can be formed in a superior/inferior direction through the body 350.

A passage 372 can be formed through the raised posterior portion 354 of the body 350. The passage 372 can extend generally through the first and second sides 360 and 362 of the stabilizing post 350 in a direction generally perpendicular to the stabilizing post aperture 370. The rotating bearing 314 can be formed from a surgical grade, low friction, and low wearing plastic, such as UHMWPE or other suitable material.

Figure 16B:
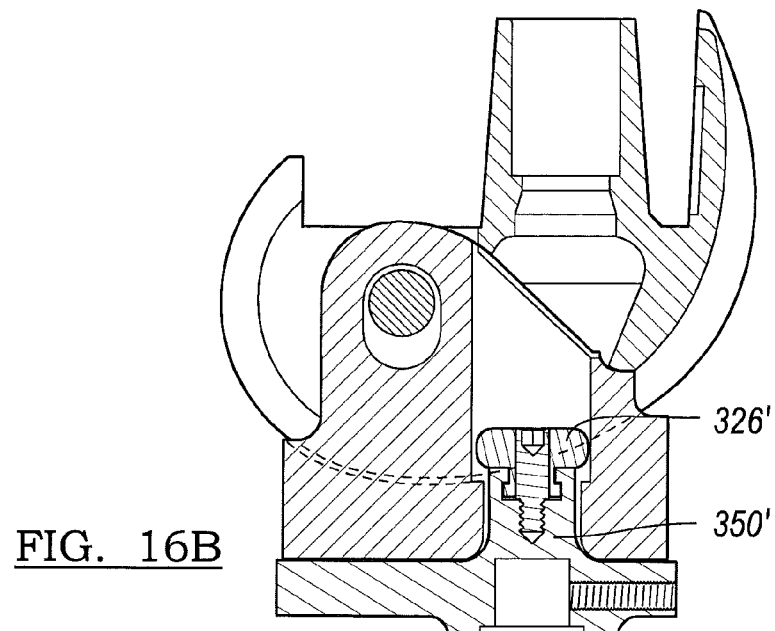
FIG. 16B is a cross-sectional view of a hinged knee prosthesis according to additional features.

An alternate stabilizing post 350' is shown in FIG. 16B that accepts a cap or fastener 326'.

The first and second condylar portions 340 and 342 of the femoral component 316 can be interconnected by an inner condylar portion 380 that defines the intercondylar recess 366. The intercondylar portion 380 can include a first lateral sidewall 382 and a second lateral sidewall 384 (FIG. 17) which can be planar and substantially parallel to each other. The first and second lateral sidewalls 382 and 384 can further define hinge passages 388 formed respectively therethrough.

Anterior portions of the first and second lateral sidewalls 382 and 384 can be connected by an anterior surface 390 (FIG. 15) of the intercondylar portion 380. In one example, the anterior surface 390 of the intercondylar portion 380 can angle anteriorly in an inferior direction at approximately 60 degrees with respect to a superior surface of the intercondylar portion 380. A superiorly extending portion 392 may be formed on the femoral component 316 and generally extend from a superior surface 394 (FIG. 16A). The superiorly extending portion 392 can include a generally cylindrical body and define a female tapered receiving portion 394.

A hinge post 396 can securably extend through the respective hinge passages 388 of the first and second lateral sidewalls 382 and 384 of the femoral component 316 and through the passage 372 in the bearing 314. Of note, the lateral sidewalls 382 and 384 of the femoral component 316 can be positioned proximate an inboard portion of the respective first and second condyles 340 and 342. In this way, host bone need not be sacrificed in areas outboard to the lateral sidewalls 382 and 384. As can be appreciated, during use, the femoral component 316 can rotate about the hinge pin 396.

Figure 19:
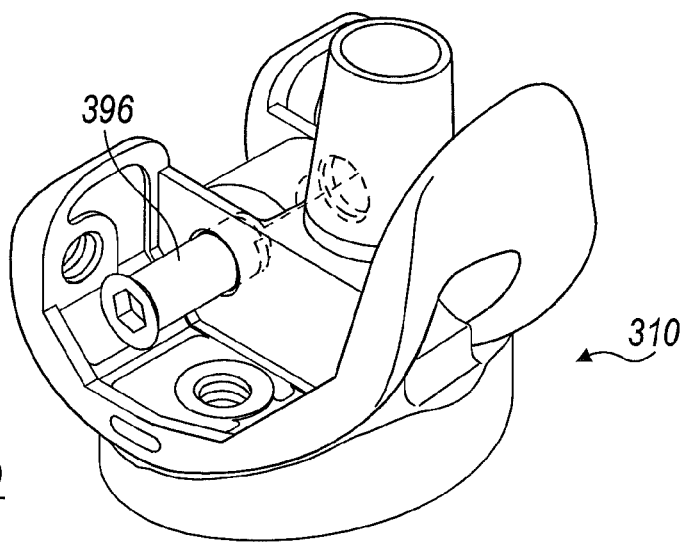
Figure 20:
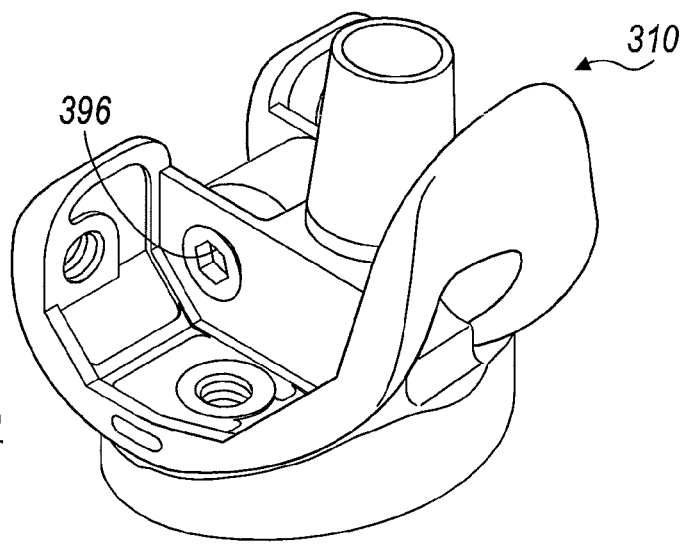
Figure 21:
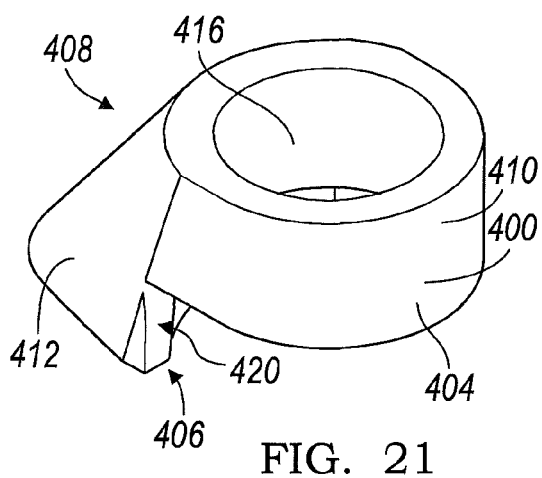
FIG. 21 is a perspective view of a first augment according to the present teachings.
Figure 22:
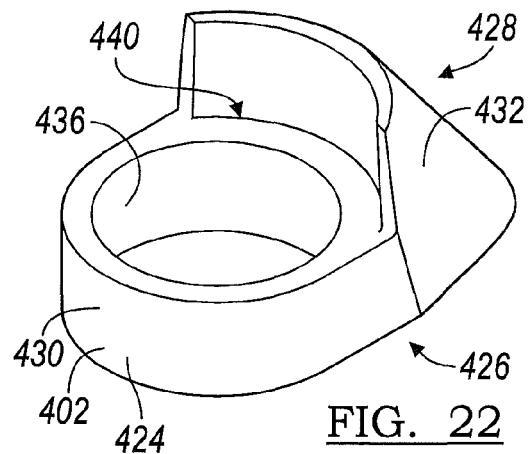
FIG. 22 is a perspective view of a second augment according to the present teachings.

With reference to FIGS. 17-20, an exemplary sequence of assembling the femoral component and bearing is shown. FIG. 17 illustrates an exploded view of the respective femoral component 310, hinge pin 396 and bearing 314. As viewed in FIG. 18, the femoral component 310 is placed onto the bearing 314 such that the respective passages 372 and 388 are aligned. FIGS. 19-20 show the hinge pin 296 inserted into the passages 372 and 388.

With reference now to FIGS. 21-25 a plurality of exemplary augments for use with any of the knee joint prostheses described above will be explained in detail. FIGS. 21-23B illustrate a first pair of augments 400 and 402. The first augment 400 can generally define a body 404 having first end 406 and a second end 408. The body 404 can further define a consistent radius portion 410 at the second end and 408 an outwardly tapered radially extending portion 412 near the first end 406. The consistent radius portion 410 can define a tapered receiving bore 416 formed therethrough. The receiving bore 416 can taper from the first end 406 to the second end 408. A first step 420 may be formed in the body 404 between the consistent radius and the radially extending portions 410 and 412, respectively. As can be appreciated, a collection of first augments may be provided having various dimensions and configurations suitable for a particular patient.

The second augment 402 can generally define a body 424 having first end 426 and a second end 428. The body 424 can further define a consistent radius portion 430 at the first end 426 and an outwardly tapered radially extending portion 432 near the second end 428. The consistent radius portion 430 can define a tapered receiving bore 436 formed therethrough. The receiving bore 436 can taper from the first end 426 to the second end 428. A second step 440 may be formed at the second end 428 between the consistent radius and the radially extending portions 430 and 432, respectively. As can be appreciated, a collection of first augments may be provided having various dimensions and configurations suitable for a particular patient.

Figure 23A:
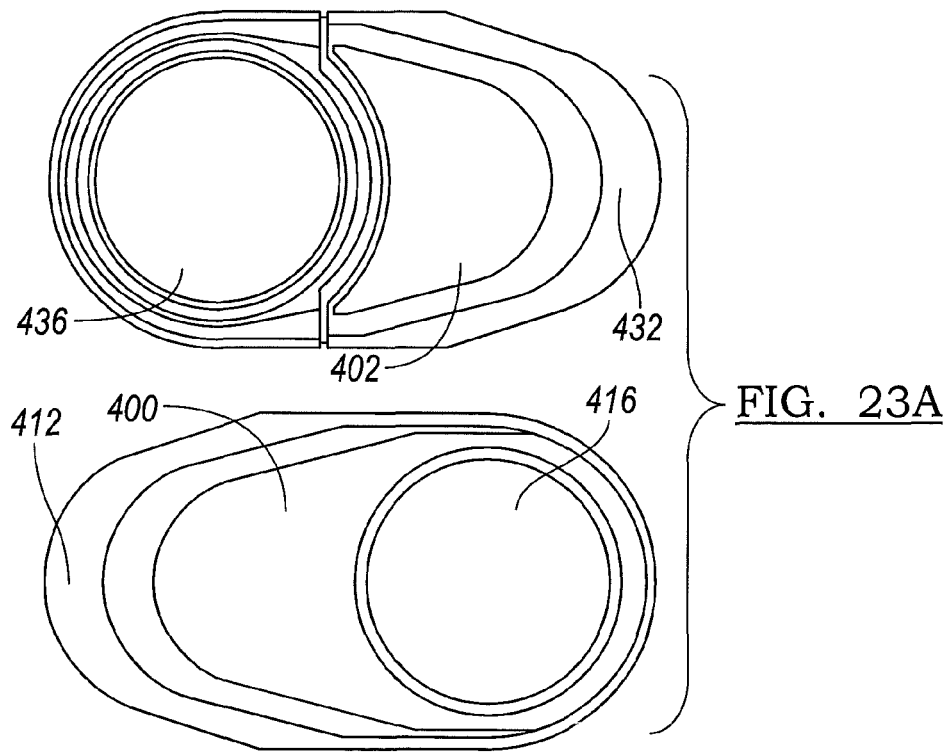
FIG. 23A is a plan view of the first and second augments of FIGS. 21 and 22.
Figure 23B:
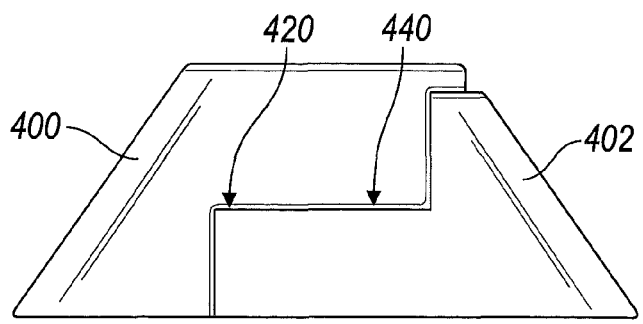
FIG. 23B is side view of the first and second augments in an mated or interlocked position.

As will be described in detail later, the first and second augments 400 and 402 may be used singly or as a combination. As shown in FIG. 23B, the first and second augments 400 and 402 can interlock or mate at the first and second steps 420 and 440 when used concurrently with any of the tibial and femoral components described above.

Figure 24:
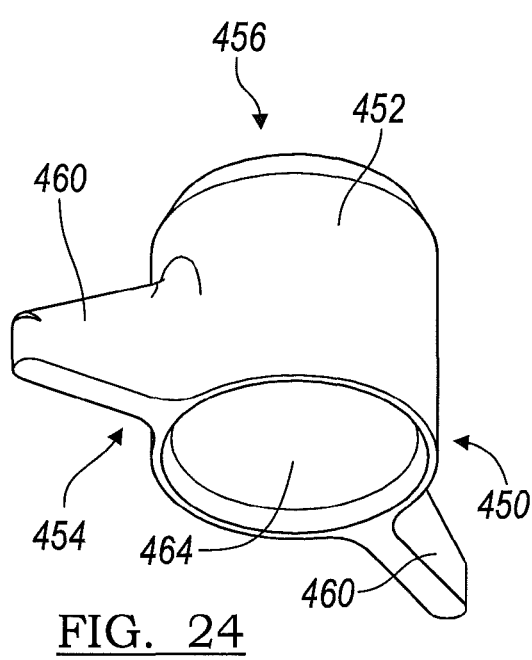
FIG. 24 is a perspective view of a third augment according to the present teachings.
Figure 25:
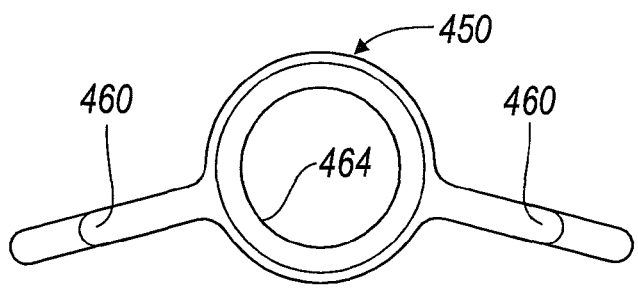
FIG. 25 is a top view of the third augment of FIG. 24.

With reference now to FIGS. 24 and 25, a third augment 450 is shown. The third augment 450 can generally define a body 452 having a first end 454 and a second end 456. The body 452 can further define a pair of wing portions 460 extending radially therefrom to provide rotational stability to either the femoral component or the tibial component. In one example, the wing portions 460 may be offset toward the first end 454. The body 452 can define a tapered receiving bore 464 formed therethrough. The receiving bore 464 can taper from the second end 456 to the first end 454.

According to the teachings of the present disclosure, the receiving bores 416, 436 and 464 of each of the augments 400, 402 and 450 can be slidably press-fit onto any of the inferior extensions of the tibial trays described above. More specifically, the receiving bores can define a tapered interlock with the tapered augment receiving surfaces of the inferior extensions of the tibial trays. Likewise, any of the same augments can also be slidably press-fit onto any of the superior extensions of the femoral components described above. More specifically, the receiving bores can define a tapered interlock with the tapered augment receiving surfaces of the superior extensions of the femoral components. As such, the respective tapered surfaces can cooperate to form a Morse taper.

Figure 26:
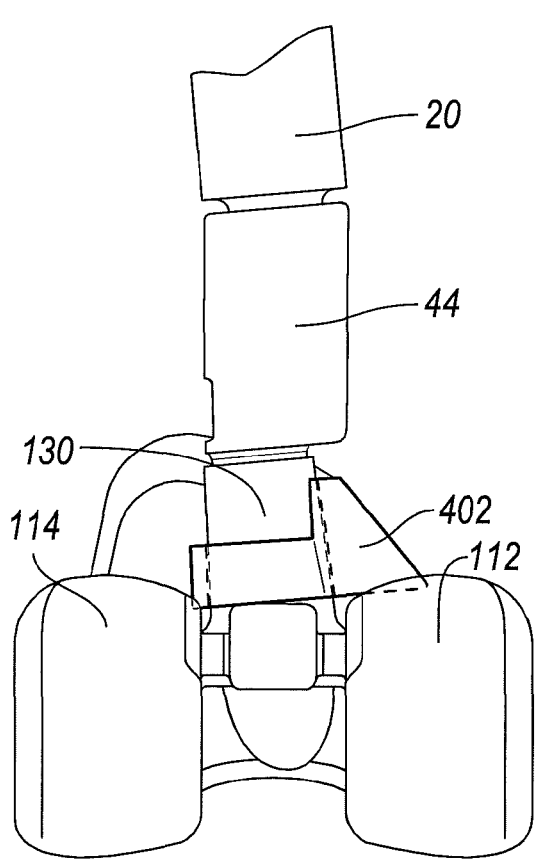
FIG. 26 is an anterior view of the femoral component of FIG. 8 shown with the first augment assembled on a superiorly extending portion.
Figure 27:
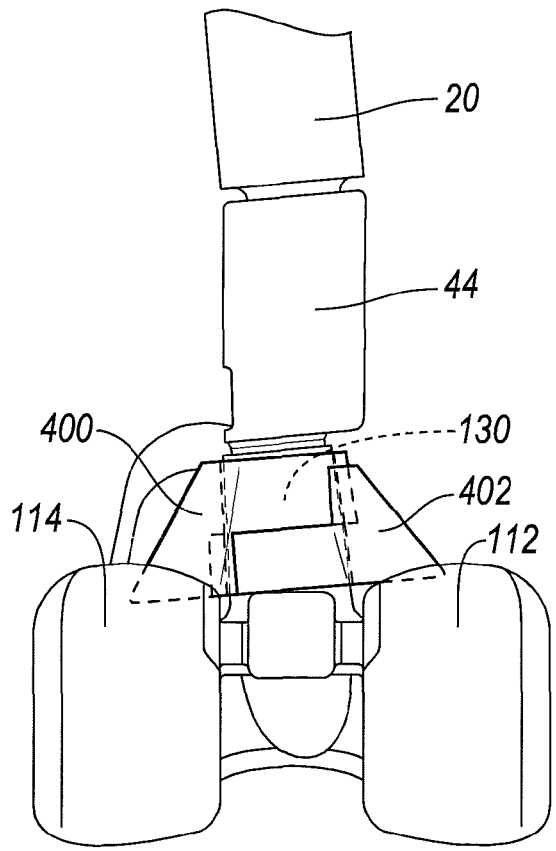
FIG. 27 is an anterior view of the femoral component of FIG. 8 shown with the first and second augments assembled on a superiorly extending portion.
Figure 28:
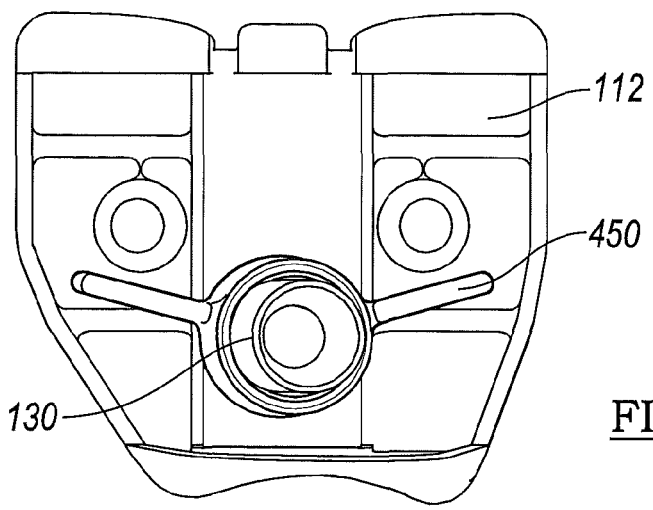
FIG. 28 is a superior view of the femoral component of FIG. 27 and shown with the augment of FIG. 24 secured to an inferiorly extending portion.

To illustrate this compatibility, a second augment 402 is shown secured to the superior extension 130 of the femoral component 112 (FIG. 26). If a surgeon desires to account for additional bone loss, the first augment 400 may also be advanced onto the superior extension 130 of the femoral component 112 (FIGS. 27 and 29). As shown, the respective first and second steps 420 and 440 cooperate to mate or form an interlock.

Figure 30:
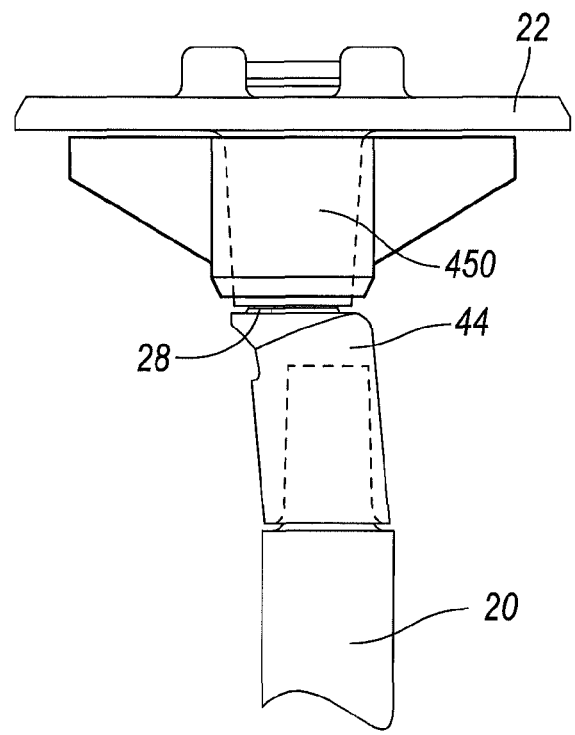
FIG. 30 is an anterior view of the tibial component of FIG. 1 shown with the third augment assembled on the inferiorly extending portion.

With reference to FIG. 29, a first and second augment 400 and 402 are shown secured to the inferior extension 28 of the tibial tray 22. Notably, the first and second augments 400 and 402 may be used with or without the adapter. It is appreciated, that any of the augments may be used with or without the adapter assemblies described above. FIG. 30 illustrates the third augment 450 secured to the inferior extension 28 of the tibial tray 22.

Figure 31:
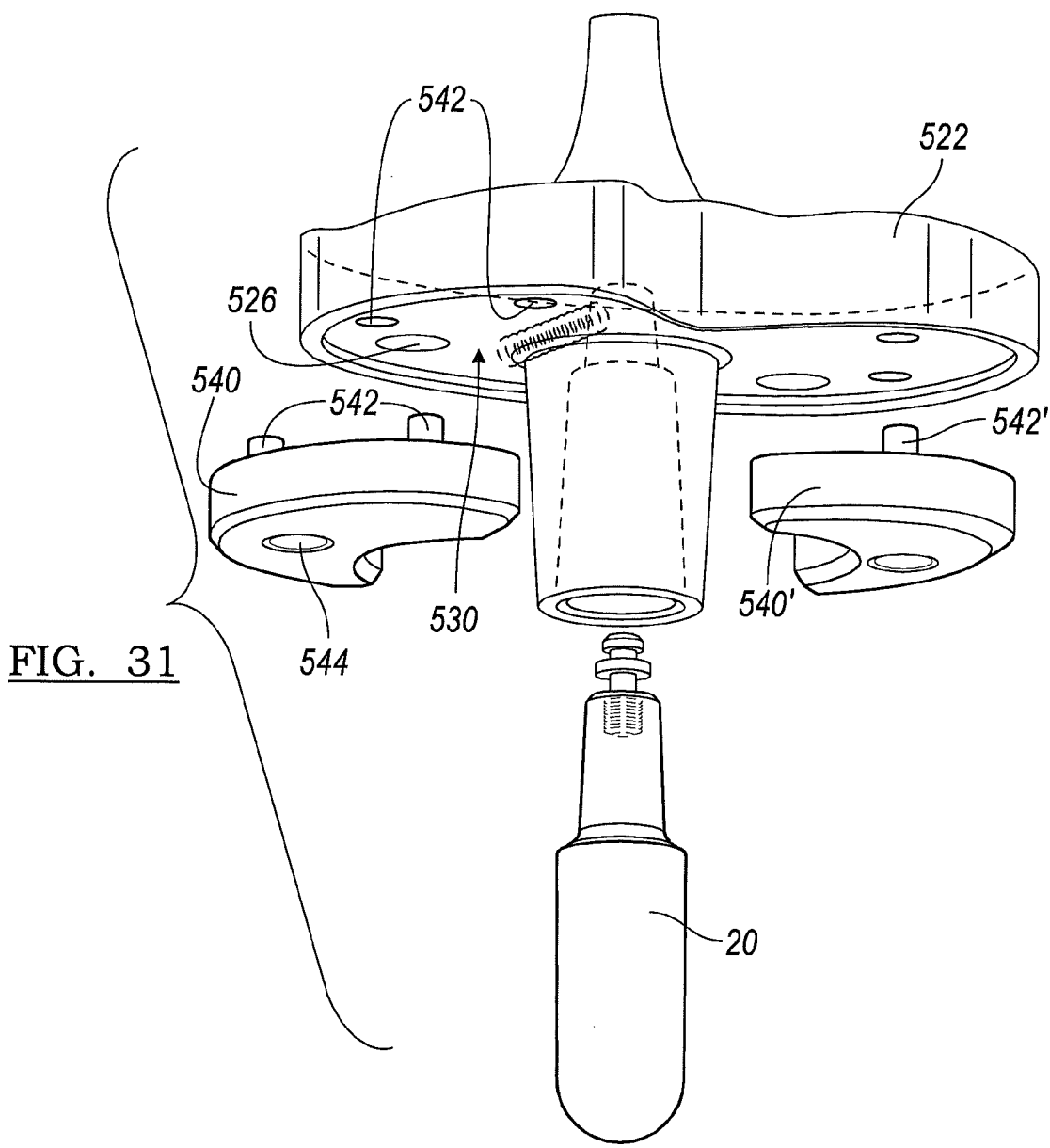
FIG. 31 is an exploded view of a modular tibial component according to additional features.
Figure 32:
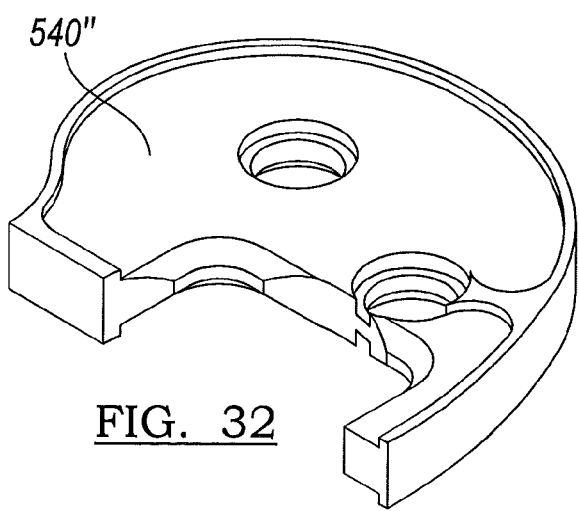
FIG. 32 is a perspective view of an augment according to additional features.

Turning now to FIGS. 31 and 32, another tibial component 522 is shown. The tibial component 522 can define one or more (such as a pair) of blind bores 524 and at least one opening 526 formed on an inferior surface. A recessed portion such as pocket 530 may also be optionally formed on an inferior surface of the tibial component 522. An augment 540 can define one or more (such as a pair) of complementary locating pegs 542 and at least one complementary opening 544. The augment 540 can be adapted to secure onto the inferior surface of the tibial component 522 to compensate for bone loss. As can be appreciated, an augment may be provided on one of a lateral or medial portion, or both, of the tibial component 522. During assembly, the locating peg 542 may nest within a blind bore 524. A fastener (not shown) may be inserted through the respective openings 526 and 544. Another augment 540' having at least one peg 542' can be provided for the opposite of the medial and lateral sides of the inferior surface of the tibial component 522. In another example (FIG. 32), an augment 540" suitable for connecting to either of the medial and lateral sides is provided. In such an example, pegs (such as pegs 542, FIG. 31) need not be provided. As can be appreciated, a plurality of augments 540 can be provided having various thicknesses such that a surgeon can assemble a particular augment suitable for a given patient. A stem 20 can be fixedly accepted into a female tapered extending portion 560 of the tray.

Figure 33:
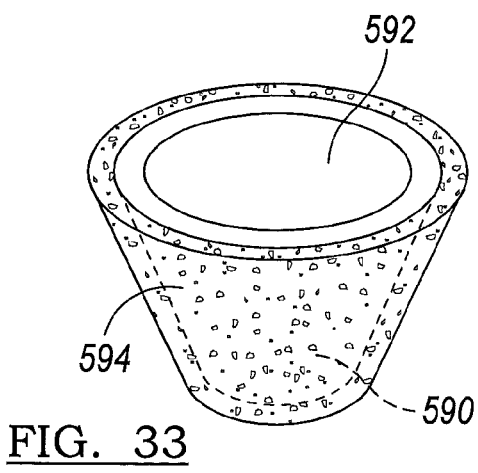
FIG. 33 is a perspective view of another augment according to the present teachings.

FIG. 33 illustrates another augment 590 that defines a tapered receiving bore 592 formed therethrough. The tapered receiving bore 592 can be slidably press-fit onto any of the inferior extensions of the tibial trays and/or the superior extensions of the femoral components described above. A portion of the augment 590 can optionally be formed of porous metal 594. The porous metal 594 can comprise porous titanium alloy for example. The augment 590 can define an inner solid metal sleeve portion and an outer porous metal sleeve portion 594. Again, according to the present teachings, the respective femoral components, tibial components, bearings and/or augments may be part of a kit wherein a surgeon may intra-operatively select a desired component or components needed for a particular patient.

Turning now to FIGS. 34-36B, the modular tibial component 22 (as described above with respect to FIGS. 1-3A) is shown cooperating with an adapter assembly 600 according to additional features. The adapter assembly 600 can cooperate with the stem 20. In a manner which will be discussed more fully below, the adapter assembly 600 can connect the tray 22 and the stem 20 so as to provide an offset to the stem 20 in the transverse or coronal plane or in any other plane. Explaining further, when the stem 20 is attached to the tray 22 through the first adapter assembly 600, the central axis 25 of the stem 20 can be offset from the central axis 27 of the inferiorly extending portion 28 of the tray 22. In the embodiment illustrated, the adapter assembly 600 can provide a first offset of approximately 5 mm. It is appreciated that the offset can range from 0 mm to approximately 5 mm or more and can be in any rotational direction relative to the central axis 27. In other words, the offset axis 25 can be rotated 360 degrees relative to the central axis 27 to provide the surgeon with various intra-operative options to select depending on the patient's needs. Alternatively, the adapter assembly 600 or stem 20 can be rotational keyed to provide only a limited range of adjustment, such as providing only a single offset or two offset positions.

With continued reference to FIGS. 34-36D and additional reference to FIGS. 37-39B, the adapter assembly 600 can generally include an adapter body 604 and a locking member or element 606. The adapter body 604 of the adapter assembly 600 can define a male tapered insertion portion 608 and a female tapered receiving portion 610. The male tapered insertion portion 608 can define a threaded bore 611. The female tapered receiving portion 610 can be formed in an offset body portion 612 of the adapter body 604 for receiving a male tapered insertion portion 58 of the stem 20. The adapter body 604 can define flats 614 on an outer surface for gripping and facilitating alignment as will be described. A skirt (not shown), similar to the skirt 54 formed on the adapter body 44 illustrated in FIG. 2, can be defined at a transition between the male tapered insertion portion 608 and the offset body portion 612. A non-skirted transition can alternatively be formed as shown herein. A bore 614 can be defined from an outer surface of the adapter body 604 to the female tapered receiving portion 610. The bore 614 can define threads 616 that threadably receive the locking member 606.

Figure 37:
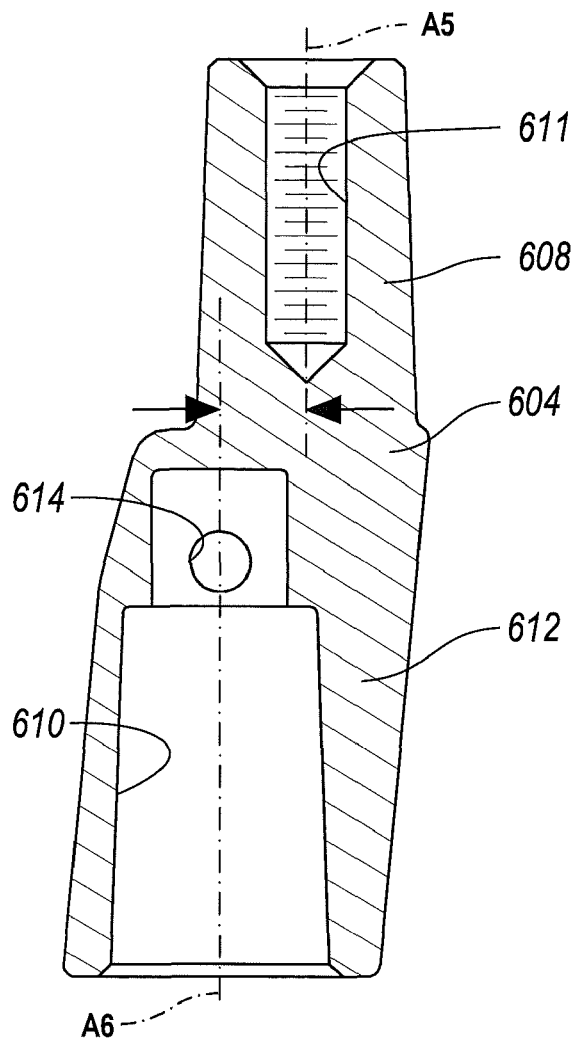
FIG. 37 is a sectional view of an exemplary adapter having a first offset.
Figure 38:
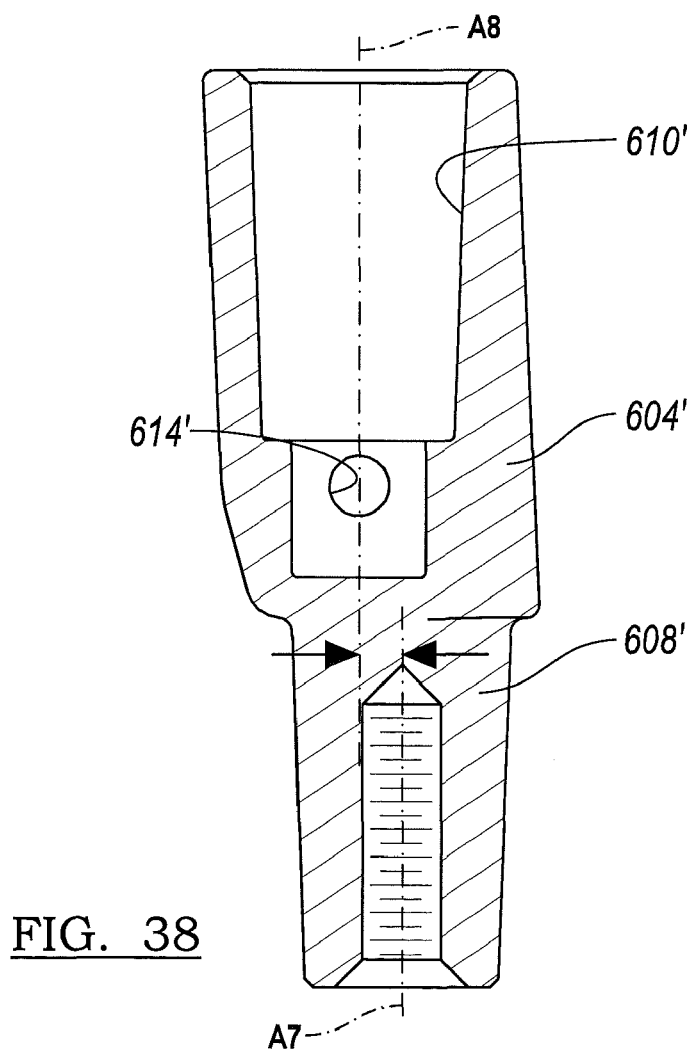
FIG. 38 is a sectional view of another exemplary adapter having a second offset.

With reference to FIG. 37, the male tapered insertion portion 608 of the adapter body 604 defines a first axis $A_5$ and the female tapered receiving portion 610 defines a second axis $A_6$. Further, in the embodiment illustrated, the first axis $A_5$ and the second axis $A_6$ are parallel to one another and spaced apart to provide the desired offset. In this regard, multiple adaptors each having a different offset can be provided to provide the surgeon with intra-operative selection depending on the patient's needs. Insofar as the adapter body 604 provides a 5 mm offset, the first and second central axes $A_5$ and $A_6$ are spaced apart 5 mm. Again, the adapter body 604 can define axes having an alternate offset. In one such alternate configuration, an adapter body 604' (FIG. 38) includes a male tapered insertion portion 608' that defines a first axis $A_7$ and the female tapered receiving portion 610' that defines a second axis $A_8$. The adapter body 604' can define an offset of 2.5 mm.

The male tapered insertion portion 608 can taper slightly as it extends away from the adapter body 604. The female tapered receiving portion 610 similarly tapers slightly as it extends into the adapter body 604 from an end of the adapter body 604. As will become appreciated from the following discussion, various male tapered insertion portions (such as portion 608) can be inserted in various female tapered receiving portions (such as portion 610) to form a locking taper or Morse taper. In a manner to be described further below, the locking member 606 can extend into the bore 614 where it ultimately engages a fastener insert 620.

The fastener insert 620 can include a distal portion 622 which can be externally threaded for engaging the internally threaded aperture 72 of the male tapered insertion portion 58 of the stem 20. The fastener insert 620 can further include a central portion 624 and a proximal portion 626. The proximal portion 626 can define a conical engaging head 630. A gripping detail 632 (such as, but not limited to, a hex-bore for receiving an Allen wrench), can be formed in an upper surface of the proximal portion 626. As will be described in more detail, the fastener insert 620, or more specifically the conical engaging head 630 can be formed of a first biocompatible material while the locking member 606 can be formed of a second biocompatible material. The second biocompatible material can be a higher durometer (harder) material than the first biocompatible material.

Figure 36A:
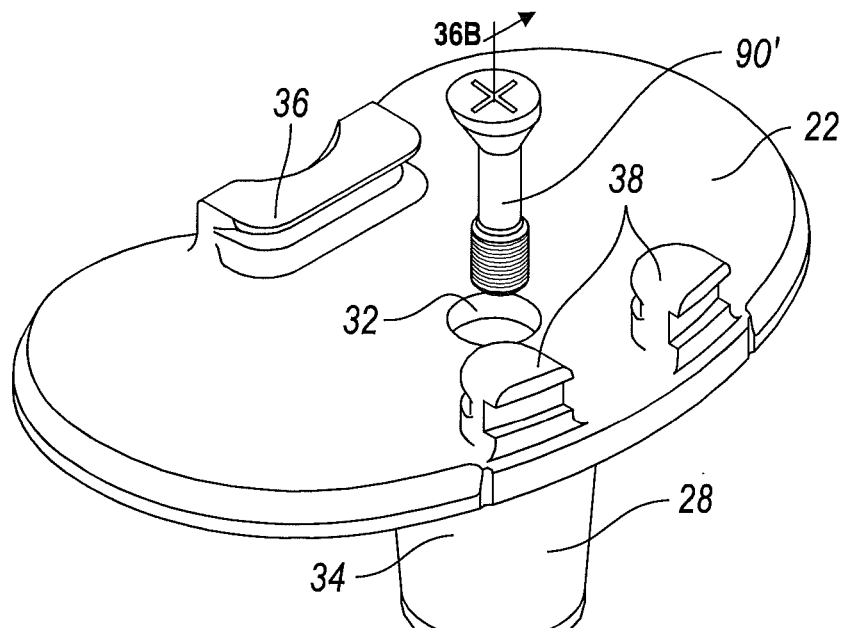
FIG. 36A is a detail exploded view of the tibial tray and adapter illustrated in FIG. 34.
Figure 36B:
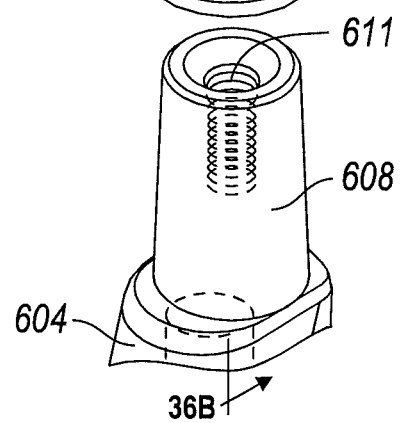
FIG. 36B is a partial sectional view taken along line 36B-36B of FIG. 36A.
Figure 36B:
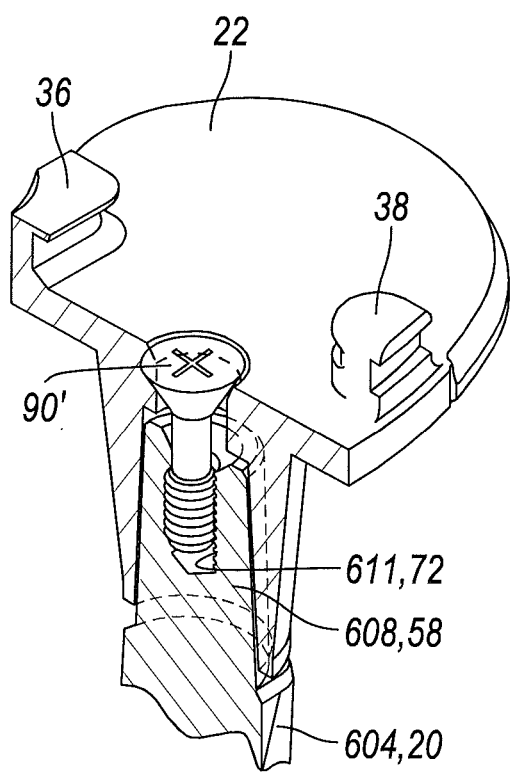
Figure 36C:
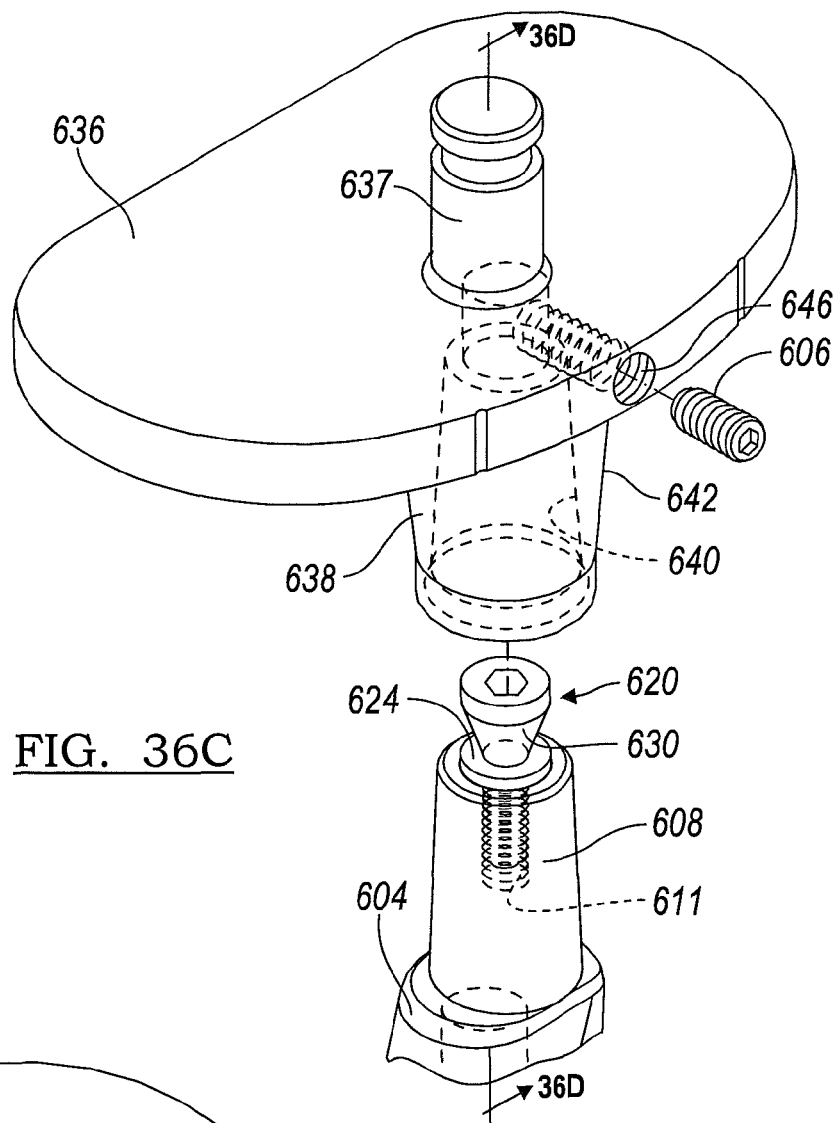
FIG. 36C is a detail exploded view of an adapter assembly cooperating with a tibial component according to additional features.
Figure 36D:
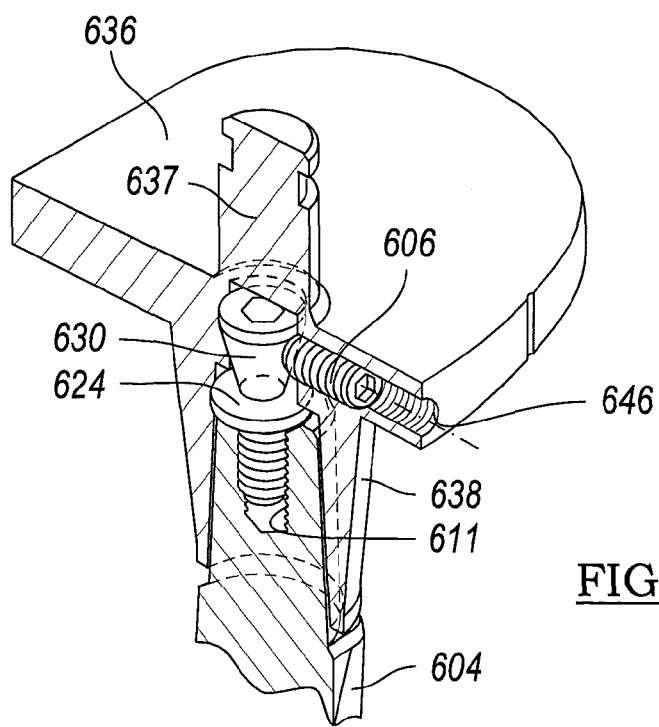
FIG. 36D is a partial sectional view taken along line 36D-36D of FIG. 36C.
Figure 48A:
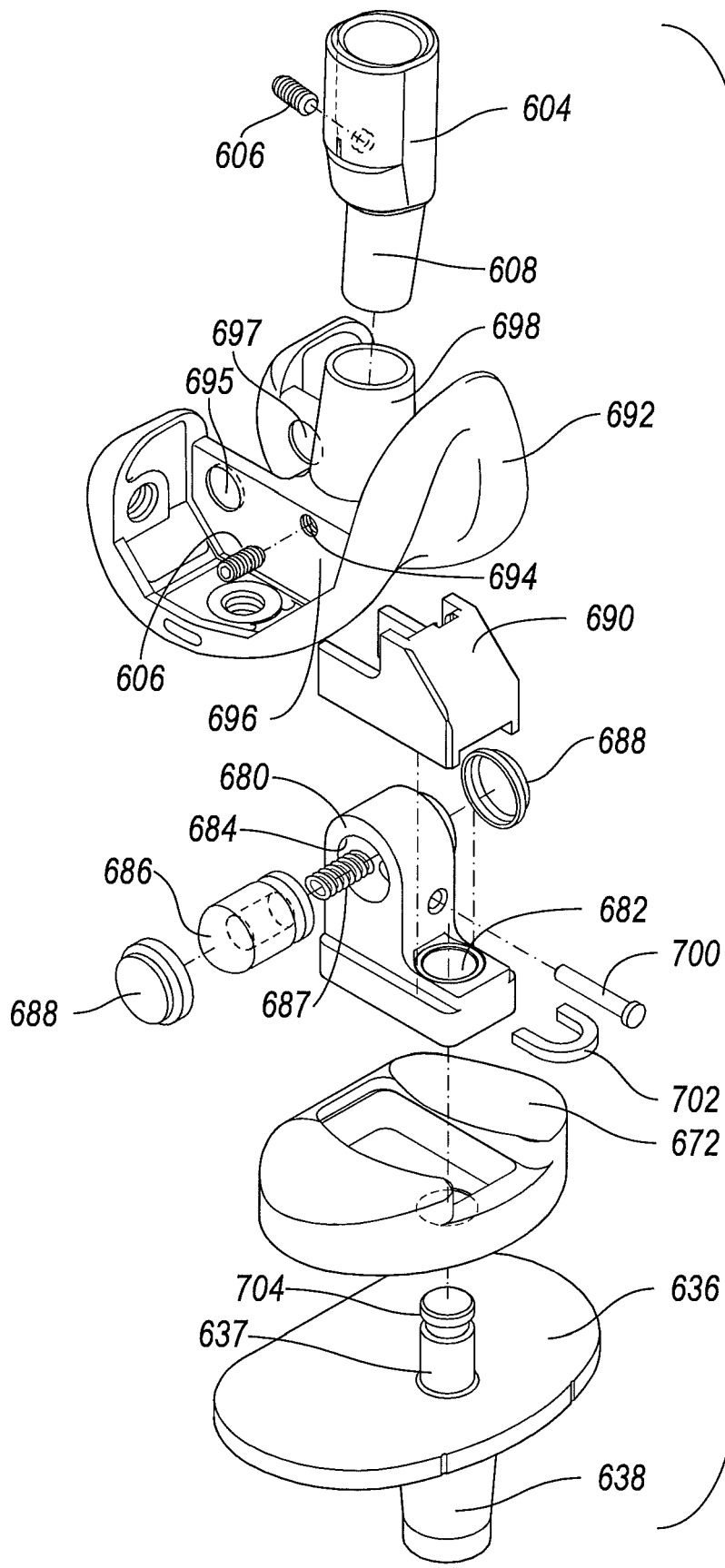
FIGS. 48A and 48B are exploded perspective views of a hinged knee prosthesis according to one example of the present teachings.
Figure 48B:
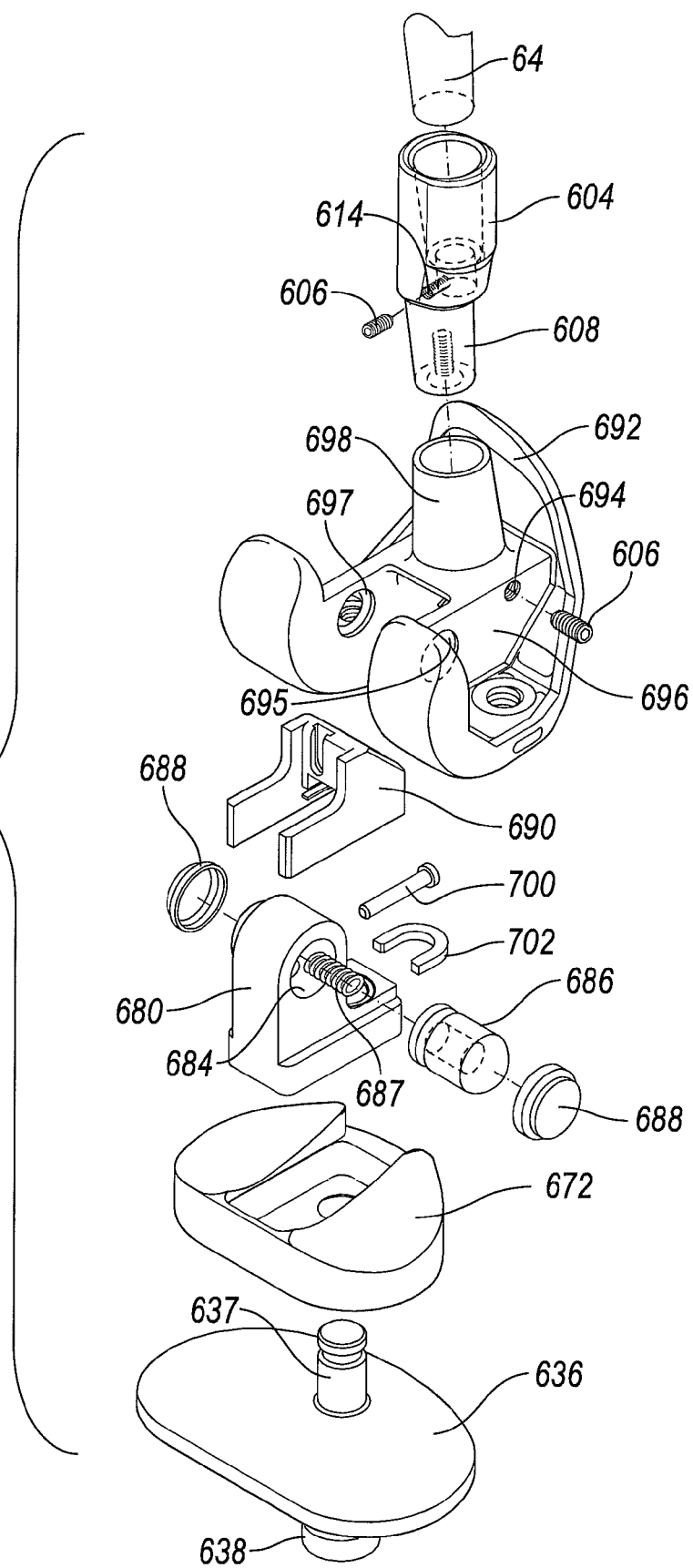
Figure 49:
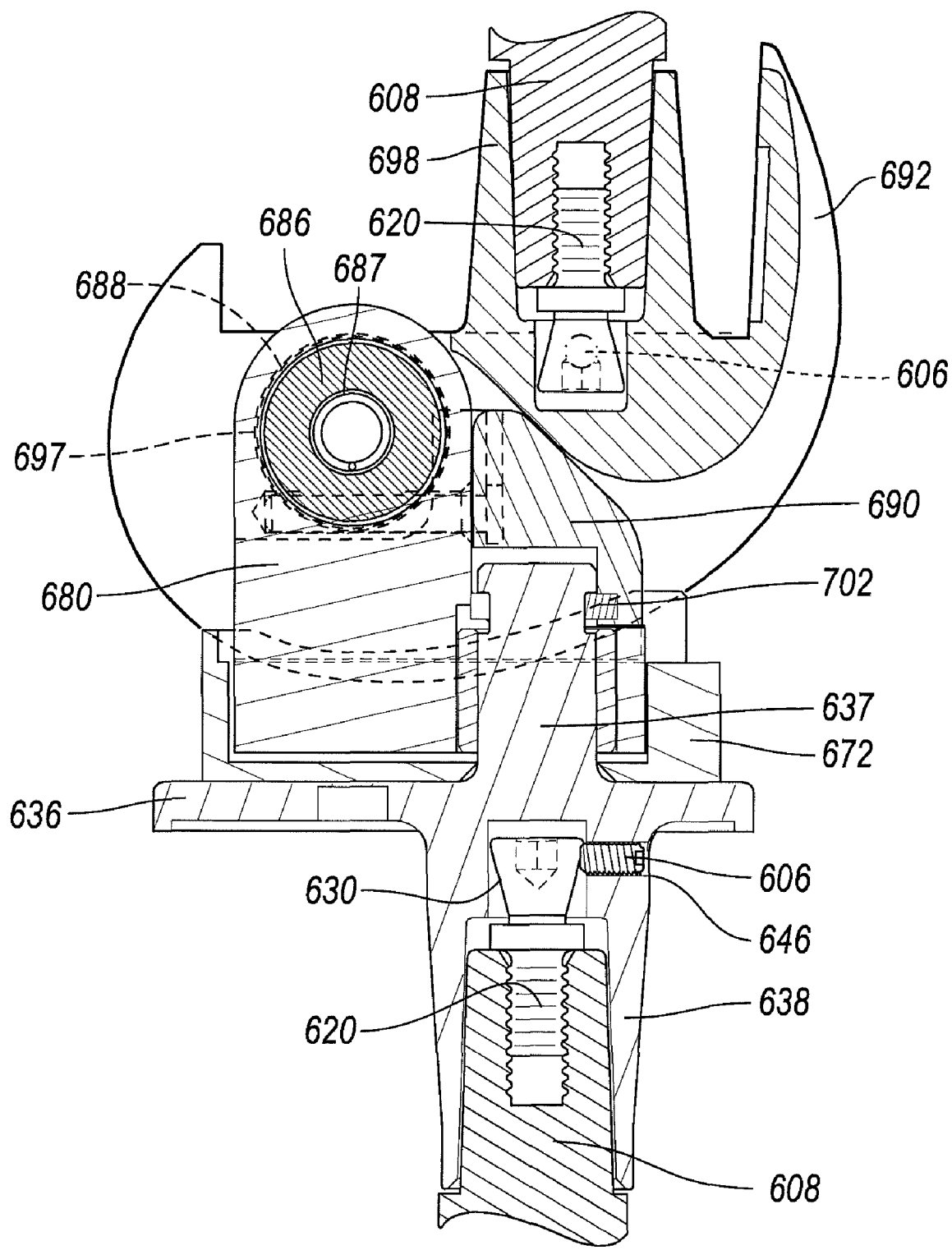
FIG. 49 is a sectional view of the hinged knee prosthesis of FIGS. 48A and 48B shown assembled.
Figure 50:
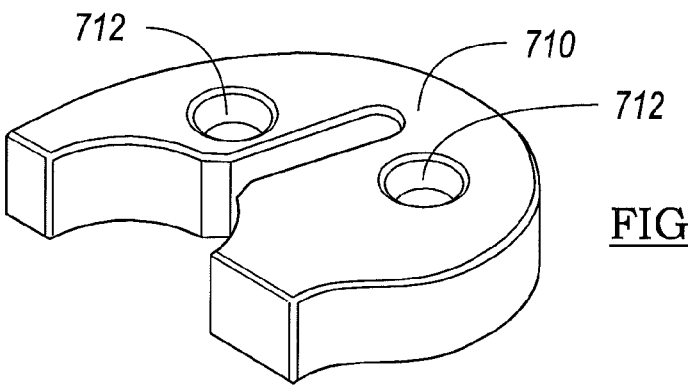
FIGS. 50-54 are perspective views of various augments according to the present teachings.
Figure 51:
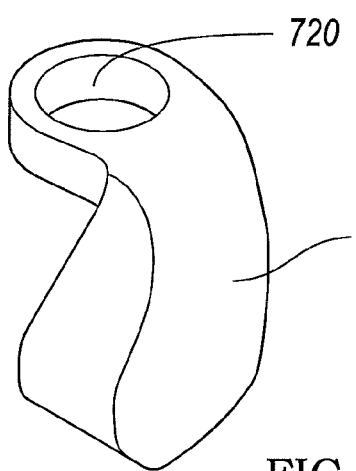
Figure 52:
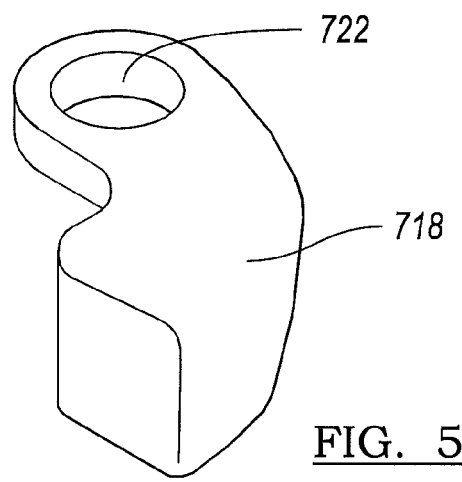
Figure 53:
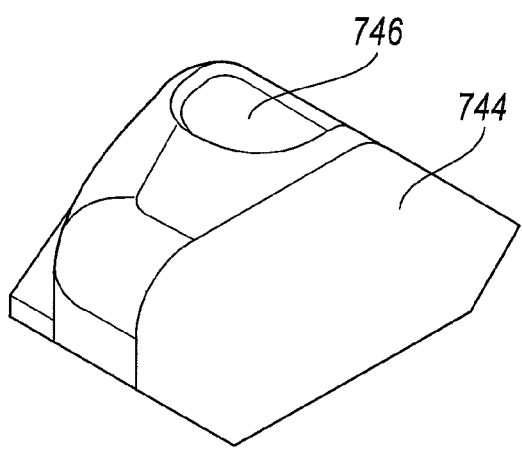

Turning now to FIGS. 36C and 36D, a tibial tray 636 according to additional features is shown. As will be described more fully herein, the tibial tray 636 can be part of a bone-conserving hinge knee prosthesis (FIG. 48A). The tibial tray 636 can define a superiorly extending stub 637 and an inferiorly extending portion 638 that defines a female tapered receiving portion 640. The inferiorly extending portion 638 can define an exterior tapered augment receiving surface 642. The tibial tray 636 can define a threaded passage 646 formed through the tray portion of the tibial tray 636. The treaded passage 646 can be adapted to threadably accept the locking member 606. Unlike the cruciate retaining tibial tray 22 (FIG. 34) that provides the central aperture 32 for receiving the fastener 90' in the superior/inferior direction, the tibial tray 636 can provide the threaded passage 646 for receiving the locking member 606 in the anterior/posterior direction.

With reference now to FIGS. 39A-40B, an exemplary sequence of assembling the tibial tray 636, the adapter body 604, and the stem 20 will be described. At the outset, the fastener insert 620 can be threaded into the threaded bore 611. In one example, the fastener insert 620 can be threaded until the central portion 624 engages a terminal surface 650 of the male tapered insertion portion 608 of the adapter body 604. At this point, the stem 20 can be coupled to the adapter body or the adapter body 604 can be coupled to the tibial tray 636. While the order can be reversed, the adapter body 604 can be coupled to the tibial tray 636, by inserting the male tapered insertion portion 608 of the adapter body 604 into the female tapered receiving portion 640 of the tibial tray 636. The surgeon can then rotate the male tapered insertion portion 608 within the female tapered receiving portion 640 to attain the desired orientation. As will be described later, the instant disclosure provides various tools for verifying a correct orientation of the adapter body 604 prior to securing the adapter body 604 in a fixed position relative to the tibial tray 636. Once the desired orientation has been attained, the locking member 606 can be threaded from an unsecured position (FIG. 36C) into engagement with the conical engaging head 630 to a secured position (FIG. 36D).

Figure 39A:
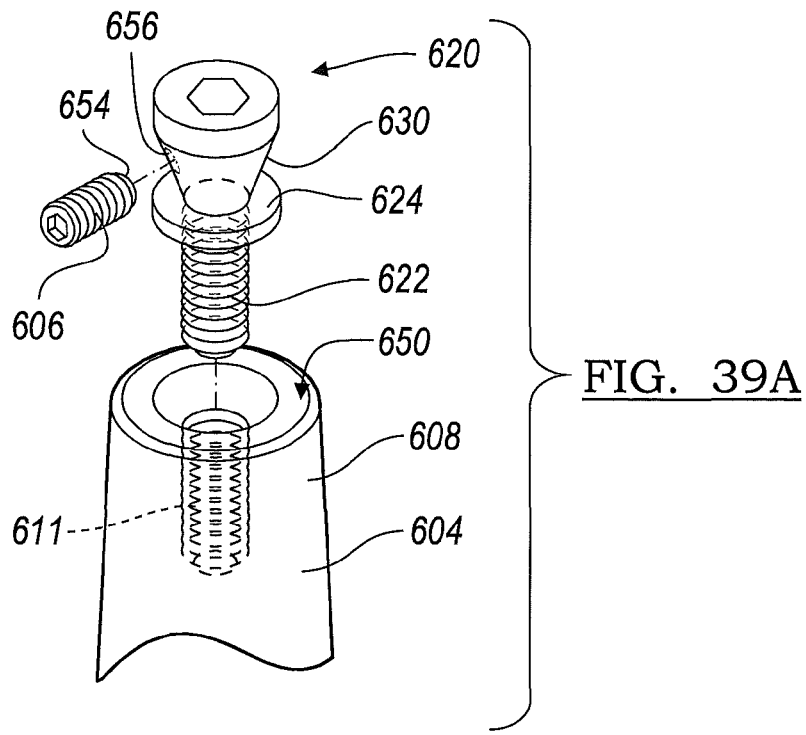
FIG. 39A is an exploded view of a fastener member and insert of the adapter assembly.
Figure 39B:
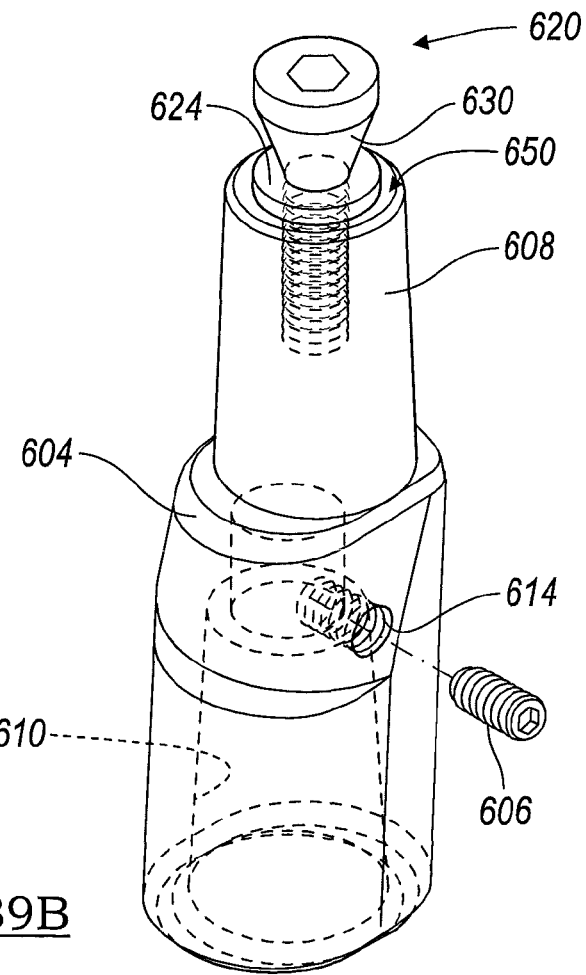
FIG. 39B is a partial exploded view of an adapter assembly.
Figure 40A:
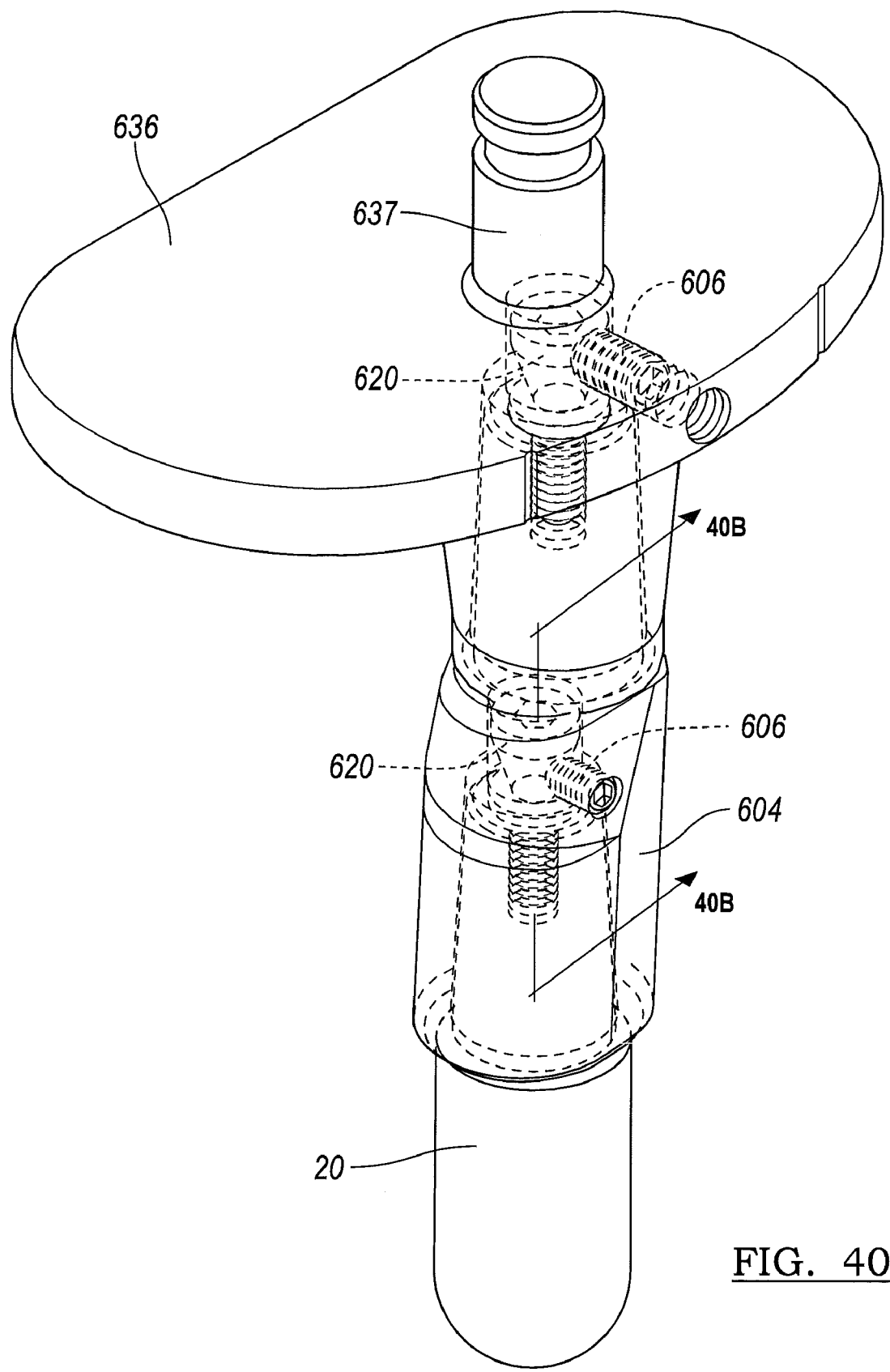
FIG. 40A is an assembled view of a tibial component, adapter assembly and stem according to one example of the present teachings.
Figure 40B:
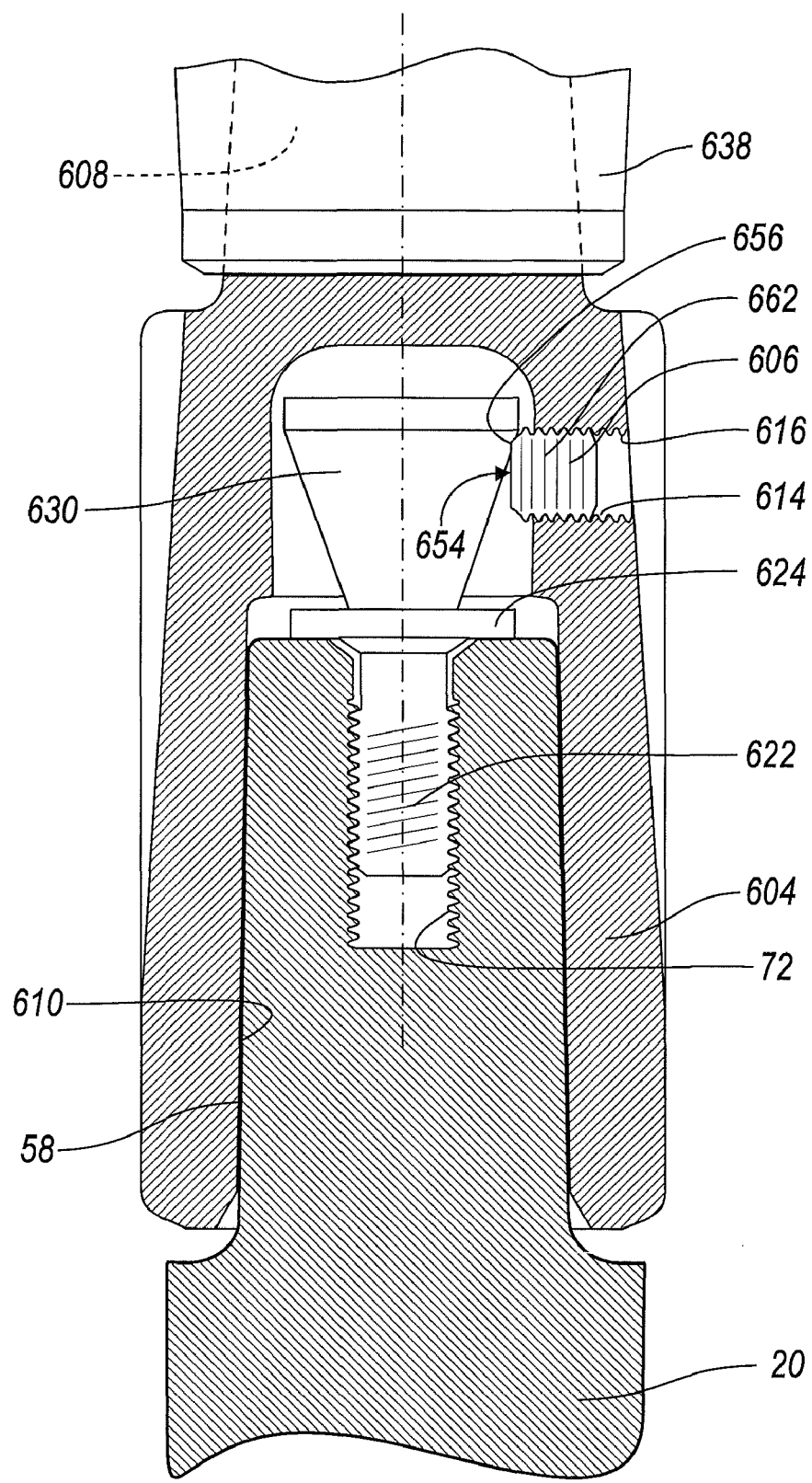
FIG. 40B is a sectional view taken along line 40B-40B of FIG. 40A.

As mentioned above, the locking member 606 can be formed of a biocompatible material that is harder than the fastener insert 620. As a result, a distal end 654 of the locking member 606 can deform (e.g. create a depression at) an interface area of the conical engaging head 630. The deformed area is identified at reference numeral 656 (FIGS. 39A and 40B). By deforming an area 656 of the fastener insert 620, the locking function of the locking member 606 can be improved by providing a greater resistance to separation. Explained further, the resultant depression can inhibit sliding, rotation, or other relative movement between the locking member 606 and the fastener insert 620.

Next, the stem 20 can be coupled to the adapter body 604 by driving the locking member 606 (i.e. another identical locking member 606) into the fastener insert 620 (i.e. another identical fastener insert 620).

According to another feature, the threads 616 defined by the bore 614 can define a thread profile that is slightly different (i.e. pitch) than threads 662 defined by the locking member 606. Alternatively, one of the threads 616 or 662 can be deformed initially. Such a relationship can allow the locking member 606 to be retained within the bore 614 upon initial handling by a surgeon. In other words, the locking member 606 can already by positioned within the bore such that the surgeon would not need to locate the distal tip 654 of the locking member 606 into the bore 616 (i.e. mate two separate components). It is appreciated that such thread configuration would not preclude rotation of the locking member 606 within the bore 616 during fastening.

Figure 41A:
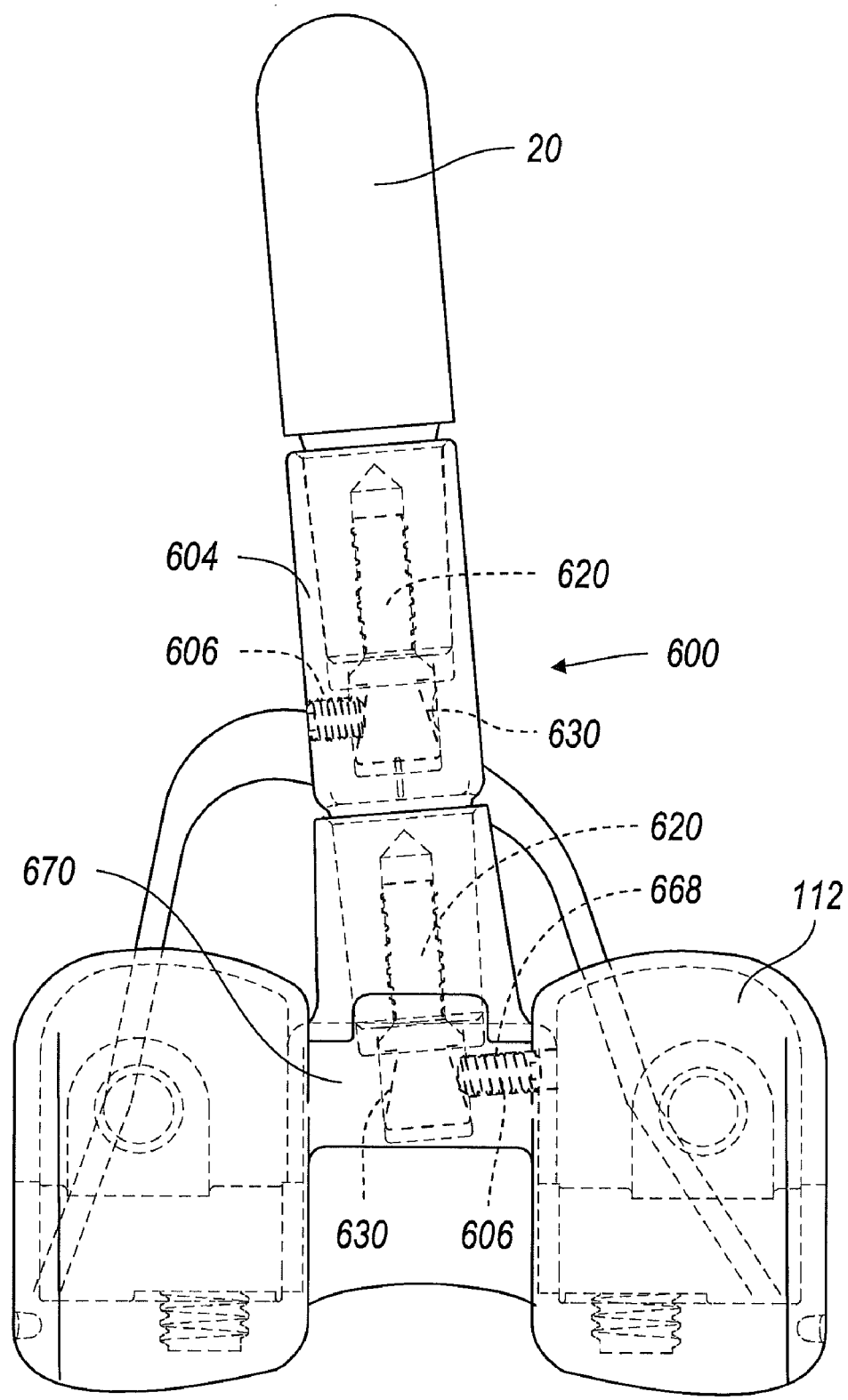
FIG. 41A is an assembled view of an exemplary femoral component, adapter assembly and stem according to one example of the present teachings.

Turning now to FIG. 41A, the adapter assembly 600 including the adapter body 604 and the locking member 606 are shown assembled with a femoral component 112'. The femoral component 112' is substantially similar to the femoral component 112 (FIG. 8), but can define a threaded bore 668 formed in a femoral box 670. As can be appreciated, the threaded bore 668 can provide a similar function to the threads 616 of the bore 614 of the adapter body 604. As a result, a locking member 606 can be driven to engage a conical engaging head 630 of fastener insert 620.

Figure 41B:
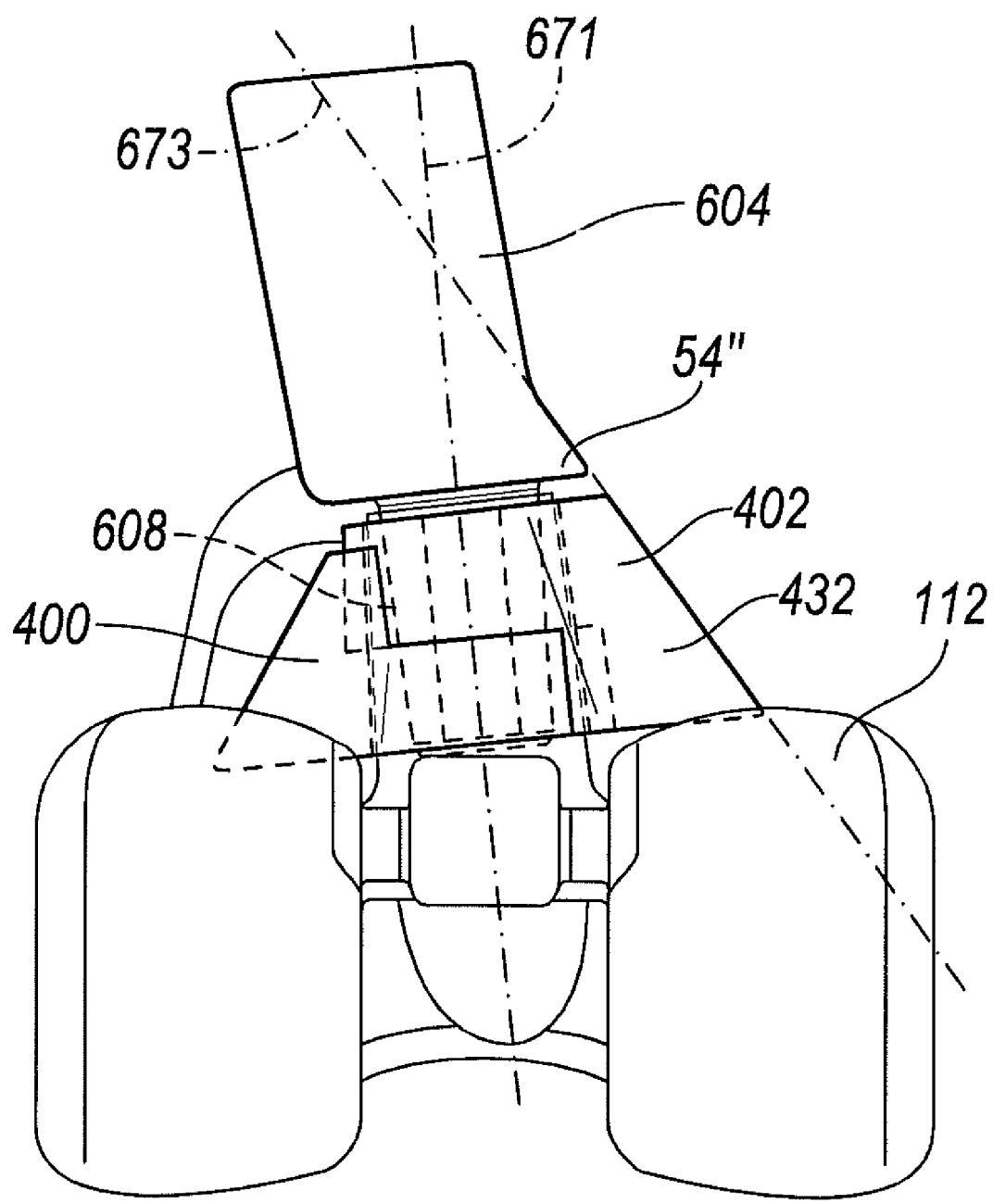
FIG. 41B is an assembled posterior perspective view of a pair of interlocking augments, adapter assembly and femoral component according to one example of the present teachings.
Figure 42:
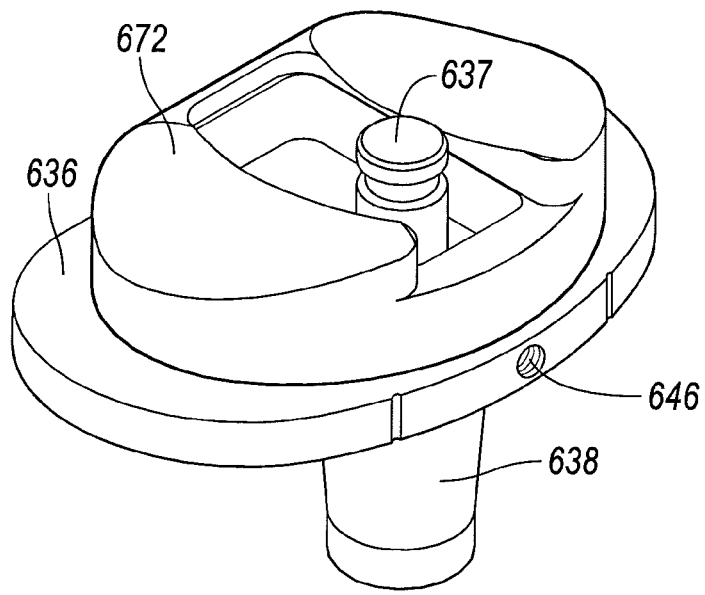
FIGS. 42-45 are perspective views of various tibial components and bearings used in cooperation with a bone conserving hinged knee.
Figure 43:
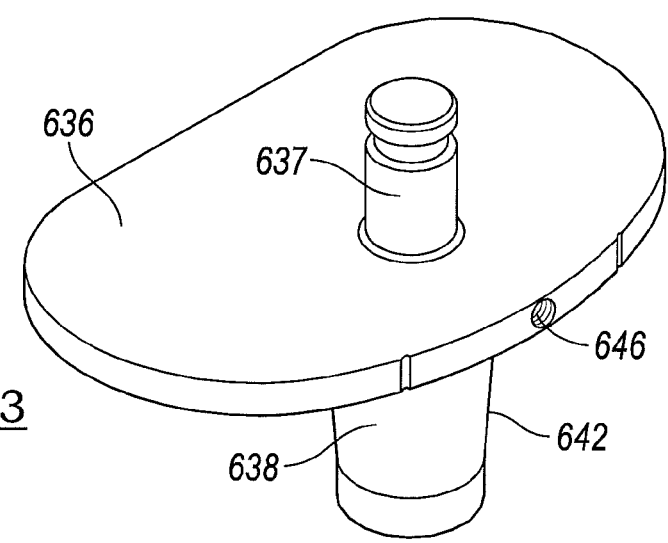
Figure 44:
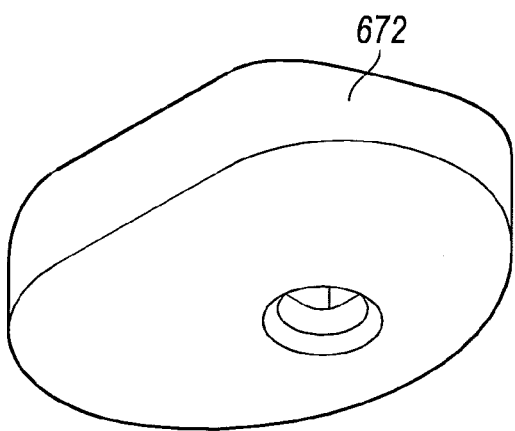
Figure 45:
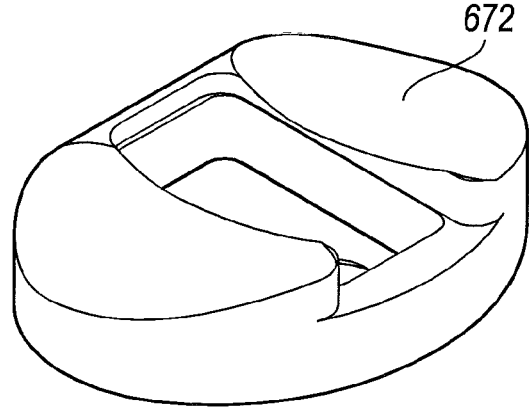
Figure 46:
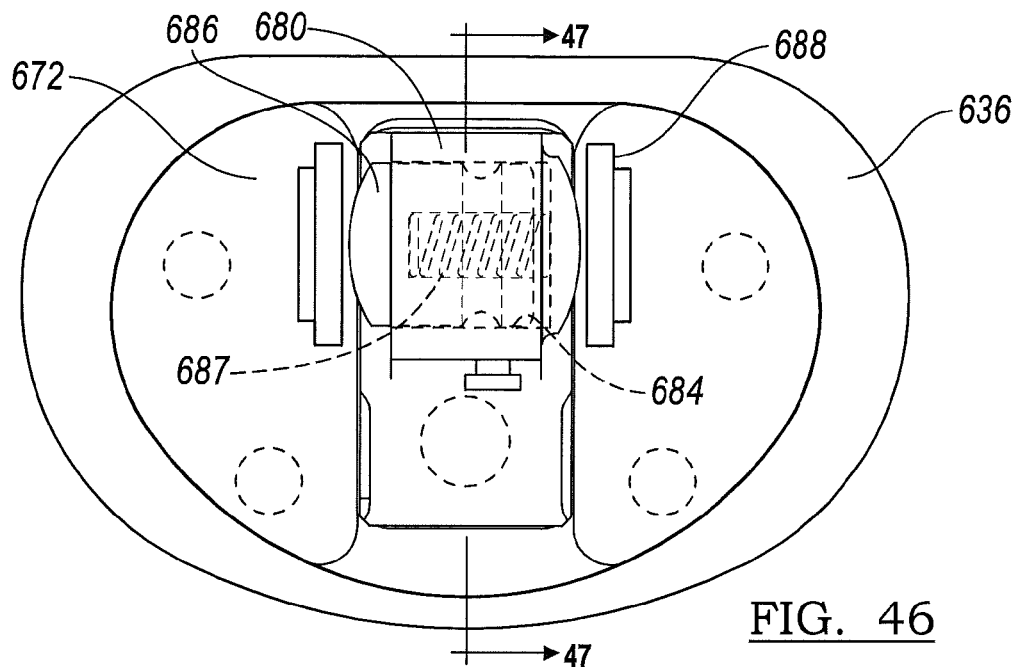
FIG. 46 is a superior view of an assembled hinged knee.
Figure 47:
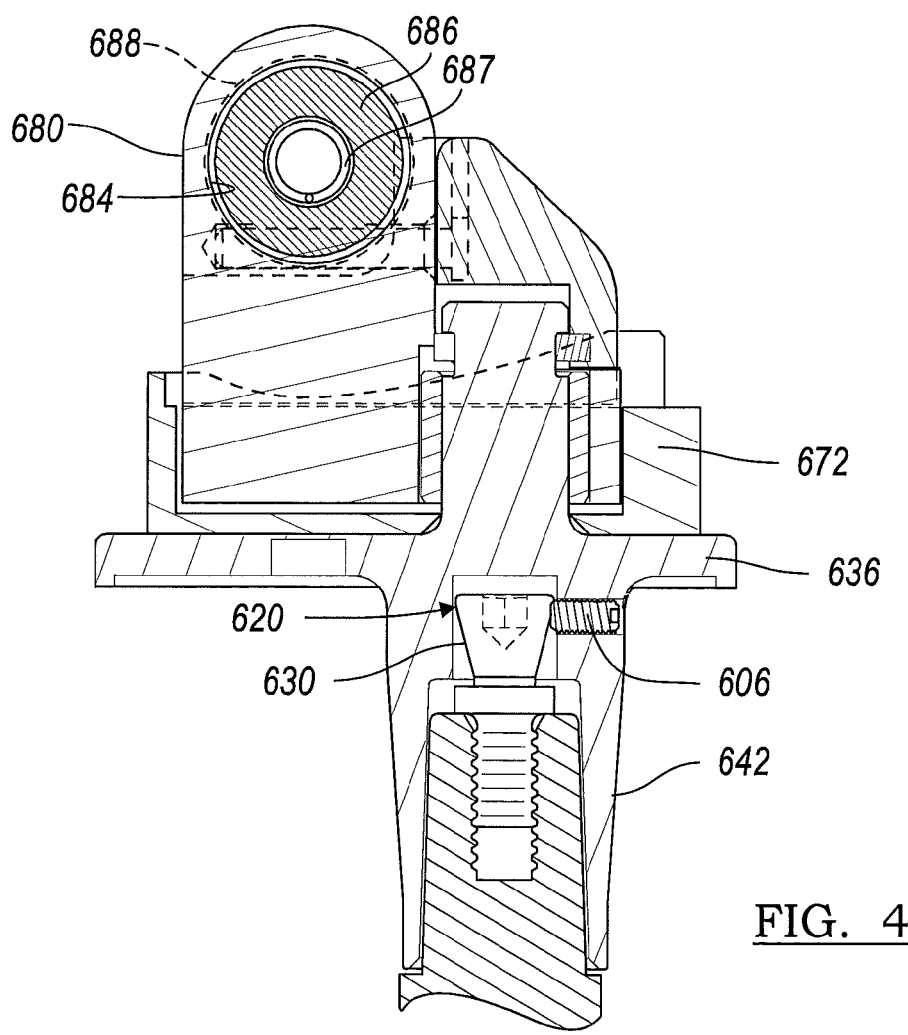
FIG. 47 is a sectional view taken along line 47-47 of FIG. 46.

As shown in FIG. 41B, a skirt 54" is shown on the adapter body 604. The skirt 54" generally defines a flared contour portion that can provide a generally smooth geometrical transition onto the outwardly tapered radially extending portion 432 (see also FIG. 21) of the augment 402. The geometrical transition between the skirt 54" and the augment 402 can reduce otherwise sharp transitions between implanted components to provide a favorable nesting configuration with surrounding bone in an implanted position. Explained more specifically, the male tapered insertion portion 608 of the adapter 604 can define an attachment axis 671. The outwardly tapered radially extending portion 432 of the body 424 can define a plane 673. The flared contour portion of the skirt 54" can taper generally along the plane 673 in an implanted position. The skirt 54" can therefore cooperate with the augment 402 to effectively fill bone voids.

Figure 35:
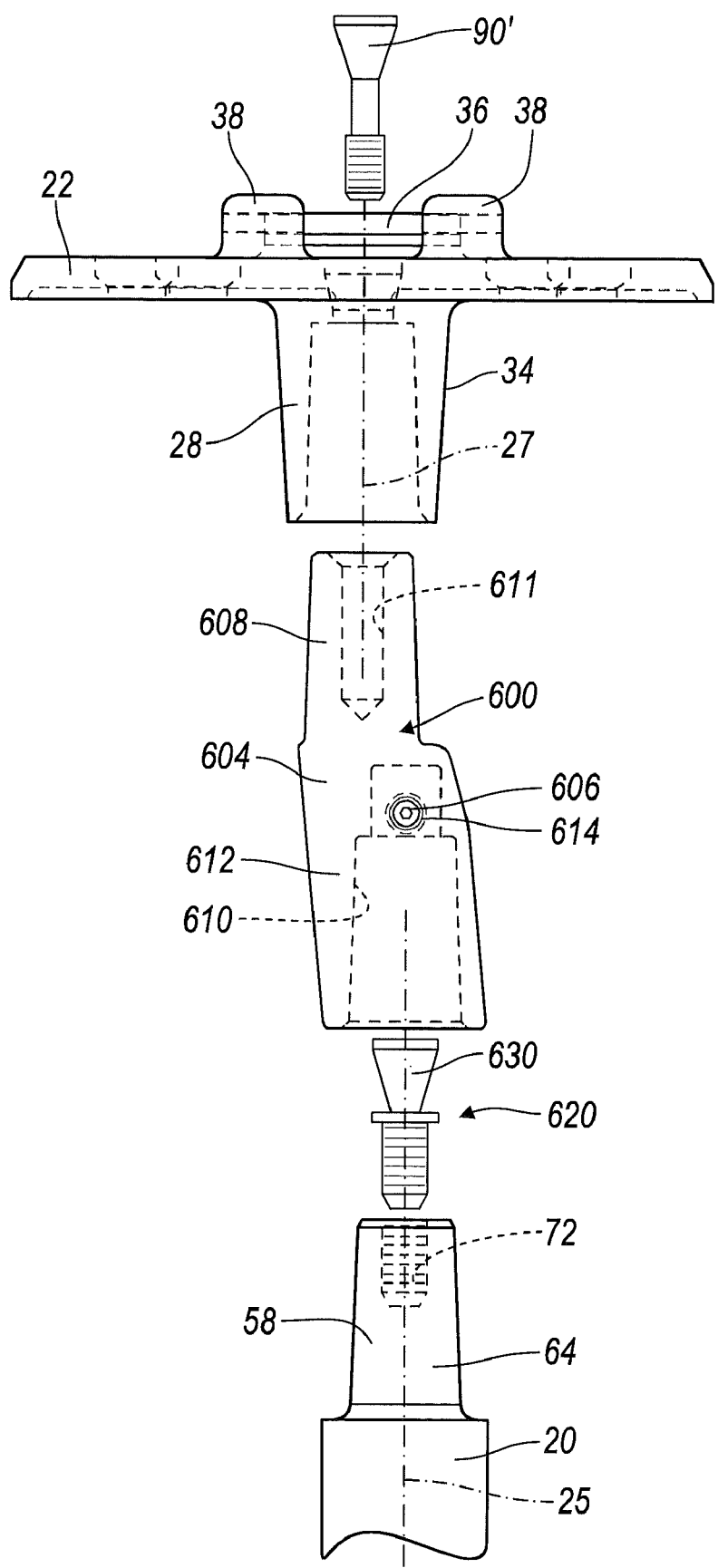
FIG. 35 is an anterior view of the prosthesis illustrated in FIG. 34.

As can now be appreciated, the instant disclosure provides a simplified set of interchangeable components wherein an adapter assembly 600 can be used on either side of the joint line (e.g. with a tibial component, such as described in relation to FIG. 35, and also a femoral component, such as described in relation to FIG. 41). Moreover, the locking member 606 and fastener insert 620 combination can be used in several distinct areas as described above. Additionally, the augments such as disclosed in FIGS. 21-25 can be used in cooperation with either a superiorly extending portion (such as portion 130, FIG. 8) of a femoral component or an inferiorly extending portion (such as portion 638, FIG. 36C) of a tibial component.

Turning now to FIGS. 42-49, additional components that may be used in cooperation with the tibial tray 636 will be described in greater detail. As explained, the tibial tray 636 can be used as part of a bone-conserving hinge knee prosthesis. The tibial tray 636 can cooperate with a bearing 672. A keel 680 can define a first bore 682 for receiving the superiorly extending stub 637, and a second bore 684 for receiving an axle 686. A pair of hubs 688 can engage opposite ends of the axle 686. In one example, a biasing member 687 can bias against an outer surface on the keel 680 to bias the axle 686 outward.

The keel 680 can be intraoperatively coupled to the femoral component 692 by depressing the axle 686 in a direction inwardly and locating the keel 680 generally into the femoral box 696 of the femoral component 692 until the axle 686 aligns with passages 695 and 697 formed in the femoral box. The hubs 688 can nest in the passages 695 and 697 on opposite ends of the axle 686. The axle 686 can bias outwardly encouraging the hubs 688 to seat into the passages 695 and 697. As can be appreciated, during use, the hubs 688 can provide a rotational surface for supporting the axle 686. The hubs 688 can be formed of any suitable bearing material such as PEEK, polyethylene, carbon reinforced PEEK. A pin 700 can then be inserted into the keel 680 to inhibit inward compression of the axle 686.

A shoe 690 can be disposed intermediate of the keel 680 and a femoral component 692. The femoral component 692 can define a threaded bore 694 through the box 696. A superiorly extending portion 698 can receive a male tapered insertion portion 608 of the adapter body 604. The locking member 606 can be used as described above to engage a fastener insert 620 (not specifically shown) extending proud from the male insertion portion 608. Alternatively, a fastener can extend superiorly though the femoral component 692 to securably mate with the adapter body 604 (such as shown in FIG. 8). A horseshoe clip 702 can securably nest in an annular pocket 704 defined on the stub 637.

Figure 58:
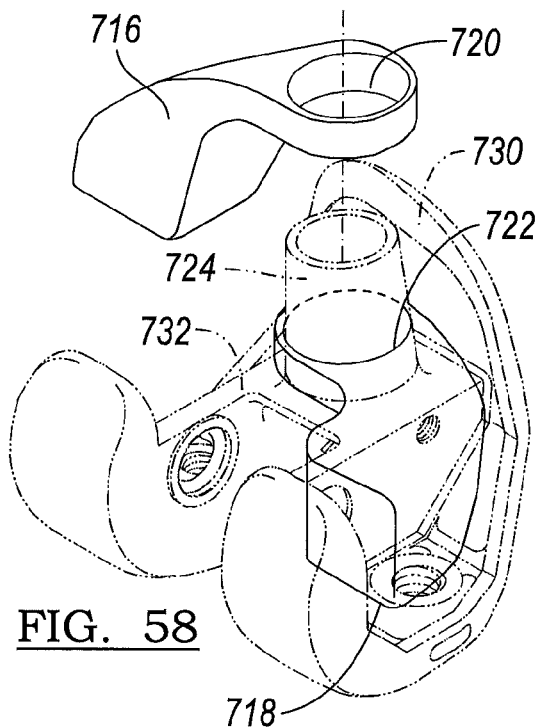
Figure 59:
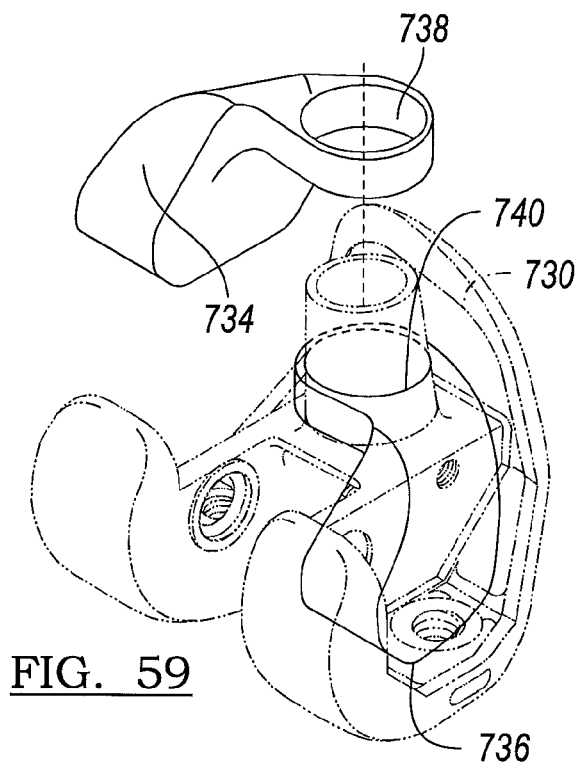

With reference now to FIGS. 50-54, additional augments are shown. An augment 710 can define a substantially symmetric profile for securing to either a medial or lateral inferior side of a tibial tray (i.e. such as a tibial tray 22D, FIG. 3D). Passages 712 can be formed through the augment 710 for receiving a fastener (not shown) in an assembled position. Augments 716 and 718 can define passages 720 and 722, respectively for receiving a superiorly extending portion 724 of a femoral component 730 (see FIG. 58). The augments 716 and 718 can define a profile unique for cooperating with a medial or lateral side of a femoral box 732. The augment 716 can be implanted to occupy an area of bone loss on a medial side of the femoral component 730. The augment 718 can be implanted to occupy an area of bone loss on a lateral side of the femoral component. Augments 734 and 736 can define passages 738 and 740 respectively (FIG. 59). The augments 734 and 736 can be used individually or in combination. The respective passages 720, 722, 738 and 740 and the superiorly extending portion 724 of the femoral component 730 can define conical engaging surfaces that are adapted to provide a friction fit formed by a Morse-type taper. The augments 734 and 736 can define a profile different than the augments 716 and 718.

Returning now to FIG. 53, another augment 744 is shown. The augment 744 can define a passage 746. In one example, the augment 744 can be symmetric for coupling to either a medial or lateral surface of the femoral component 730. Threaded blind bores 750 and 752 can be defined on the femoral component 730 for accepting a fastener (not shown) for securing an augment 744. Another augment 744' can be provided (that can have a mirror image profile relative to the augment 744) for compatibility with only the medial (or lateral) side of the femoral component.

Figure 54:
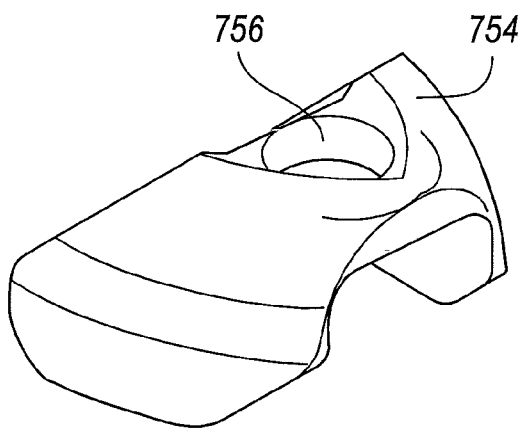
Figure 57:
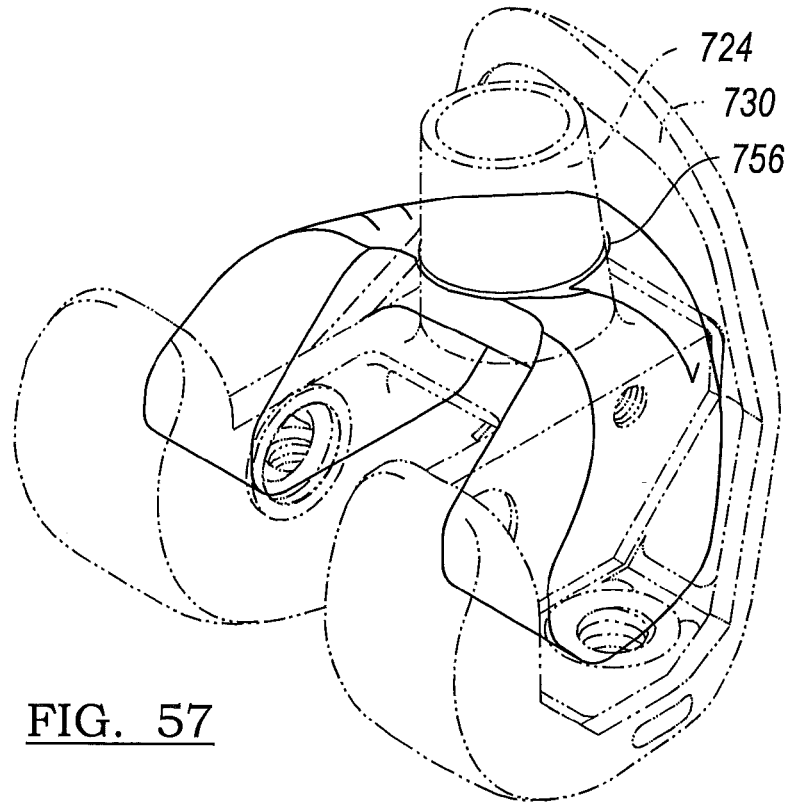
Figure 60:
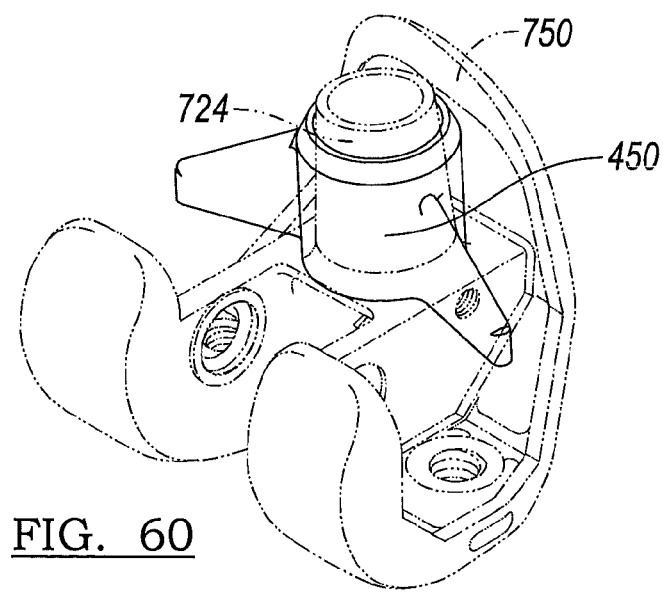

With reference to FIGS. 54 and 57, a saddlebag augment 754 having a central passage 756 is shown. The central passage 756 can receive the superiorly extending portion 724 of a femoral component 730. As with the other augments provided herein, the central passage 756 and the superiorly extending portion 724 can define conical engaging surfaces that are adapted to provide a friction fit formed by a Morse-type taper. FIG. 60 illustrates a femoral component 730 having the winged augment 450 (FIG. 24) secured to the superiorly extending portion 724.

Each of the augments disclosed herein can be formed of biocompatible material such as solid metal, porous metal or a combination of solid metal and porous metal. In one example, the solid metal or porous metal can comprise stainless steel, titanium, titanium alloys, cobalt-chromium alloys and other materials that are suited for use in a biocompatible environment. As is generally known in the art, porous metal can provide a suitable surface area for encouraging ingrowth of natural bone and/or soft tissue. Various compositions and methods of making such porous metal may be found in co-pending applications, U.S. Ser. No. 11/111,123, filed Apr. 21, 2005; Ser. No. 11/294,692, filed Dec. 5, 2005; Ser. No. 11/357,868, filed Feb. 17, 2006 each entitled "Method and Apparatus for Use of Porous Implants"; U.S. Ser. No. 11/546,500, filed Oct. 11, 2006, entitled "Method for Use of Porous Implants"; U.S. Ser. No. 11/709,549, filed Feb. 22, 2007, entitled "Porous Metal Cup with Cobalt Bearing Surface"; and U.S. Ser. No. 11/357,929, filed Feb. 17, 2006, entitled "Method and Apparatus for Forming Porous Metal Implants", all of which are also assigned to Biomet, Inc., of Warsaw Ind., which are incorporated herein by reference.

Figure 55A:
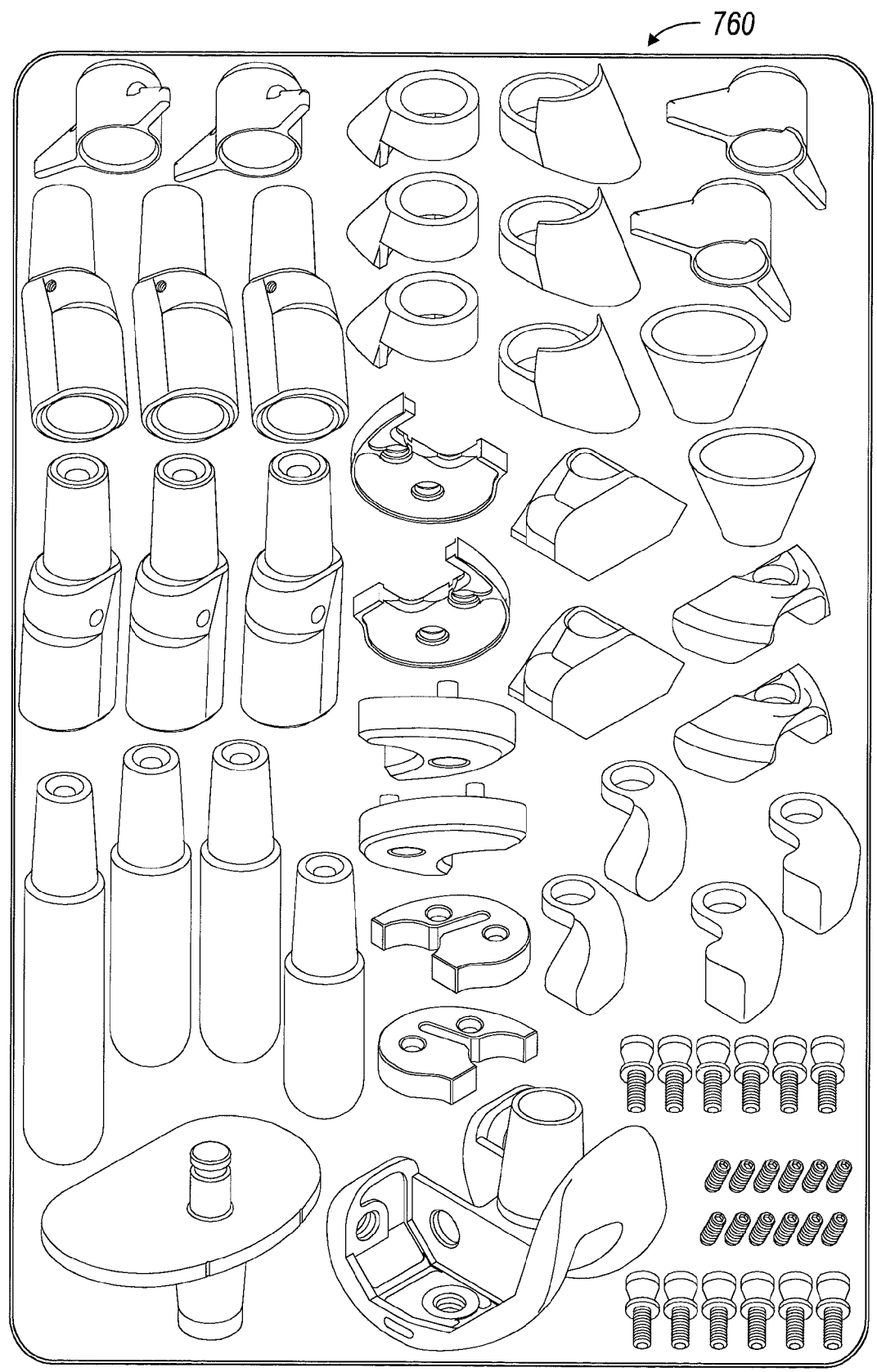
FIGS. 55A and 55B illustrates a kit of implants according to the present teachings.
Figure 55B:
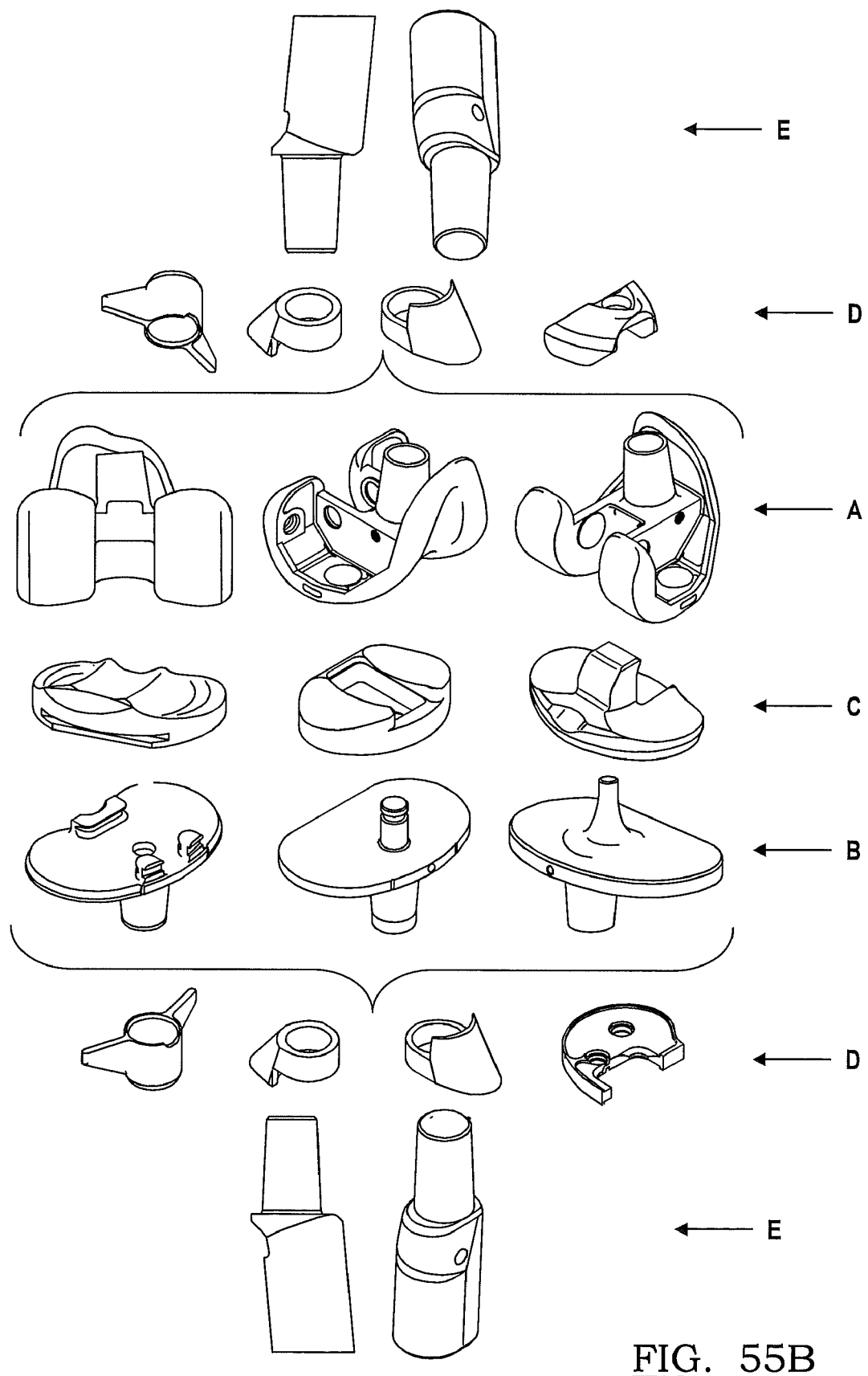
Figure 56:
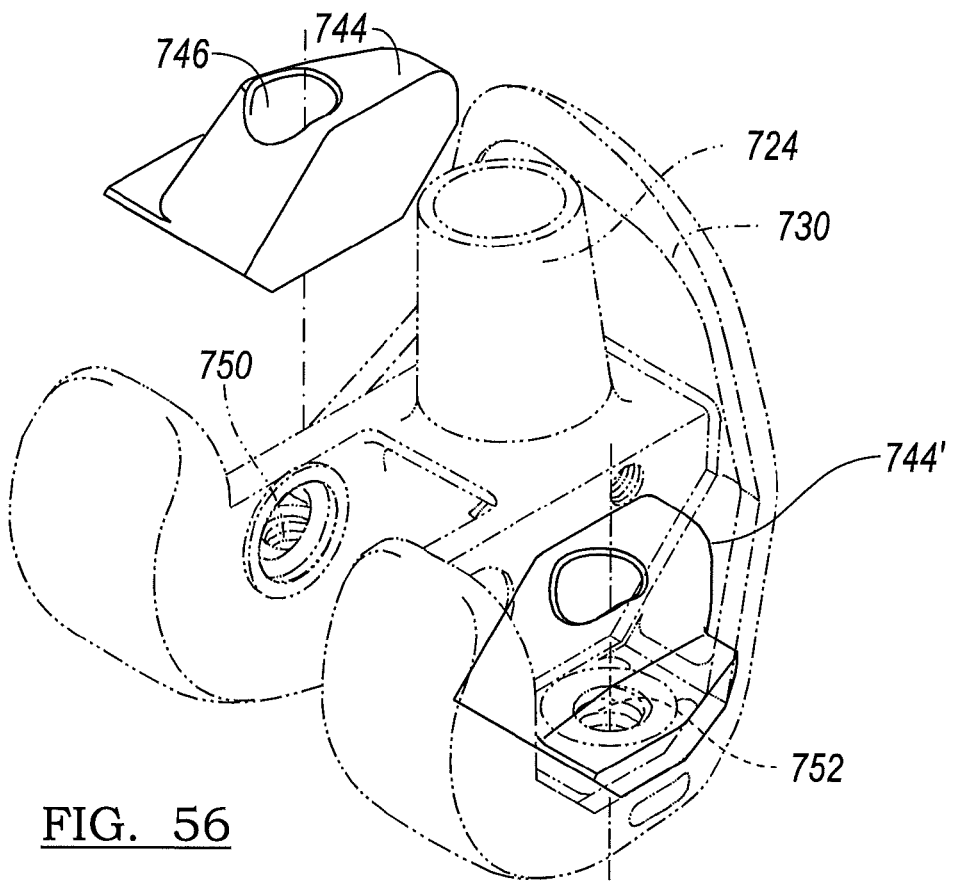
FIGS. 56-60 illustrate various augments shown during stages of assembly.

FIG. 55A illustrates a kit of components 760. The kit of components can be used interchangeably as discussed herein. The stems can define various lengths and diameters. The adapters can define various offsets. FIG. 55B illustrates such interchangeability. For instance, a surgeon can intraoperatively select a desired femoral component A, a tibial component B, a bearing C, and augment D and an offset adapter E. While not shown, a suitable stem (such as stem 20) can also be coupled to the offset adapter E as described herein.

As described herein, the tapered female receiving portions have been described as receiving the tapered male insertion portions by way of press-fit. Explained further, the female receiving portions and male insertion portions all define conical engaging surfaces adapted to provide a friction fit formed by a Morse-type taper.

With reference now to FIGS. 61-77, exemplary tools for implanting a femoral component and offset adapter according to the present teachings are shown. A distal resection cutting guide 800 (FIG. 61) can include a distal resection block 802 and a removable bracket portion 804 having a pair of dials 806, 808 for selecting a desired orientation (i.e. valgus angle etc.). The distal resection block 802 can define resection slots of +0, +4, +8, and +12 mm, collectively referred to at reference 810 for distal resection. In one example, the +0 slot can resect from the most prominent condyle as a clean-up cut. Other configurations are contemplated. If there is a defect, the +4, +8, or the +12 mm slot can be used for later use with a respective 4, 8 or 12 mm distal augmentation block.

A distal cutting block 812 (FIGS. 62A-62D) can define lateral anterior and posterior slots 822 and 824 and anterior and posterior chamfer slots 826 and 828. The distal cutting block 812 can be referred to herein as a "cutting" block. First and second partially overlapping bores 830 and 832 can be defined through a central portion 834 of the distal cutting block 812. As will become appreciated, one of the bores 830 or 832 can be aligned for use with a right femur while the other can be aligned for use with a left femur. A mark 836, 837 can be defined adjacent to the respective bores 830, 832. A rotatable offset bushing 838 (FIG. 66) can be selectively received within either of the overlapping bores 830 and 832. The offset bushing 838 can define an offset passage 840 and indicia 842. The offset passage 840 can be laterally offset relative to a longitudinal axis of the offset bushing 838. A plurality of offset bushings (such as offset bushing 838', FIG. 67) can be provided that provide various offsets suitable for a range of patient needs. In the examples shown, the offset bushing 838 can provide a 5 mm offset and the offset bushing 838' can provide a 2.5 mm offset. A bushing 838" (FIG. 68) can have a zero offset. Augment trials 844 (FIG. 63A) can be selectively secured to an inboard face 868 (FIG. 62B) of the distal cutting block 812. The augment trials 844 can define a series of detents 870 for selectively capturing around a fastener 872 (FIGS. 64A and 64B). The series of detents 870 can locate the augment trials 844 at a desired location.

Figure 78:
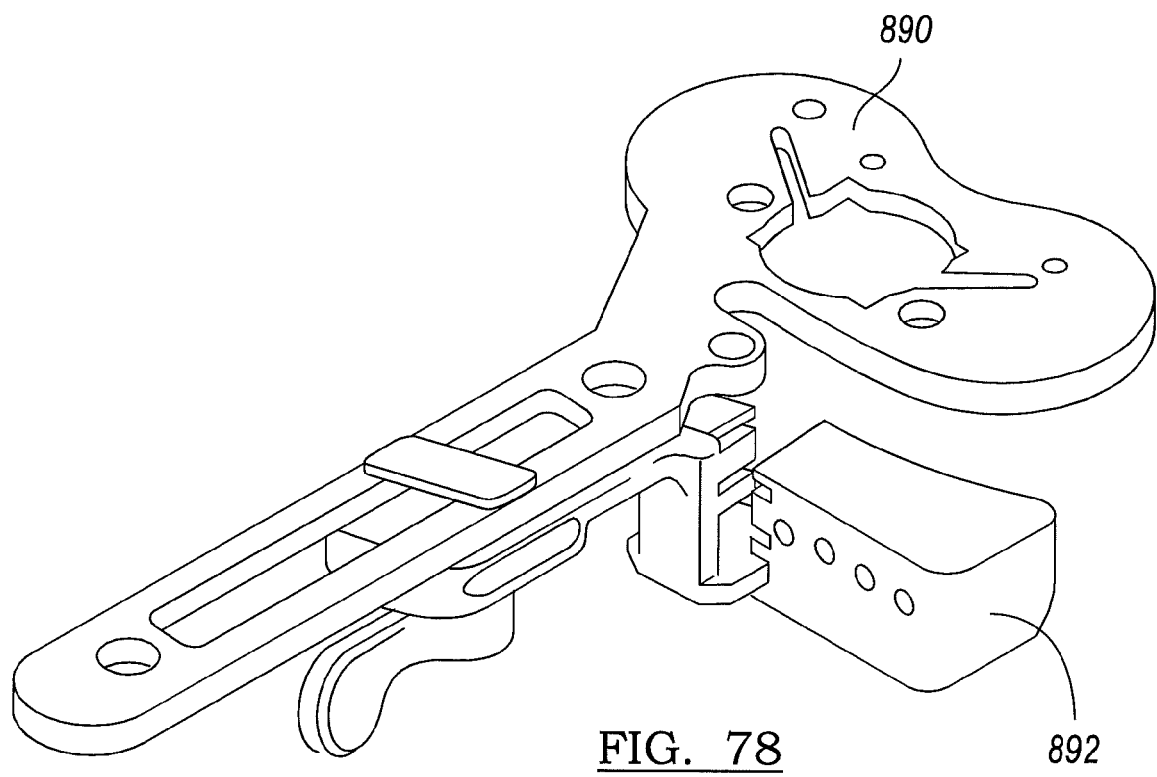
Figure 79:
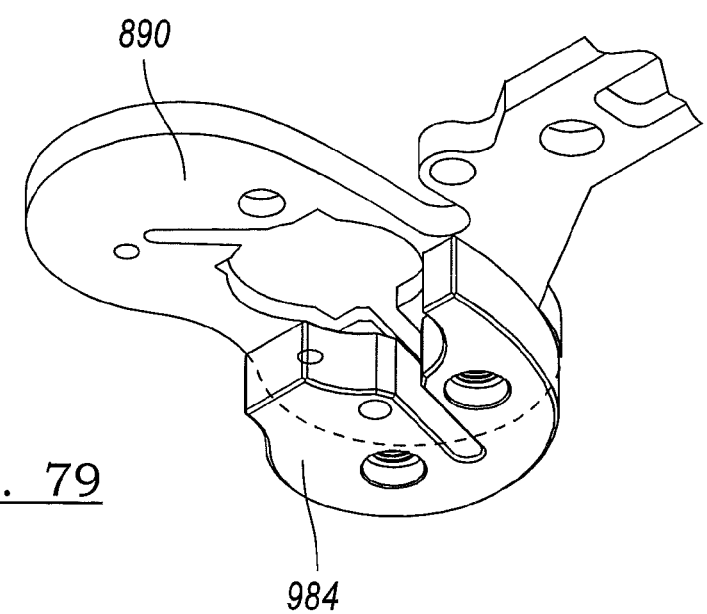

A femoral offset template 876 (FIGS. 70A and 70B) can define a plurality of apertures 880 for locating the fastener 872 and augment trial 844 at various locations. In one example, an offset template can be unique to a left femur (e.g. FIGS. 70A and 70B) or right femur (e.g. template 876', FIG. 71). A universal revision alignment member 882 (FIG. 69) can define a pocket 884 for receiving the bushing 838 (or 838'). A mark 886 can be defined on the pocket 884 for aligning with the indicia 842. A tibial template 890 (FIG. 78) can be provided for use during tibial preparation. Additional description of the tibial template 890 may be found in commonly owned patent application Ser. No. 10/702,335, entitled "Tibial Preparation Apparatus and Method", filed Nov. 6, 2003, the disclosure of which is incorporated herein by reference. The tibial template 890 can cooperate with an augment cut block 892. An implant boss reamer bushing 896 (FIG. 76) can be provided for receipt into the pocket 884 of the alignment member 882. Of note, the universal revision alignment member 882, offset bushing 838, and reamer bushing 896 can all be used with either the femoral offset template 876 or the tibial template 890.

Figure 34:
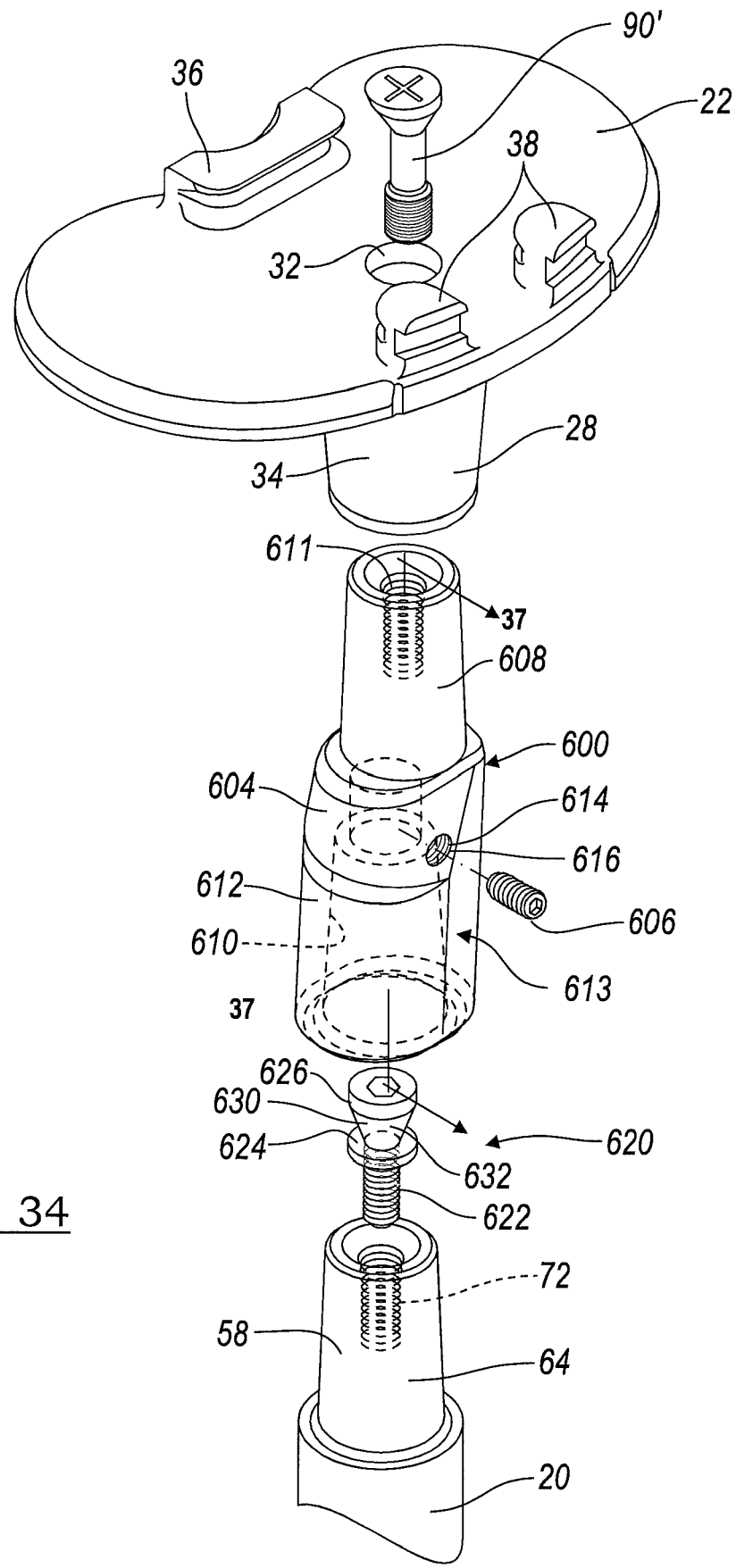
FIG. 34 is an exploded perspective view of an adapter assembly according to additional features and shown with an exemplary tibial component and stem.
Figure 65:
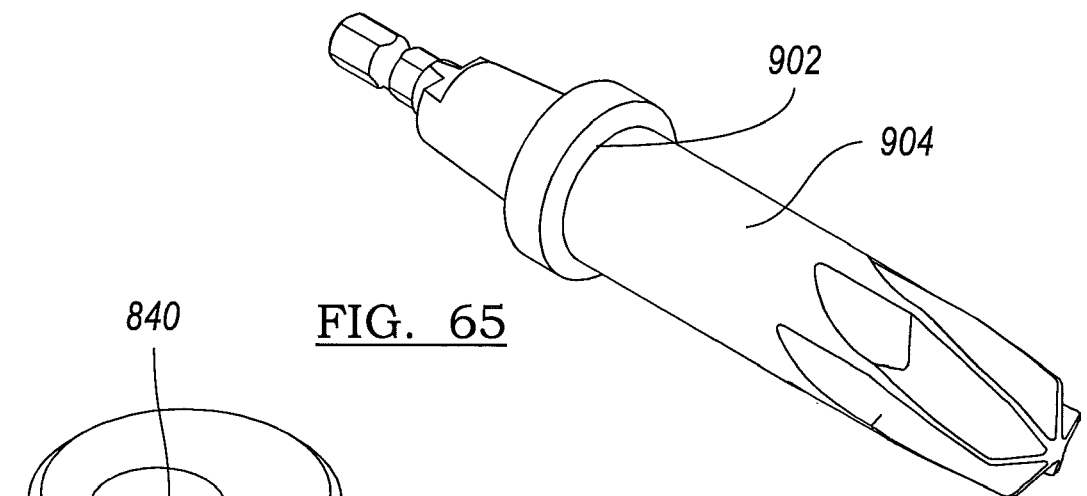
Figure 66:
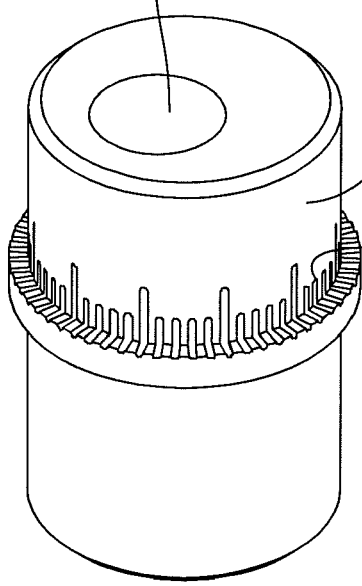
Figure 67:
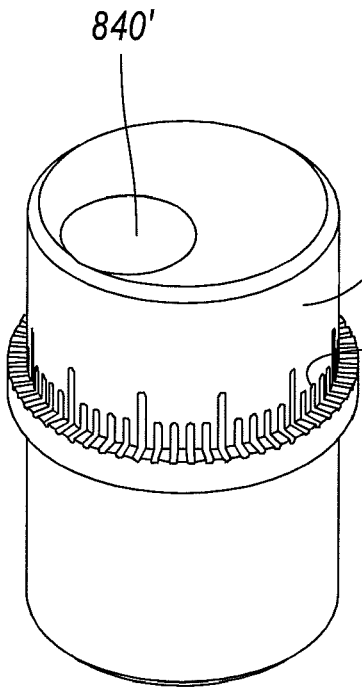
Figure 68:
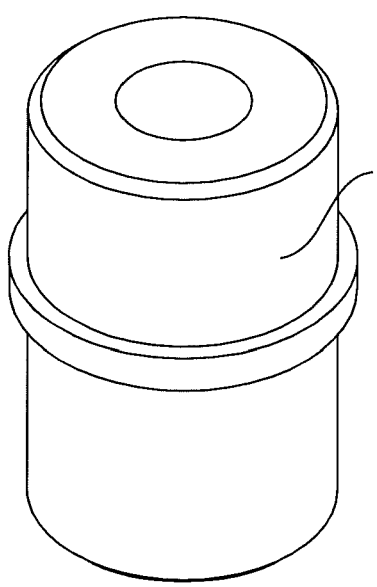
Figure 69:
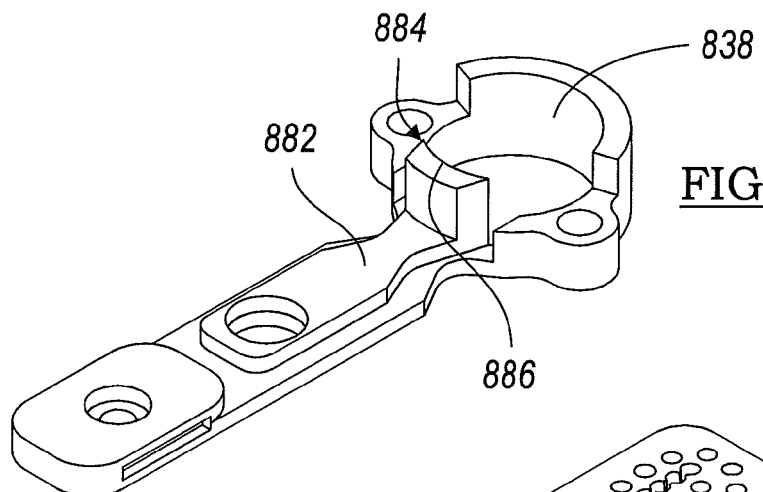
Figure 70A:
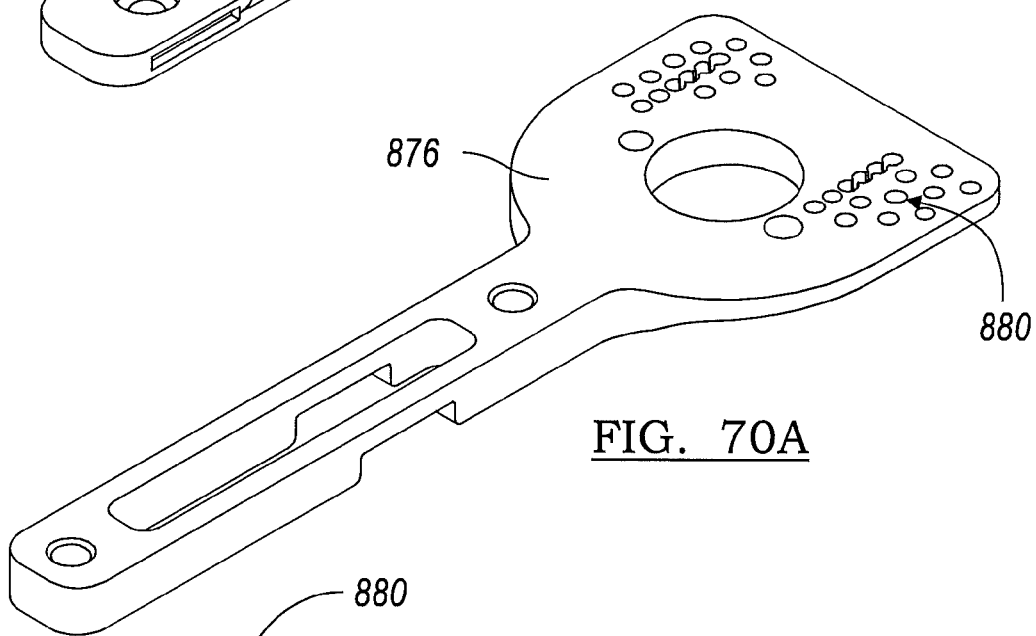
Figure 70B:
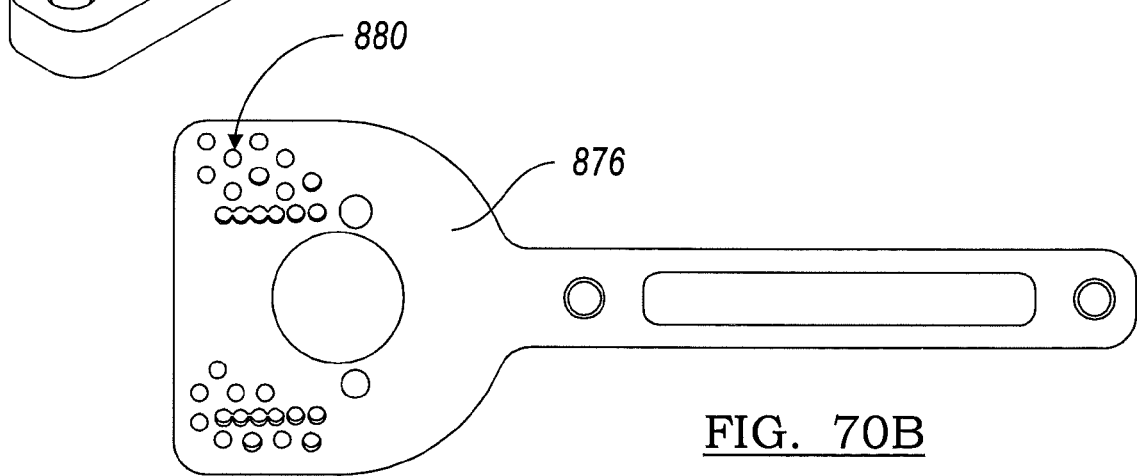
Figure 70C:
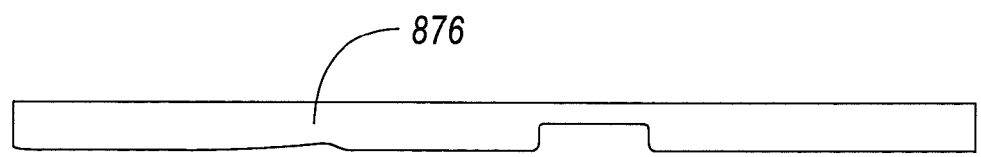
Figure 74:
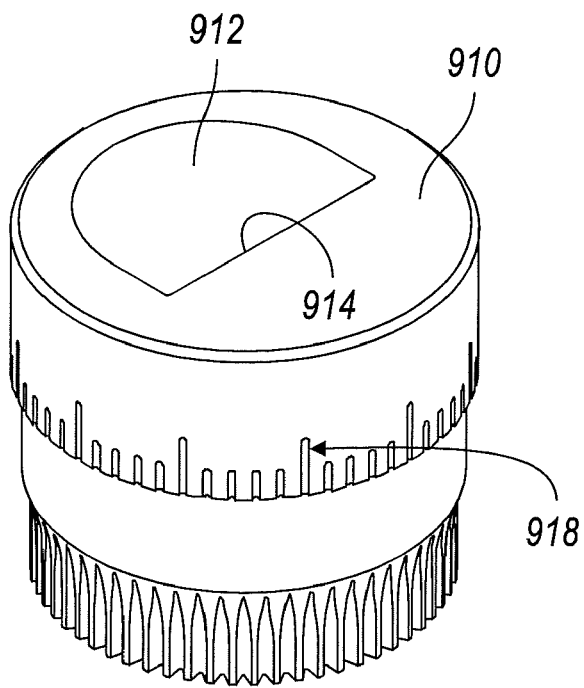
Figure 75:
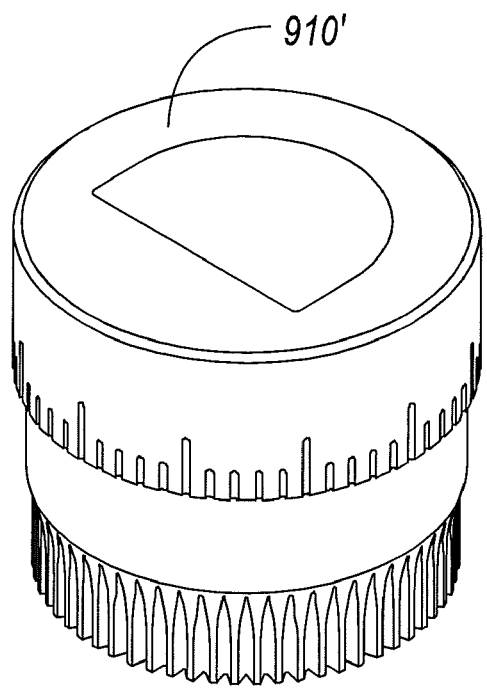
Figure 76:
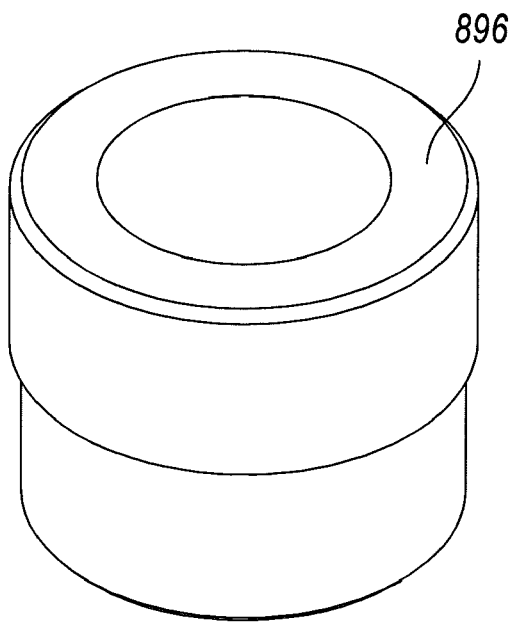
Figure 77:
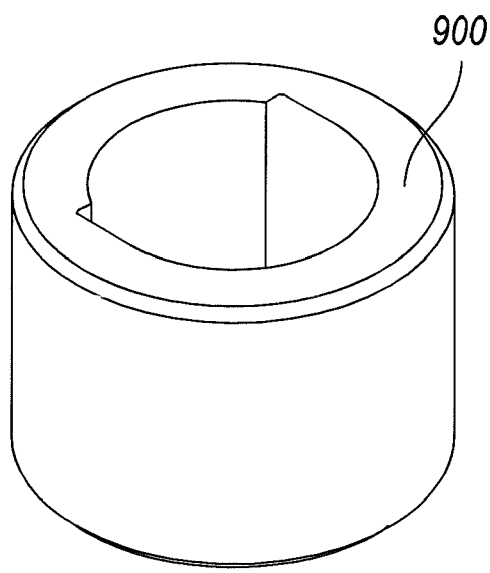

A tibial bushing stop 900 (FIG. 77) can be provided for locating between the reamer bushing 896 and a collar 902 of a reamer bit 904 (FIG. 65). The tibial bushing stop 900 can be used to limit a reaming depth in the tibial canal when reaming a tibial bore. As can be appreciated, the depth of a reamed tibial canal can be shallower than a depth of a reamed femoral canal. An offset adapter rasp bushing 910 (FIG. 74) can define a half-moon shaped passage 912. The half-moon shaped passage 912 can define a flat 914. The offset adapter rasp bushing 910 can cooperate with the pocket 884 of the universal revision alignment member 882 (during either femoral or tibial offset bore preparation). The offset adapter rasp bushing 910 can define indicia 918 for aligning with the mark 886 on the pocket 884. As will be described, the offset adapter rasp bushing 910 can be rotated to dial in a desired orientation that corresponds to the desired offset orientation of the adapter body 604 (FIG. 34). Another offset adapter rasp bushing 710' (FIG. 75) can define another offset.

A rasp 922 (FIGS. 72A and 72B) can define an impacting portion 924 on a distal end 926, and a handle 930 on a proximal end 932. A planar surface 934 can be defined along the impacting portion 924. The planar surface 934 can cooperate with the flat 914 of the offset adapter rasp bushing 910 to locate the rasp 922 in a desired orientation.

Figure 80A:
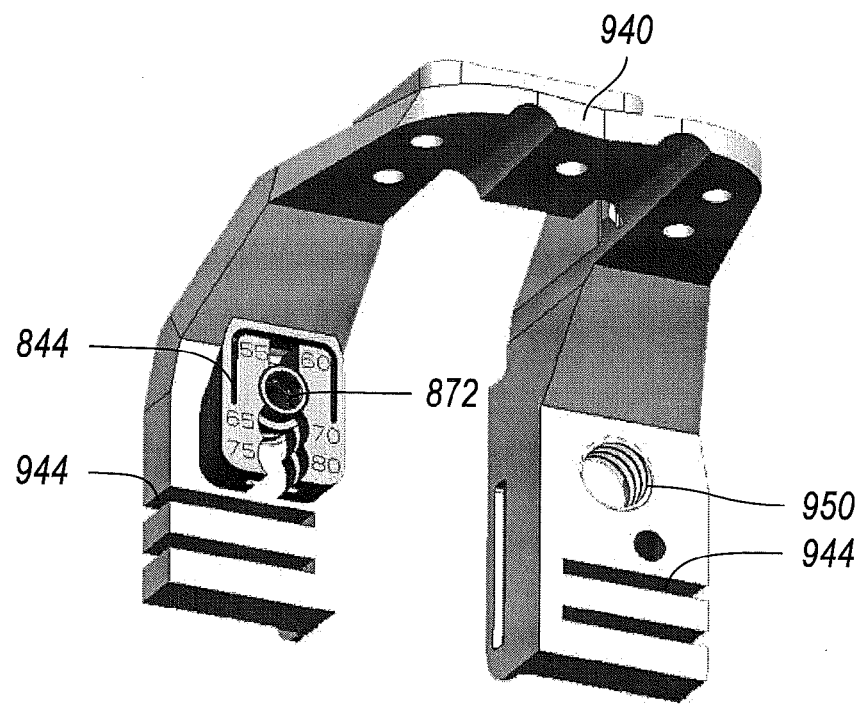
Figure 80B:
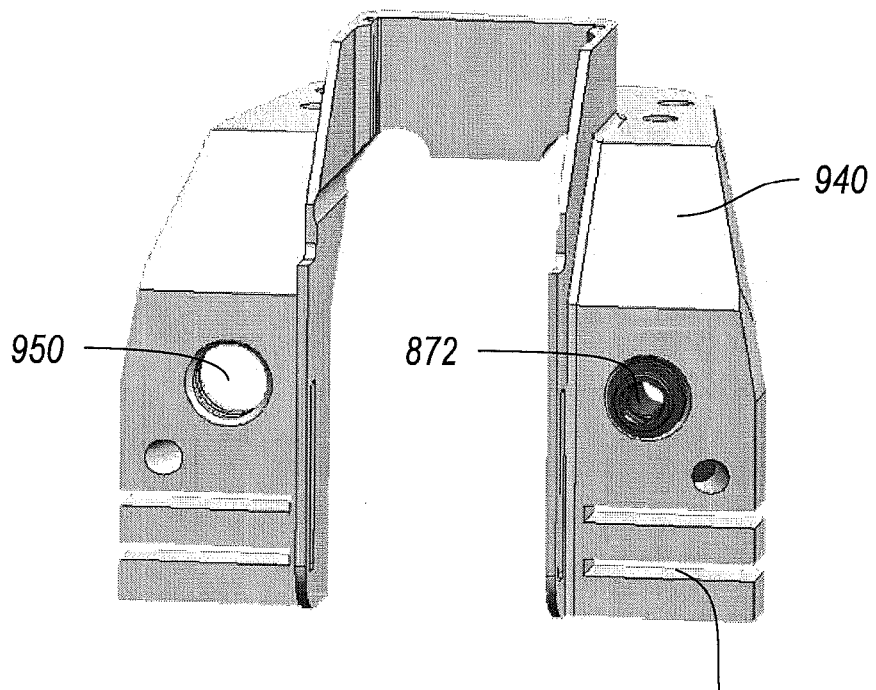

A posterior stabilized box guide 940 or 942 (FIGS. 80A and 80B) or can be provided for preparation of a posterior stabilized femur. Slots 944, 946 can be defined through the posterior stabilized box guide 940 and 942, respectively for guiding a cutting member at a given location. The posterior stabilized box guide 940 can define passages 950 for accepting the augment trials 844 in a similar manner described above.

Figure 81:
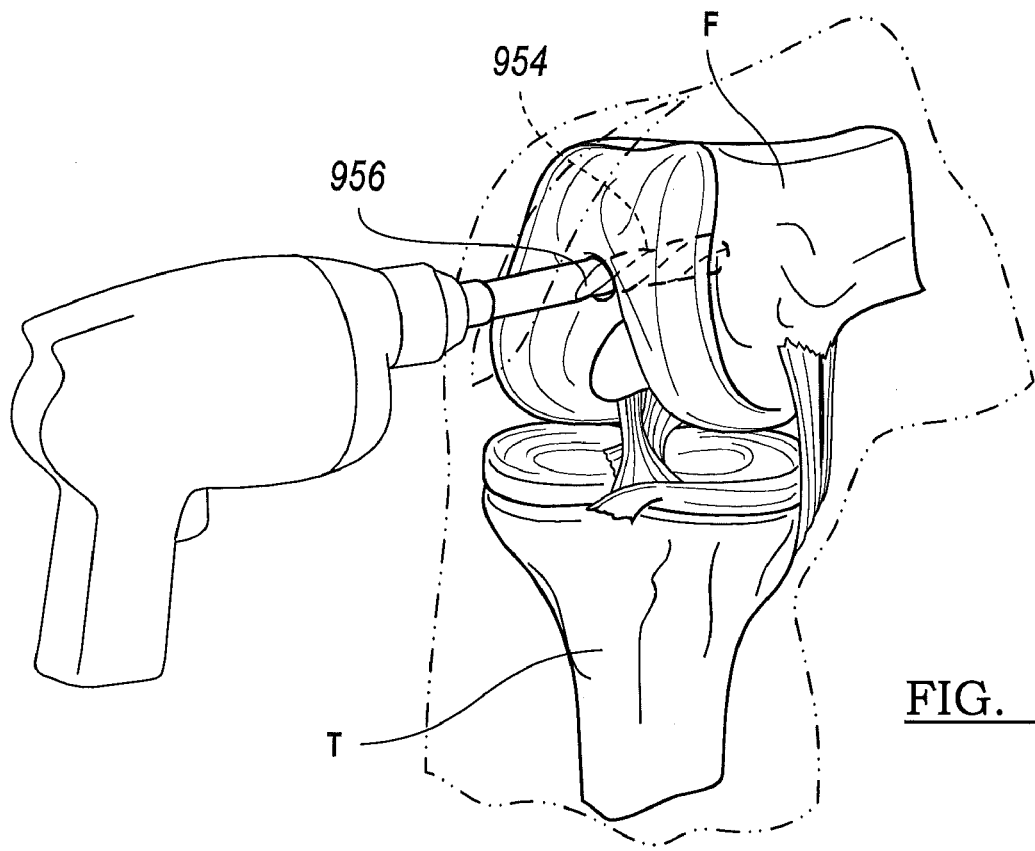
FIG. 81-104 illustrate exemplary sequences of using the instruments of FIGS. 61-80B.

An exemplary sequence of preparing a femur F for accepting a femoral component having an offset adapter will now be described. At the outset, the distal femur F can be exposed and a femoral (intramedullary) canal 954 can be reamed until cortical contact is achieved using a reamer 956 (FIG. 81). Next, the distal cutting guide 810 can be secured to the distal femur F and aligned to a desired orientation using the dials 806, 808. The bracket portion 804 can then be removed from the block 802, leaving the distal resection block 802 on the anterior bone. The reamer 956 may be left in the bone F. While avoiding the reamer 956, distal resection through the selected slots 810 can be performed using a sawblade 960. The distal cutting guide 810 can be removed while leaving in the reamer 956 (FIG. 83B).

Figure 83A:
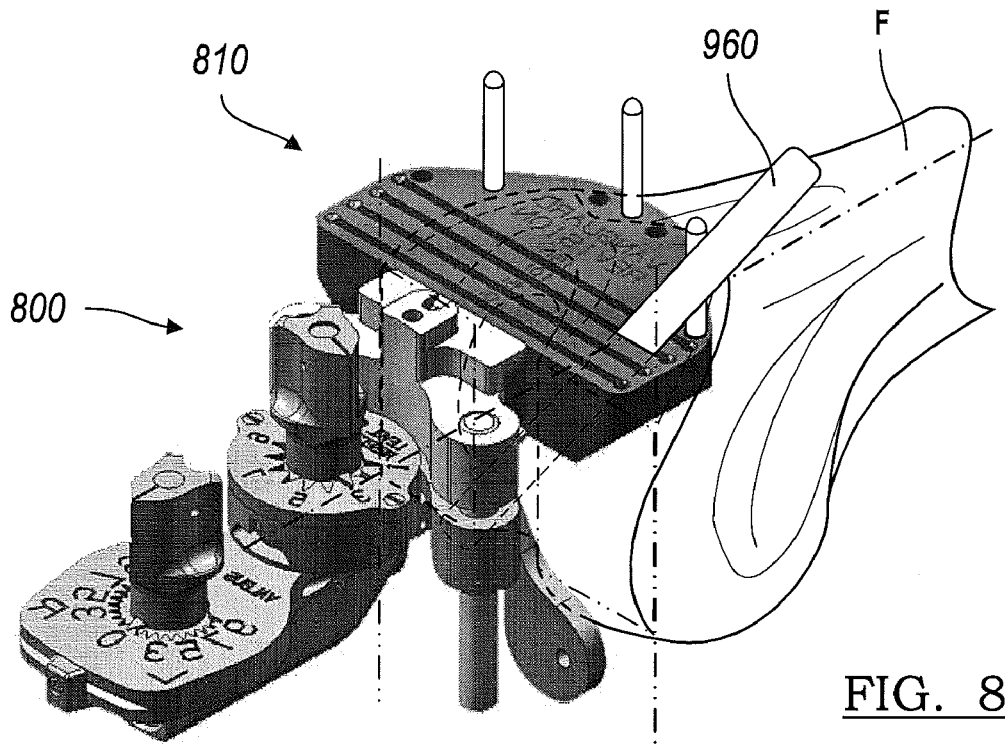
Figure 83B:
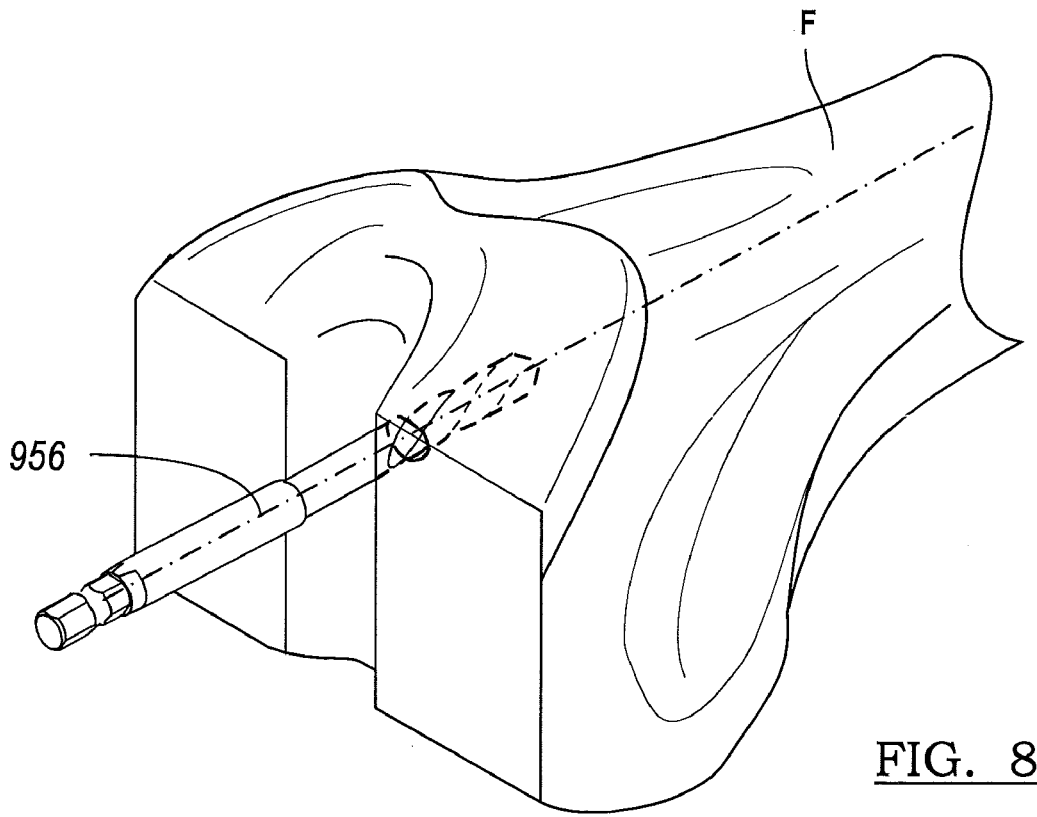
Figure 83C:
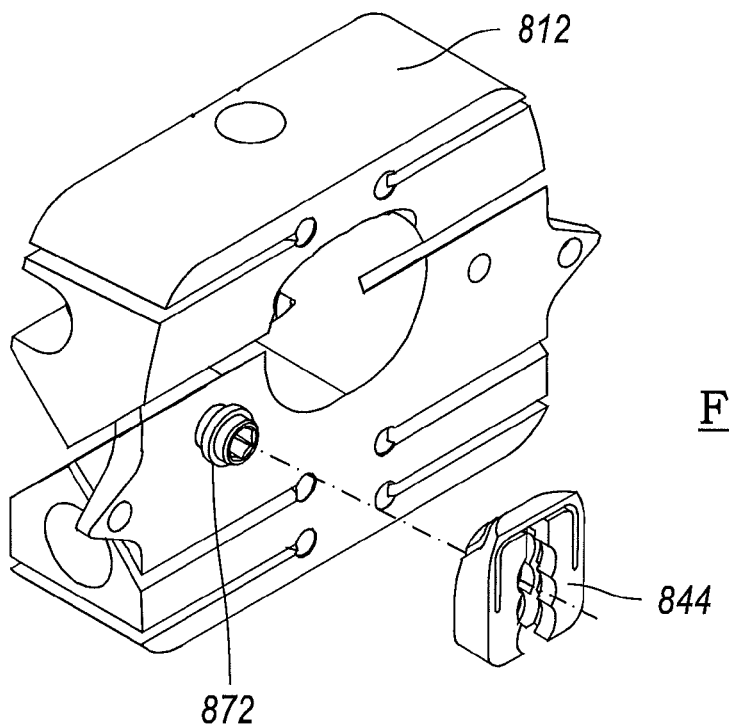
Figure 84:
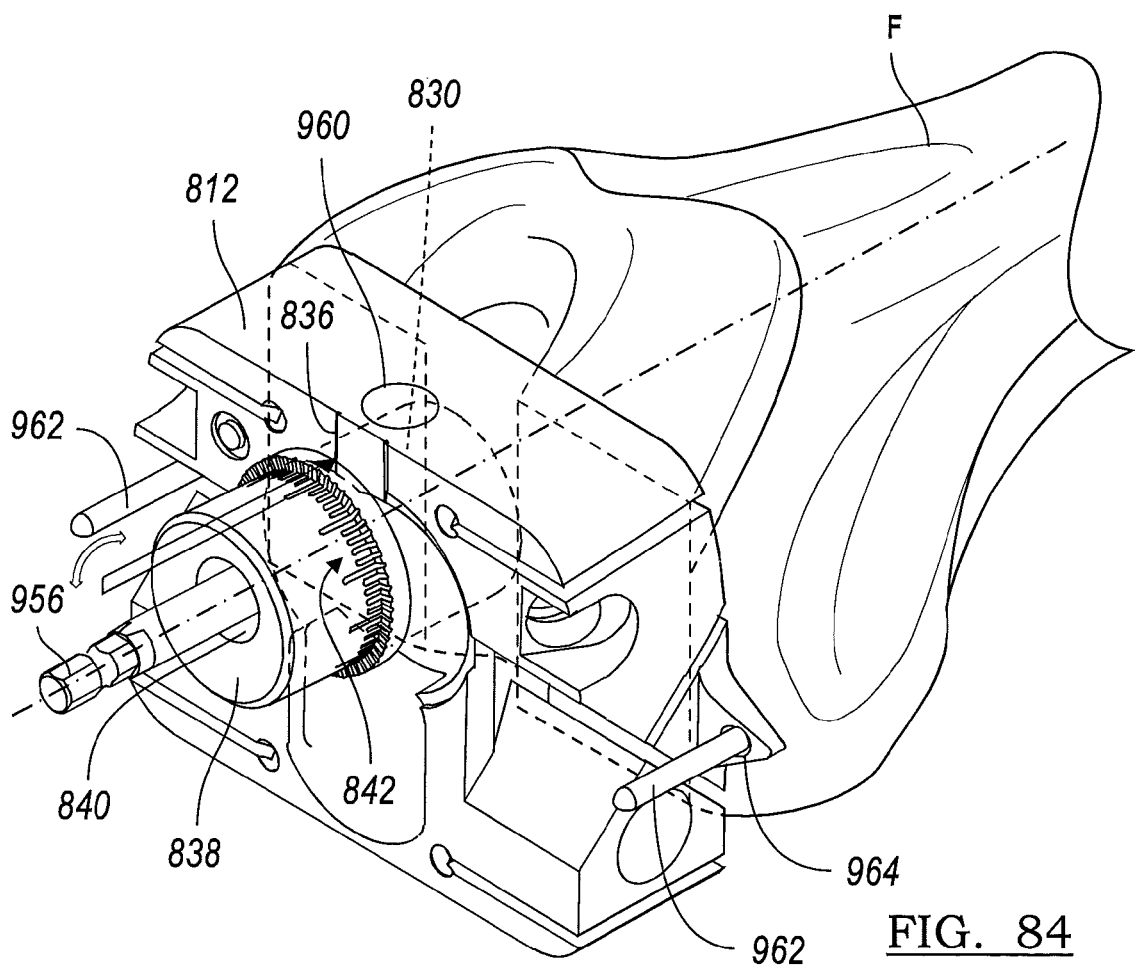
Figure 85:
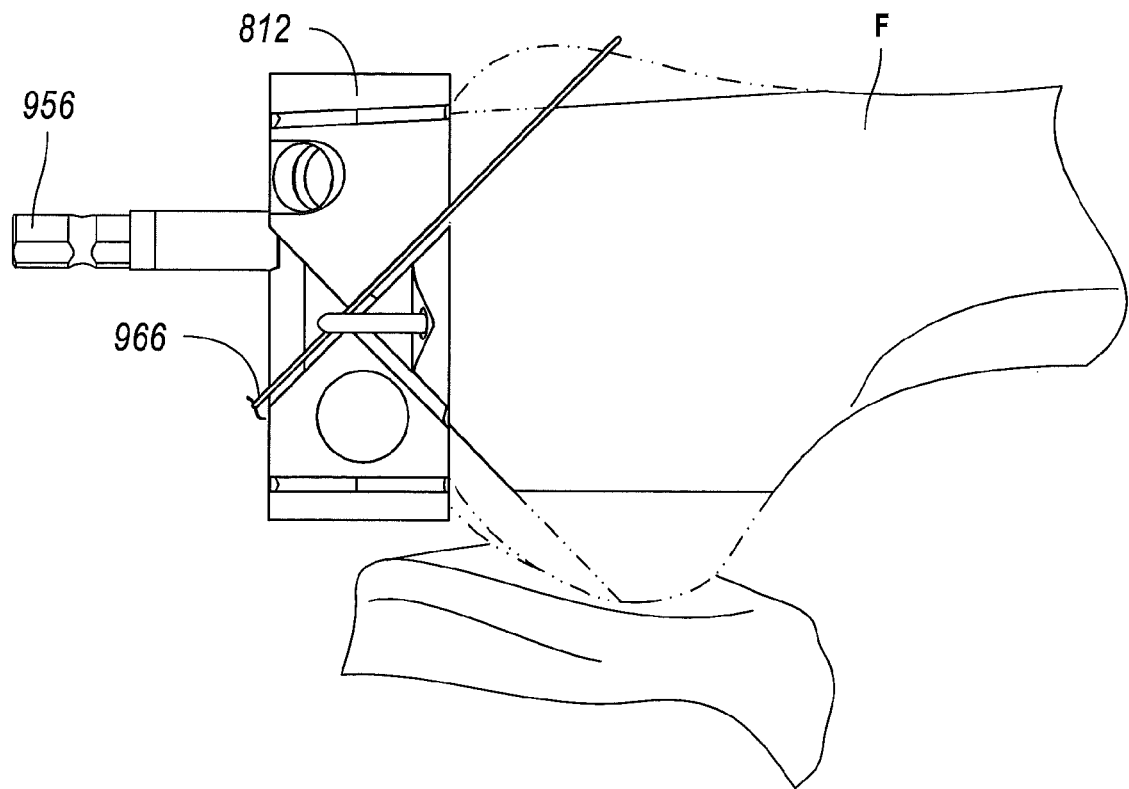

If a distal augment cut is required, an augment trial 844 (or trials) can then be snapped onto the back side of the cutting block 812 (FIG. 83C). Next, the offset bushing 838 can be inserted into the appropriate overlapping bore 830 of the cutting block 812. The cutting block 812 is then inserted over the reamer shaft 956 such that the reamer shaft 956 locates through the offset bore 840 of the offset bushing 838 (FIG. 84). The offset bushing 838 is then rotated (thereby translating the cutting block 812 around the distal femur F) until the desired position of the cutting block 812 is attained. A bolt (not shown) extending through an anterior passage 960 in the cutting block 812 can then be tightened to preclude further movement of the offset bushing 838. The cutting block 812 can then be secured to the distal femur F such as by driving nails 962 through holes 964 provided on the cutting block 812. The alignment number (i.e. the indicia 842 corresponding to the mark 836) is noted. The offset bushing 838 can then be removed. The anterior and posterior bone can be resected followed by the anterior and posterior chamfer cuts using a sawblade 966 (FIG. 85).

Figure 86:
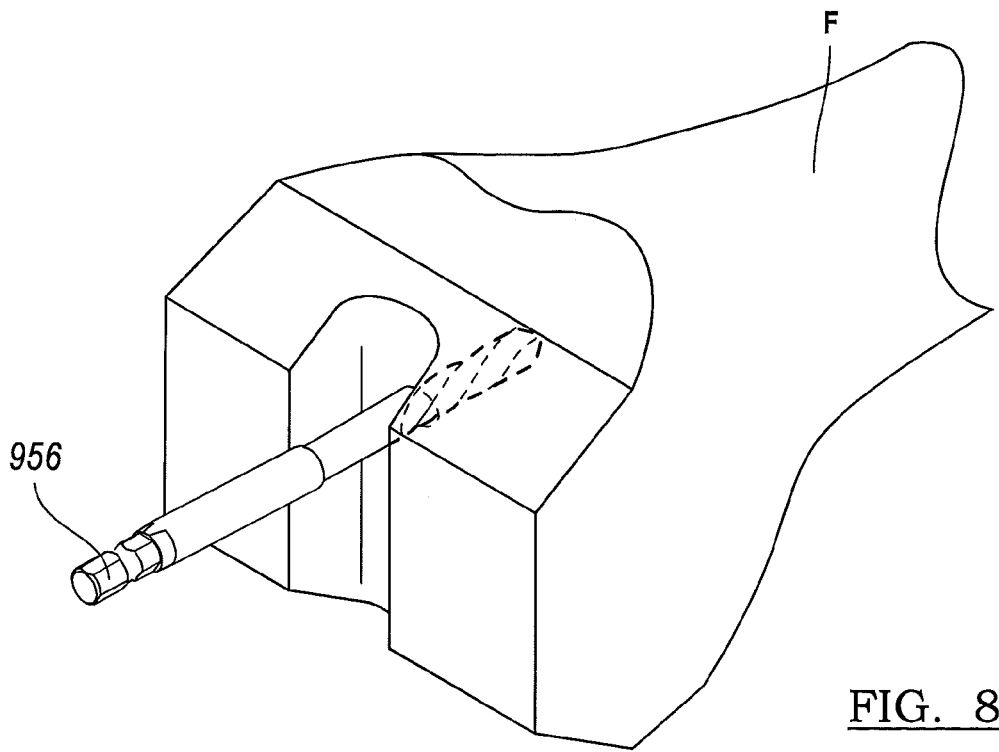
Figure 87:
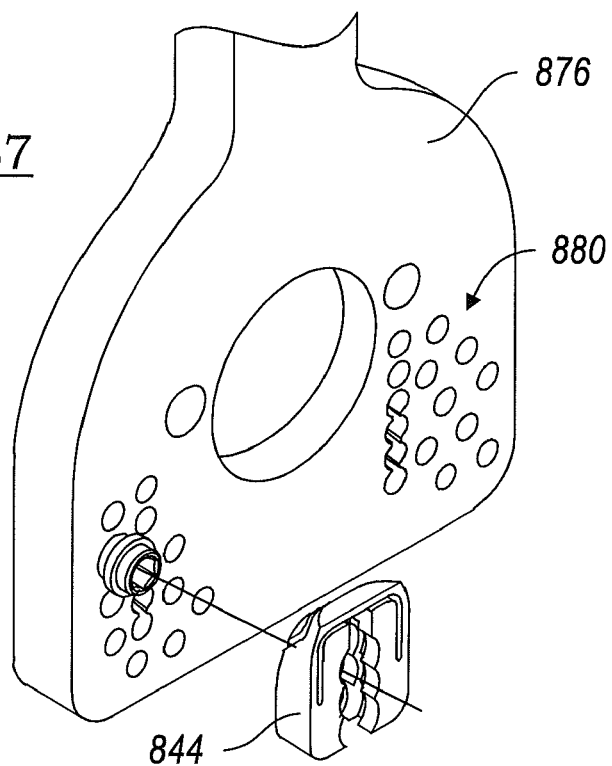
Figure 88:
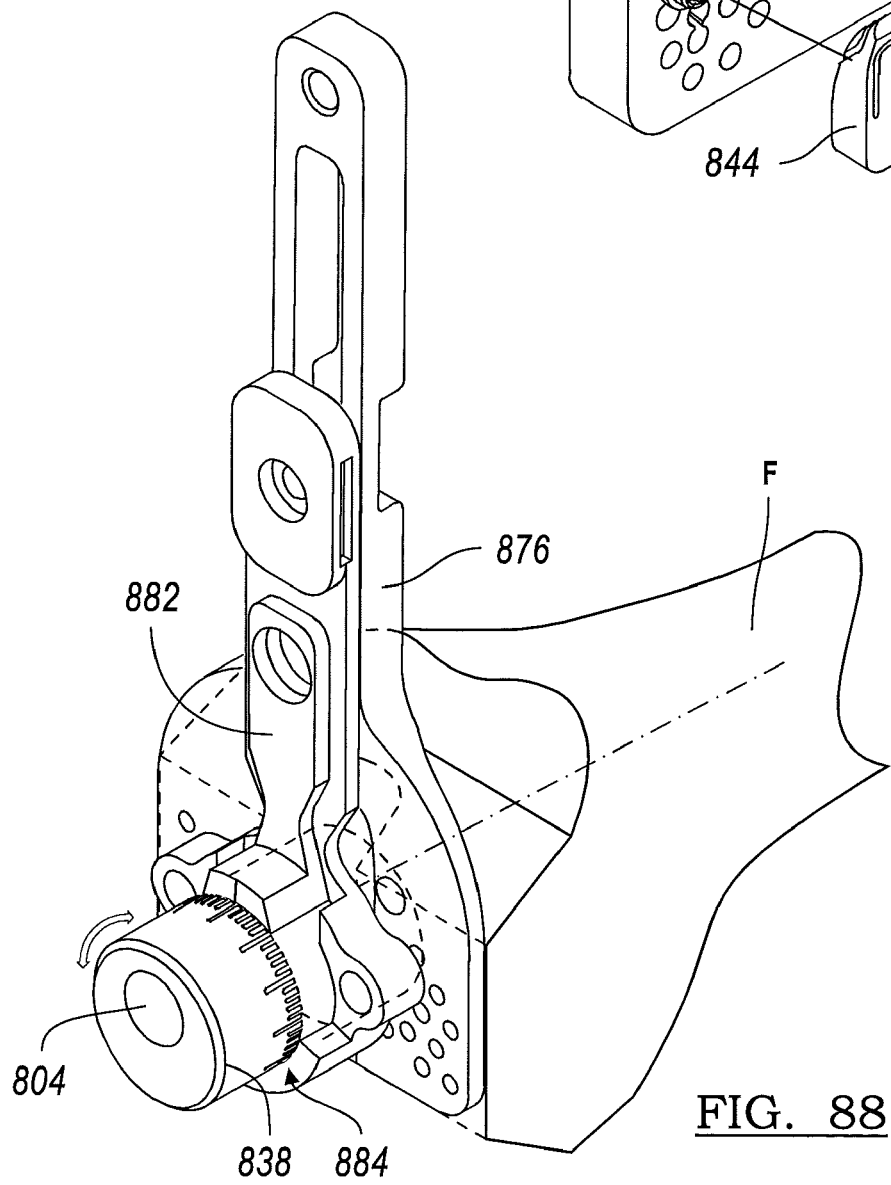
Figure 89:
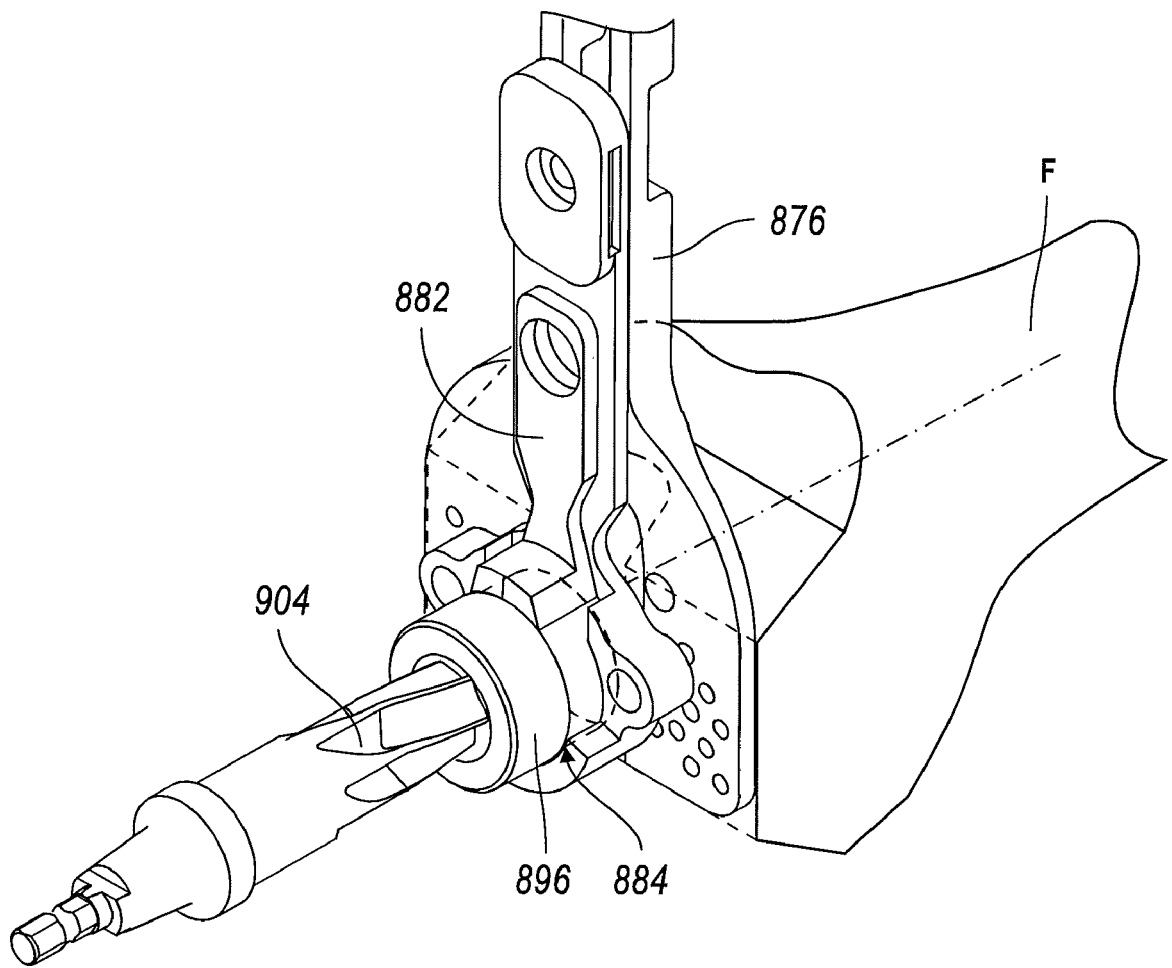
Figure 90:
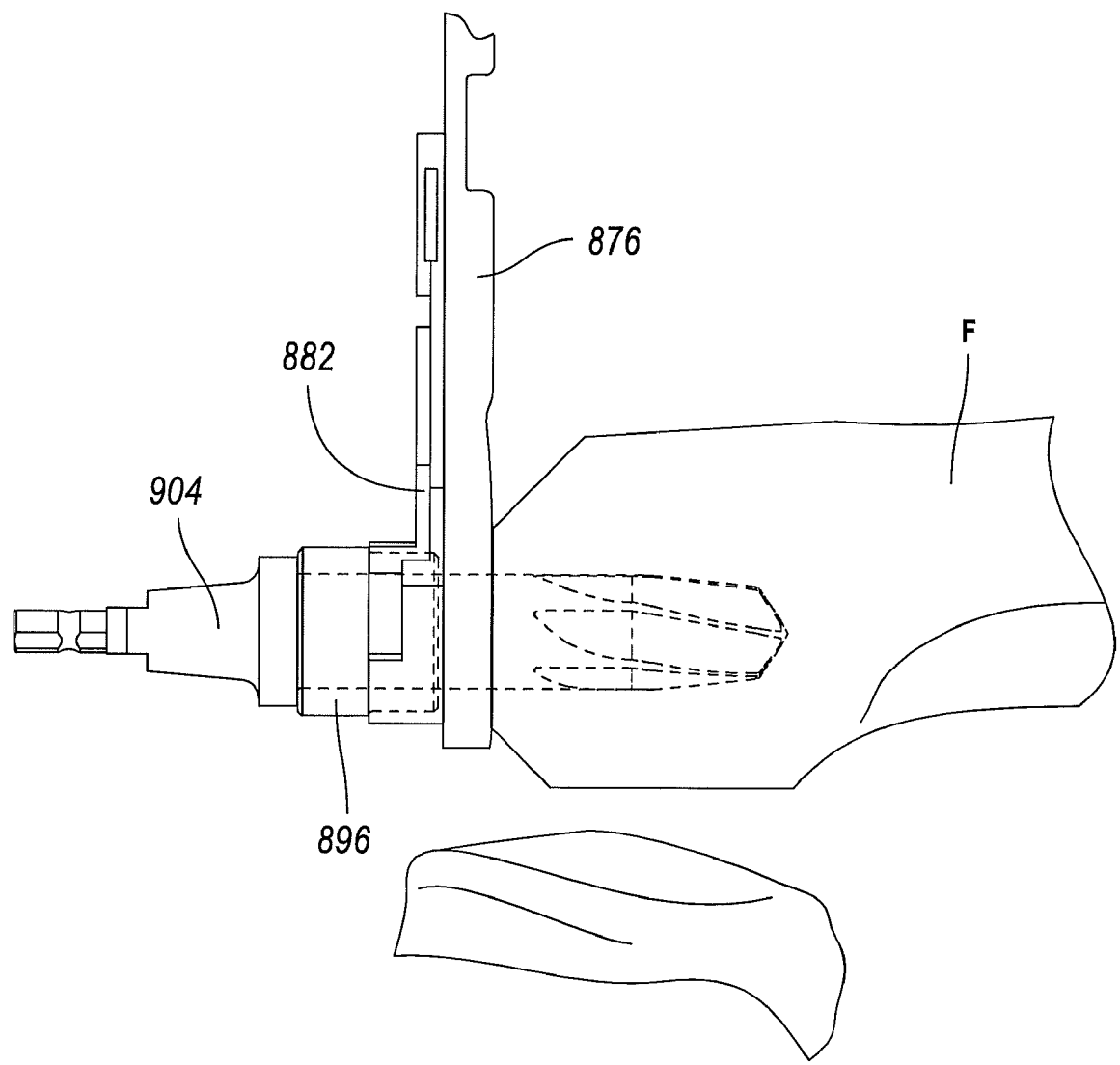
Figure 91:
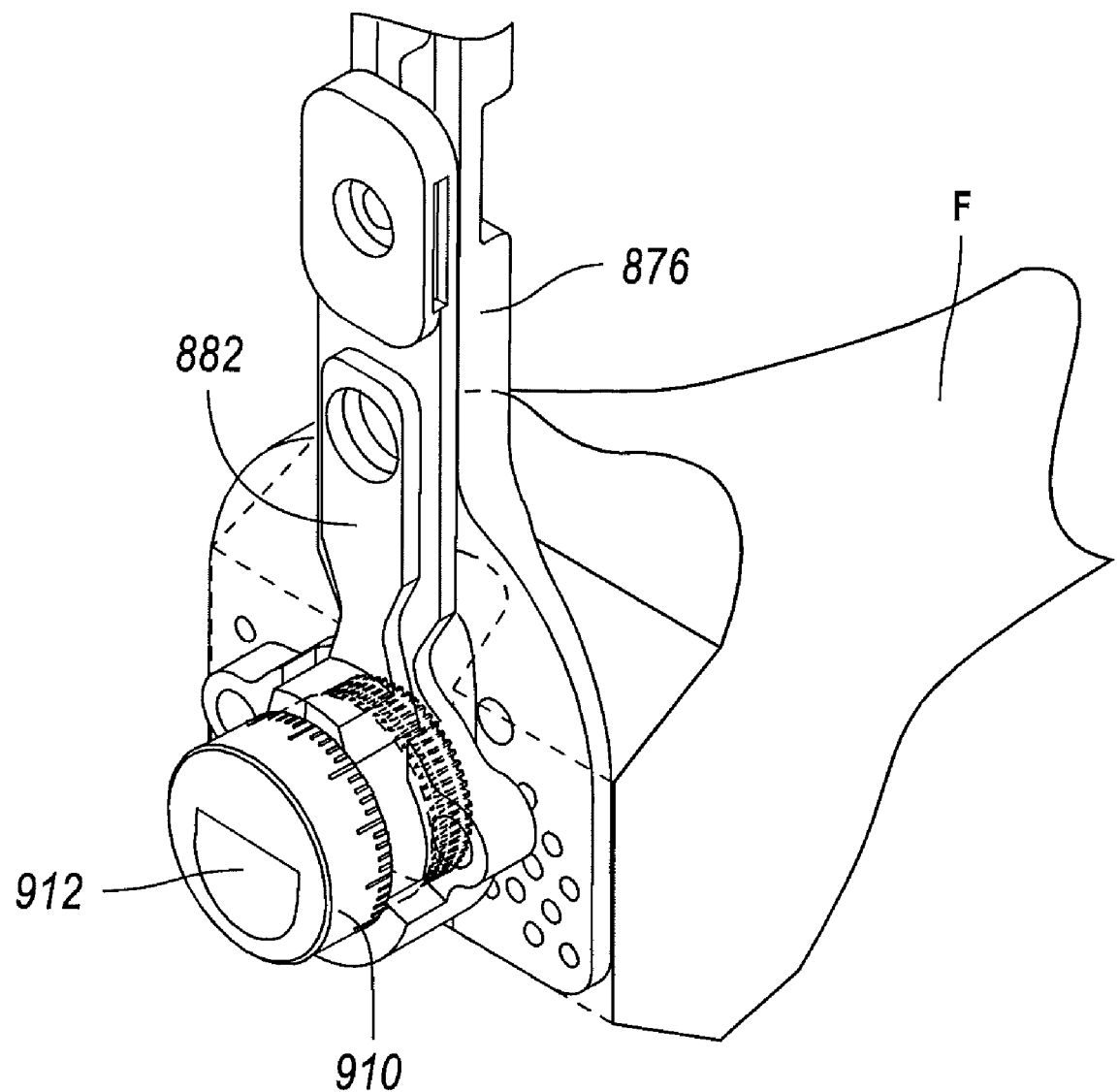
Figure 92:
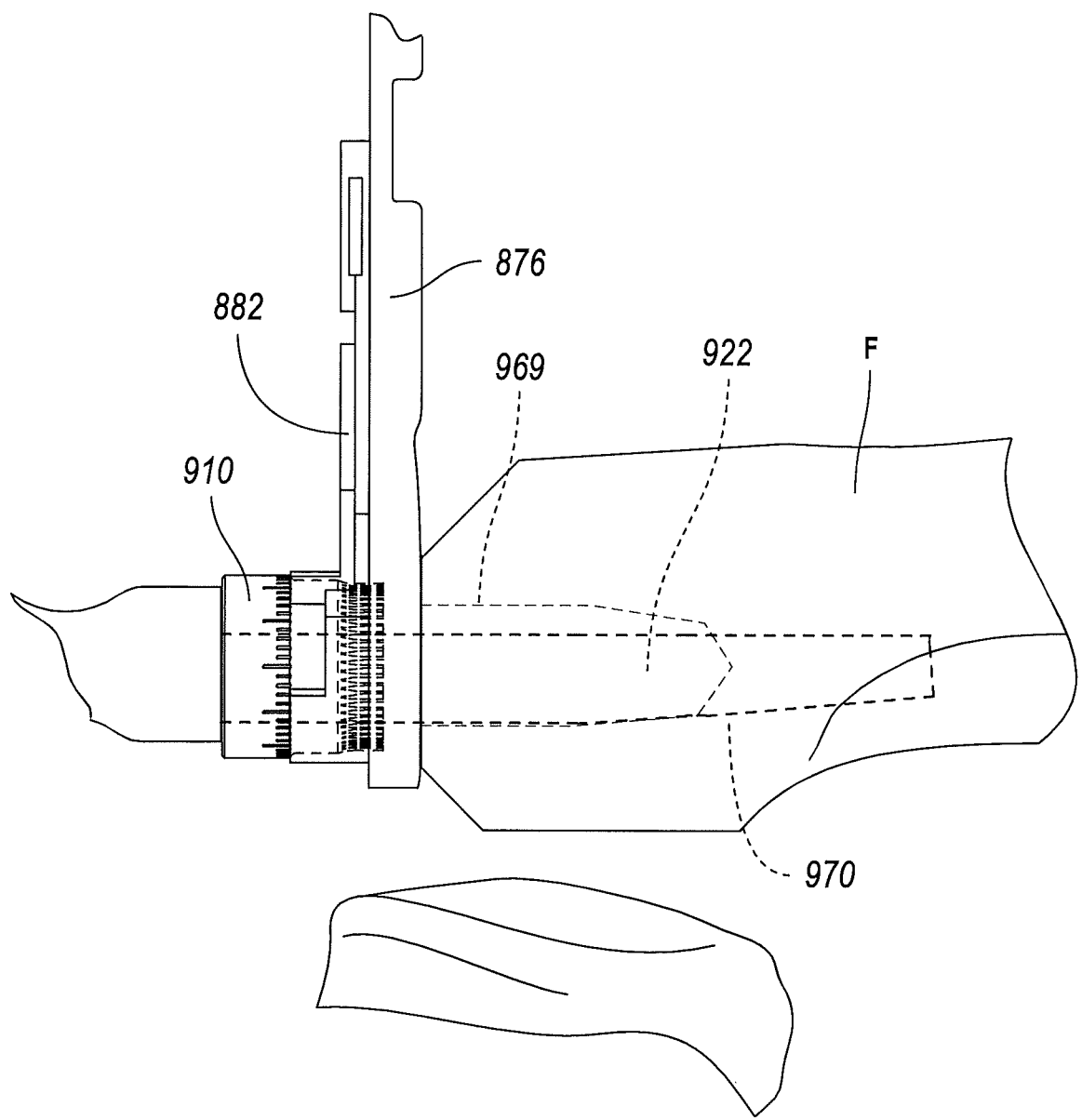

The cutting block 812 can then be removed from the distal femur F while leaving the reamer 956 in place (FIG. 86). Augment trials 844 can then be coupled to the back side of the femoral offset template 876 using a desired hole 880. Next, the universal revision alignment member 882 can be coupled to top side of the femoral template 876 (FIG. 88). The offset bushing 838 can be inserted into the pocket 884. The reamer bit 904 can be inserted through the passage 804 in the offset bushing 838 and the assembly can be dropped onto the distal femur F. The offset bushing 838 can then be rotated to the alignment number 842 noted from above. The femoral offset template 876 can be secured to the distal femur F. The offset bushing 838 can then be removed from the pocket 884. The implant boss reamer bushing 896 can then be inserted into the pocket 884 (FIG. 89). The reamer bit 904 can be directed through the implant boss reamer bushing 896 to ream an implant boss 969 (FIGS. 90 and 92).

Figure 93:
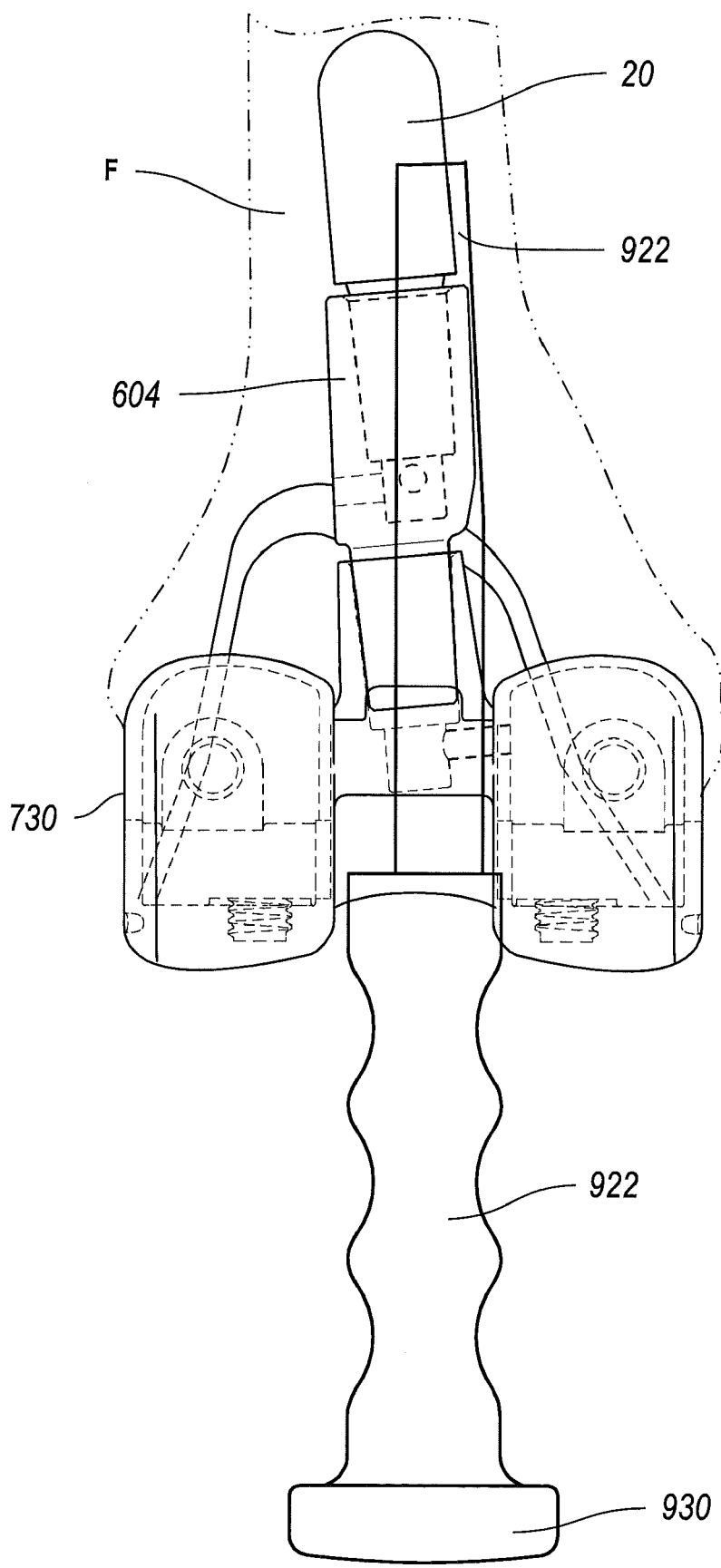

The implant boss reamer bushing 896 can then be removed from the pocket 884 and swapped out for the offset adapter rasp bushing 910. The rotational orientation can be verified (i.e. to match the alignment number noted above). The rasp 922 can be driven (i.e. repeatedly) through the half-moon shaped passage 912 of the offset adapter rasp bushing 910 (to create an offset bore portion 970). Again, the offset adapter rasp bushing 910 aligns the rasp 922 for preparing an offset passage within the femoral bore. The offset passage can substantially correspond to the profile (and rotational orientation) of the offset adapter (see superimposed components, FIG. 93).

Figure 94A:
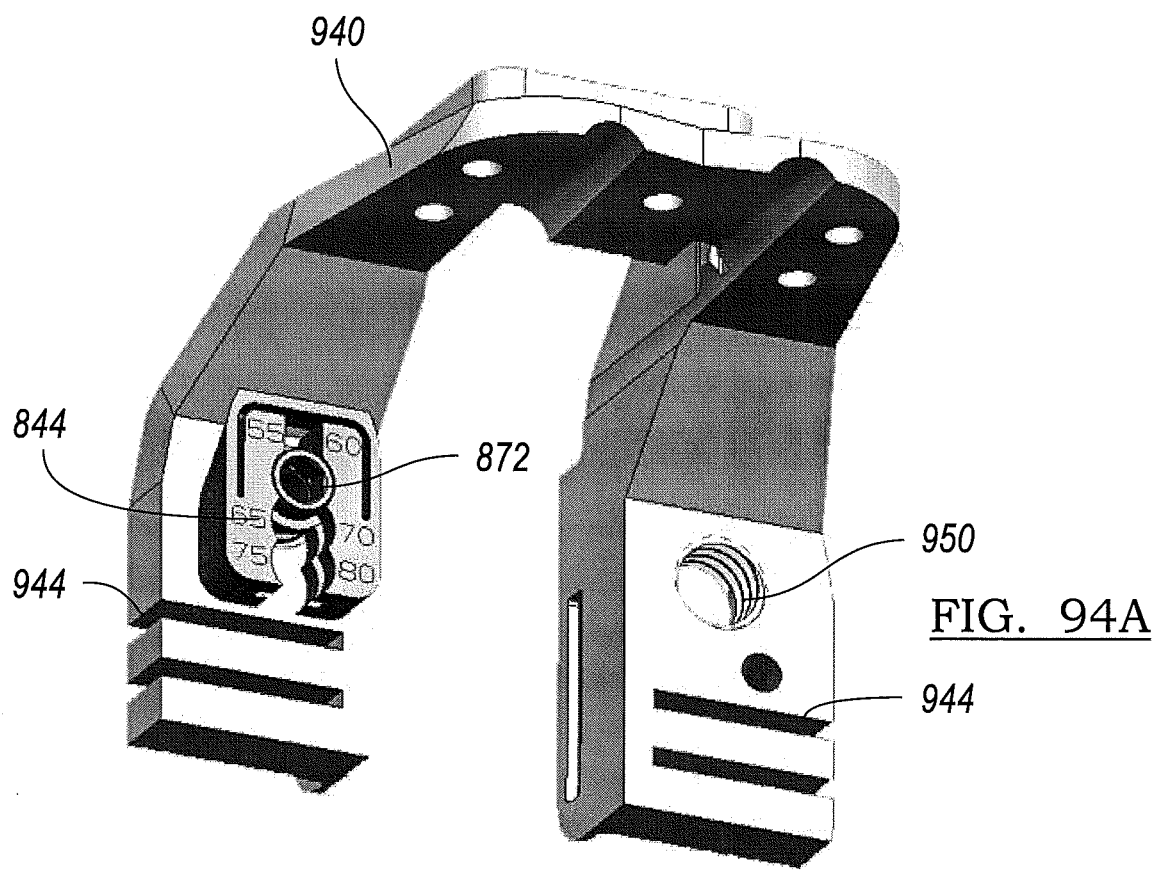
Figure 94B:
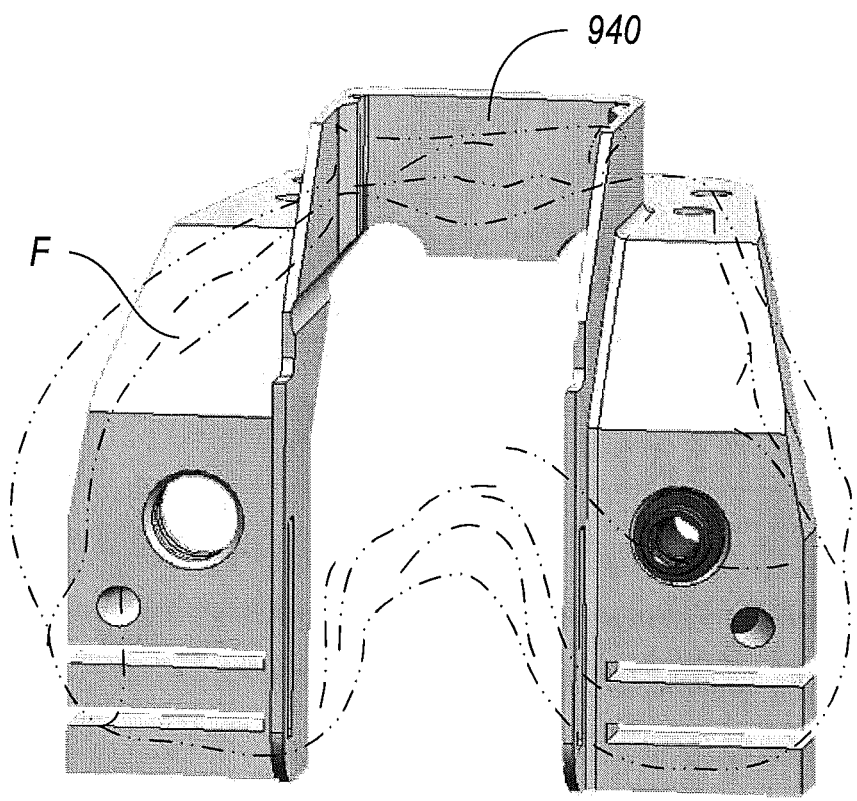
Figure 95:
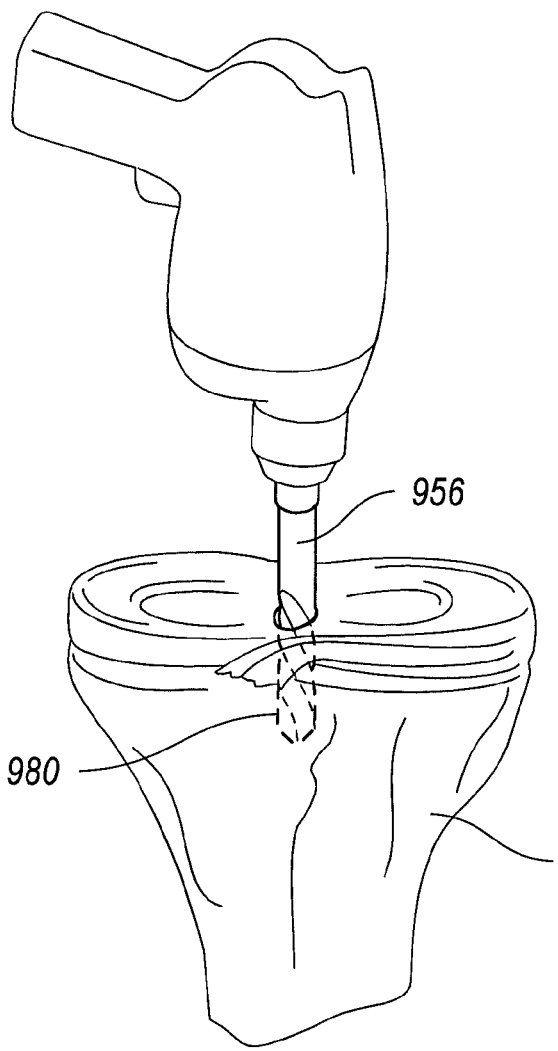

If desired, the posterior stabilized box guide 740 (FIGS. 94A and 94B) can be used to create a PS box at the outset of femoral preparation as is known in the art.

An exemplary sequence of preparing a tibia T for accepting a tibial component having an offset adapter will now be described. At the outset, the proximal tibia T can be exposed and resected. A tibial (intramedullary) canal 980 can be reamed using a reamer 956.

Figure 96:
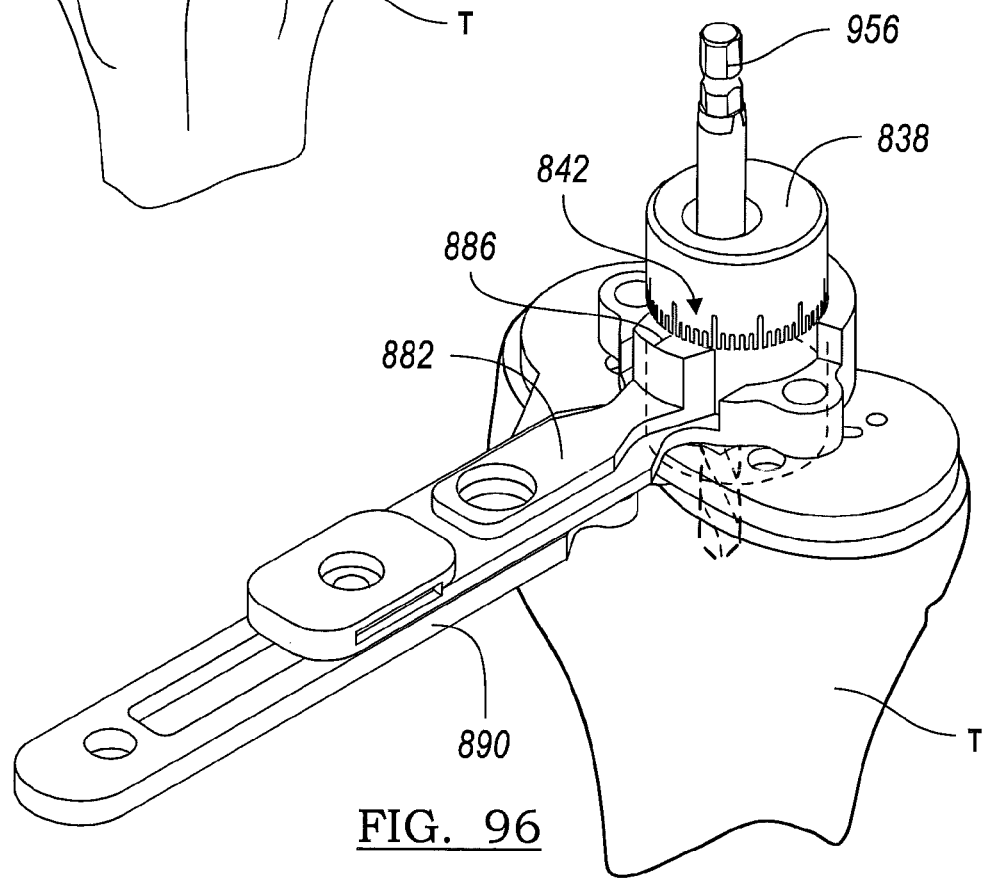
Figure 97:
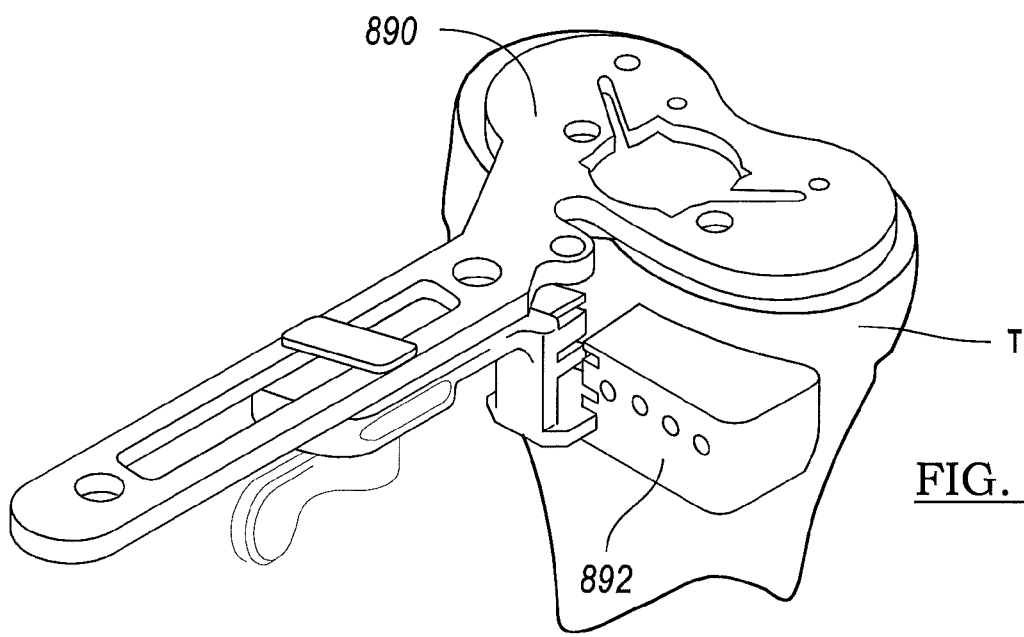

Next, the universal revision alignment member 882 can be coupled to top side of the tibial template 890. The offset bushing 838 can be inserted into the pocket 884 of the universal revision alignment member 882. The reamer shaft 956 can be inserted through the passage 840 in the offset bushing 838 and the assembly can be dropped onto the proximal tibia T (FIG. 96). The offset bushing 838 can then be rotated causing the tibial template 890 to translate around the proximal tibia T until optimal tibial coverage is attained. The tibial template 890 is then secured to the proximal tibia T. The alignment number is noted.

Figure 98A:
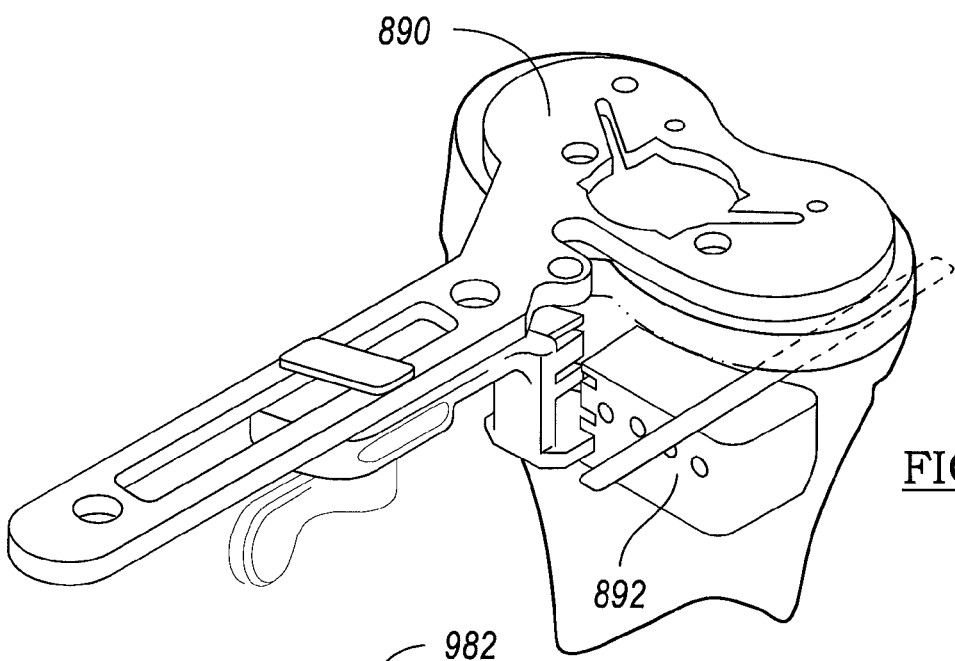
Figure 98B:
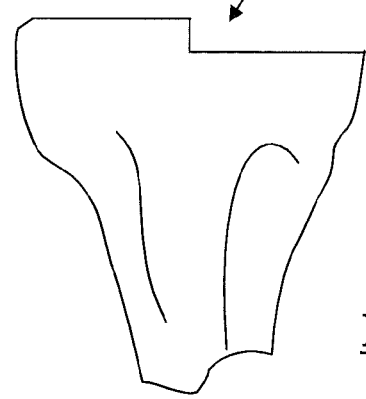
Figure 99:
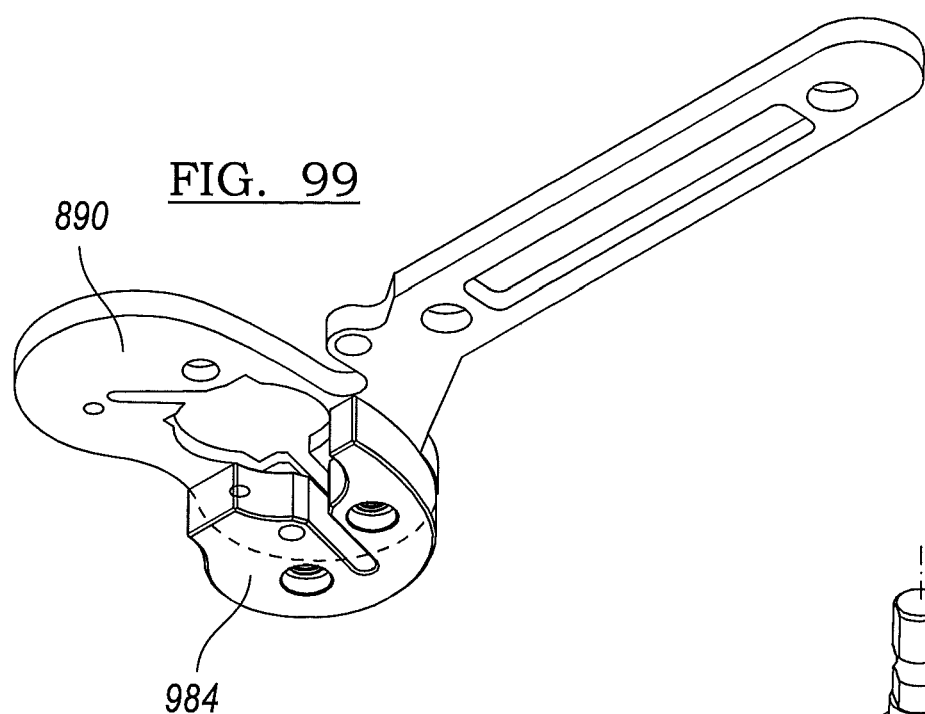
Figure 100:
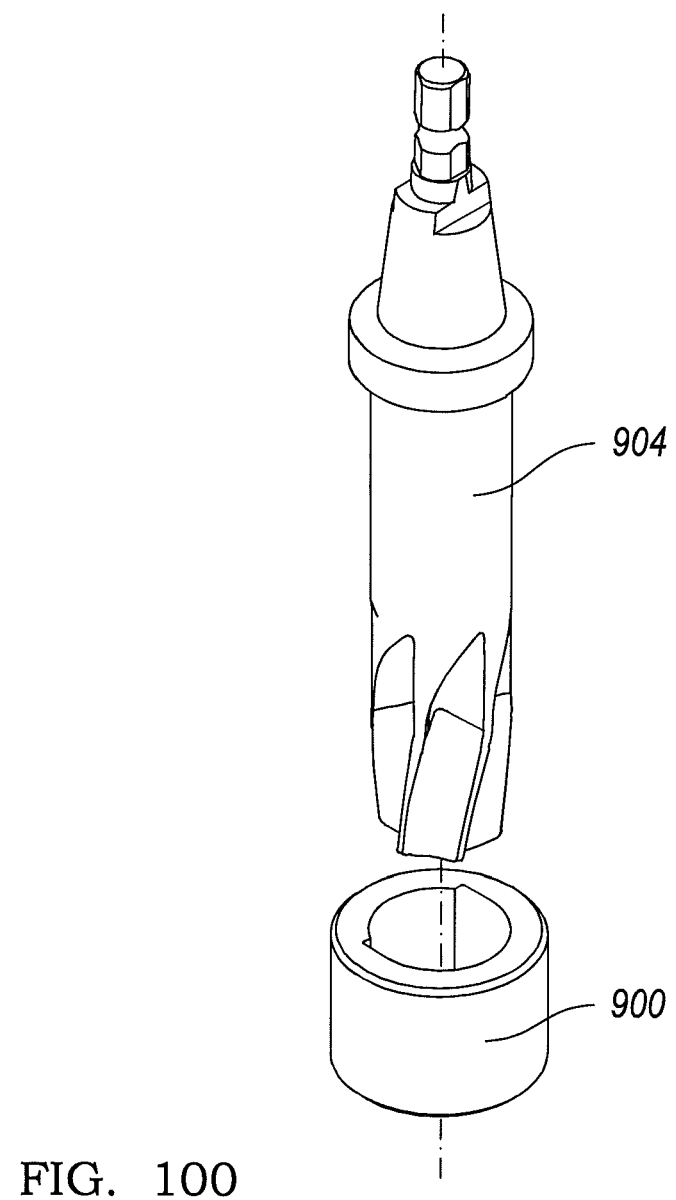

If a proximal augment cut is required, the tibial template 890 with augment cut block 892 can be secured to the proximal tibia T. The proximal tibia T can then be cut such as to form a notch 982 (FIG. 98B) on the proximal tibia T. A trial augment 984 can then be inserted onto the bottom surface of the tibial template 890.

Figures 101, 102:
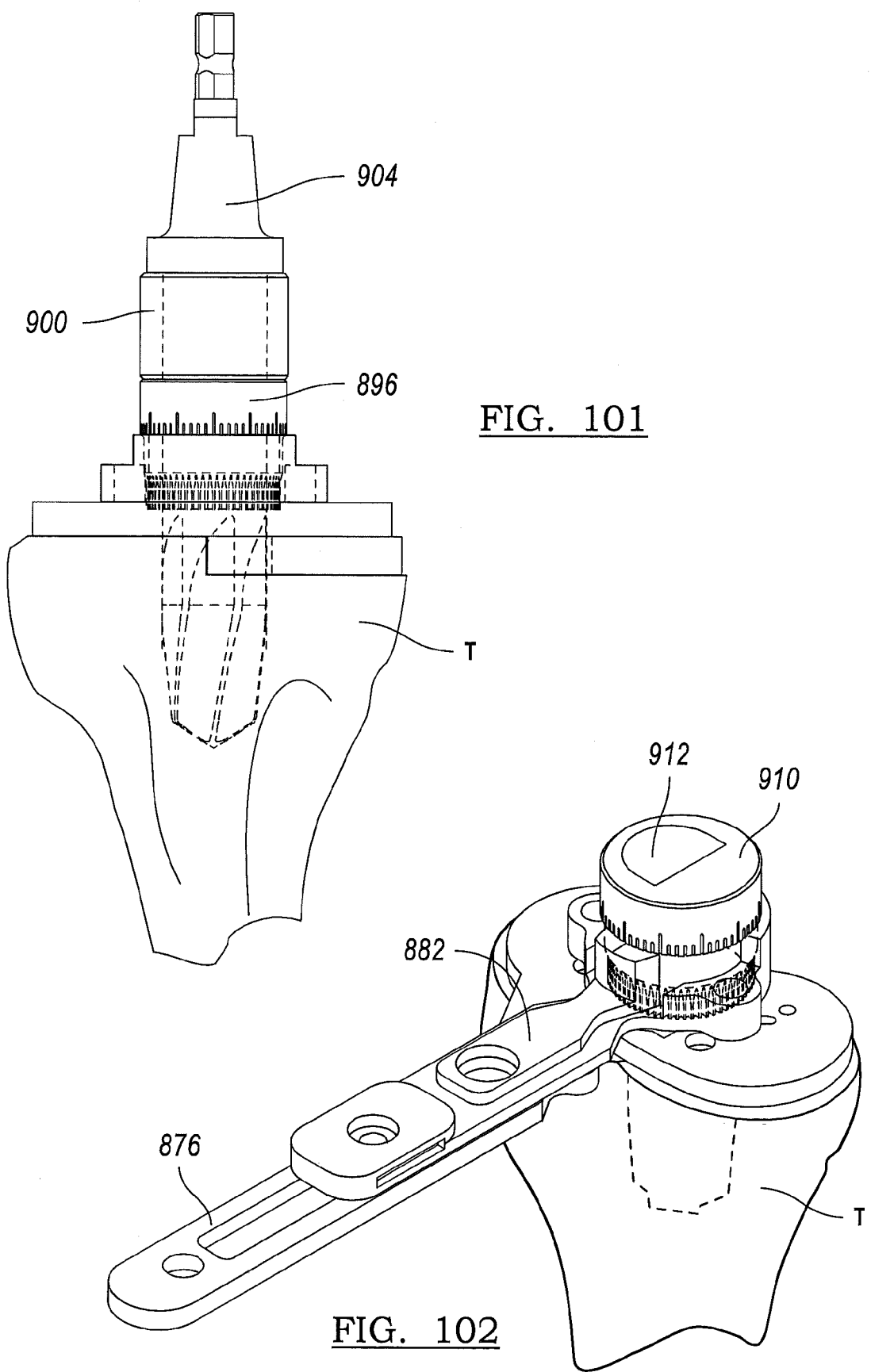
Figure 103:
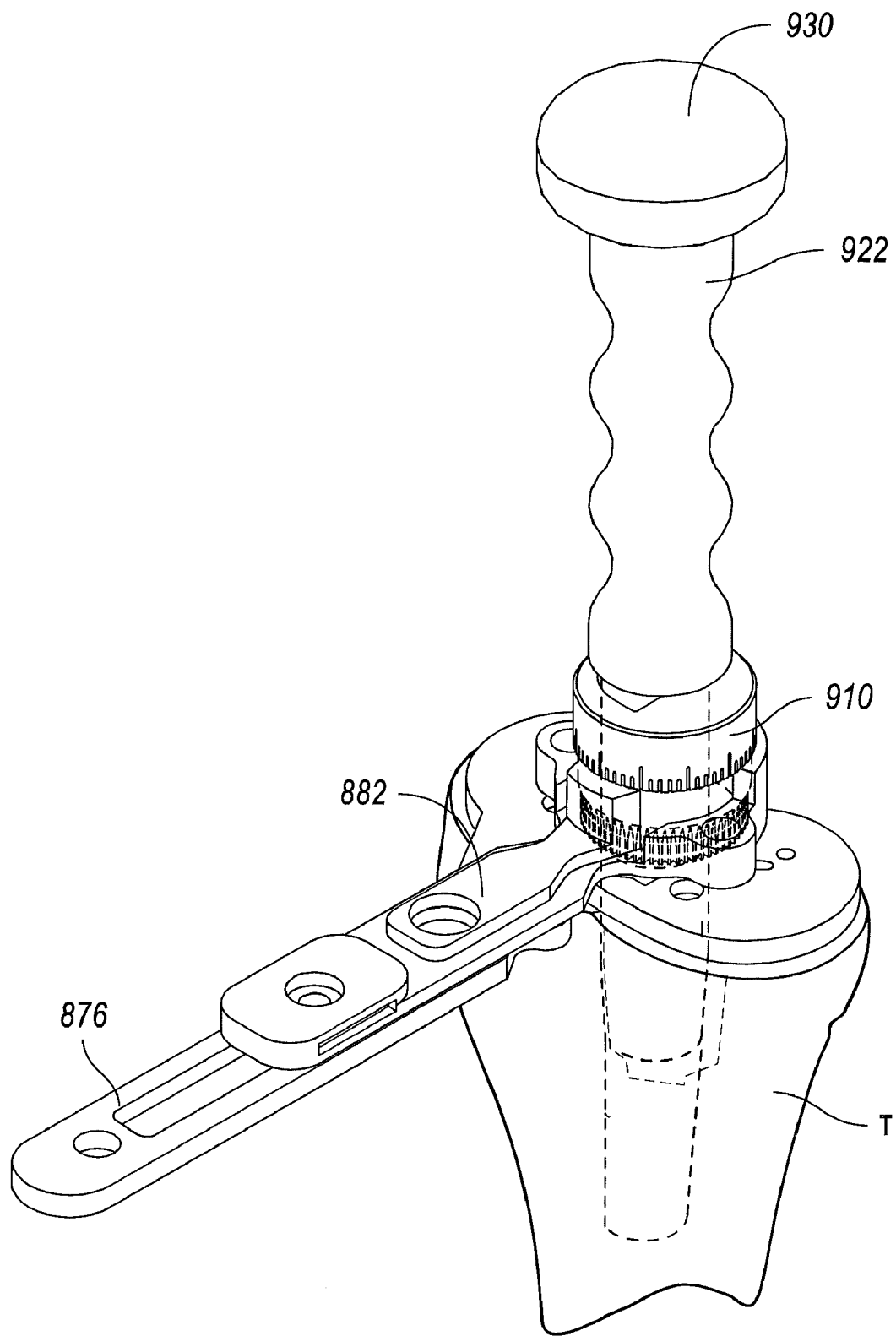
Figure 104:
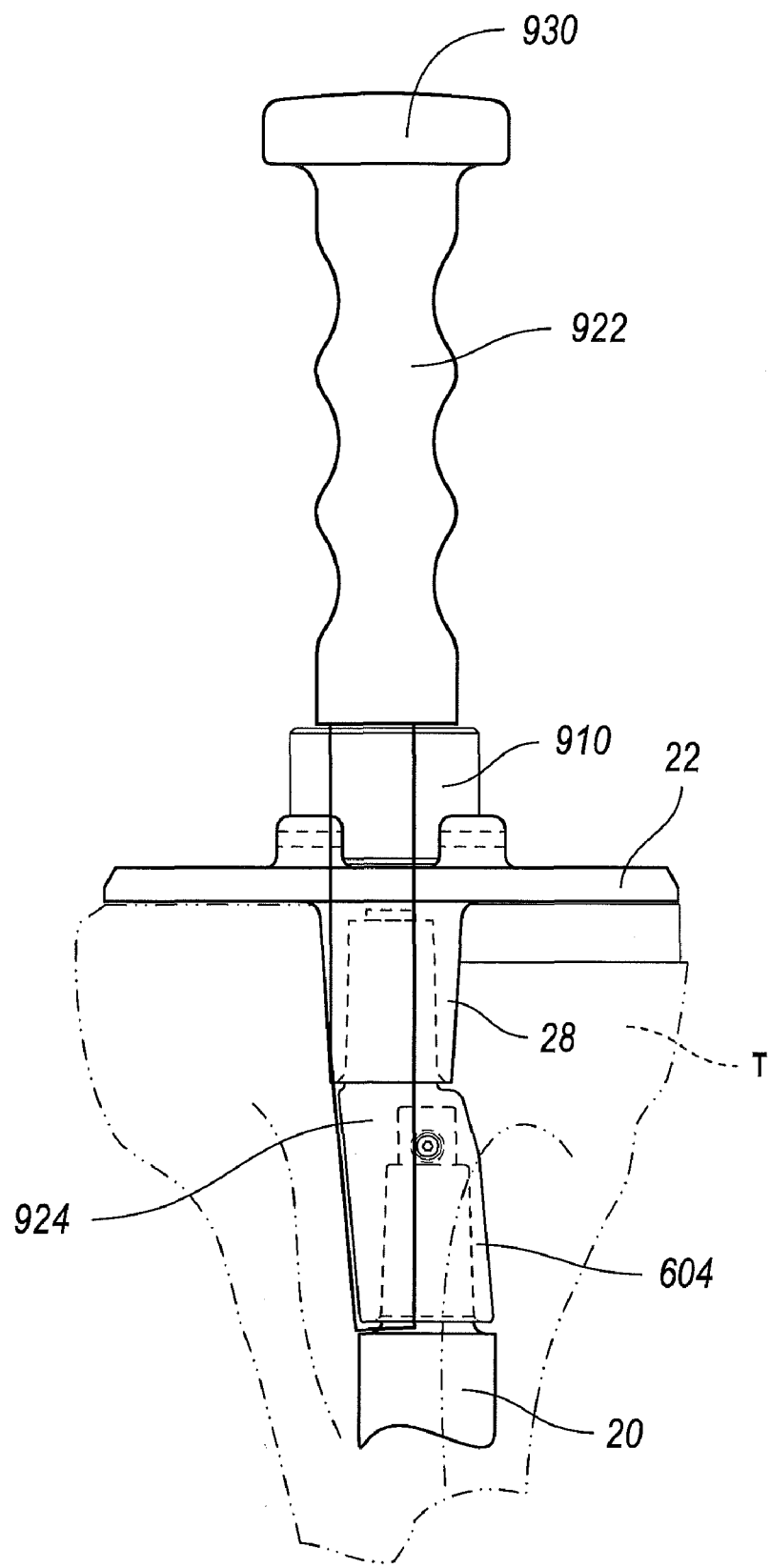

Next, the implant boss reamer bushing 896 can then be inserted into the pocket 884. The tibial bushing stop 900 is then located between the collar 902 of the reamer bit 904 and the implant boss reamer bushing 896 (to limit the depth of cut). The reamer bit 904 can be directed through the implant boss reamer bushing 896 to ream the implant boss (FIG. 101). The implant boss reamer bushing 896 and tibial bushing step 900 can then be removed from the pocket 884 and swapped out for the offset adapter rasp bushing 910. The rotational orientation can be verified (i.e. to match the alignment number noted above). The rasp 922 can be driven (i.e. repeatedly) through the half-moon shaped passage 912 of the offset adapter rasp bushing 910 to create the offset bore portion. Again, the offset adapter rasp bushing 910 aligns the rasp 922 for preparing an offset passage within the tibial bore (FIG. 104). The offset passage can substantially correspond to the profile (and rotational orientation) of the offset adapter body 604.

Figure 105:
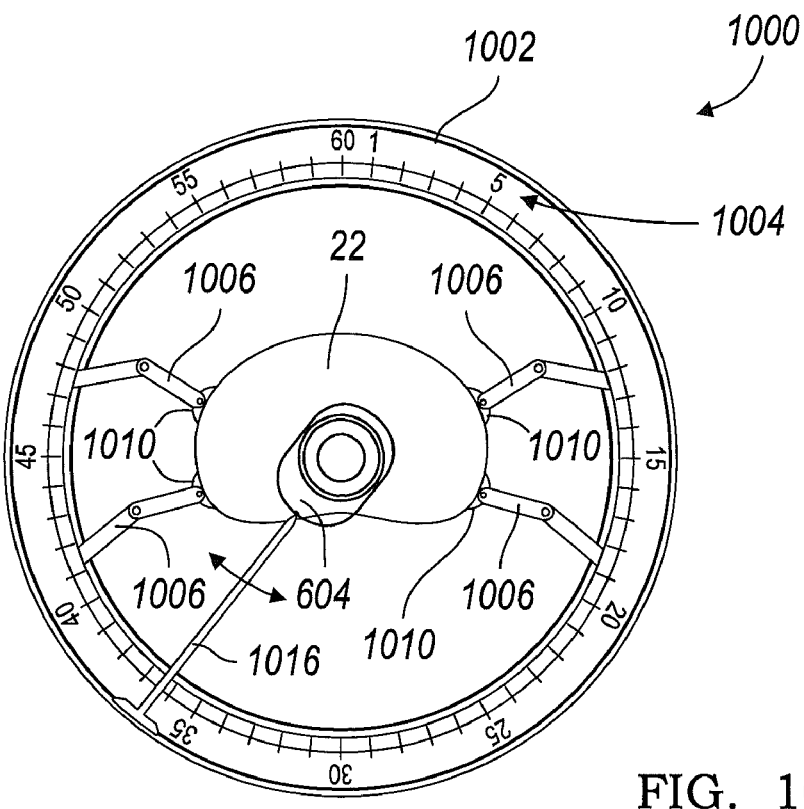
FIGS. 105-107 illustrate various apparatus for aligning an offset adapter at a desired orientation prior to joining with a desired femoral or tibial component.

With reference to FIG. 105, an apparatus 1000 for aligning an offset adapter body 604 rotationally with a receiving portion of an implant (i.e. female tapered receiving portion of a tibial component or a femoral component). In the example shown in FIG. 105, the apparatus 1000 is shown securing a tibial component 22, while it is appreciated that the apparatus can also secure a femoral component (such as any femoral component disclosed herein). The apparatus 1000 can generally define an outer frame 1002 defining a scale of indicia 1004 thereon. A plurality of arms 1006 can be movably secured to the outer frame 1002. A corresponding plurality of hands 1010 can be defined on distal ends of the arms 1006. Once the plurality of arms 1006 and hands 1010 are positioned to securably retain the implant (i.e. tray 22), the arms 1006 and hands 1010 can be locked in position. In one example, the implant (i.e. tray 22) can be secured in a known position. In the example shown, the known position can be such that the tibial tray 22 is positioned with the anterior portion aligned with the indicia 1004 (i.e. at indicia numeral "60"). A pointer 1016 can be mounted for rotation around the outer frame 1002.

The indicia 1004 can be at a known location relative to the indicia 842 on the offset bushing 838. The pointer can then be rotated around the dial 1004 to correspond to the noted number dialed in with the offset bushing 838. Next, a mark 1020 (see FIG. 106) can be aligned with the pointer 1016 and dropped into the female tapered receiving portion 30 of the tibial tray 22. The Morse-type taper interface, as described in detail, can secure the adapter body 604 relative to the tray 22 until supplemental mechanical securement (such as the fastener 90', FIG. 34, or locking element 606, FIG. 36D).

Figure 106:
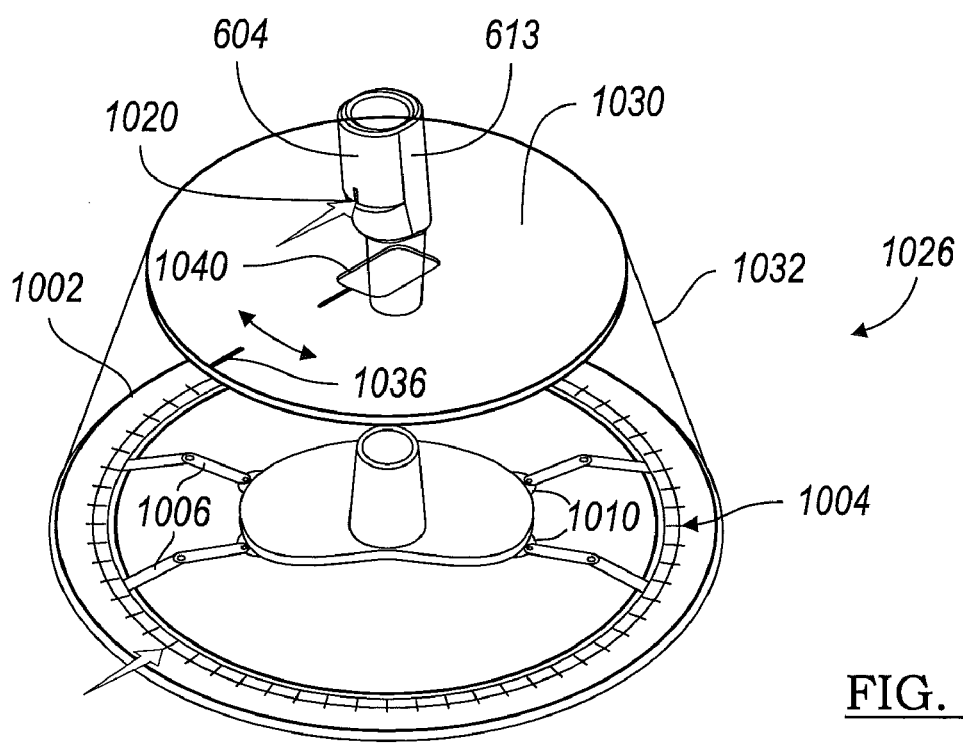

Another apparatus 1026 for aligning an offset adapter body 604 rotationally with a receiving portion of an implant (i.e. female tapered receiving portion of a tibial component or a femoral component) is shown in FIG. 106. The apparatus 1026 can include the dial 1002, arms 1006 and hands 1010 as described above (or any suitable securing device). A dial 1030 can be rotatably suspended above the tibial tray 22. In one example, the dial 1030 can rotate within a halo 1032 extending above the dial 1002. The dial 1030 can define a mark 1036 and a keyhole 1040. The keyhole can correspond to a footprint that slidably accepts the flats 613 of the adapter body 604 so that the adapter body is rotatably fixed in the keyhole 1040. The dial 1030 can be rotated until the mark 1036 aligns with the noted number dialed in with the offset bushing 838. The adapter can then be dropped through the keyhole 1040 and into the female tapered receiving portion 30 of the tibial tray 22. The Morse-type taper interface, as described in detail, can secure the adapter body 604 relative to the tray 22 until supplemental mechanical securement (such as the fastener 90', FIG. 34, or locking element 606, FIG. 36D).

Figure 107:
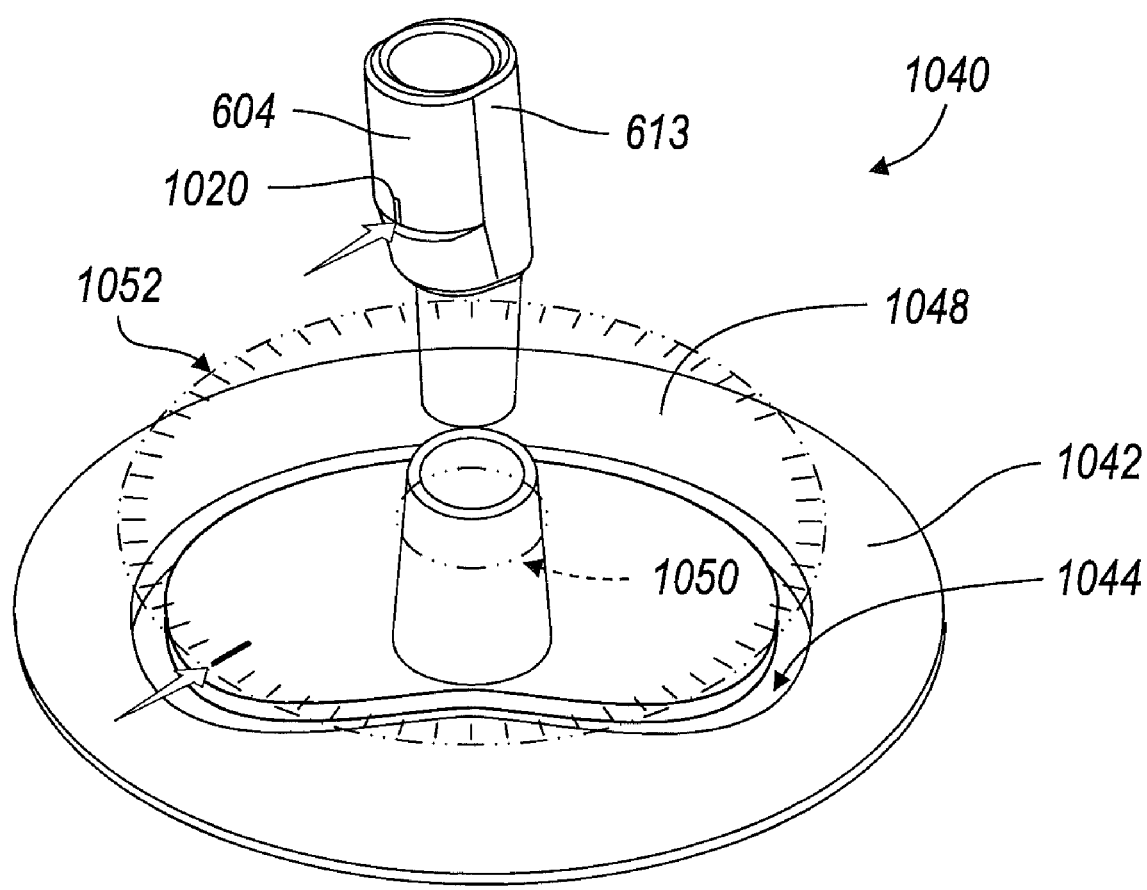

Another apparatus 1040 for aligning an offset adapter body 604 rotationally with a receiving portion of an implant (i.e. female tapered receiving portion of a tibial component or a femoral component) is shown in FIG. 107. The apparatus can include a blister package 1042. The blister package 1042 can define a pocket 1044 that defines a profile substantially corresponding to the footprint of an implant (such as any femoral or tibial component described herein). In the example shown, the tibial tray 22 nests in a secure position within the pocket 1044. A disposable dial 1048 can be loosely provided within the blister package 1042. Alternatively, the seal of the blister package or removable top can act as the dial 1048 and have indicia 1052 printed on the inside of the top. The disposable dial 1048 or top can define a perforation 1050 and scaled indicia 1052. The disposable dial 1048 can be dropped over the tapered extension portion of the packaged implant (the inferiorly extending portion 28 of the tibial tray 22, as shown) such that the tapered extension portion breaks through the perforation 1050. The dial 1048 can then be rotated until the mark 1020 aligns with a number of the indicia 1052 that corresponds with the noted number dialed in with the offset bushing 838. The adapter 604 can then be dropped into the female tapered receiving portion 30 of the tibial tray 22. The Morse-type taper interface, as described in detail, can secure the adapter body 604 relative to the tray 22 until supplemental mechanical securement (such as the fastener 90', FIG. 34, or locking element 606, FIG. 36D).

Figure 108:
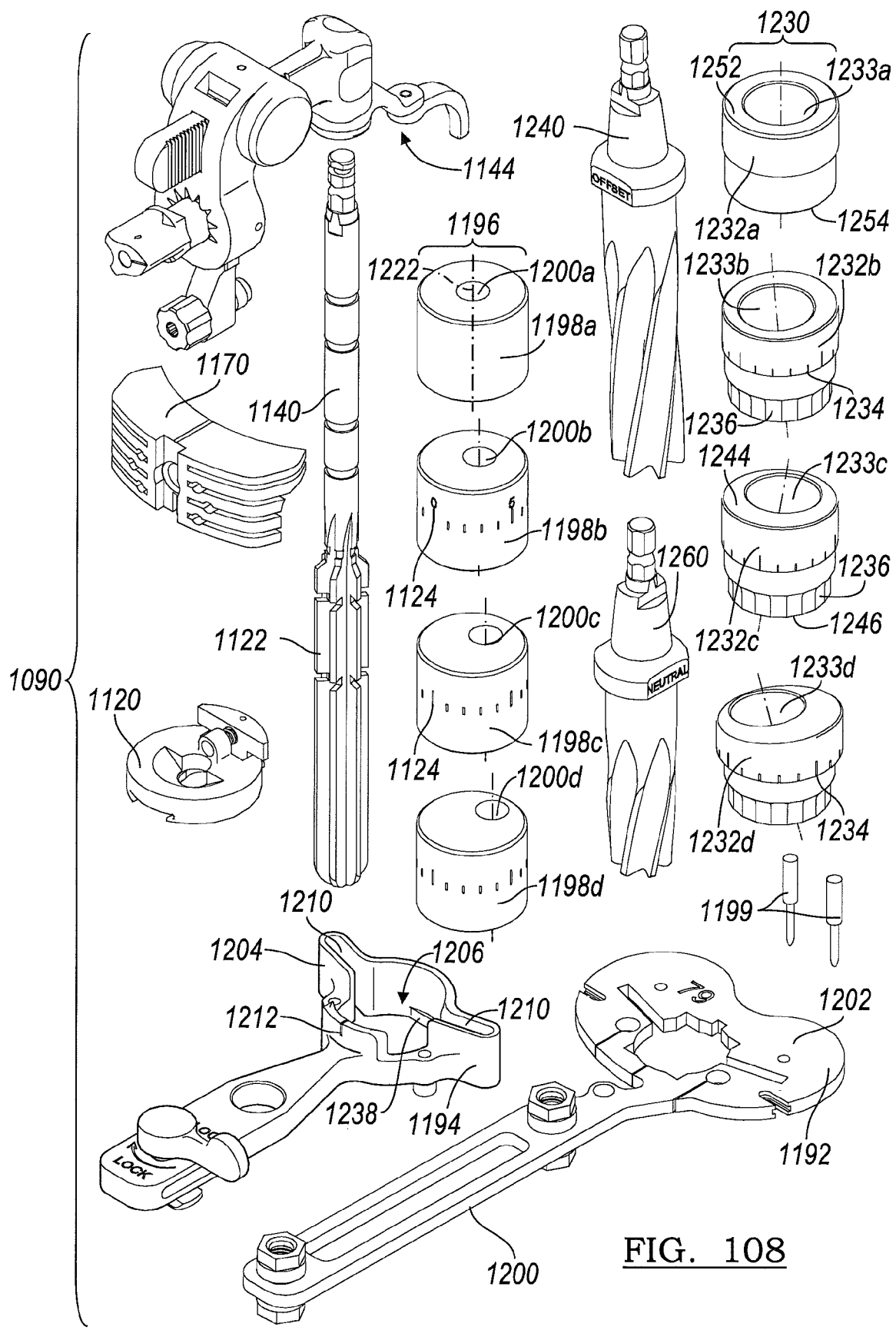
Figure 109A:
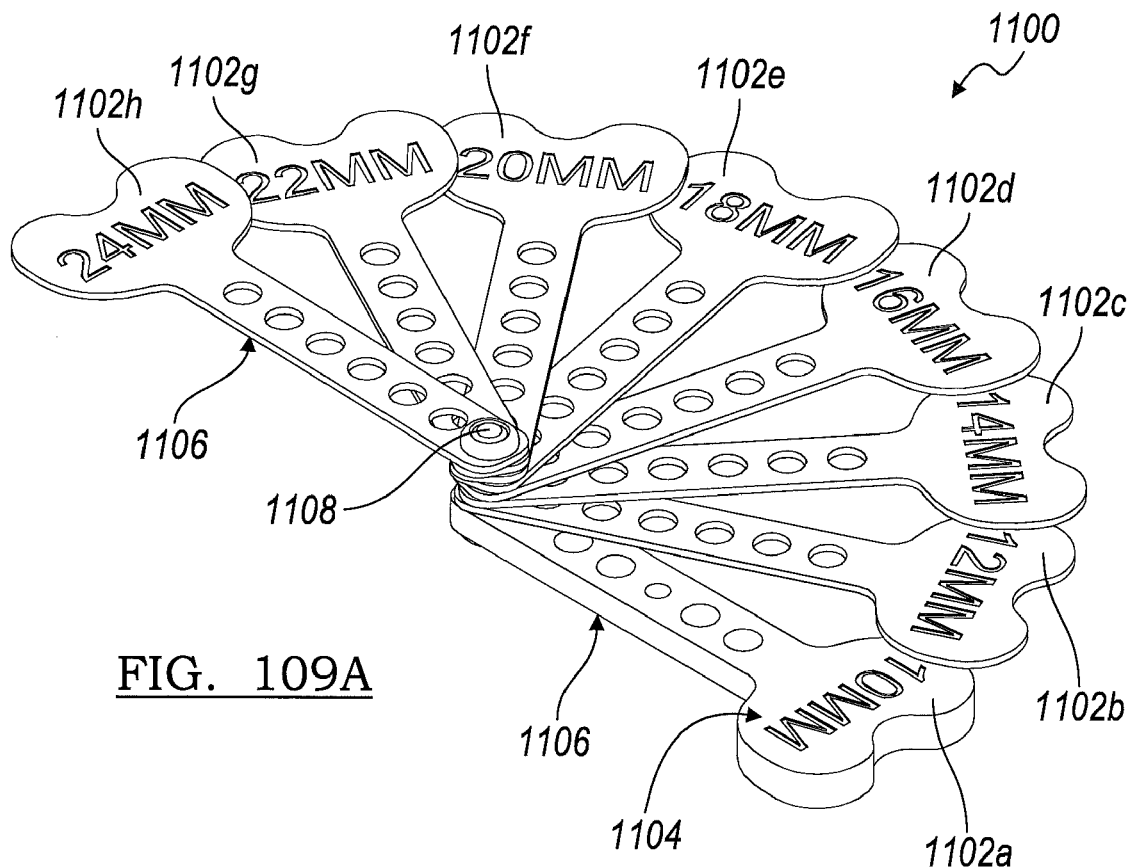
Figure 109B:
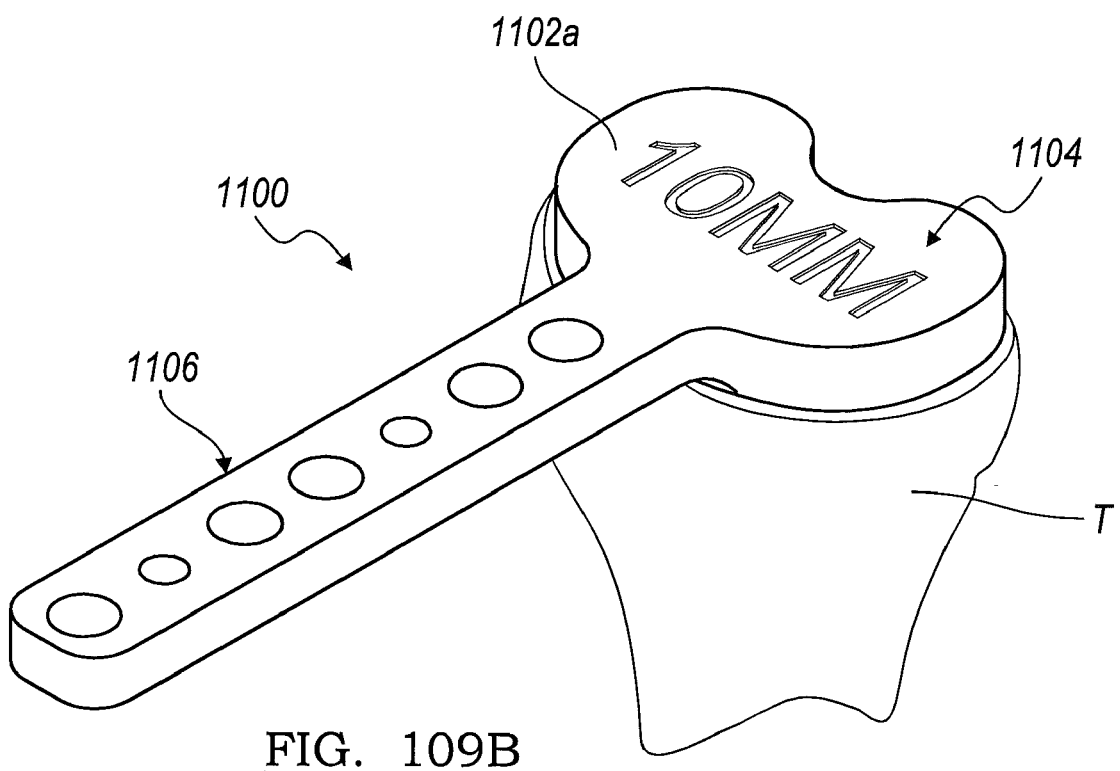

With reference to FIGS. 108-119, another exemplary method for preparing a tibia during revision surgery will be described. Those skilled in the art will appreciate that with revision surgery, the existing (i.e., prior implanted) tibial component (e.g. tibial tray, bearing, etc.) is removed from the tibia. A system or kit of tools 1090 are shown in FIG. 108. As illustrated in FIG. 109A, a tibial spacer assembly 1000 is shown. In the depicted example, tibial spacers 1102a, 1102b, 1102c, 1102d, 1102e, 1102f, 1102g, and 1102h are provided. The tibial spacer 1102a has a thickness of 10 mm. The remaining tibial spacers 1102b-1102h each have a thickness of 2 mm. The tibial spacer assembly 1100 can be stacked, as needed, to achieve a desired height. The thickness of a given stack of tibial spacers 1102a-1102h (or just the tibial spacer 1102a used alone) represents a desired thickness of a tibial bearing that will be implanted at the proximal tibia. In the examples provided, the tibial spacer 1102b can be stacked onto the tibial spacer 1102a to collectively define a thickness of 12 mm. As can be appreciated, the tibial spacers 1102c-1102h can be sequentially stacked to achieve additional increments of 2 mm. The tibial spacer 1102c represents (e.g., the cumulative thickness of the tibial spacer 1102c, the tibial spacer 1102b and the tibial spacer 1102a) a thickness of 14 mm. The tibial spacer 1102d represents a thickness of 16 mm, and the tibial spacer 1102e represents a thickness of 18 mm. The tibial spacer 1102f represents a thickness of 20 mm. The spacer 1102g represents a thickness of 22 mm. The spacer 1102h represents a thickness of 24 mm. In other embodiments, other thicknesses of the assembly 1100 and the individual spacers 1102a-1102h are contemplated. As shown, the respective spacers 1102a-1102h can each include a tibial plateau portion, collectively referred to by reference numeral 1104, and a handle portion, collectively referred to by reference numeral 1106. Each of the tibial spacers 1102a-1102h are rotatably connected at terminal ends by way of a fastener 1108. The respective tibial spacers 1102a-1102h can each pivotally rotate about the fastener 1108 in order to isolate a desired tibial spacer 1102a-1102h from the remainder of the spacers 1102a-1102h. It is appreciated that while the respective tibial spacers 1102a-1102h are shown attached to each other through the fastener 1108, they may alternatively be unattached, separate pieces.

The tibial spacer assembly 1100 can be used to find the joint line of a tibia T using anatomical landmarks. More specifically, the tibial plateau portion 1104 of a given tibial spacer 1102a-1102h can be placed atop the tibial plateau of the tibia T or atop the resected proximal end of the tibia. In other words, the primary tibia is removed and the selected spacer 1102a-1102h is positioned on the previously resected proximal tibia. In the depicted embodiment, the spacers 1102a-1102h are universal and can accommodate a left or a right tibia. The appropriate joint line will be confirmed when the proper thickness spacer 1102a-1102h is placed on the tibial plateau and presents a desired height (i.e., superiorly from the tibial plateau) relative to anatomical landmarks. At this time, a thickness of optional, supplemental augments (i.e., such as those illustrated in FIGS. 55A and 55B) can be determined. It is appreciated that it may be necessary to provide supplemental augments on any combination of the medial and lateral sides of the tibia. The joint line relative to the tibia is known once the desired thickness of the identified spacer 1102a-1102h and the augmentation need is confirmed and noted. The spacer assembly 1100 is then removed from the tibia.

Once the joint line has been determined relative to the tibia, an intramedullary (IM) reamer stop 1120 (FIG. 110A) can be coupled to a reamer 1122. The reamer 1122 can cooperate with the IM reamer stop 1120 to prepare the IM canal of the tibia. During use, the reamer 1122 is able to ream a distance into the IM canal until the reamer stop 1120 comes into contact with the proximal tibia.

The IM reamer stop 1120 and the reamer 1122 will now be described in greater detail with reference to FIGS. 110A and 110B. The IM reamer stop 1120 has a superior surface 1126, an inferior surface 1128 and defines an opening 1130 that extends through the IM reamer stop 1120 from the superior surface 1126 to the inferior surface 1128. A finger support 1132 can be supported on the superior surface 1126 of the IM reamer stop 1120. A button 1133 can be coupled to a locating finger 1134. The locating finger 1134 can be movably fixed to the finger support 1132. In one example, the locating finger 1134 can move (e.g., such as by depression of the button 1133) along an axis that is substantially transverse to an axis defined by the reamer 1122. In one example, a biasing member 1136, such as a spring in the depicted embodiment, can bias the locating finger 1134 into engagement with the reamer 1122.

The reamer 1122 can define a reamer shaft 1140 having a plurality of annular grooves, collectively referred to at reference 1142 formed thereon. As can be appreciated, the grooves 1142 provide a nesting location for the locating finger 1134 to control the depth of reaming for the reamer 1122. According to one example, the grooves 1142 can be marked with indicia (not specifically shown) that identify various depths of reaming for the tibia T (as will become appreciated from the following discussion, the reamer 1122 and the IM reamer stop 1120 can also be used for preparation of the IM canal in the femur). As such, the grooves 1142 can also correspond to various depths of reaming in the femur as well. For exemplary purposes, the grooves 1142 can correspond to 40 mm, 80 mm, 200 mm and other depths of reaming to correspond to a desired stem length. As can be appreciated, the various depths of cut can correspond to the various lengths of tibial stems, such as the tibial stem 20 illustrated in FIG. 29 or any of the tibial stems illustrated in FIG. 55A. It is also appreciated in some instances it may be necessary to implant an offset adapter, such as the offset adapter 600 illustrated in FIG. 35 or any of the other offset adapters described herein, such as the offset adapters illustrated in FIGS. 55A and 55B. In those examples wherein an offset adapter is needed in conjunction with a stem, the grooves 1142 will correspond to different lengths of stems. For example, if a 40 mm offset adapter will be used, the groove that corresponds to an 80 mm tibial stem will also correspond to a 40 mm tibial stem with a 40 mm tibial offset adapter. Those skilled in the art will appreciate that the dimensions described herein are merely exemplary. In this way, grooves can be provided in any combination of configurations along the reamer 1122 for identifying a depth of reaming that can accommodate any combination of stems and/or offset adapters described herein.

Figure 111:
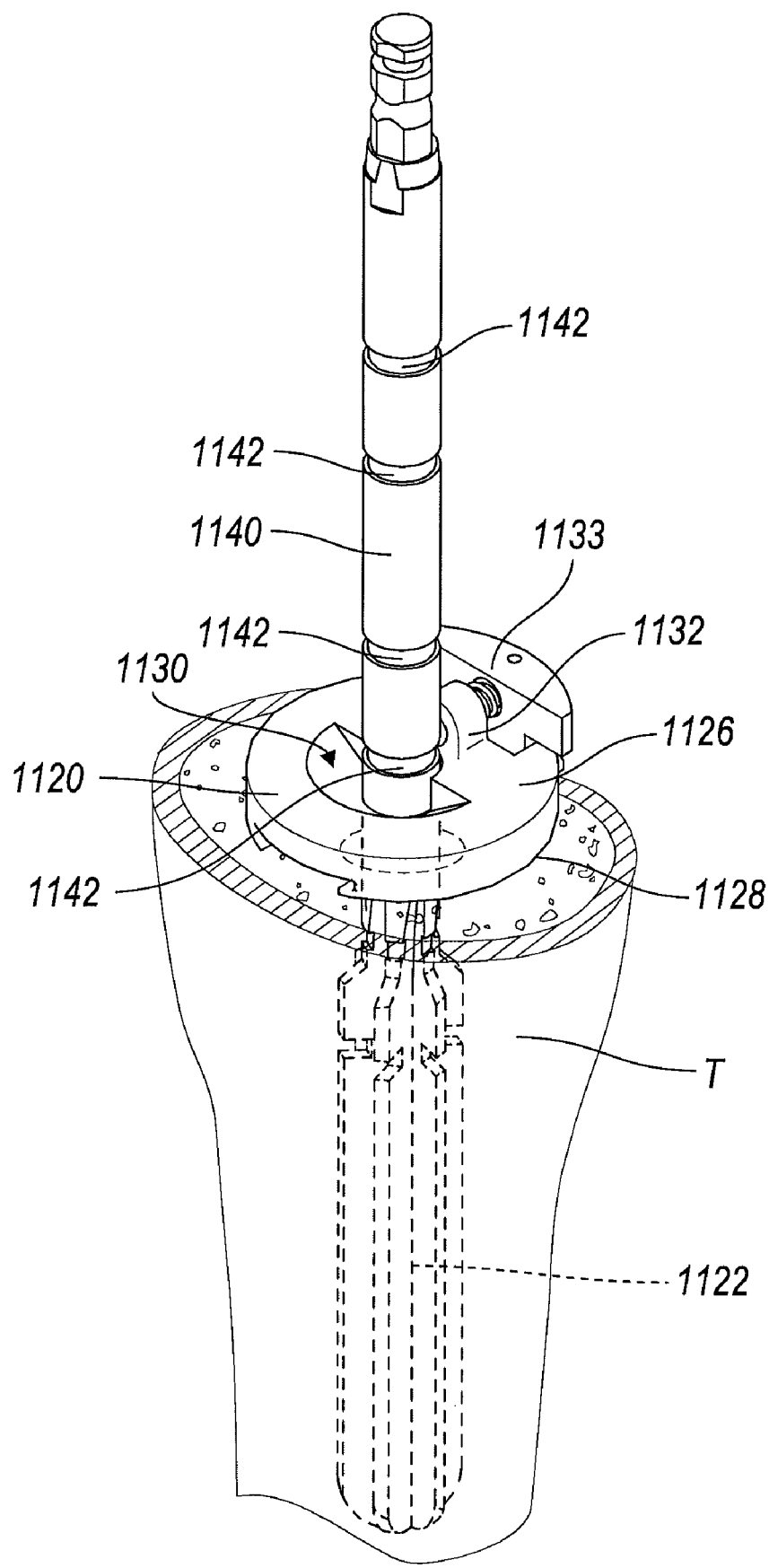

During use, such as the example shown in FIG. 111, various reamers 1122 having distinct diameters can be used until adequate cortical contact is achieved in the tibia T. Multiple IM reamer stops 1120 can be provided, each being operatively connected to a reamer 1122 having a distinct diameter. In this way, a surgeon, when switching to a reamer having a bigger diameter, can simply remove the combination of reamer 1122 and IM reamer stop 1120 and utilize another collective set of reamer and IM reamer stop. As can be appreciated, this can minimize the amount of time that may be required to remove a reamer 1122 from the opening 1130 in an IM reamer stop 1120 and replace it with a reamer having another diameter.

Figure 112A:
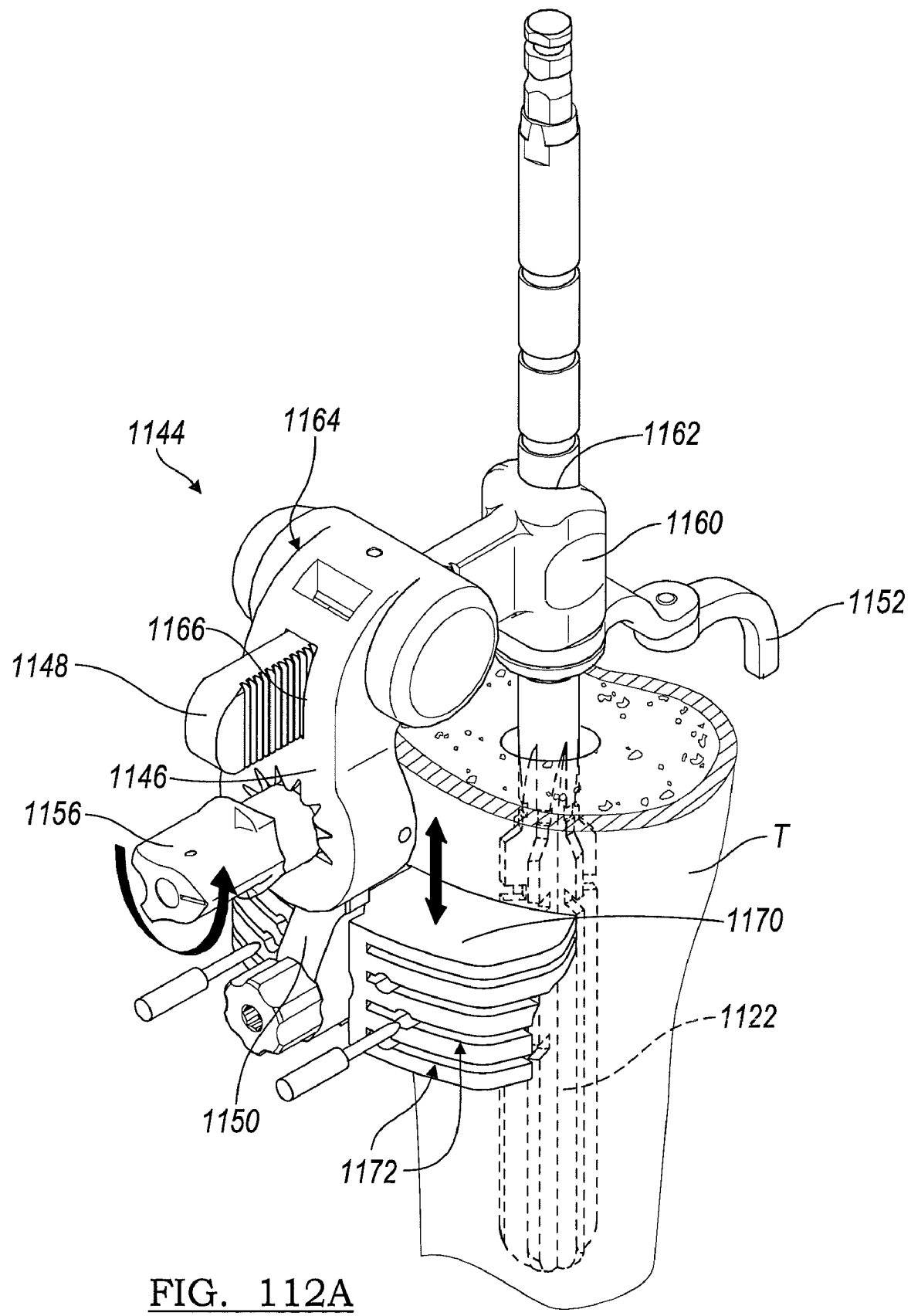
Figure 112B:
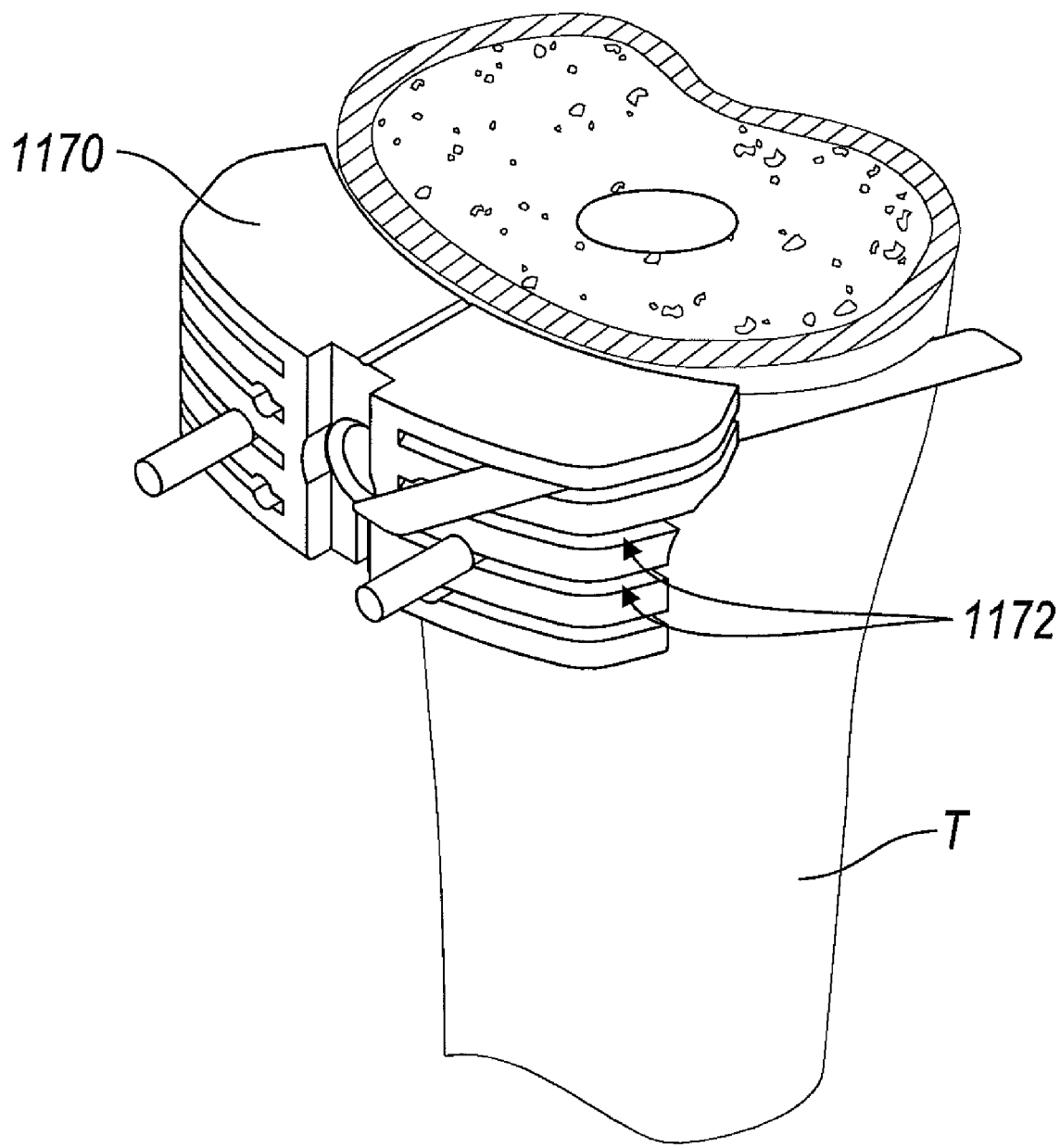

Once the IM canal of the tibia has been sufficiently prepared, as shown in FIG. 111, the IM reamer stop 1120 can be removed from the reamer 1122. The reamer 1122 remains in the IM canal. At this point, the reamer 1122 is securably retained in a fixed position by the cortical bone of the tibia T. Next, as illustrated in FIG. 112A, an IM tibial resection guide 1144 can be slid over the reamer 1122. The IM tibial resection guide 1144 can generally comprise a body 1146, an adjustment arm 1148, a block arm 1150 and a stylus or finger, 1152. The body 1146 can include a resection level adjustment knob 1156. The adjustment arm 1148 includes a hub 1160 that has a passage 1162 formed therethrough. The passage 1162, as shown, can slidably receive the reamer shaft 1140 of the reamer 1122. A coupler 1164 can adjustably secure the adjustment arm 1148 through a slot 1166 formed through the body 1146. The resection block 1170 can then be secured to the block arm 1150. The resection block 1170 can define a series of slots 1172 on a medial and lateral side. In embodiments, a trial stem (not shown) may be inserted into the intramedullary canal in order to act as a positioning reference in place of the reamer 1122.

The body 1146 can be adjusted along the adjustment arm 1148 to position the resection block 1170 against the tibia T. The resection level adjustment knob 1156 can be rotated to place the resection block 1170 at a desired level (i.e., relative to a proximal surface of the tibia). Once the desired location of the resection block 1170 has been achieved, the resection block 1170 can be fixed to the tibia (such as by pins 1174). The remainder of the IM tibial resection guide 1144 along with the reamer 1122 can be removed.

Figure 113:
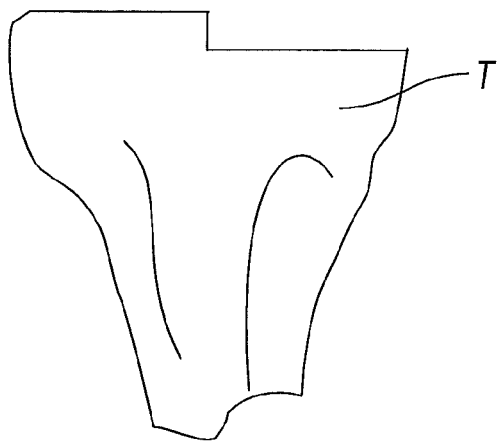

An exemplary sequence for preparing the proximal tibia for receipt of a 5 mm medial augment and a 10 mm lateral augment will now be described. It is appreciated that the medial and lateral cuts can be made to accommodate any of the tibial augments described herein, such as, but not limited to augments 540 and 540' (FIG. 31), augment 540" (FIG. 32), augment 710 (FIG. 50) or any other of the augments shown in FIGS. 55A and 55B. The resection level of the IM tibial resection guide 1144 can be set by rotating the resection level adjustment knob 1156 to the desired position. In one example, rotation of the resection level adjustment knob 1156 can adjust the block arm 1150 between a distance of 0 and 8 mm along a longitudinal axis of the block arm 1150, which moves the cutting slots 1172 in the resection block a certain distance from the top of the stylus or finger 1152 in the direction of the longitudinal axis of the block arm 1150. It is appreciated that the resection level adjustment knob 1156 can be configured to adjust the block arm 1150 to other distances. It is further appreciated that other IM tibial resection guides may be used. Once the resection level is set, a clean-up cut can be made through the 0 slot of the slots 1172 on the medial side of the resection block 1170. Similarly, a cut can be made through the 5 slot of the slots 1172 on the lateral side of the resection block 1170. An exemplary tibia is shown in FIG. 113 after cutting, while using the resection block 1170. It is appreciated that the depths of cut described above are merely exemplary. Those skilled in the art will appreciate that a depth of cut will be made that is consistent with the joint line determined as described above that can accommodate a thickness of a given bearing (i.e., such as any of the bearings discussed herein including 14 (FIG. 1), 214 (FIG. 9), 314 (FIG. 15) and 672 (FIG. 42)) and a thickness of a given augment (if necessary). Once the proximal tibia has been prepared using the resection block 1170, the resection block 1170 can be removed from the tibia T. The reamer 1122 can then be re-inserted into the IM canal.

Figure 114:
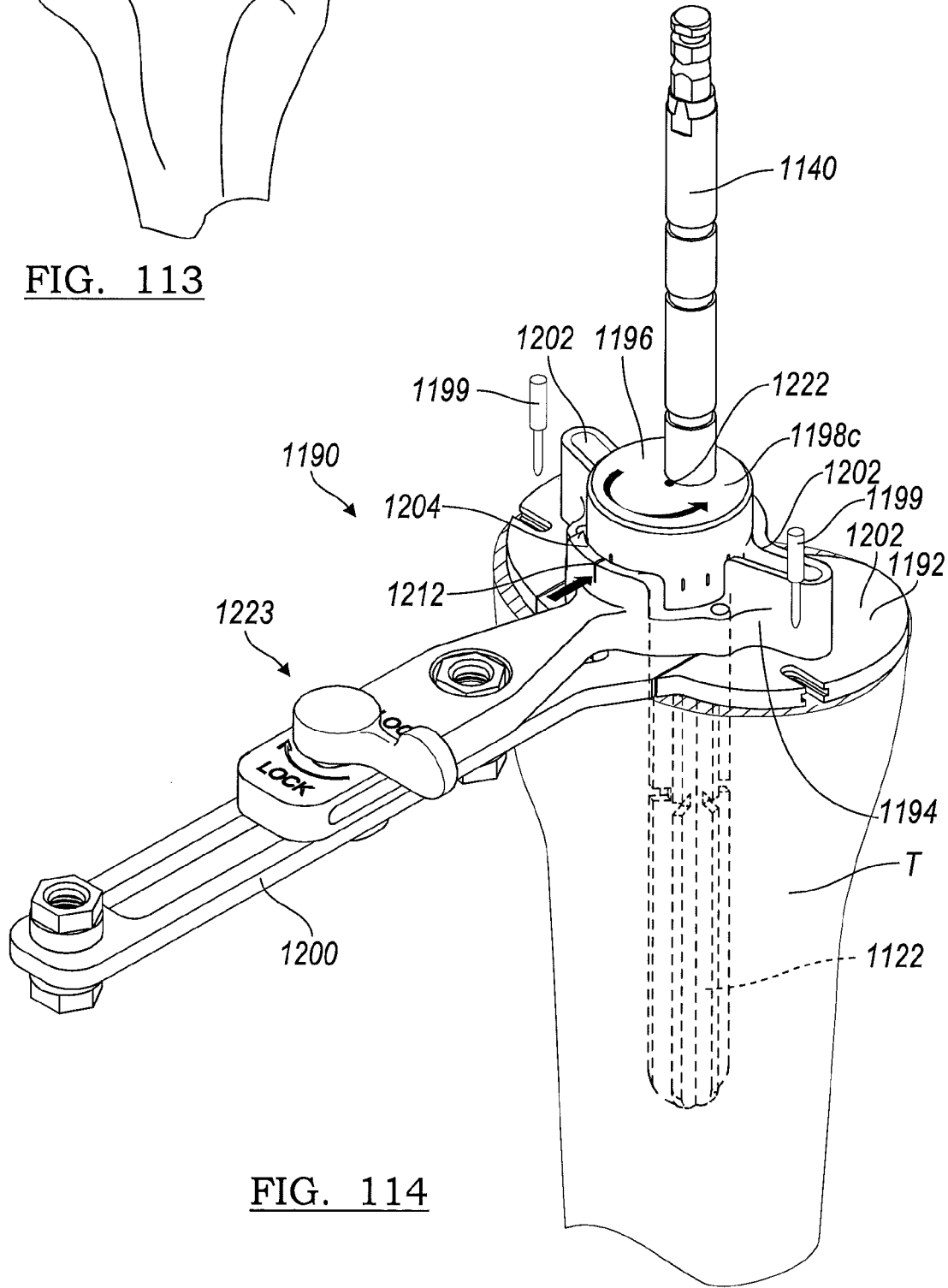

With reference now to FIGS. 108 and 114, the offset position of the reamer 1122 will be determined using a tibial offset positioning assembly 1190. The tibial offset positioning assembly 1190 can generally comprise a tibial template 1192, a tibial alignment member 1194, and a series of positioning sleeves collectively referred to by reference 1196. The tibial template 1192 can generally include a handle portion 1200 and a tibial profile portion 1202 (also see FIG. 108). The tibial alignment member 1194 can generally comprise a body 1204 that defines a bore 1206 (for rotatably receiving the positioning sleeve 1196) and a pair of radial slot passages 1210. The body 1204 can define an alignment marker 1212 formed thereon. The positioning sleeves 1196 (FIG. 108) can include a neutral positioning sleeve 1198a (0 offset), an offset sleeve 1198b (2.5 mm offset), an offset sleeve 1198c (5 mm offset) and an offset sleeve 1198d (7.5 mm offset). The positioning sleeves 1196 can each define a throughbore 1220a, 1220b, 1220c, and 1220d, respectively that is offset a distance from a longitudinal axis 1222 of the positioning sleeves 1196. The positioning sleeves 1196 include indicia, collectively referenced by numeral 1124. In the example shown in FIG. 114, the offset sleeve 1198c is received in the bore 1206 of the tibial alignment member 1194. The tibial alignment member 1194 can be fixed to the tibial template 1192 by a locking mechanism 1223.

At this point, it is important to recognize that only the reamer 1122 is fixed relative to the tibia T. The positioning sleeve 1196 is able to rotate around its longitudinal axis 1222 causing the tibial alignment member 1194 (and the tibial template 1192) to move around the proximal tibia. The positioning sleeve 1196 is rotated (e.g. by the surgeon) around its longitudinal axis 1222 until a position is attained in which the tibial profile portion 1200 achieves optimal coverage over the proximal tibia T. In some instances, the surgeon may need to swap out various offset sleeves (such as other positioning sleeves 1196) in order to attain the best possible coverage of the proximal tibia. Once the desired proximal tibial coverage is verified, the tibial template 1192 is fixed relative to the tibia T, such as by pins 1199. At this point, the surgeon can make a note of the indicia 1224 relative to the mark 1212 on the tibial alignment member 1194. This will correspond to the tibial offset position. In some instances, no offset will be necessary (i.e., optimal coverage is confirmed with the 0 positioning sleeve 1198a).

Figure 115:
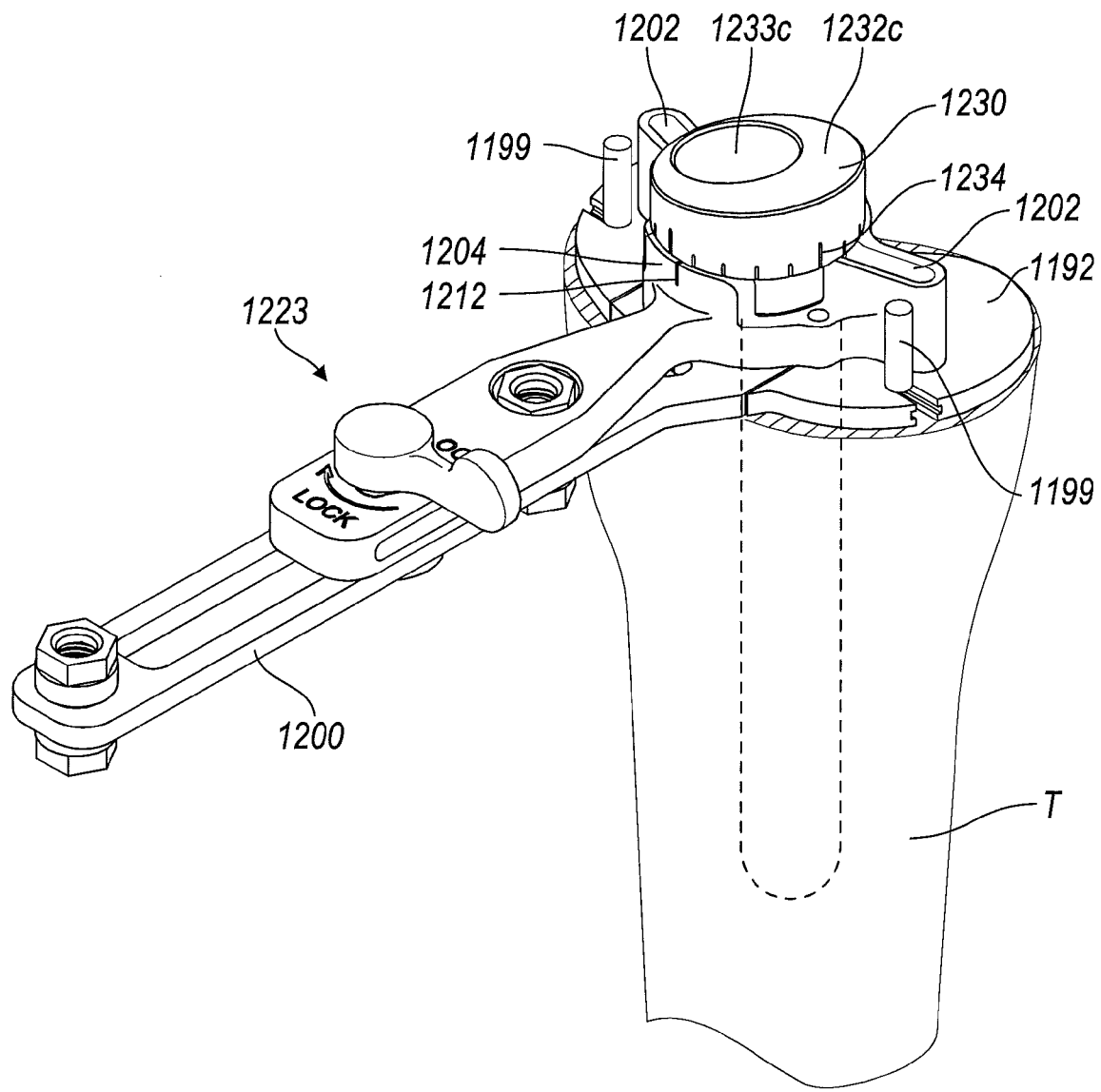

Once the tibial template 1192 has been secured to the proximal tibia T with the pins 1198, the positioning sleeve 1196 can be removed from the alignment member 1194. The reamer 1122 can also be removed at this point. One reamer sleeve selected from a group collectively referenced by numeral 1230 (FIG. 108), can then be located into the bore 1206 of the tibial alignment member 1194 (FIG. 115). The collective reamer sleeves 1230 (FIG. 108) can include a neutral reamer sleeve 1232*a* (0 mm offset, or neutral offset), an offset reamer sleeve 1232*b* (2.5 mm offset), an offset reamer sleeve 1232*c* (5 mm offset), and an offset reamer sleeve 1232*d* (7.5 mm offset). The reamer sleeves 1230 can each define a throughbore 1233*a*, 1233*b*, 1233*c* and 1233*d*, respectively. As can be appreciated, each offset corresponds to a radial offset from the longitudinal axis of the tibia T. Each of the reamer sleeves 1230 can correspond to a respective positioning sleeve 1196. In this way, a surgeon will select an offset reamer sleeve 1230 having a similar offset as the positioning sleeve 1196 identified above. The reamer sleeves 1230 can define indicia 1234 and facets 1235 around its radial surface. The surgeon then rotates the offset reamer sleeve 1230 within the bore 1206 of the tibial alignment member 1194 to align the indicia 1234 with the mark 1212 of the tibial alignment member 1194. It is important to recognize that the surgeon rotates the reamer bushing 1230 in order to align a common indicia 1234 of the reamer bushing 1230 with the same indicia 1224 that was determined by the positioning sleeve 1196 (FIG. 114). Once the reamer bushing 1230 has been rotated to the desired orientation, the reamer bushing 1230 can be advanced toward the tibial alignment member 1194 such that the facets 1235 interface with a series of flats 1238 (only one flat specifically shown in FIG. 108 formed on the tibial alignment member 1194).

Figure 116A:
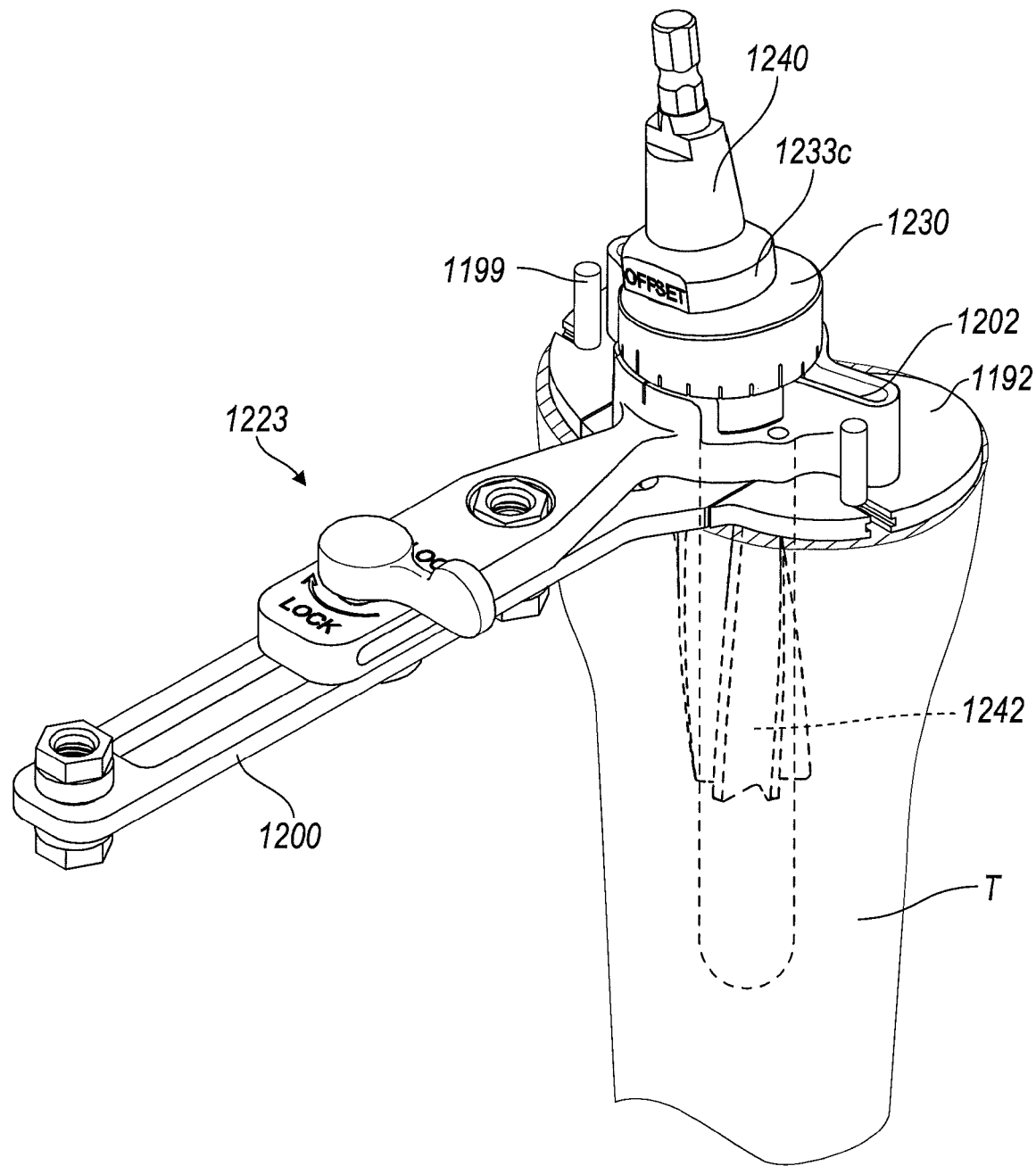
Figure 116B:
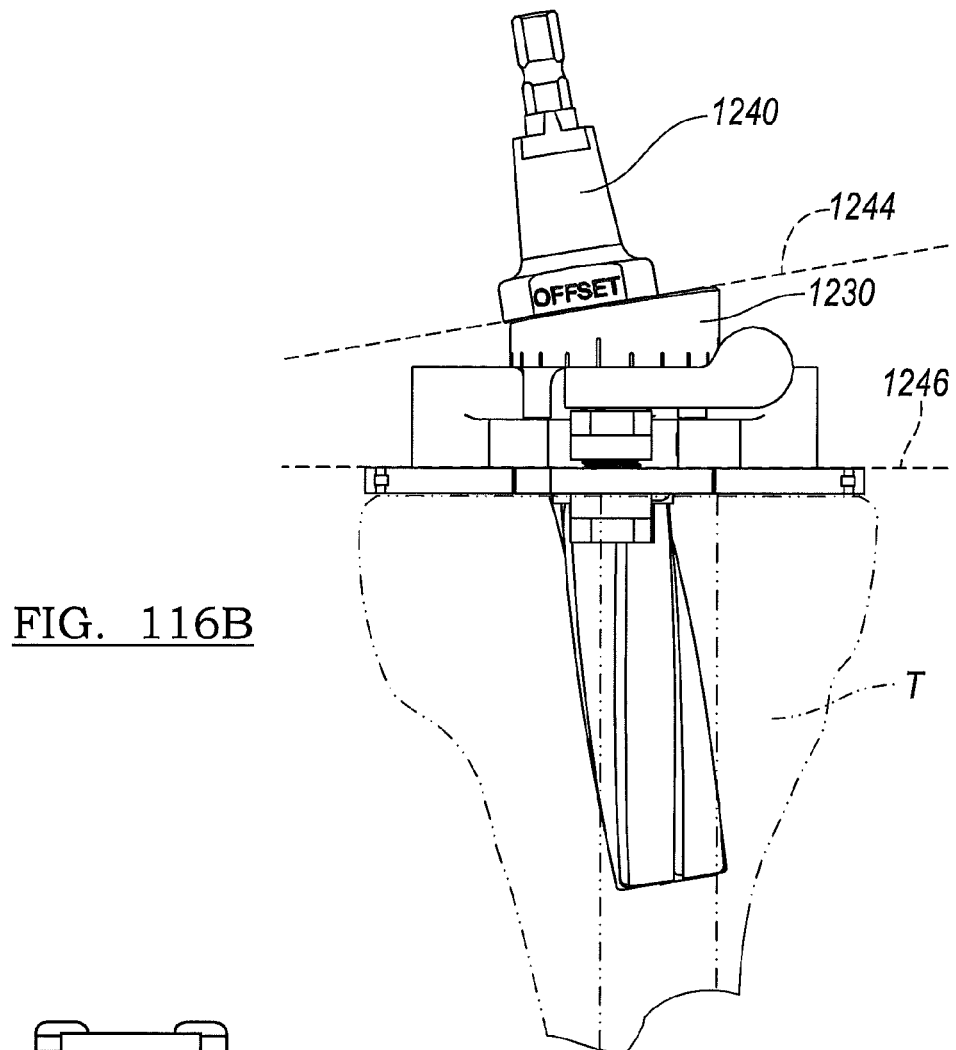
Figure 117:
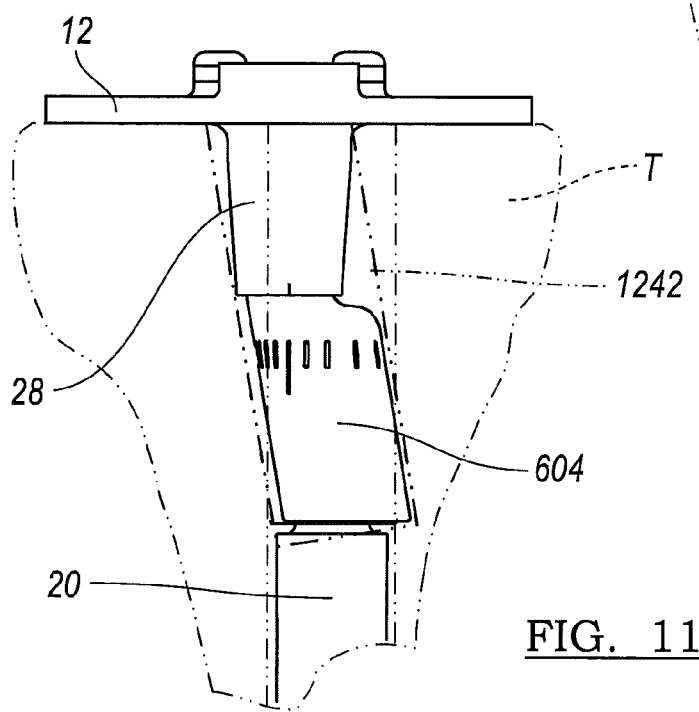

Turning now to FIGS. 116A and 116B, once the offset reamer sleeve 1230 has been rotated to the desired location, a reamer 1240 is inserted through the reamer bore (i.e., 1233*c*) and an offset cavity 1242 is reamed to accommodate an implant boss (such as the implant boss 28, FIG. 34) and an offset adapter (such as the adapter body 604, FIG. 34). Notably, as illustrated in FIG. 116B, the offset reamer sleeve 1230 defines an upper plane 1244 and a lower plane 1246 that are non-parallel. As can be appreciated, the series of offset reamer sleeves 1230 can be provided having various upper and lower planes that diverge at various distinct angles. As can be appreciated, each offset reamer bushing (such as 1230) can correspond to an angle of reaming that will accommodate the profile of any of the given offset adapters (such as the adapter 604, FIG. 35) disclosed herein. As illustrated in FIG. 117, the cavity 1242 can accommodate the adapter body.

Figure 118B:
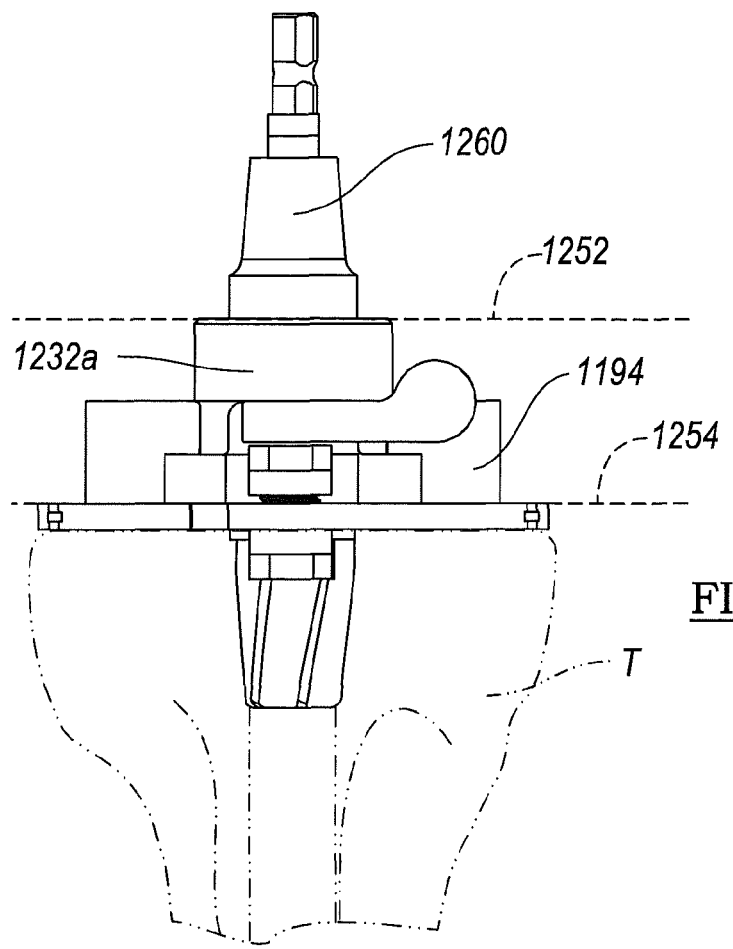
Figure 118A:
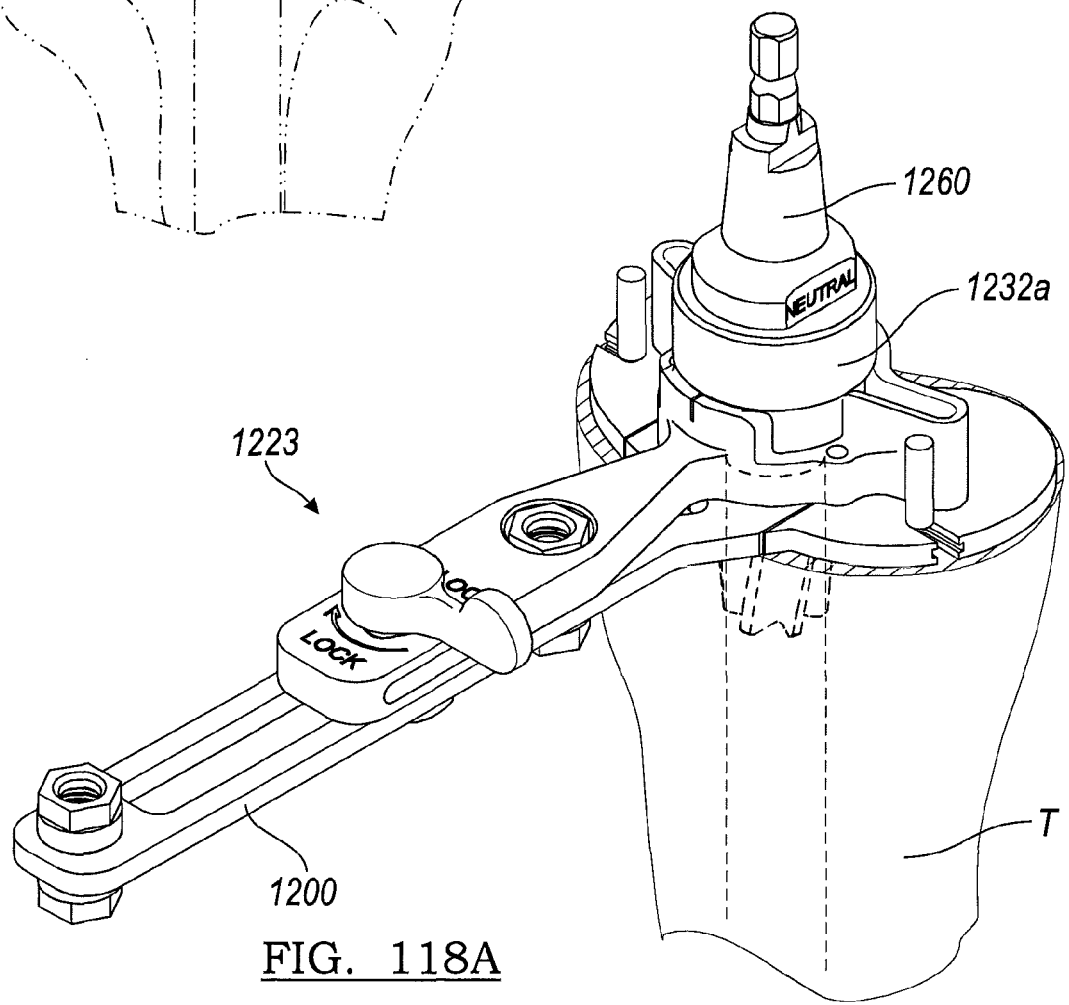
Figure 119:
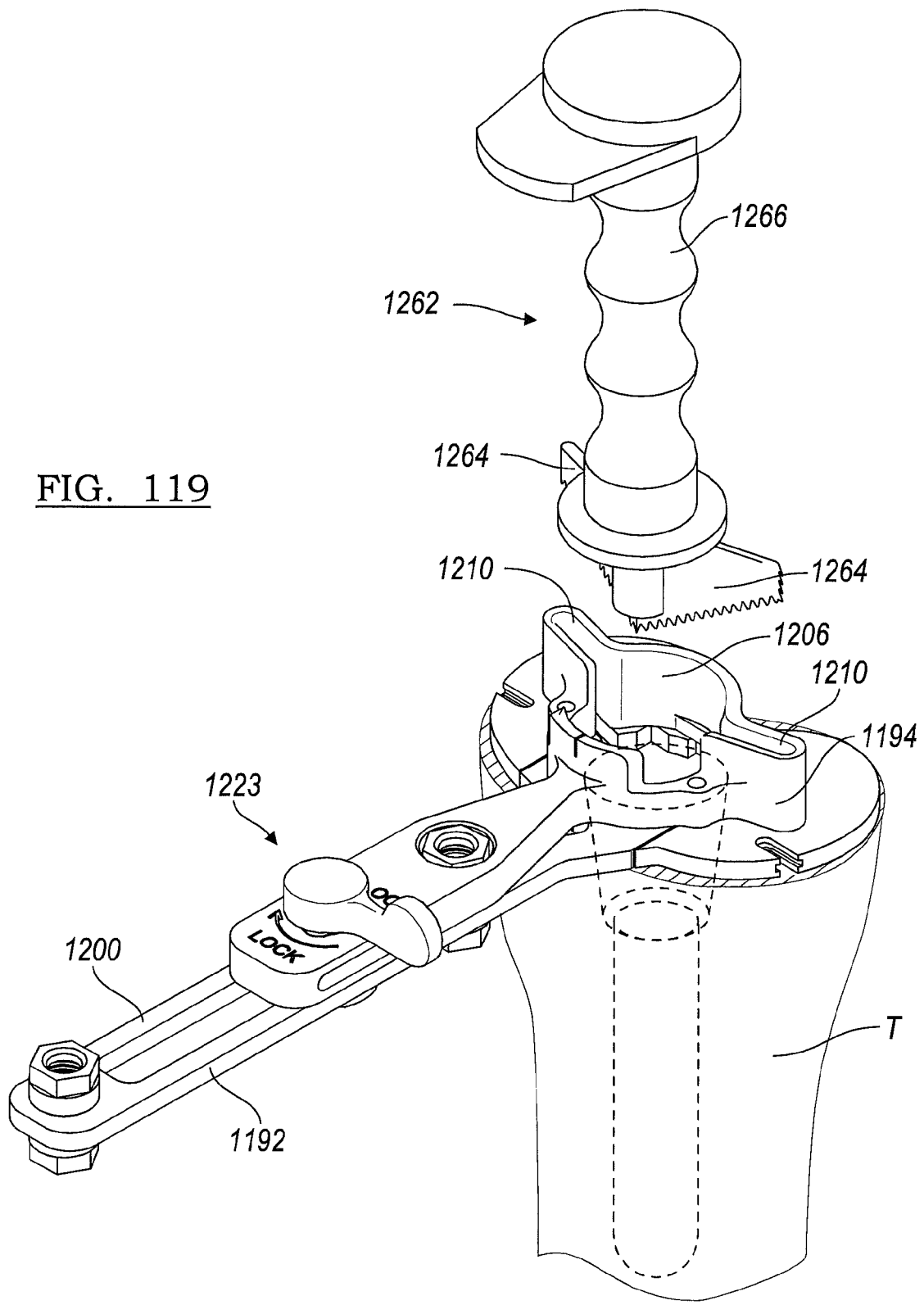

In some examples, the neutral offset bushing 1232*a* can be used in instances where an offset adapter is unnecessary. As best shown in FIGS. 118A and 118B, the neutral offset bushing 1232*a* defines an upper surface 1252 and a lower surface 1254 that are parallel. A reamer 1260 can be used to ream an opening in the proximal tibia that will accommodate the tibial implant boss (such as reference numeral 28, FIG. 35).

Figure 120:
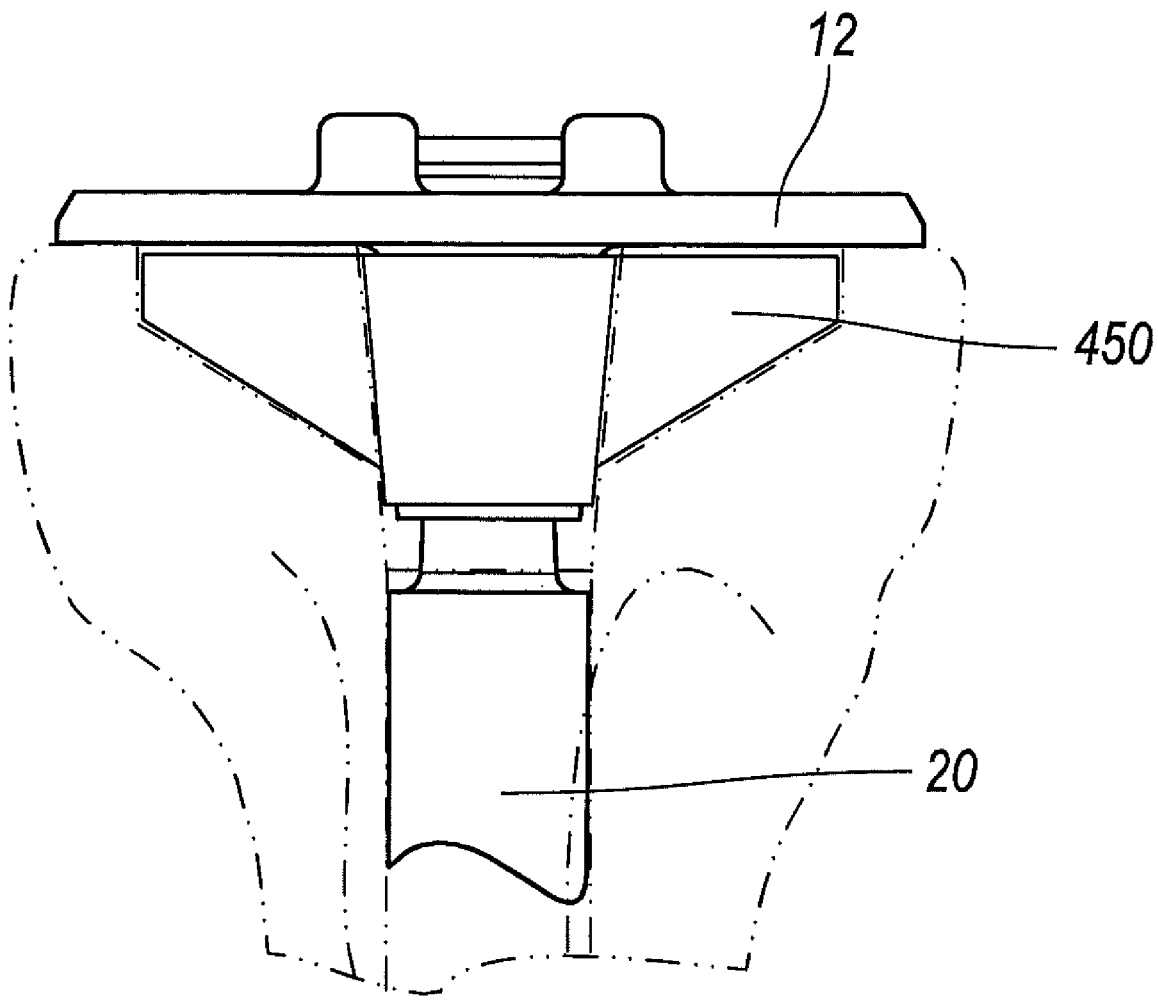

In examples where the tibia T must be prepared for receipt of a cruciate augment (such as augment 450, illustrated in FIG. 60), a cruciate augment punch 1262 (FIG. 119) can be passed through the bore 1206 of the tibial alignment member 1194. More specifically, the punch 1262 can define a winged plate with cutting teeth 1264 that can pass through the slot passages 1210 formed on the tibial alignment member 1194 while a surgeon grasps the ribbed handle portion 1266. The surgeon can repeatedly axially drive the punch 1260 through the tibial alignment member 1194 creating the complementary passages in the proximal tibia to receive the winged portions of the augment 450, as shown in FIG. 120.

With reference now to FIGS. 121-140, another exemplary method for preparing a femur during revision surgery will be described. Again it is appreciated that in a revision surgery, it may be necessary to remove a prior implanted femoral component in any suitable manner. At the outset, the IM reamer stop 1120 can be coupled to the reamer shaft 1140 at the desired location. The reamer 1122 can cooperate with the IM reamer stop 1120 to prepare the IM canal of the femur in a similar manner as described above with respect to preparation of the IM canal of the tibia (see FIGS. 111 and 112). Also, as discussed above, the grooves 1142 can correspond to various depths of reaming into the femur. As can be appreciated, the various depths of reaming can correspond to various lengths of femoral stems, such as the femoral stem 20 illustrated in FIG. 26 or any of the femoral stems illustrated in FIG. 55A.

Figures 121, 122A:
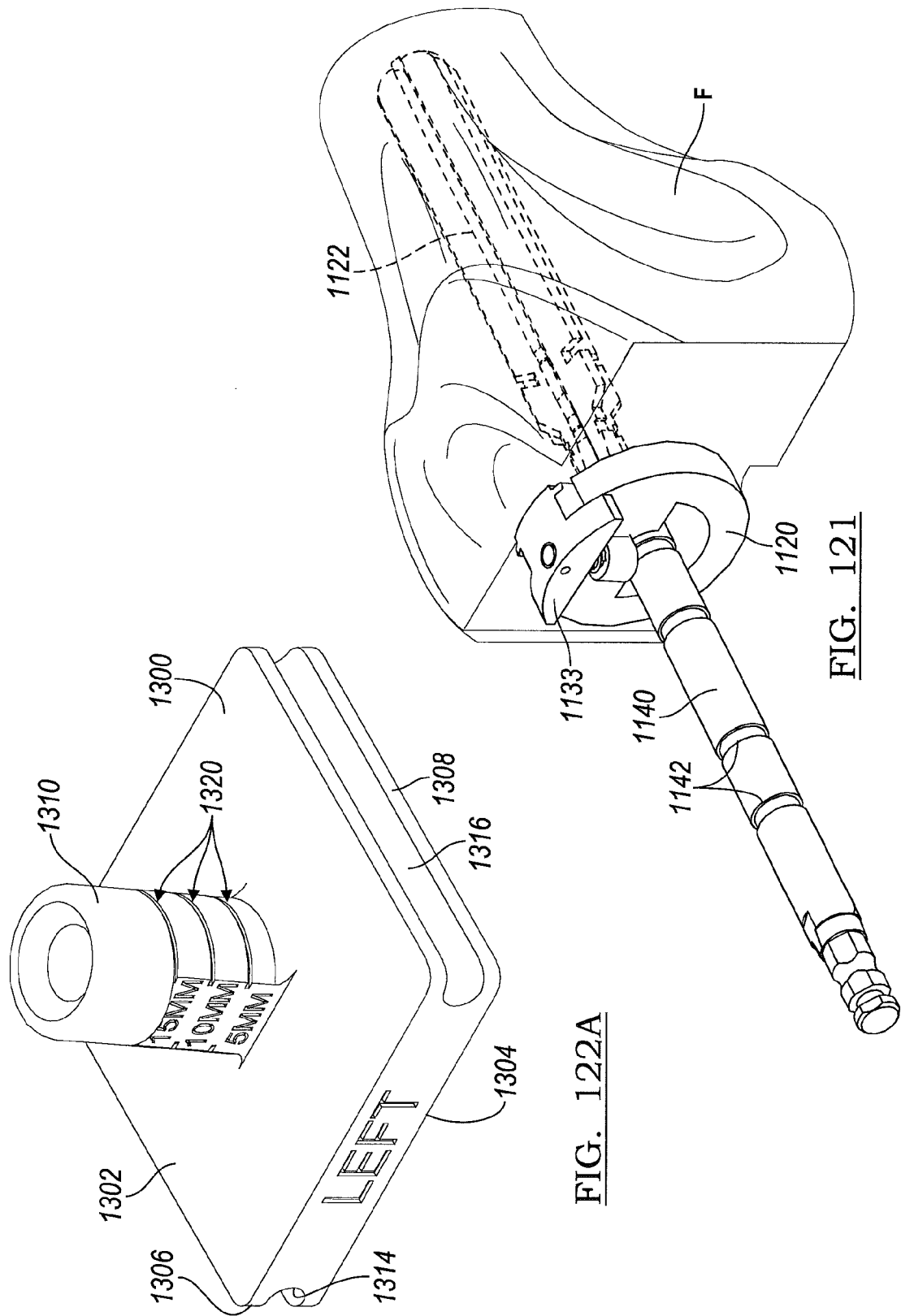
FIGS. 121-140 illustrate various instruments and a related sequence for preparing a femur for receipt of a femoral prosthesis.

As with the tibia, in some instances it may be necessary to implant an offset adapter, such as the offset adapter 600, FIG. 35 or any of the other offset adapters described herein, such as the adapters illustrated in FIGS. 55A and 55B. In those examples wherein an offset adapter is needed in conjunction with a stem, the grooves 1142 will correspond to different lengths of stems. For example, if a 40 mm offset adapter will be used, the groove that corresponds to an 80 mm femoral stem (used alone) will also correspond to a 40 mm femoral stem that will be used in conjunction with a 40 mm femoral offset adapter. Again, the grooves can be provided in any combination of configurations along the reamer 1122 for identifying a depth of reaming that can accommodate any combination of stems and/or offset adapters described herein. Various reamers 1122 having distinct diameters can be used until adequate cortical contact is achieved in the femur F (FIG. 121). As explained above, multiple IM reamer stops 1120 can be provided, each being operatively connected to a reamer 1122 having a distinct diameter.

Turning now to FIG. 122A, a femoral spacer 1300 is shown. The femoral spacer 1300 generally comprises a superior surface 1302, an inferior surface 1304, a medial surface 1306, a lateral surface 1308 and a boss 1310. A medial slot 1314 can be formed along the medial surface 1306. A lateral slot 1316 can be formed along the lateral surface 1308. A series of depth markings 1320 can be formed on the boss 1310. The depth markings 1320, as will be described, can be referenced to identify any potential augment requirement on the distal femur. As described above, with reference to FIGS. 26 and 27, in some instances it may be necessary to implant distal femoral augments, such as identified at reference numeral 400 and 402, or any other of the augments identified herein, such as the augment 450, FIG. 24, the augment 590, FIG. 33, or any of the other augments identified herein, such as illustrated in FIGS. 55A and 55B.

Figure 122B:
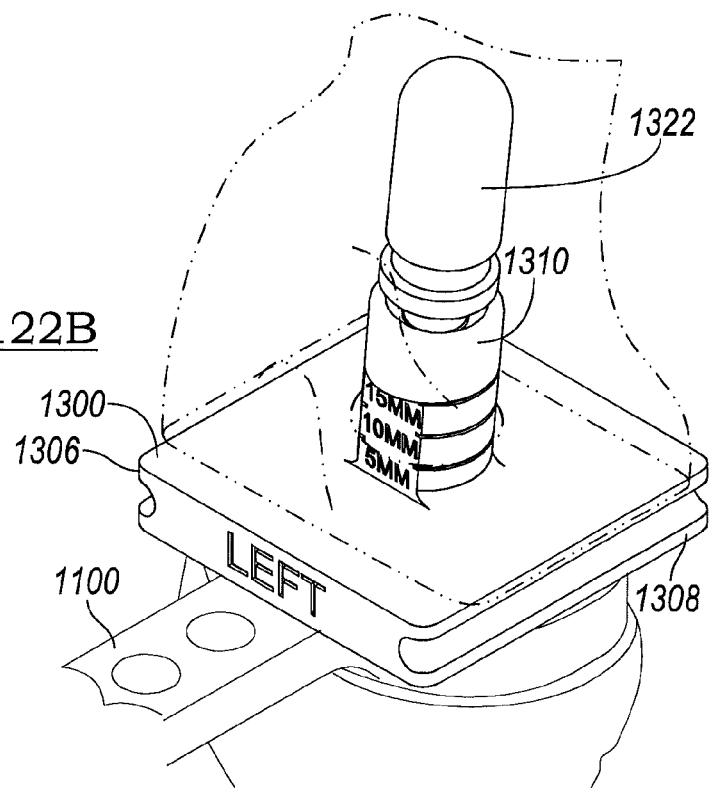
Figure 122C:
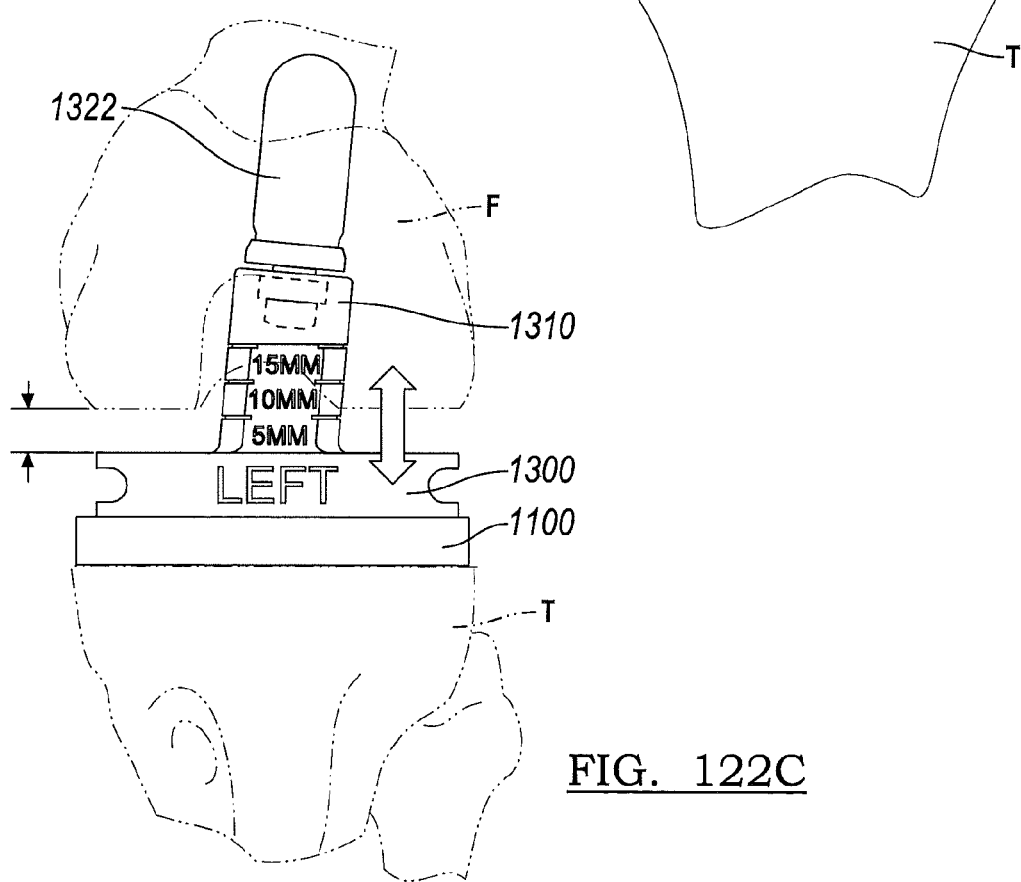

Once the IM canal has been reamed, the reamer 1122 (along with the reamer stop 1120) can be removed from the femur F. A trial stem 1322 with a diameter corresponding to the reamer previously used, can be attached to the boss of the femoral spacer. The boss 1310 of the femoral spacer 1300 in combination with a trial stem can be inserted into the IM canal of the femur F (FIGS. 122B and 122C). The joint line with respect to the tibia can be re-visualized using one of the same tibial spacers 1100 as when preparing the tibia. The tibia T and femur F can then be brought into extension while keeping the respective femoral spacer 1300 and tibial spacer 1100 placed on the femur and tibia, respectively. The joint line is represented by the tibial plateau portion 1104 of the tibial spacer 1100, which is determined based on anatomical landmarks. At this time, the distal augmentation needs for the tibia T and femur F can be determined by allowing the inferior surface 1304 of the femoral spacer 1300 to meet the tibial plateau portions 1104 of the tibial spacer 1100. Once the two surfaces have met, a number of depth markings 1320 may be visible on the medial or lateral side of the femur to imply that a corresponding distal augment may be needed. Likewise, a thickness of a bearing (such as bearing 14, FIG. 3A or any of the other bearings identified herein) can be re-verified. In one example, the femoral spacer 1300 can be adapted for use with either a left or a right femur. The femoral spacer 1300 can be rotated 180 degrees about a boss 1310 for use between a right or left femur. In other examples, a dedicated femoral spacer 1300 can be provided that is specifically configured for each of a right or left femur.

Figure 123:
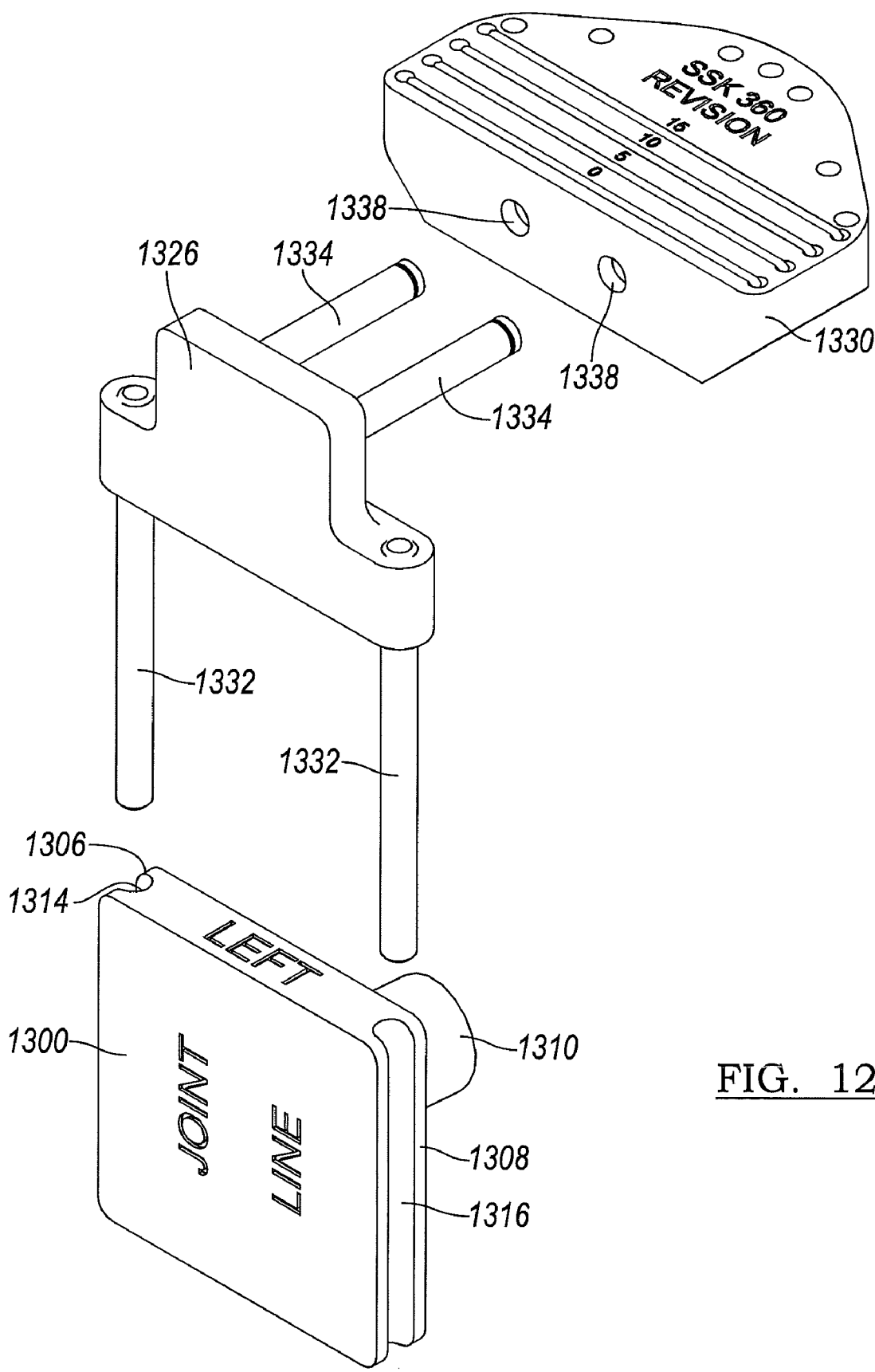
Figure 124A:
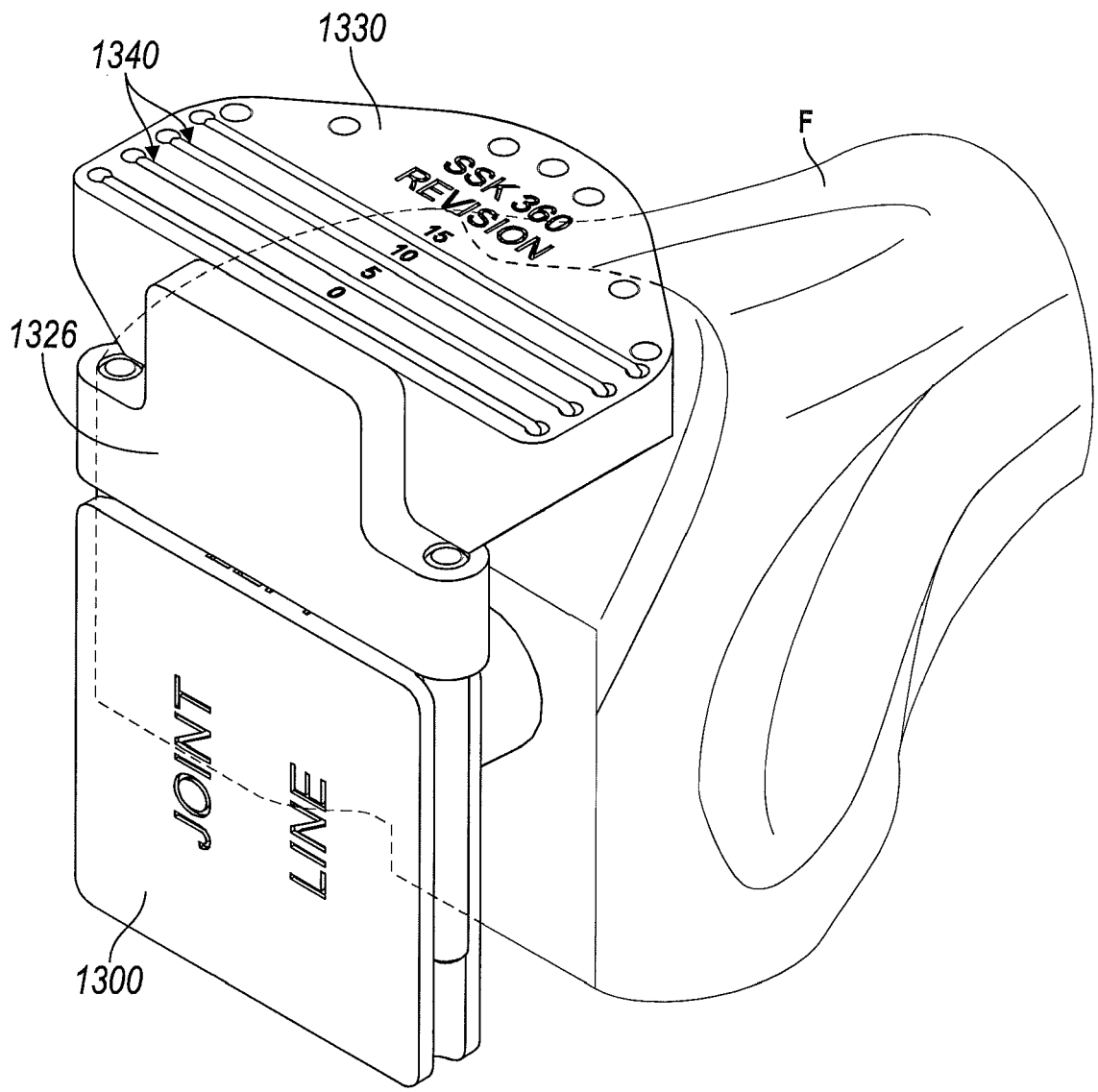
Figure 124B:
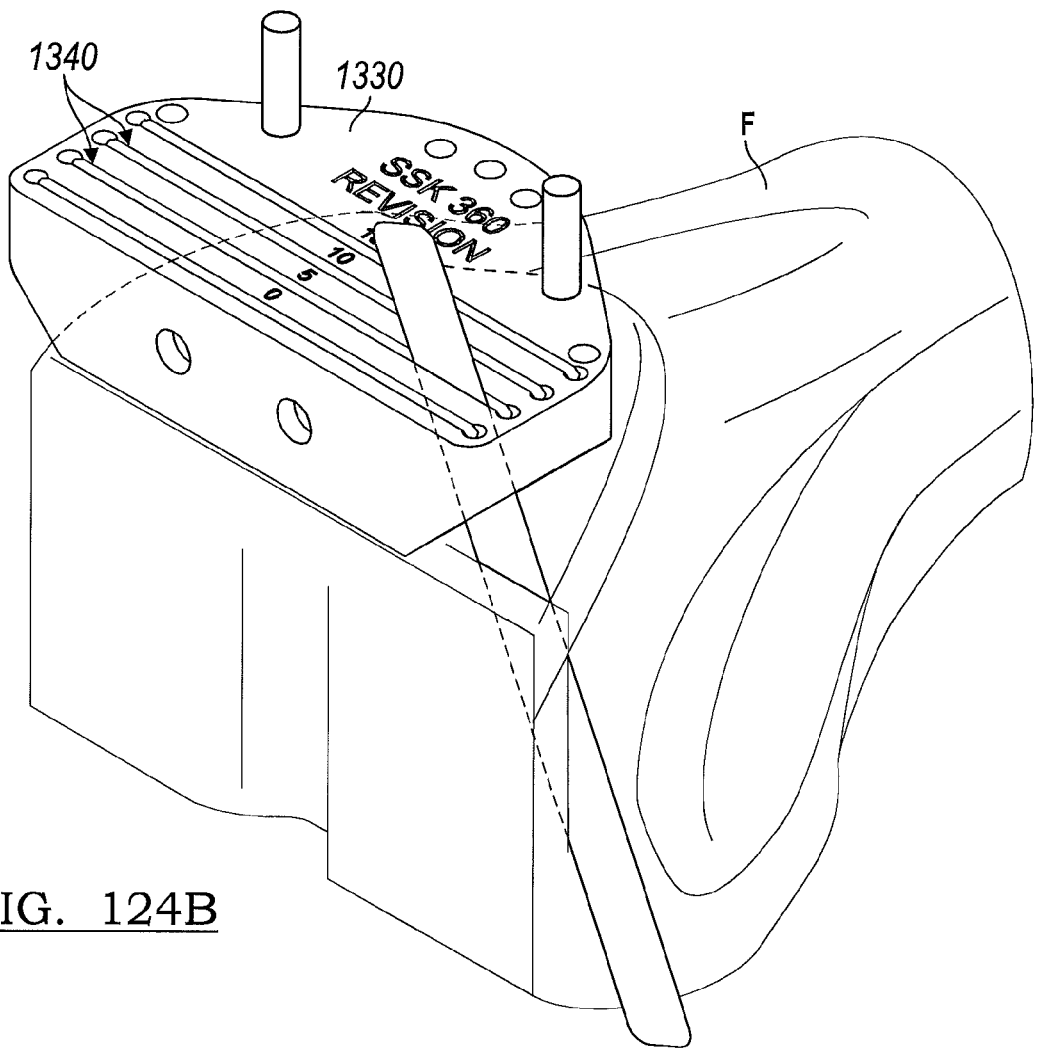
Figure 125:
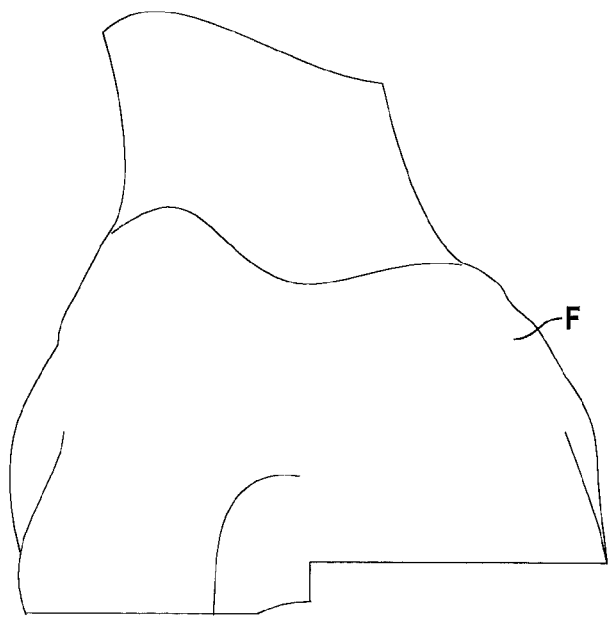

With reference now to FIG. 123, the femoral spacer 1300 can cooperatively mate with a tower 1326. The tower 1326 can operatively connect to a distal revision block 1330. Specifically, the tower 1326 can include spacer posts 1332 that can slidably advance along the respective medial and lateral slots 1314 and 1316 defined on the femoral spacer 1300. Block posts 1334 can slidably advance into bores 1338 defined in the distal revision block 1330. In one example, the tower 1326 and the distal revision block 1330 can be connected to the femoral spacer 1300 while the boss 1310 of the femoral spacer 1300 remains in the IM canal of the femur F. Once the tower 1326 is advanced into a connected relationship with the femoral spacer 1300 and the distal revision block 1330 is advanced into a connected relationship with the tower 1326, the distal revision block 1330 can be secured to the femur F and the reamer 1122, the tower 1326 and femoral spacer 1300 can be removed from the femur F (FIG. 124B). Distal cuts can be made on the femur F using any of the slots 1340 defined in the distal revision block 1330 (see FIG. 125) in order to make a distal resection or prepare for distal augments, if necessary.

Figure 126A:
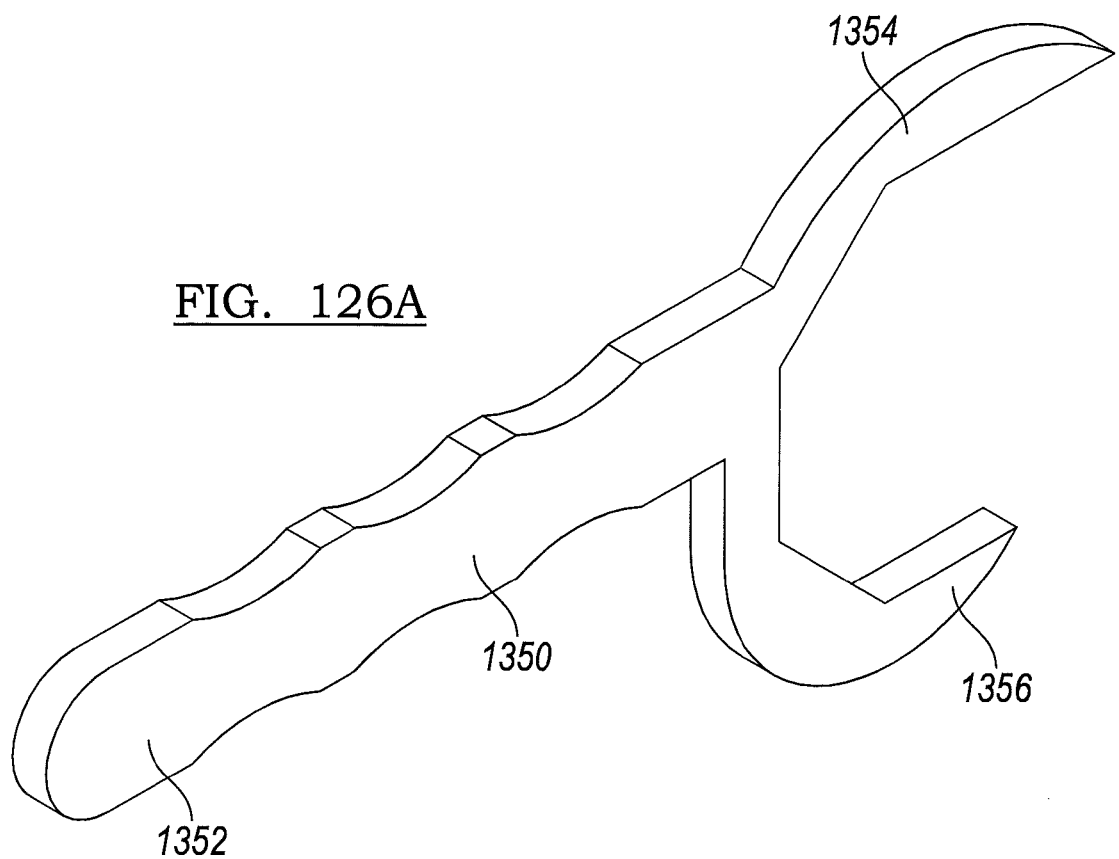
Figure 126B:
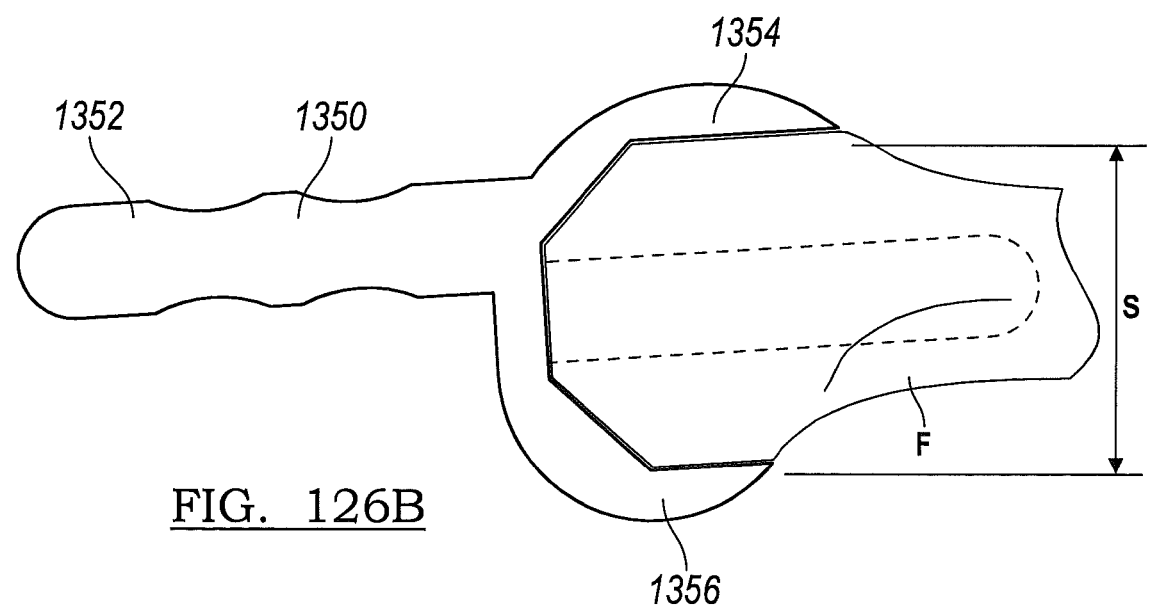

With reference now to FIGS. 126A and 126B, a femoral sizer tool 1350 is shown. The femoral sizer tool 1350 can be used to approximate the desired size of femoral component (i.e., reference number 112, FIG. 8) and/or scaffold, skeleton or frame 1362 (described later herein). The femoral sizer tool 1350 can generally include a handle portion 1352, an anterior finger 1354 and a posterior finger 1356. As shown in FIG. 126B, the femoral sizer tool 1350 can be used to approximate the anterior/posterior size of the distal femur F. The femoral sizer tool 1350 can be advanced toward the distal femur F, such that the anterior finger 1354 and the posterior finger 1356 locate adjacent to the respective posterior and anterior surfaces of the femur F. A plurality of femoral sizer tools can be provided each having a distinct span S between respective anterior and posterior fingers 1354, 1356. As such, if a selected femoral sizer tool 1350 does not satisfactorily fit against an anterior and posterior side of the femur F (see FIG. 126B), another femoral sizer tool having a different span S between respective anterior and posterior fingers 1354, 1356 can be used.

Figure 127:
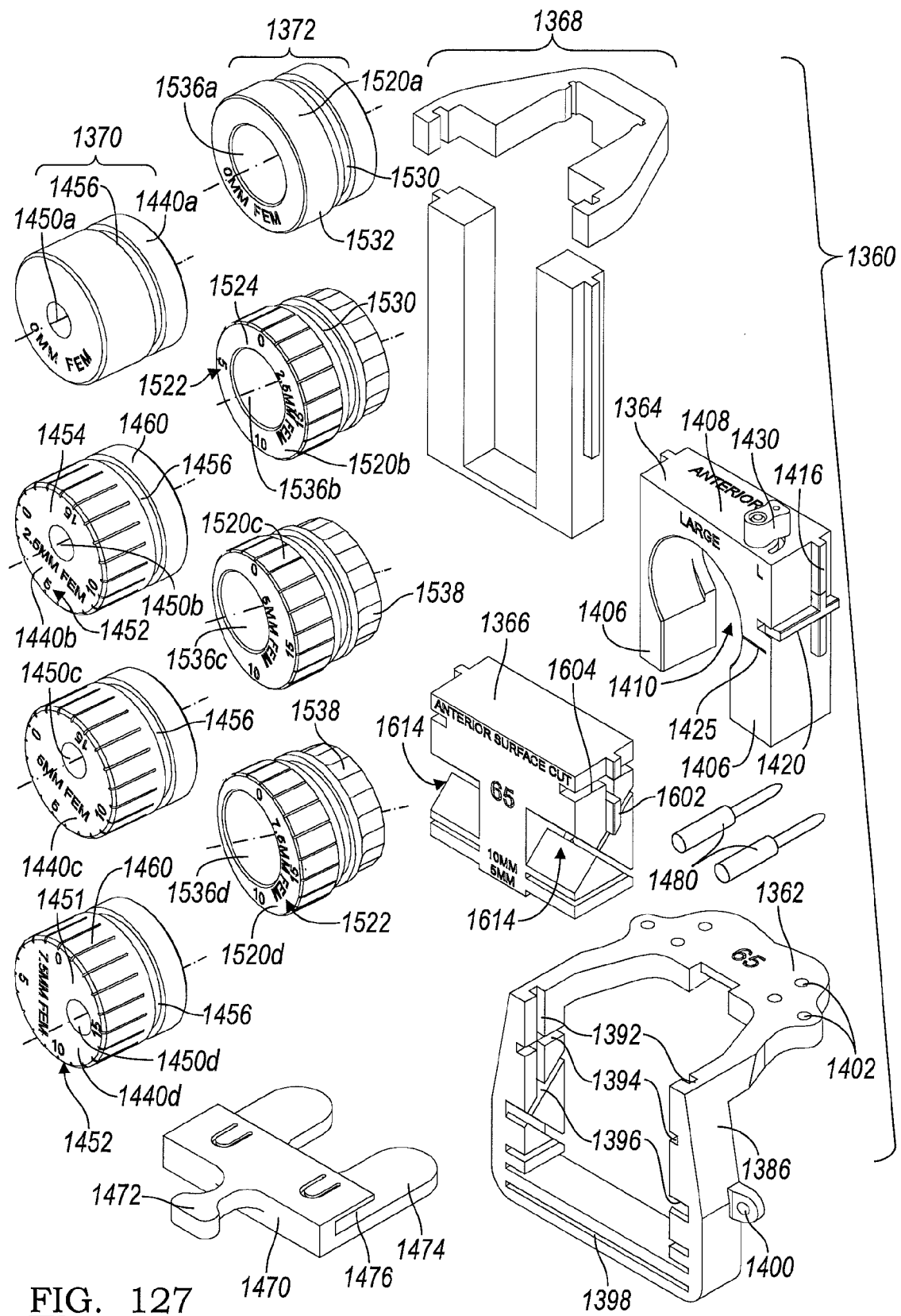

Turning now to FIG. 127, a system or kit 1360 having a collection of components adapted for use in preparing a distal femur according to one example of the present teachings is shown. The kit 1360 can include a plurality of different sized scaffold, skeleton or frames 1362, a mask or femoral alignment member 1364, a cutting block 1366, a posterior stabilized (PS) box guide assembly 1368, a series of locating bushings, collectively referenced by numeral 1370, and a collection of reamer bushings, collectively referenced by numeral 1372. The alignment member 1364 and the series of locating bushings 1370 and the collection of reamer bushings 1372 can collectively define an alignment assembly. As will become appreciated from the following discussion, the kit 1360 of the present teachings allows a surgeon to selectively and alternatively attach, in sequence, the alignment member 1364, the cutting block 1366, and the PS box guide assembly 1368 to the frame 1362. In sum, the alignment member 1364 (in combination with the locating bushing 1370 and the reamer bushing 1372) can be coupled to the frame 1362 for preparation of a bore reamed in the distal femur. The alignment member 1364 can then be removed from the frame 1362. The cutting block 1366 can then be coupled to the frame 1362 for preparation of the distal femoral cuts. The cutting block 1366 can then be removed from the frame 1362. The PS box guide assembly 1368 can then be coupled to the frame 1362 and then necessary cuts for the PS box can then be made in the distal femur. As will become appreciated from the following discussion, by using the frame 1362 as a fixed reference while simply exchanging other components of the kit 1360 into the frame 1362, an accurate and efficient system is provided for preparing the distal femur.

Figure 128:
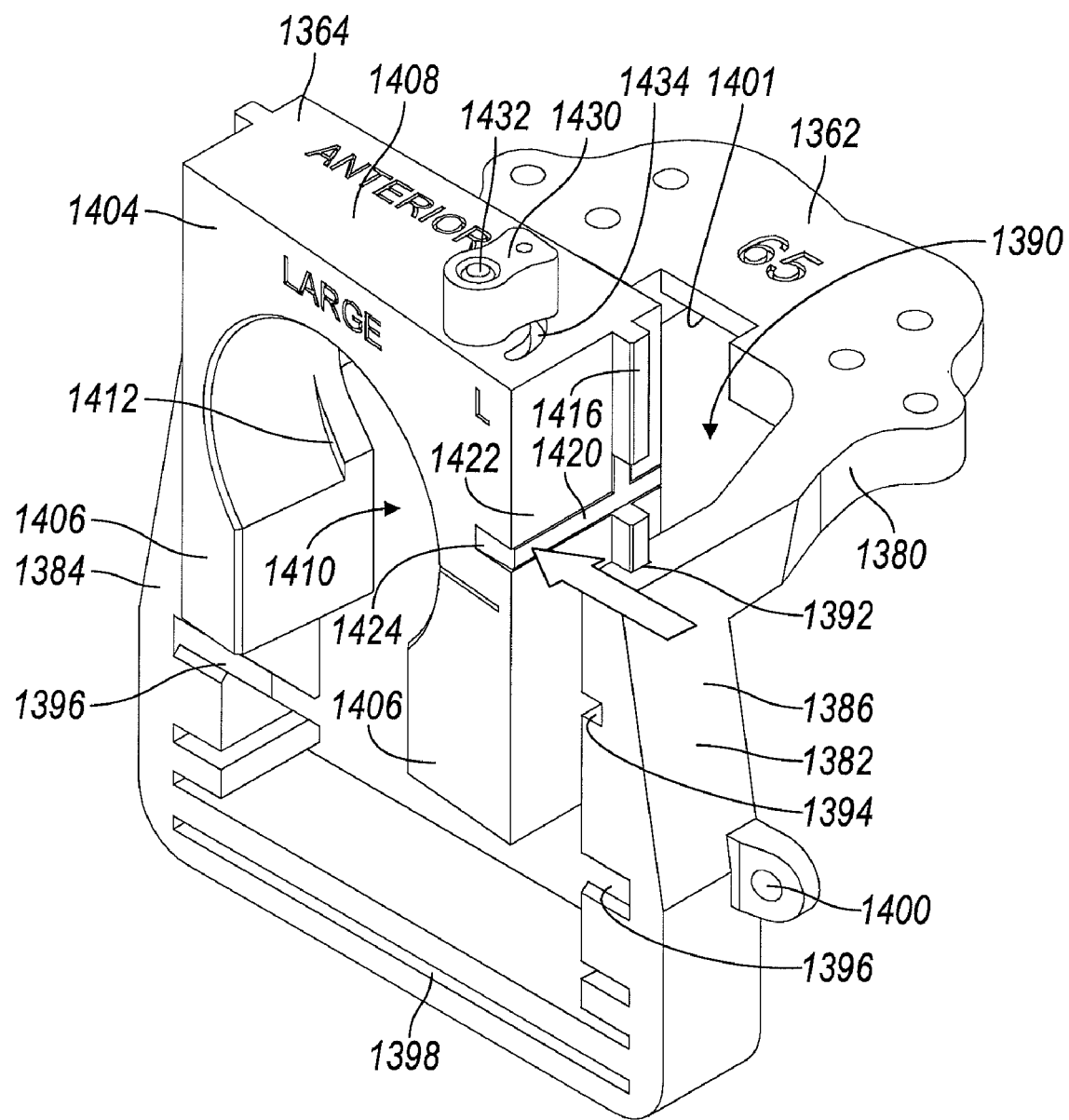
Figure 129:
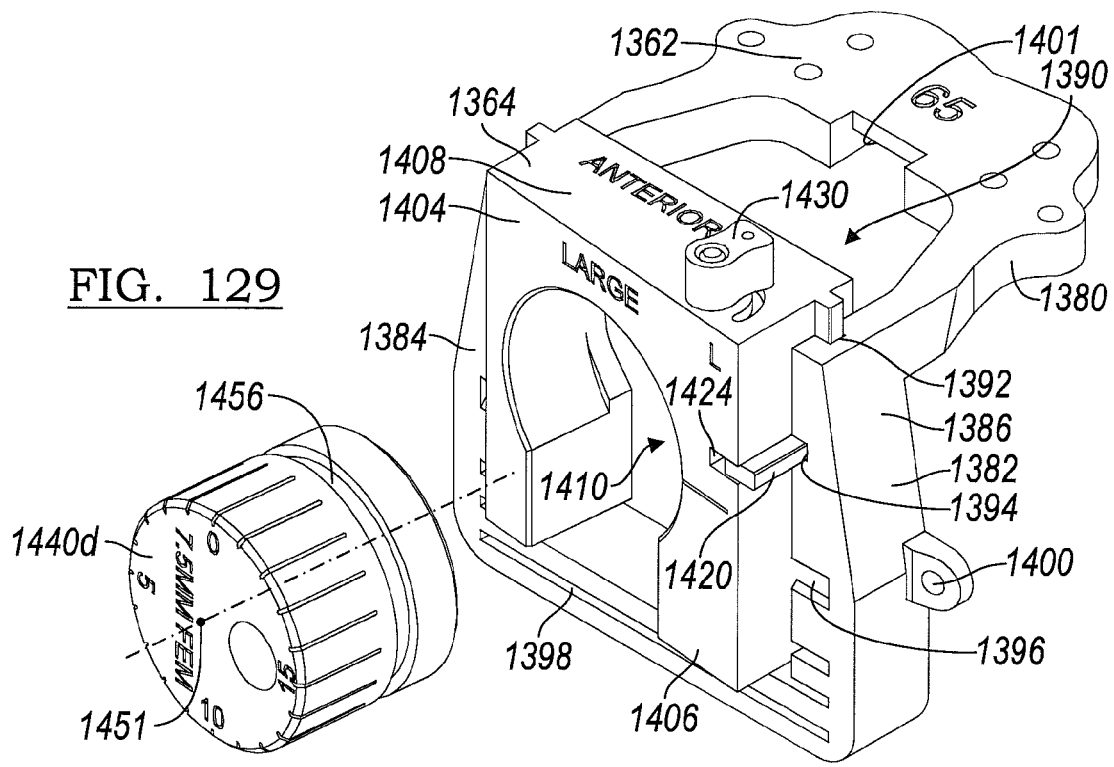
Figure 130:
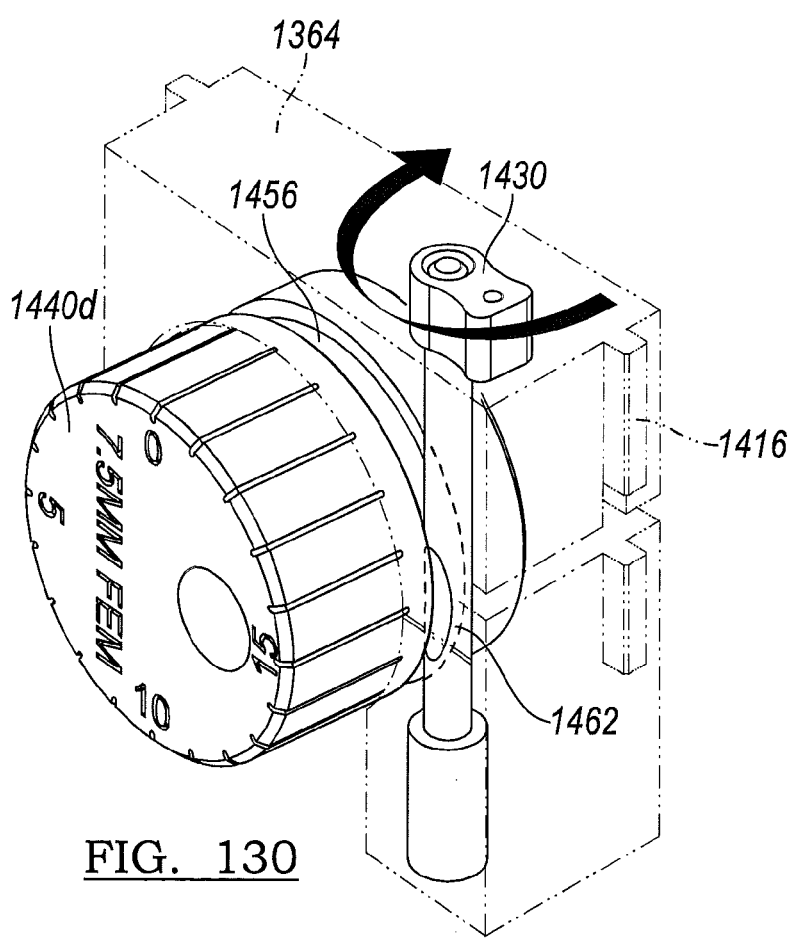

With continued reference to FIG. 127 and additional reference to FIG. 128, the frame 1362 and the alignment member 1364 will be described in greater detail. The frame 1362 can generally comprise an anterior section 1380 and a distal section 1382. The distal section 1382 can comprise a medial frame portion 1384 and a lateral frame portion 1386. The medial frame portion 1384 and the lateral frame portion 1386, along with the anterior section 1380, can collectively define an entryway 1390. The distal section 1382 can include a first pair of opposing attachment portions or guide slots 1392 formed along the respective medial and lateral frame portions 1384 and 1386. The distal section 1382 can further comprise a second pair of opposing locking slots 1394 formed along the medial and lateral frame portions 1384 and 1386. The distal section 1382 can further comprise cutting surface extensions 1396 formed in the medial and lateral frame portions 1384 and 1386, respectively. The distal section 1382 can further comprise a posterior cutting slot 1398. A pair of eyelets 1400 can be formed on the distal section 1382. The anterior section 1380 can define a shelf 1401 and a plurality of passages 1402 formed therethrough.

The alignment member 1364 can comprise a body 1404. The body 1404 can generally comprise a pair of lateral sections 1406 and an upper section 1408. The lateral sections 1406 and the upper section 1408 can cooperate to define a receiving portion or keyway 1410 defined through the body 1404. An axial stop 1412 can be formed on the lateral section 1406. The axial stop 1412 generally extends into the keyway 1410. A pair of lateral rails 1416 can extend from the respective lateral sections 1406. A locking or transverse rail 1420 can extend from one of the lateral sections 1406. A biasing member 1422 can bias the transverse rail 1420 in a direction generally outwardly from the lateral section 1406. The transverse rail 1420 can be depressed into a channel 1424 defined in the lateral section 1406 against the bias of the biasing member 1422. A knob 1430 can be rotatably fixed to the upper section 1408 of the alignment member 1364. The knob 1430 can be operable to rotate about an axis 1432 and follow an arcuate path defined by a slot 1434 formed in the upper section 1408 of the alignment member 1364.

Assembly of the alignment member 1364 into the frame 1362 according to one example of the present teachings will now be described. At the outset, a surgeon can depress the transverse rail 1420 into the channel 1424 of the body 1404. In one example, the transverse rail 1420 can be flush or substantially flush with an outer surface of the lateral section 1406. Next, the surgeon can advance the alignment member 1364 into the entryway 1390 of the frame 1362. More specifically, the lateral rails 1416 of the alignment member 1364 can be aligned with the first pair of guide slots 1392 of the frame 1362. While the transverse rail 1420 remains depressed, the lateral rails 1416 of the alignment member 1364 can be advanced along the first pair of guide slots 1392 of the frame 1362. Once the transverse rail 1420 advances to a location beyond the anterior section 1380, the lateral frame portion 1386 will maintain the transverse rail 1420 in a depressed position until the transverse rail 1420 is aligned with the opposing slot 1394 of the second pair of opposing slots 1394 formed on the lateral frame portion 1386. The biasing member 1422 will then urge the transverse rail 1420 into a nested position in the slot 1394 of the second pair of opposing slots. The alignment member 1364 is now secured to the frame 1362. The alignment member 1364, being secured along two directions (i.e., lateral rail 1416 and transverse rail 1420), provides a secure, robust connection. It is appreciated that while the first pair of guide slots 1392 are shown on the frame 1362 and the lateral and transverse rails 1416 and 1420 are shown on the alignment member 1364, they may be provided on opposite components. In other words, the guide slots 1392 can be formed on the alignment member 1364 and the lateral and transverse rails 1416 and 1420 can be formed on the frame 1362. Other configurations are contemplated.

Figure 131:
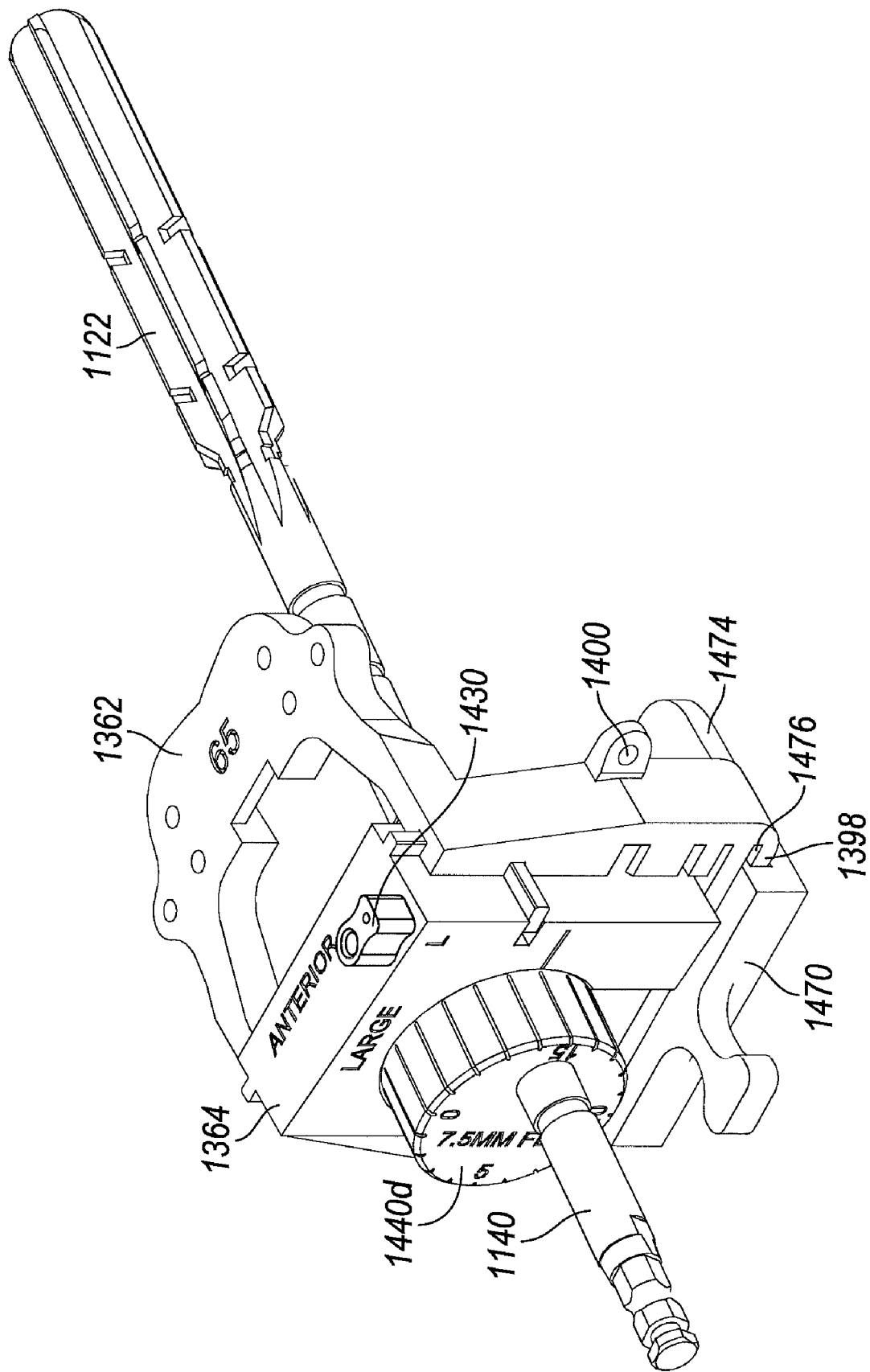

Referencing now to FIG. 127, the series of locating bushings 1370 will be described in greater detail. Similar to the positioning sleeves 1196 associated with preparation of the tibia above, the series of locating bushings 1370 can include a neutral locating bushing 1440a (0 offset or "neutral offset"), an offset locating bushing 1440b (2.5 mm offset), an offset locating bushing 1440c (5 mm offset) and an offset locating bushing 1440d (7.5 mm offset). Bores 1450a, 1450b, 1450c and 1450d can be formed through each of the locating bushings 1370, respectively. Indicia marks 1452 can be defined around a front face 1454 of each of the locating bushings 1370. An annular groove 1456 can be defined around a circumferential surface 1460 of each of the locating bushings 1370. A locating bushing 1370 can be selected from the series of locating bushings 1370 and be advanced into the keyway 1410 of the alignment member 1364 until engaging the axial stop 1412. The axial stop 1412 can preclude the locating bushing 1370 from advancing further axially. Next, the knob 1430 can be rotated from the position shown in FIG. 130 to a position shown in FIG. 131. By rotating the knob 1430 around the axis 1432, a scalloped shaft 1462 can extend into the keyway 1410 and therefore into a nested position in the annular groove 1456 formed around the circumferential wall 1460 of the locating bushing 1370, whereas prior to rotating the knob 1430 the scallop of the shaft was positioned to allow the diameter of the locating bushing to pass by. With the knob 1430 rotated in the locked position as shown in FIG. 131, the shaft 1462 will preclude withdrawal of the locating bushing 1370 from the keyway 1410. The locating bushing 1370 is still permitted to rotate around its axis 1451 within the keyway 1410.

Figure 132:
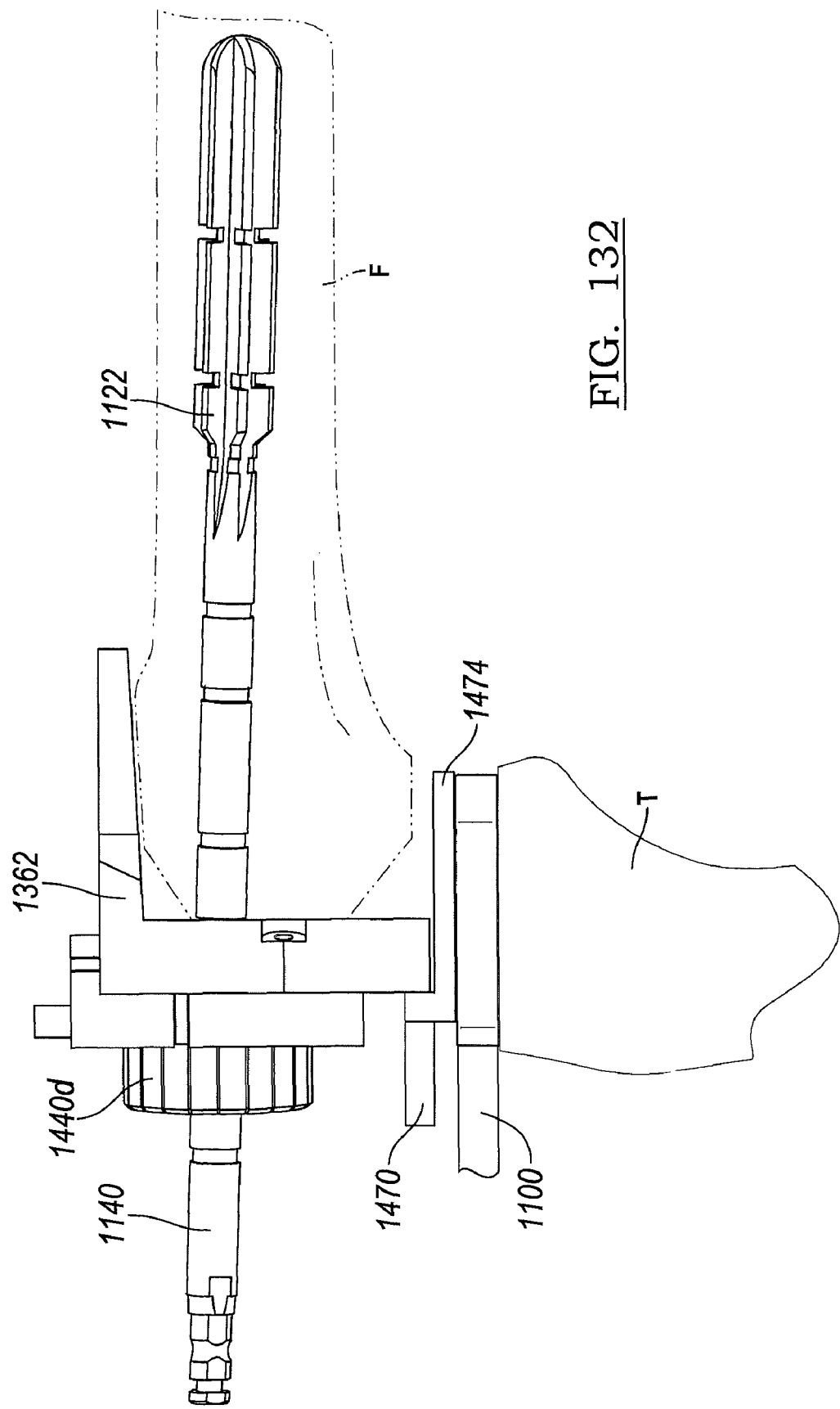

Next, a posterior foot 1470 will be described in greater detail. The posterior foot 1470 can generally comprise a handle portion 1472, a fin portion 1474 and a catch 1476. The posterior foot 1470 can be selectively coupled to the frame 1362 as illustrated in FIGS. 131 and 132. Specifically, in one example, the catch 1476 (FIG. 127) can be inserted into the posterior foot slot 1398 of the distal section 1382 on the frame 1362. The posterior foot 1470 can be used along with the tibia spacers 1100 to match the flexion gap as illustrated in FIG. 132 (i.e., the tibia and femur positioned in flexion) to the extension gap (the tibia and femur positioned in extension as described above with respect to FIGS. 122B and 122C). It will be appreciated that it may be necessary to change the frame 1362 to a different sized frame if the discrepancy between flexion and extension gaps is unsatisfactory or similarly to use a different size offset or different offset position.

Figure 133:
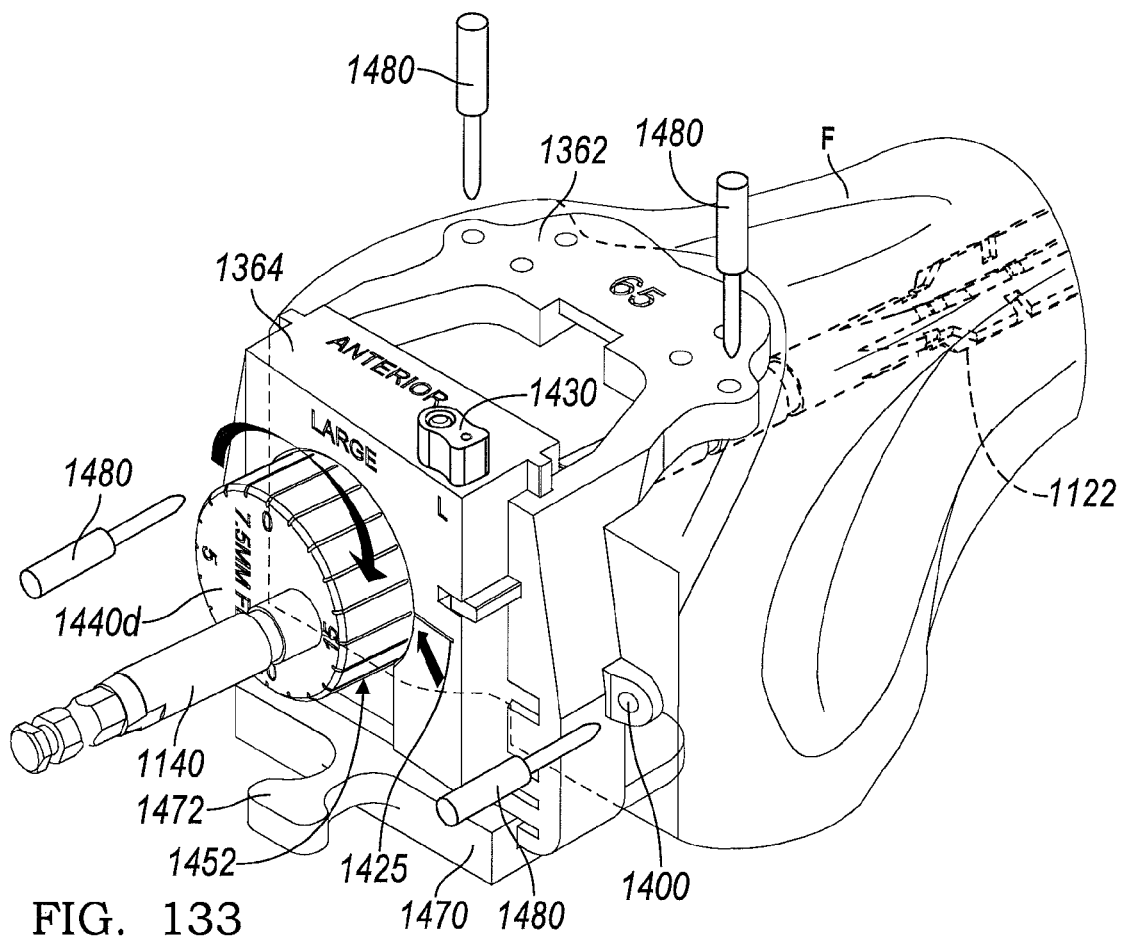

With the reamer 1122 extending through the offset bore 1450 of the locating bushing 1370, the locating bushing 1370 can be rotated (e.g., by the surgeon) around its longitudinal axis 1451 (FIG. 129) until a position is attained in which the frame 1362 achieves optimal coverage over the distal femur. In one example, while rotating the locating bushing 1370, the surgeon can refer to the position of the posterior foot 1470 and the tibia spacer 1100 as reference (FIG. 133). In some instances, the frame 1362 can occupy a position on the distal femur that satisfies adequate bone coverage, but the flexion gap does not match the extension gap. In this case, it may be necessary to change the femoral size (change the frame 1362 to a different sized frame). It is appreciated that it may be necessary to swap out locating bushings 1370 until a locating bushing 1370 having an offset (or a neutral offset) that corresponds to the best distal femoral coverage is achieved.

Once optimal coverage of the distal femur is attained and the flexion gap and the extension gap are matched, the frame 1362 can be secured in place relative to the distal femur. In one example, pins or fasteners 1480 can be inserted through the eyelets 1400 defined on the frame 1362. Again, it is important to note that once the frame 1362 is sufficiently secured to the distal femur, the other components of the kit 1360 (the alignment member 1364, the cutting block 1366, and the PS box guide assembly 1368) can all be switched out while the frame 1362 remains fixed to the distal femur. Those skilled in the art will appreciate that by using the frame 1362 as a fixed reference, accuracy can be improved during formation of the offset bore, the cuts, and the PS box cuts. Likewise, it is appreciated that by providing a common reference point (the frame 1362), a surgeon may require less time to accomplish preparation of the distal femur.

Figure 134:
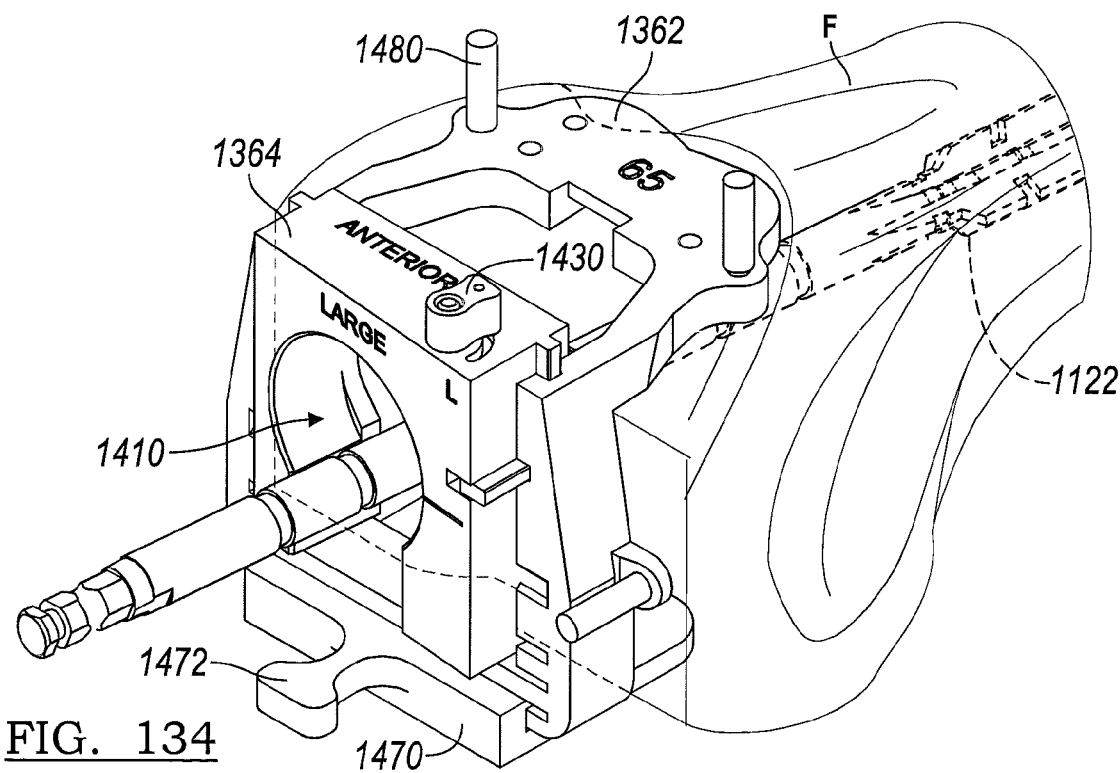
Figure 135:
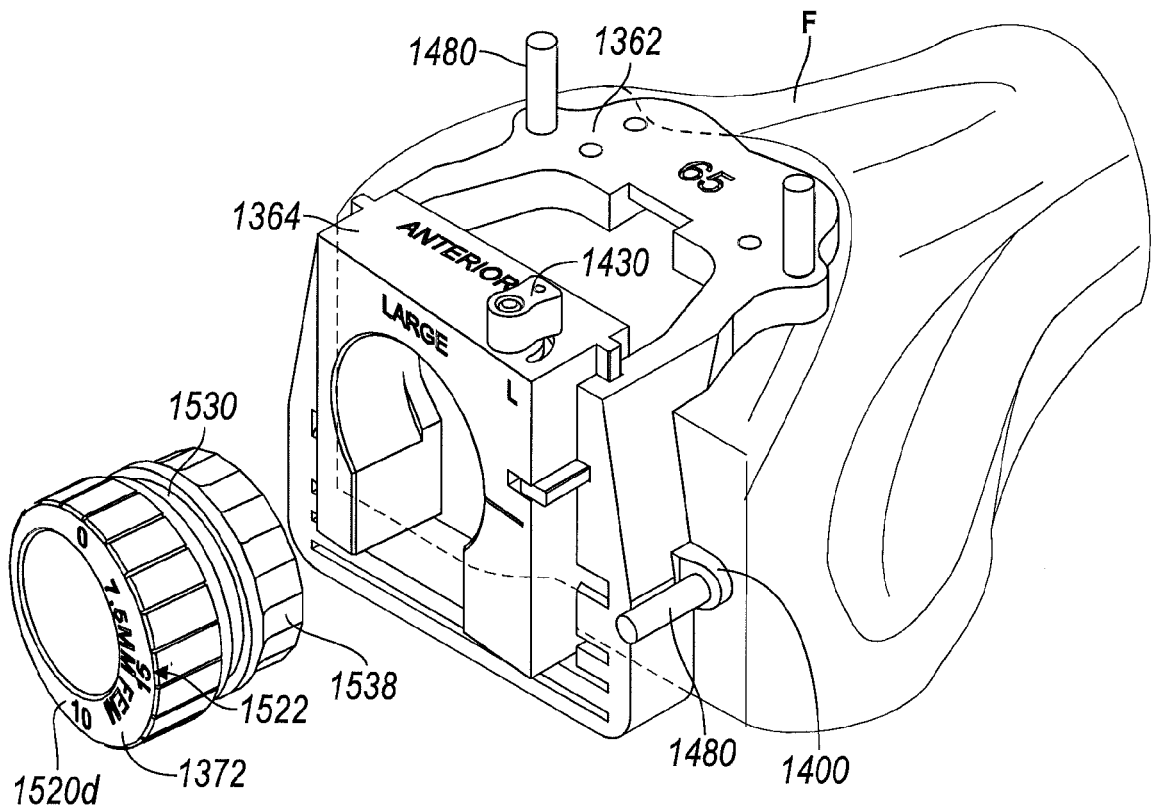

A surgeon then makes a note of the indicia mark 1452 that is aligned with the alignment indicator 1425 of the alignment member 1364. Next, the locating bushing 1370 is removed from the alignment member 1364 (FIG. 134). To remove the locating bushing 1370 from the alignment member 1364 a surgeon can rotate the knob 1430 around the axis 1432 into the unlocked position (FIG. 134). The locating bushing 1370 can then be withdrawn from the keyway 1410. The reamer 1122 can also be removed through the keyway 1410. In some examples, it may be necessary to remove the alignment member 1364 from the frame 1362 prior to withdrawal of the reamer 1120 from the keyway 1410. In such an example, a surgeon can simply depress the transverse rail 1420 into the channel 1424 and remove the alignment member 1364 by sliding the lateral rails 1416 from the first pair of guide slots 1392 defined in the frame 1362.

Next, a reamer bushing 1372 can be inserted into the keyway 1410 of the alignment member 1364. Returning now to FIG. 127, the reamer bushings 1372 can include a neutral reamer bushing 1520a (0 mm offset or "neutral offset"), an offset reamer bushing 1520b (2.5 mm offset), an offset reamer bushing 1520c (5 mm offset) and an offset reamer bushing 1520d (7.5 mm offset). A front face 1524 of each of the reamer bushing 1372 includes indicia marks 1522, respectively. An annular groove 1530 can be defined around a circumferential surface 1532 of each of the reamer bushings 1372. Offset bores 1536a, 1536b, 1536c and 1536d can be formed through each of the reamer bushings 1372, respectively. Facets 1538 can be formed on each of the reamer bushings 1372. The reamer bushings 1372 each define a longitudinal axis 1540. The selected reamer bushing 1372 can be advanced into the keyway 1410 of the alignment member 1364 until engaging the front face 1404 (the reamer bushings have a ledge to stop them from moving further axially. The angled surfaces interface with the facets on the reamer bushings to lock the reamer bushings in the desired position.

Figure 136A:
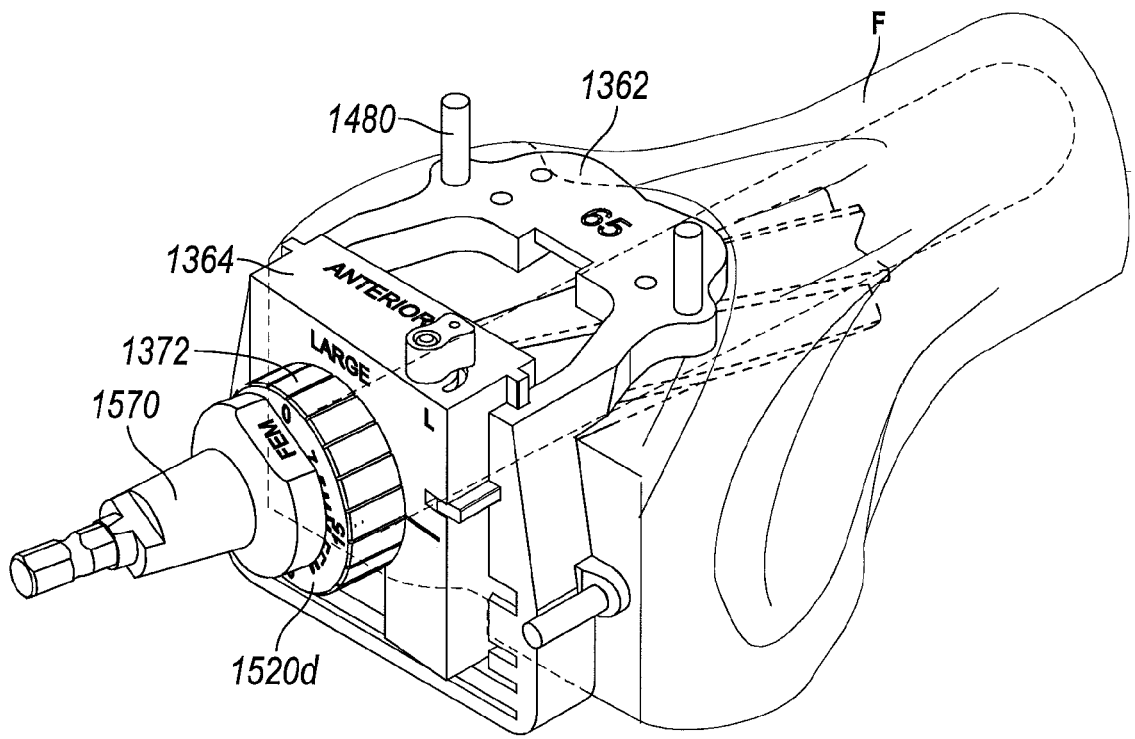
Figure 136B:
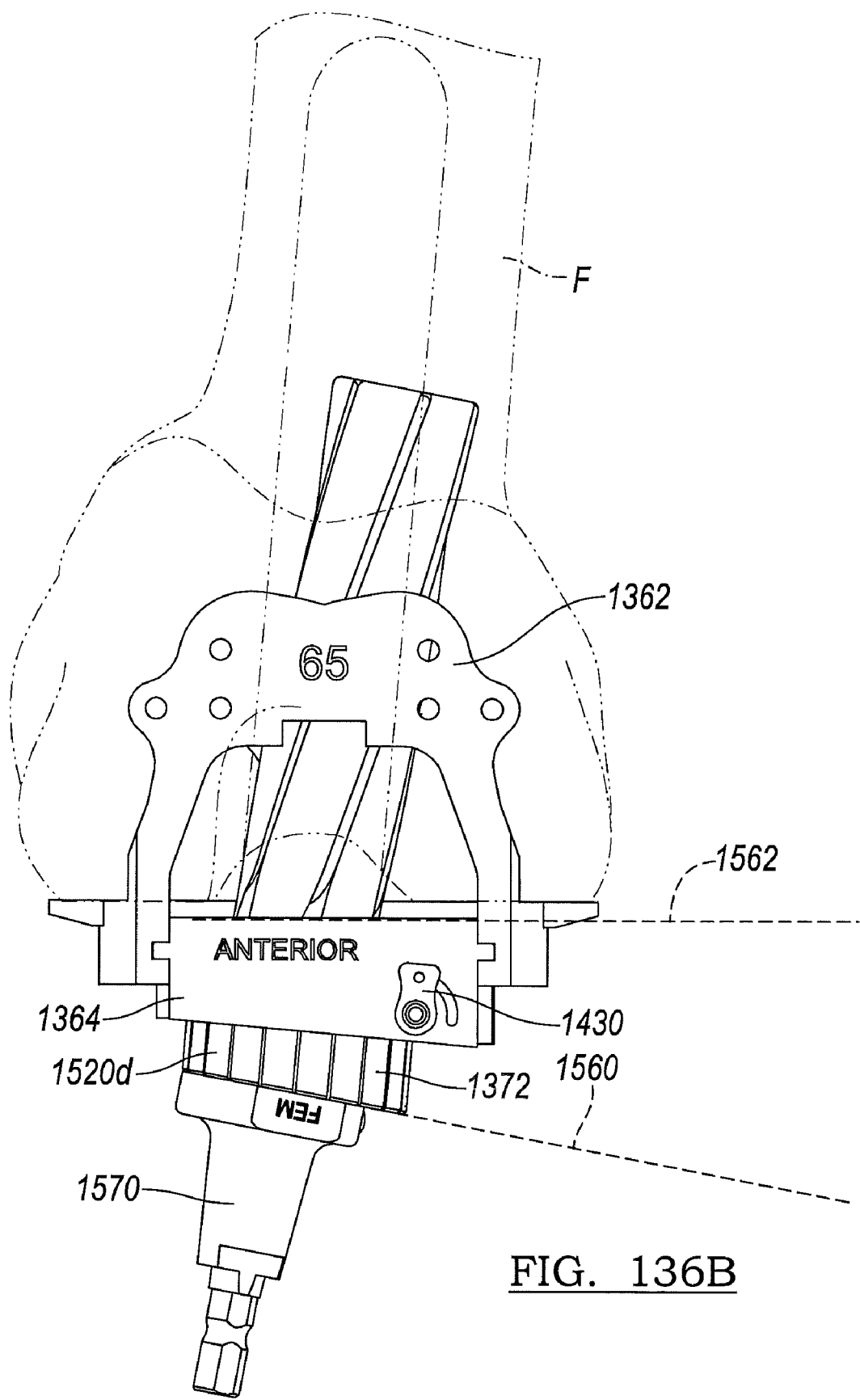
Figure 137A:
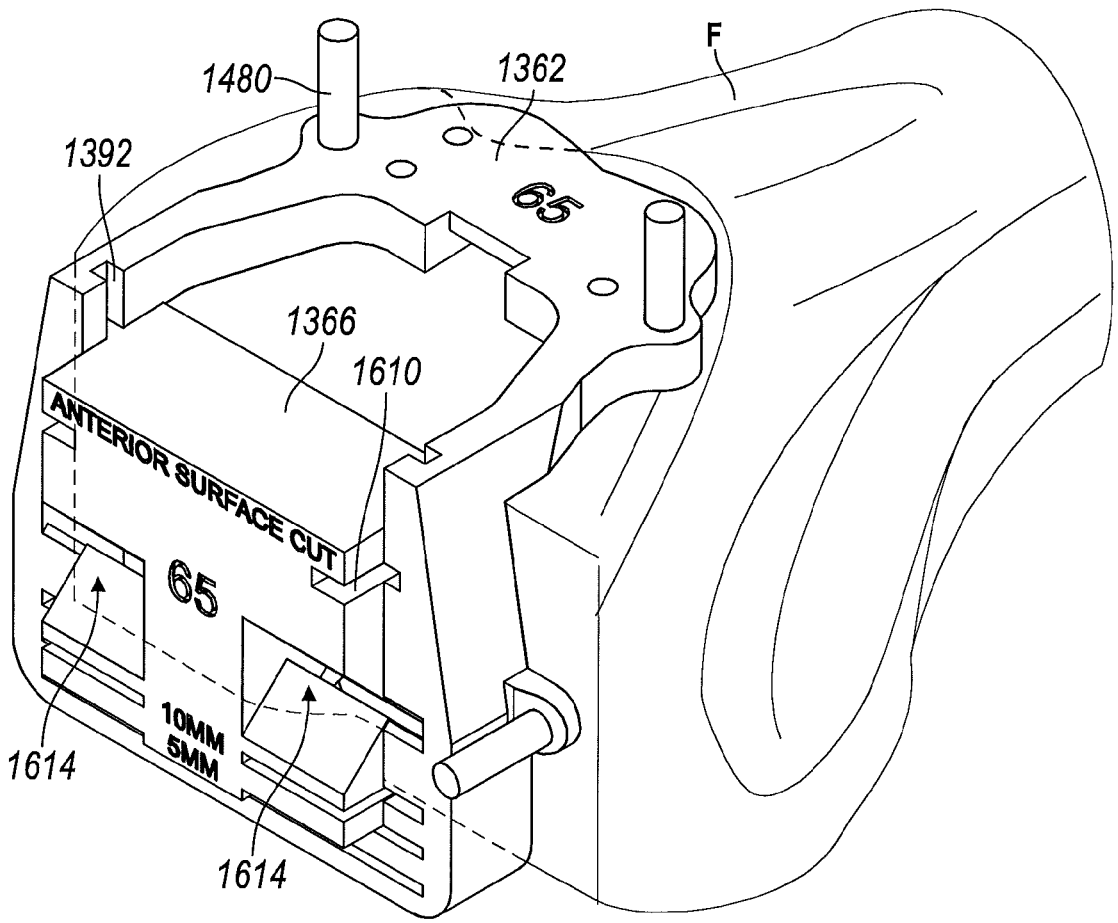
Figure 137B:
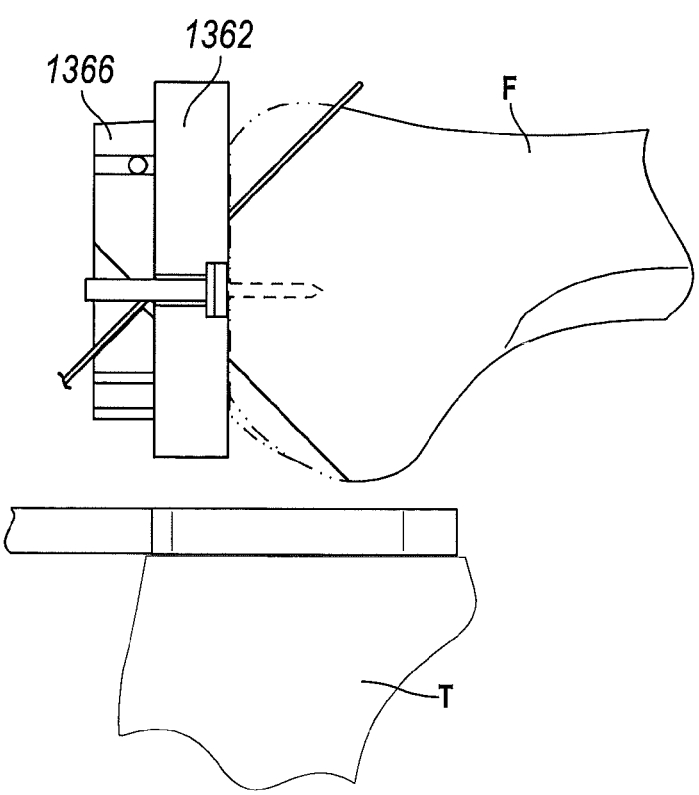

The surgeon then rotates the reamer bushing 1372 within the keyway 1410 of the alignment member 1364 to align the indicia marks 1522 with the noted indicia mark 1452 that was aligned with the alignment indicator 1425 above. The reamer bushing 1372 can then be advanced further into the keyway 1410 to the position shown in FIG. 136A. The knob 1430 can then be rotated along its axis 1432 causing the shaft 1462 to nest into the annular groove 1530 defined around the circumferential surface 1532. As with the locating bushing 1370 described above, the shaft 1462 can preclude withdrawal of the reamer bushing 1372 from the keyway 1410. The reamer bushing 1372 cannot rotate because it locks into place when the facets 1538 interface with 3 flats/axial stops formed on the alignment member 1364. As can be appreciated, each of the reamer bushings 1372 correspond to a respective locating bushing 1370. In this way, a surgeon will select a reamer bushing 1372 having a similar offset as the locating bushing 1370 identified above. As shown in FIG. 136B, the offset reamer bushing 1520*d* defines a first plane 1560 and a second plane 1562 that are non-parallel. As can be appreciated, the series of reamer bushings 1372 can be provided having various first and second planes that diverge at various distinct angles. As can be appreciated, each reamer bushing 1372 can correspond to an angle of reaming that will accommodate the profile of any of the given offset adapters (such as the adapter 604, FIG. 41A) disclosed herein. In some examples, a neutral reamer bushing 1520*a* can be used in instances where an offset adapter is unnecessary.

A reamer 1570 can be used to ream an opening in the distal femur that will accommodate the femoral implant boss (such as reference numeral 130, illustrated in FIG. 8) as well as an offset adapter such as 604 if necessary. The reamer 1570 is guided by the offset bore 1536 of the reamer bushing 1372.

The alignment member 1364 is then removed from the frame 1362. In order to remove the alignment member 1364 from the frame 1362, in one example, a surgeon can depress the transverse rail 1420 such that it withdraws from the second opposing slot 1394. The alignment member 1364 can then be withdrawn from the entryway 1390 by traversing the lateral rails 1416 of the alignment member 1364 along the first pair of guide slots 1392 of the frame 1362.

Next, the cutting block 1366 is coupled to the frame 1362. Again, it is appreciated that the frame 1362 remains fixed to the distal femur. The cutting block 1366 attaches to the frame 1362 in the same manner as described above with respect to the alignment member 1364. The cutting block 1366 includes lateral rails 1602 (FIG. 127) and transverse rails 1604. In one example, such as the one shown in FIGS. 137*a* and 137*b*, transverse rails 1604 can be included on opposite lateral sides of the cutting block. The transverse rails 1604 can each be biased by a biasing member 1606 in a direction generally outwardly from the cutting block 1366. The transverse rails 1604 can be depressed into respective channels 1610 against the bias of the biasing member 1606 of the cutting block 1366. The cutting block 1366 can further define a plurality of tool guides 1614 formed thereon. The tool guides 1614 can be configured to guide a blade of a bone saw.

In one example, according to the present teachings, a surgeon can depress the transverse rails 1604 into the respective channels 1610 of the cutting block 1366. The transverse rails 1604 can be flush or substantially flush with an outer surface of the cutting block 1366. Next, the surgeon can advance the cutting block 1366 into the entryway 1390 of the frame 1362. More specifically, the lateral rails 1602 of the cutting block 1366 can be aligned with the first pair of guide slots 1392 of the frame 1362. While the transverse rails 1604 remain depressed, the lateral rails 1602 of the cutting block 1366 can be advanced along the first pair of guide slots 1392 of the frame 1362. Once the transverse rails 1604 advance to a location beyond an outer surface of the frame 1362, the transverse rails 1604 will remain in a depressed position until they are aligned with the second pair of opposing slots 1394 formed on the lateral frame portion 1386 of the frame 1362. The biasing members 1606 will then urge the respective transverse rails 1604 into a nested position in the respective opposing slots 1394. The cutting block 1366 is now secured to the frame 1362. Next, a surgeon can perform the cuts, such as chamfer cuts, posterior augment cuts through the tool guides 1614 in a manner known in the art. An anterior surface cut can also be performed on the femur. The posterior cut may be made through the posterior cutting slot in the frame 1362.

Once the distal femur has been prepared with the cutting block 1366, the cutting block 1366 can be removed from the frame 1362. To remove the cutting block 1366 from the frame 1362 according to one example of the present teachings, the transverse rails 1604 can be depressed into their respective channels 1610. The cutting block 1366 can then be withdrawn from the frame 1362 by sliding the lateral rails 1602 from the first pair of guide slots 1392 defined in the frame 1362.

Figure 138:
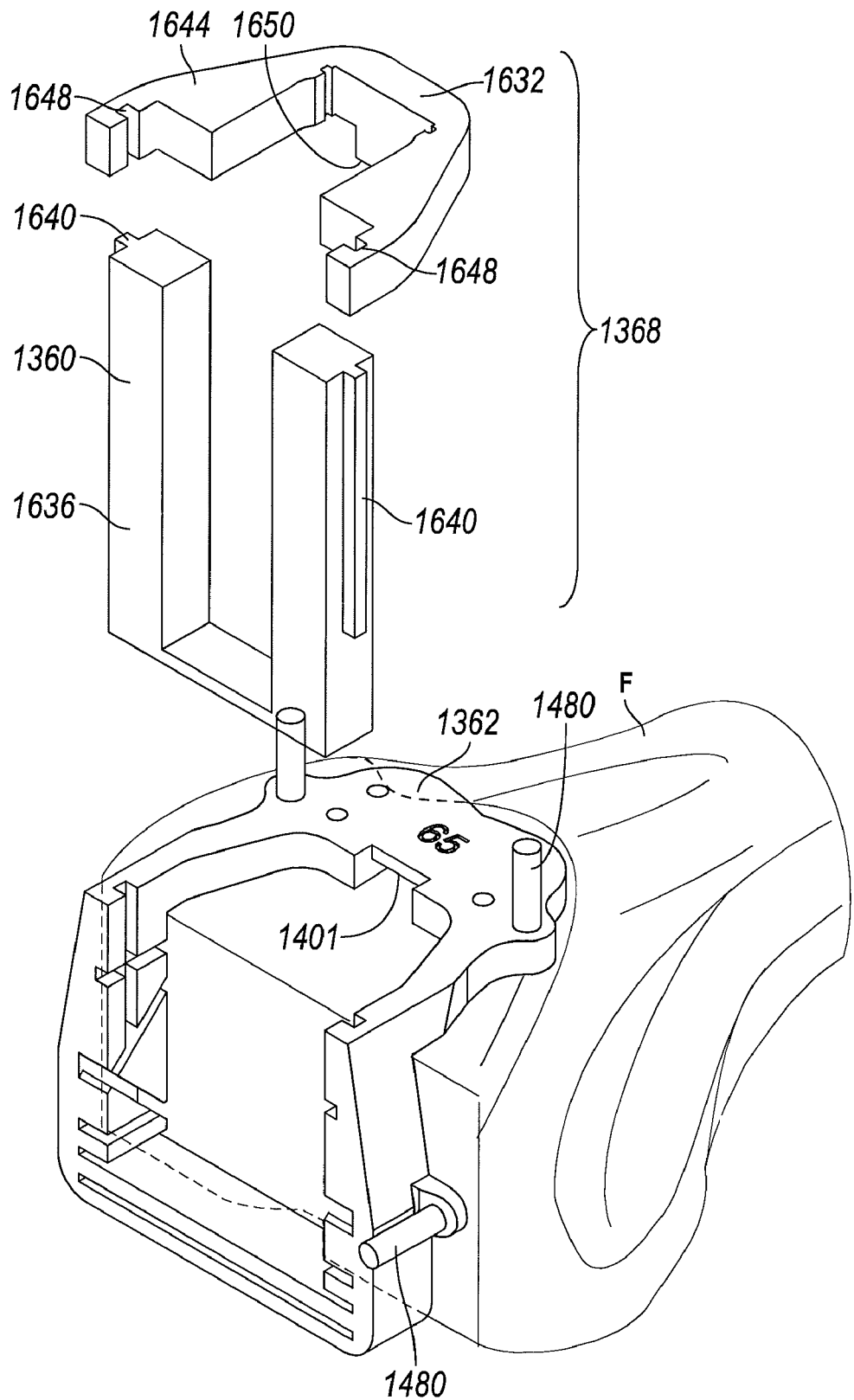
Figure 139:
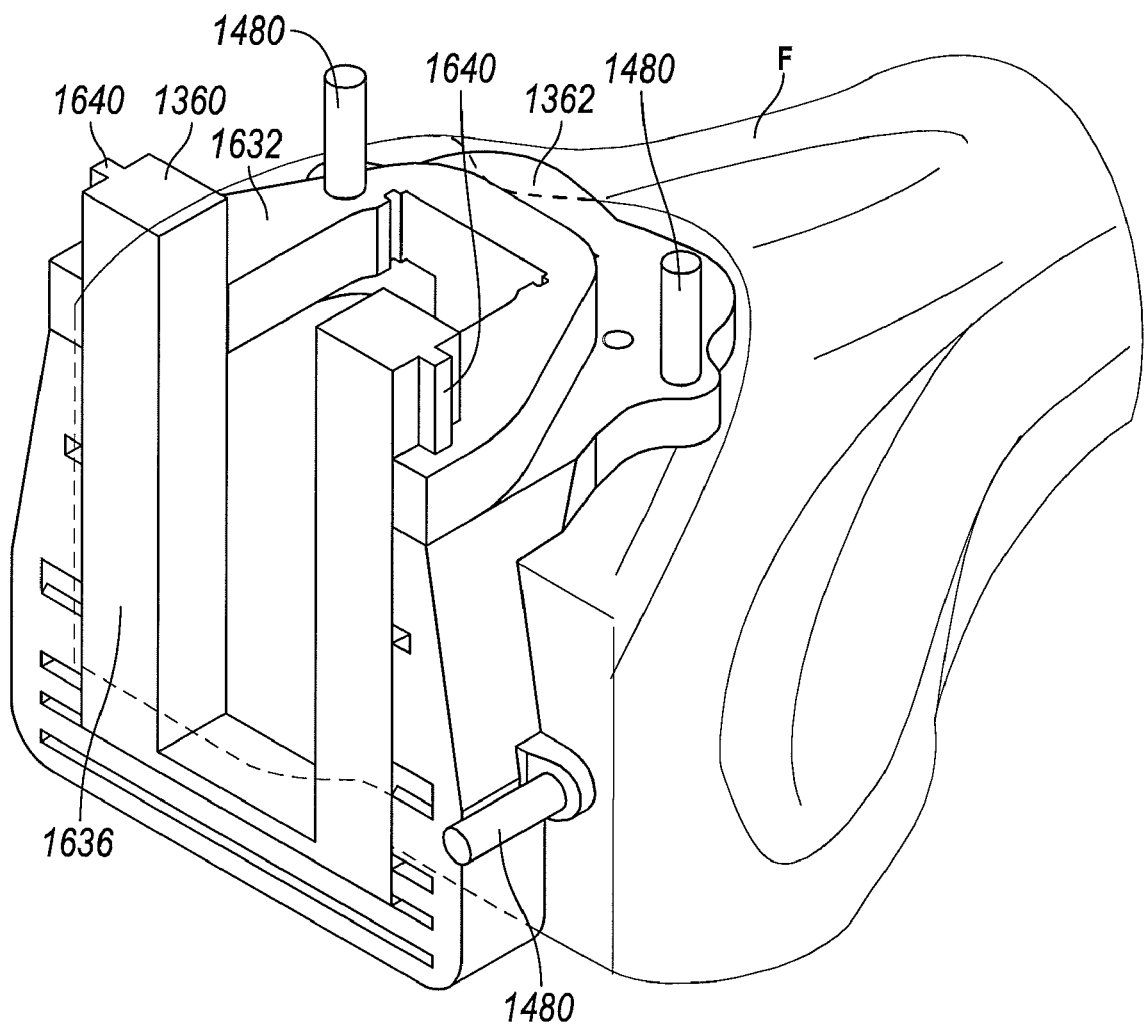
Figure 140:
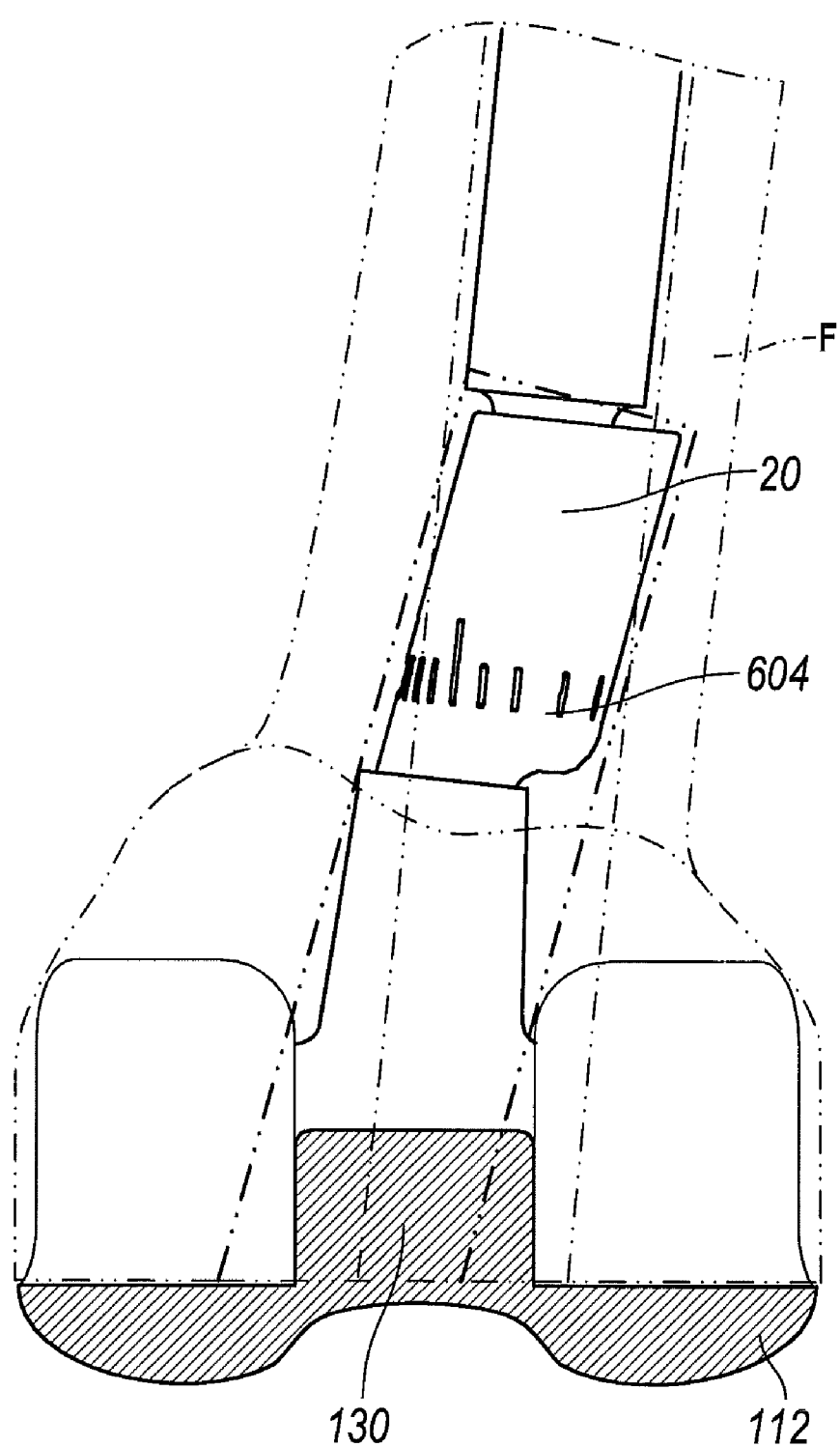

Next, referring to FIGS. 138 and 139, the PS box guide assembly 1368 is coupled to the frame 1362. Again, it is appreciated that the frame 1362 remains fixed to the distal femur. The PS box guide assembly 1368 can generally comprise a first PS box guide component 1360 and a second PS box guide component 1632. The first PS box guide component 1360 can generally comprise a U-shaped body 1636 having rails 1640 defined along its lateral sides. The second PS box guide component 1632 can generally comprise a C-shaped body 1644. The C-shaped body 1644 can define retaining slots 1648 and a catch 1650. In one example, the second PS box guide component 1632 can be located against the anterior section 1380 of the frame 1362, such that the catch 1650 locates onto the shelf 1401 of the anterior section 1380. The rails 1640 of the first PS box guide component 1630 can then slidably locate through the retaining slot 1648 of the second PS box guide component 1632 and the first pair of guide slots 1392 of the frame 1362. The PS box can then be resected in a manner known in the art. Next, the PS box guide assembly 1368 can be removed from the frame 1362 and the frame 1362 can be removed from the distal femur. Trial components can then be used to trial the distal femur in a manner known in the art. As shown in FIG. 140, a femoral component 112 having a femoral boss 130, offset adapter 604 and stem 20, such as described herein, can then be implanted onto the distal femur F.

While the above discussion has been generally directed toward instrumentation and a method for performing revision knee surgery, a primary knee replacement surgery can be similarly performed. One method for preparing a tibia during primary knee replacement surgery according to one example of the present teachings will now be described in greater detail.

At the outset, an IM canal can be reamed with a starter reamer in the tibia as is known in the art. The reamer 1122 can then be used with the reamer stop 1120, as discussed above, to ream the IM canal of the tibia until adequate cortical bone is contacted. It should be noted that the proximal tibia shall be resected using an IM tibial resection guide assembly. The remainder of the procedure for preparing a tibia for a primary knee replacement surgery is substantially similar to the procedure described above with respect to preparation of a tibia during a revision procedure.

Figure 141:
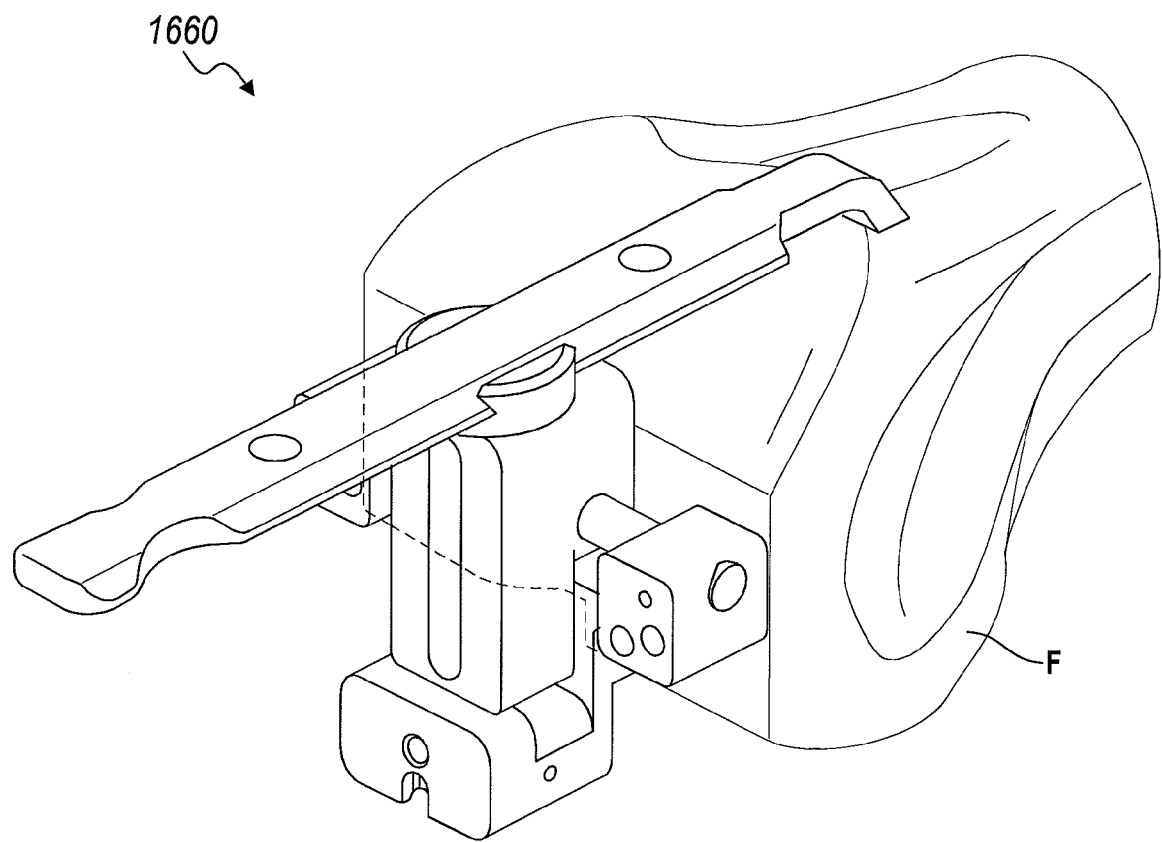
FIGS. 141 and 142 illustrate various instruments and a related sequence for preparing a femur during a primary knee procedure.

One method for preparing a femur during primary knee replacement surgery according to one example of the present teachings will now be described in greater detail. At the outset, an IM canal can be reamed with a starter reamer in the femur as is known in the art. Next, with reference to FIG. 141, an AP sizer 1660 can be used to determine the anterior/posterior size of the distal femur. Other tools may be used to determine the anterior/posterior size of the femur.

Figure 61:
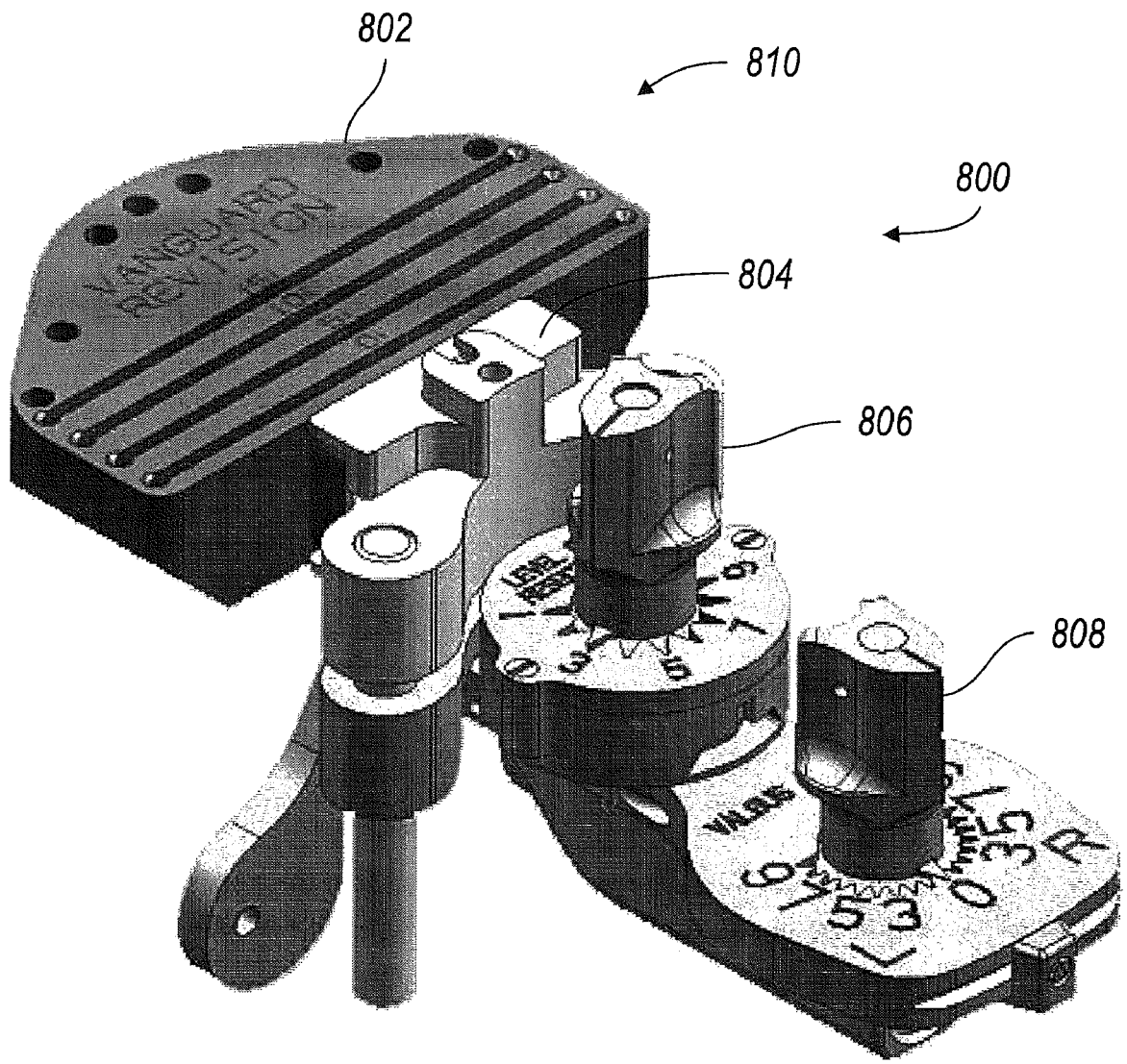
Figure 82:
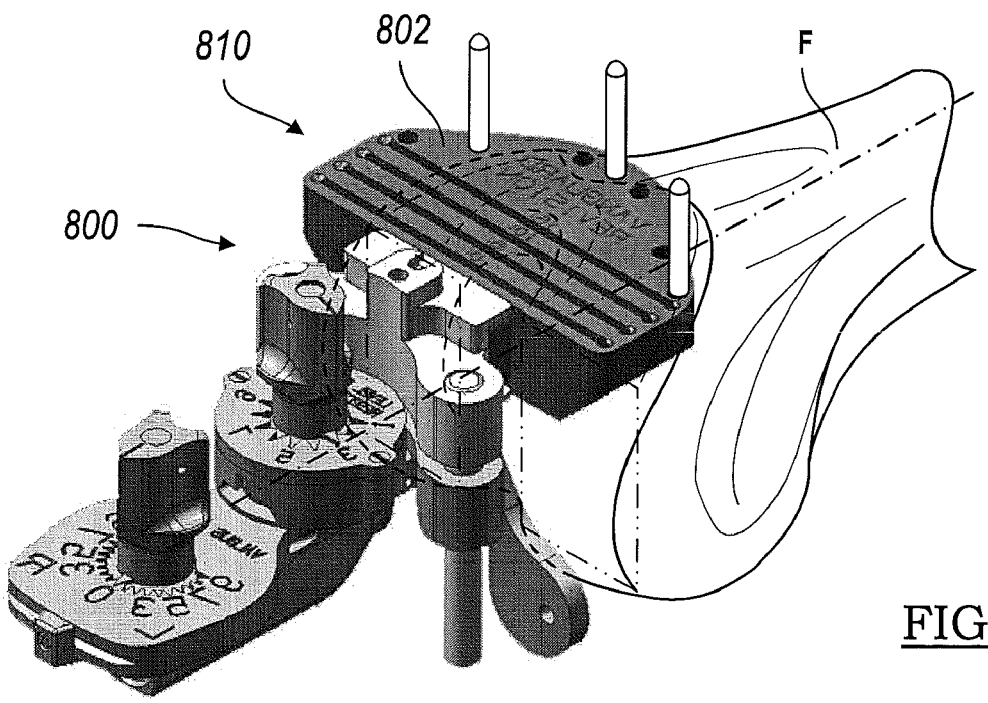

Next, a distal resection guide, such as guide 800 FIG. 61 can be used to perform distal and/or augment cuts (i.e. such as at 5 degrees), see FIGS. 82 and 83. The reamer 1122 can then be used with the reamer stop 1120 as discussed above to ream the IM canal of the femur until adequate cortical bone is contacted. It will be appreciated for a primary femoral procedure, the distal resection will decrease the depth of the initial ream.

Figure 142:
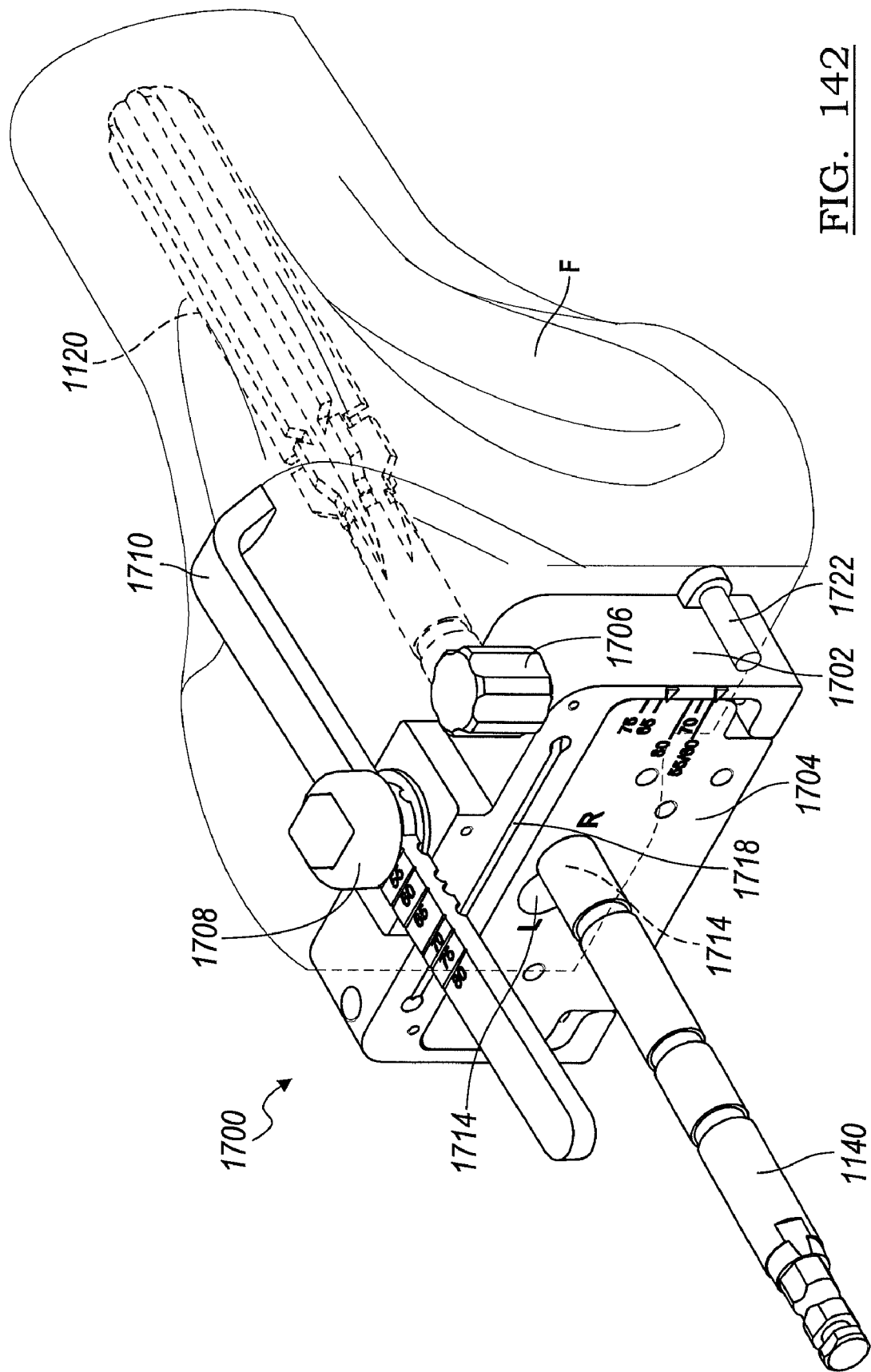

With reference now to FIG. 142, an anterior final cutter 1700 can be used to make the final anterior cut on the distal femur. The anterior final cutter can include body 1702, a central block 1704, a knob 1706, a knuckle 1708 and a finger 1710. The central block 1704 can define a pair of overlapping bores 1714 that correspond to a right and left femur. A respective bore 1714 can receive the reamer shaft 1140. A slot 1718 can be formed in the body 1702 for receiving a cutting during cutting of the anterior femur. During use, the anterior final cutter 1700 can be advanced over the reamer shaft 1140 (e.g. through the identified bore). The knob 1706 can then be rotated causing the body 1702 to move in the anterior/posterior direction relative to the central block 1704. Once the femoral size corresponds to that determined by the AP sizer, the body 1702 is pinned in place by pins 1722 on the distal femur. The anterior final cut can then be made through the slot 1718. As can be appreciated, the anterior section 1380 of the frame can reference the anterior final cut on the distal femur.

The remainder of the procedure for preparing a femur for a primary knee replacement surgery is substantially similar to described above with respect to preparation of a femur during a revision procedure.

While the disclosure has been described in the specification and illustrated in the drawings with reference to a preferred embodiment, it will be understood by those skilled in the art that various changes may be made and equivalents may be substituted for elements thereof without departing from the scope of the disclosure as defined in the claims. In addition, many modifications may be made to adapt a particular situation or material to the teachings of the disclosure without departing from the essential scope thereof. Therefore, it is intended that the disclosure not be limited to the particular embodiment illustrated by the drawings and described in the specification as the best mode presently contemplated for carrying out this disclosure, but that the disclosure will include any embodiments falling within the description of the appended claims.

What is claimed is:

1. A system for cooperating with an elongated intramedullary (IM) member during preparation of a bone for receiving a prosthesis, the system comprising:
    a frame;
    an alignment assembly selectively coupled to the frame, the alignment assembly cooperating with the IM member to position the frame relative to the bone, the alignment assembly including an alignment member having a receiving portion and a bushing selectively received by the receiving portion of the alignment member, the bushing defining a longitudinal axis, an annular groove and a bore configured to accept the IM member therethrough, the alignment member further comprising an engaging portion, wherein the bushing is selectively received by the receiving portion of the alignment member and the engaging portion is movable from a disengaged position to an engaged position, wherein in the engaged position, the engaging portion nests in the annular groove and substantially inhibits movement of the bushing along the longitudinal axis while permitting rotation of the bushing around the longitudinal axis; and
    a cutting block selectively coupled to the frame wherein the engaging portion comprises a knob coupled to a foot, wherein the knob is movable between the disengaged and engaged positions causing the foot to move from a position generally within the body of the alignment member to a position generally into the receiving portion of the alignment member.

2. The system of claim 1, further comprising a posterior stabilized (PS) box guide assembly having a PS box guide attachment portion that selectively couples with a first attachment portion of the frame.

3. The system of claim 1, further comprising a posterior foot that selectively couples with a second attachment portion on the frame, the posterior foot positioned to occupy space of a joint line in an installed position.

4. The system of claim 1 wherein the knob rotates about an axis between the disengaged and engaged positions.

5. The system of claim 1, further comprising a plurality of bushings each having a longitudinal axis and a bore formed through the bushing wherein the respective bores of each of the bushings are defined at distinct positions relative to the corresponding longitudinal axes.

6. A system for cooperating with an intramedullary (IM) member during preparation of at least a first bone for receiving a prosthesis, the system comprising:
    a frame having an attachment portion defining a slot and that includes a sliding portion and a locking portion formed thereon;
    an alignment member having a body that defines a receiving portion and an alignment member attachment portion, wherein the alignment member attachment portion selectively couples with the attachment portion of the frame in an installed position;
    a bushing selectively received by the receiving portion of the alignment member, the bushing defining a bore configured to accept the IM member therethrough;
    a block having a plurality of tool guides formed thereon configured to guide a blade of a bone saw, the block having a block attachment portion that selectively couples with the attachment portion of the frame in an installed position; and
    a posterior stabilized (PS) box guide assembly having a PS box guide attachment portion that selectively couples with the attachment portion of the frame in an installed position;
    wherein each of the alignment member, the block and the PS box guide all include a rail that is selectively and alternatively slidably coupled to the slot of the attachment portion of the frame during preparation of the bone; and
    wherein the rail of the alignment member attachment portion includes a first portion that extends along the body in a first direction and a second portion that extends along the body in a second direction, the second direction being distinct from the first direction; and
    wherein the second portion is movable between an assembly position and an installed position, wherein in the assembly position, the second portion is substantially flush with the body, and in the installed position, the second portion extends a distance outward from the body and securably nests in the locking portion of the slot, wherein in the installed position, slidable movement of the first portion of the rail along the sliding portion of the slot is substantially inhibited.

7. The system of claim 6, further comprising an engaging portion formed on the alignment member, wherein the bushing is selectively received by the receiving portion of the alignment member and the engaging portion is movable from a disengaged position to an engaged position, wherein in the engaged position, the engaging portion substantially inhibits movement of the bushing along the longitudinal axis while permitting rotation of the bushing around the longitudinal axis.

8. The system of claim 6 wherein the bushing defines facets that selectively cooperate with structure on the alignment member to inhibit rotation around the longitudinal axis.

9. The system of claim 7 wherein the bushing defines an annular groove and wherein the engaging portion nests in the annular groove of the bushing in the engaged position.

10. The system of claim 9 wherein the engaging portion comprises a knob coupled to a shaft, wherein the knob is movable between the disengaged and engaged positions causing the shaft to move from a position generally within the body of the alignment member to a position generally into the receiving portion of the alignment member.

11. The system of claim 10 wherein the knob rotates about an axis between the disengaged and engaged positions.

12. The system of claim 6 wherein the alignment member further comprises a biasing member that biases the second portion toward the installed position.

13. The system of claim 6 wherein the alignment member includes a stop that generally extends into the receiving portion wherein axial movement of the bushing is limited by the stop.

14. The system of claim 6, further comprising a posterior foot that selectively couples to a distal resection surface of the frame in an installed position, the posterior foot positioned to occupy space of a joint line in the installed position.

15. A system for cooperating with an intramedullary (IM) member during preparation of a bone for receiving a prosthesis, the system comprising:
a frame having a plurality of attachment portions formed thereon;
an alignment member having a body that defines a receiving portion, an engaging portion and an alignment member attachment portion, the alignment member attachment portion selectively coupling with a first attachment portion of the plurality of attachment portions of the frame in an installed position wherein the engaging portion comprises a knob coupled to a foot, wherein the knob is movable between the disengaged and engaged positions causing the foot to move from a position generally within the body of the alignment member to a position generally into the receiving portion of the alignment member;
a bushing extending along a longitudinal axis and having a circumferential surface defining an annular groove formed thereon, and a bore formed through the bushing, the bore configured to accept the IM member therethrough; and
wherein the bushing is selectively received by the receiving portion of the alignment member and the engaging portion is movable from a disengaged position to an engaged position, wherein in the engaged position, the engaging portion nests in the annular groove of the bushing thereby substantially inhibiting movement of the bushing along the longitudinal axis while permitting rotation of the bushing around the longitudinal axis.

16. The system of claim 15 wherein the first attachment portion defines one of a rail or a slot and the alignment member attachment portion defines the other of the rail or slot, wherein the slot slidably accepts the rail in the installed position.

17. The system of claim 16 wherein the alignment member attachment portion defines a rail having a first portion that extends along the body in a first direction and a second portion that extends along the body in a second direction, the second direction being distinct from the first direction.

18. The system of claim 17 wherein the first attachment portion defines a slot having a sliding portion and a locking portion.

19. The system of claim 18 wherein the second portion is movable between an assembly position and an installed position, wherein in the assembly position, the second portion is substantially flush with the body, and in the installed position, the second portion extends a distance outward from the body and securably nests in the locking portion of the slot, wherein in the installed position, slidable movement of the first portion of the rail along the sliding portion of the slot is substantially inhibited.

20. The system of claim 18 wherein the alignment member further comprises a biasing member that biases the second portion toward the installed position.

21. The system of claim 15 wherein the knob rotates about an axis between the disengaged and engaged positions.

22. The system of claim 21 wherein the alignment member includes a stop that generally extends into the receiving portion wherein axial movement of the bushing is limited by the stop.

23. The system of claim 15, further comprising a block having a plurality of tool guides formed thereon configured to guide a blade of a bone saw, the block having a block attachment portion that selectively couples with the first attachment portion of the plurality of attachment portions of the frame in an installed position.

24. The system of claim 23 wherein the block attachment portion includes a rail having a first portion that extends along the body in a first direction and a second portion that extends along the body in a second direction, the second direction being distinct from the first direction.

25. The system of claim 24 wherein the second portion is movable between an assembly position and an installed position, wherein in the assembly position, the second portion is substantially flush with the body and in the installed position, the second portion extends a distance outward from the body.

26. The system of claim 25 wherein the block further comprises a biasing member that biases the second portion toward the installed position.

27. The system of claim 23, further comprising a posterior stabilized (PS) box guide assembly having a PS box guide attachment portion that selectively couples with the first attachment portion of the plurality of attachment portions of the frame in an installed position.

28. A system for cooperating with an intramedullary (IM) member during preparation of a bone for receiving a prosthesis, the system comprising:
a frame having a plurality of attachment portions formed thereon;
an alignment member having a body that defines a receiving portion, an engaging portion and an alignment member attachment portion, the alignment member attachment portion selectively coupling with a first attachment portion of the plurality of attachment portions of the frame in an installed position;

a bushing extending along a longitudinal axis and having a circumferential surface defining an annular groove formed thereon, and a bore formed through the bushing, the bore configured to accept the IM member therethrough;

wherein the bushing is selectively received by the receiving portion of the alignment member and the engaging portion is movable from a disengaged position to an engaged position, wherein in the engaged position, the engaging portion nests in the annular groove of the bushing thereby substantially inhibiting movement of the bushing along the longitudinal axis while permitting rotation of the bushing around the longitudinal axis; and a block having a plurality of tool guides formed thereon configured to guide a blade of a bone saw, the block having a block attachment portion that selectively couples with the first attachment portion of the plurality of attachment portions of the frame in an installed position;

wherein the block attachment portion includes a rail having a first portion that extends along the body in a first direction and a second portion that extends along the body in a second direction, the second direction being distinct from the first direction, wherein the second portion is movable between an assembly position and an installed position, wherein in the assembly position, the second portion is substantially flush with the body and in the installed position, the second portion extends a distance outward from the body.

29. The system of claim 28 wherein the block further comprises a biasing member that biases the second portion toward the installed position.

* * * * *